US012600776B2

(12) United States Patent
Chae et al.

(10) Patent No.: US 12,600,776 B2
(45) Date of Patent: Apr. 14, 2026

(54) ANTI-L1CAM ANTIBODY OR ANTIGEN-BINDING FRAGMENT THEREOF AND CHIMERIC ANTIGEN RECEPTOR COMPRISING SAME

(71) Applicant: CARTEXELL INC., Seoul (KR)

(72) Inventors: Jin-A Chae, Seoul (KR); Jae-Gyun Jeong, Seoul (KR); Dae Young Kim, Chungcheongbuk-do (KR); Yu Jung Kim, Chungcheongbuk-do (KR); Bin Yoo, Chungcheongbuk-do (KR)

(73) Assignee: CARTEXELL INC., Seoul (KR)

( * ) Notice: Subject to any disclaimer, the term of this patent is extended or adjusted under 35 U.S.C. 154(b) by 1216 days.

(21) Appl. No.: 17/285,184

(22) PCT Filed: Oct. 21, 2019

(86) PCT No.: PCT/KR2019/013820
§ 371 (c)(1),
(2) Date: Apr. 18, 2022

(87) PCT Pub. No.: WO2020/080908
PCT Pub. Date: Apr. 23, 2020

(65) Prior Publication Data
US 2022/0242948 A1 Aug. 4, 2022

(30) Foreign Application Priority Data
Oct. 19, 2018 (KR) ......................... 10-2018-0125538

(51) Int. Cl.
| | |
|---|---|
| *A61K 40/31* | (2025.01) |
| *A61K 40/11* | (2025.01) |
| *A61K 40/42* | (2025.01) |
| *A61P 35/00* | (2006.01) |
| *C07K 14/705* | (2006.01) |
| *C07K 14/715* | (2006.01) |
| *C07K 14/725* | (2006.01) |
| *C07K 14/73* | (2006.01) |
| *C07K 16/28* | (2006.01) |
| *C12N 5/0783* | (2010.01) |

(52) U.S. Cl.
CPC .......... *C07K 16/2803* (2013.01); *A61K 40/11* (2025.01); *A61K 40/31* (2025.01); *A61K 40/4254* (2025.01); *C07K 14/7051* (2013.01); *C07K 14/70514* (2013.01); *C07K 14/70517* (2013.01); *C07K 14/70521* (2013.01); *C07K 14/70532* (2013.01); *C07K 14/70575* (2013.01); *C07K 14/70589* (2013.01); *C07K 14/7151* (2013.01); *C12N 5/0636* (2013.01); *A61K 2239/31* (2023.05); *A61K 2239/38* (2023.05); *A61K 2239/59* (2023.05); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 8,138,313 B2 | 3/2012 | Kelm et al. | |
| 9,447,194 B2 | 9/2016 | Jensen | |
| 9,777,060 B2 | 10/2017 | Hong et al. | |
| 10,189,903 B2 | 1/2019 | Jensen | |
| 2015/0038684 A1 | 2/2015 | Jensen | |
| 2015/0344571 A1 | 12/2015 | Hong et al. | |
| 2017/0107285 A1 | 4/2017 | Jensen | |
| 2018/0009891 A1* | 1/2018 | Jensen | ............... C07K 14/7051 |
| 2019/0119382 A1 | 4/2019 | Jensen | |
| 2020/0237825 A1* | 7/2020 | Li | ........................ C12N 5/0646 |
| 2021/0085719 A1* | 3/2021 | Jensen | ............... A61K 40/4204 |
| 2023/0130938 A1* | 4/2023 | Jensen | ................. A61K 31/713 |
| | | | 424/130.1 |

FOREIGN PATENT DOCUMENTS

| | | |
|---|---|---|
| CN | 107523549 A | 12/2017 |
| CN | 107709356 A | 2/2018 |
| JP | 2015-513394 A | 5/2015 |
| KR | 10-2010-0064985 A | 6/2010 |
| KR | 10-2014-0066101 A | 5/2014 |
| WO | WO-2014/077648 A1 | 5/2014 |

OTHER PUBLICATIONS

Hong Hao et al: "Diverse solid tumors expressing a restricted epitope of L1-CAM can be targeted by chimeric antigen receptor redirected T lymphocytes", Journal of Immunotherapy, Lippincott Williams & Wilkins, US, vol. 37, No. 2, Feb. 1, 2014 (Feb. 1, 2014) , pp. 93-104.

Julie R Park et al: "Adoptive Transfer of Chimeric Antigen Receptor Re-directed Cytolytic T Lymphocyte Clones in Patients with Neuroblastoma", Molecular Therapy, Jan. 1, 2007.

Hao Hong et al: "Development of chimeric antigen receptor-redirected T cell therapy targeting LI-GAM in ovarian cancer": Journal for Immunotherapy of Cancer, Biomed Central, London, GB, vol. 1, No. Suppl 1, Nov. 7, 2013 (Nov. 7, 2013) , p. 16.

(Continued)

*Primary Examiner* — Ilia I Ouspenski
(74) *Attorney, Agent, or Firm* — Harness, Dickey & Pierce, P.L.C.

(57) ABSTRACT

The present invention relates to an anti-L1CAM antibody specifically binding to L1CAM antigen or an antigen-binding fragment thereof, a chimeric antigen receptor comprising same, and uses thereof. The anti-L1CAM antibody or the antigen-binding fragment of the present invention is excellent in specificity and affinity to L1CAM and thus may be used in the treatment and diagnosis of cancers related to high expression of L1CAM and diseases related to inflammatory disorders. In particular, when the chimeric antigen receptor comprising the anti-L1CAM antibody of the present invention is expressed in effector cells such as T lymphocytes, the chimeric antigen receptor may be effectively used as immunotherapy for cancers related to L1CAM and inflammatory disorders.

5 Claims, 109 Drawing Sheets

Specification includes a Sequence Listing.

(56)                    References Cited

OTHER PUBLICATIONS

Sergio Gonzalez et al: "Genetic engineering of cytolytic T lympho-
cytes for adoptive T-cell therapy of neuroblastoma", The Journal of
Gene Medicine, vol. 6, No. 6, May 26, 2004 (May 26, 2004), pp.
704-711.
Irina V. Kholodenko et al: "Neuroblastoma Origin and Therapeutic
Targets for Immunotherapy", Journal of Immunology Research, vol.
2018, Jul. 11, 2018 (Jul. 11, 2018), pp. 1-25.
Supplementary Search Report from corresponding European Patent
Application No. 19873014.5 dated Dec. 21, 2021.
International Search Report from corresponding PCT Application
No. PCT/KR2019/013820, dated Feb. 21, 2020.
Hong, H., et al.; "L1 cell adhesion molecule-specific chimeric
antigen receptor-redicrected human T cells exhibit specific and
efficient antitumor activity against human ovairan cancer in mice",
PLOS ONE, Jan. 13, 2016, vol. 11, No. 1, thesis No. e0146885,
inner pp. 1-18.
Schafer, H., et al.; "TGF-$\beta$1-dependent L1CAM expression has an
essential role in macrophage-induced apoptosis resistance and cell
migration of human intestinal epithelial cells" Oncogene, 2013, vol.
32, pp. 180-189.

Cho, S., et al.; Generation, characterization and preclinical studies
of a human anti-L1CAM monoclonal antibody that cross-reacts
with rodent L1CAM, MABS, 2016, vol. 8, No. 2, pp. 414-425.
Office Action from corresponding Japanese Patent Application No.
2021-547023, dated Apr. 25, 2022.
Arlt M.J.E et al., Efficient inhibition of intra-peritoneal tumor
growth and dissemination of human ovarian carcinoma cells in nude
mice by anti-L1-cell adhesion molecule monoclonal antibody treat-
ment, Cancer Research, 2006, vol. 66, No. 2, pp. 936-943.
Wolterink S. et al., Therapeutic Antibodies to Human L1CAM:
Functional Characterization and Application in a Mouse Model for
Ovarian Carcinoma, Cancer Research, 2010, vol. 70 No. 6, pp.
2504-2515.
Pavlova A.A. et al., Adoptitive immunotherapy with genetically
engineered T lymphocytes modified to express chimeric antigen
receptors.
Office Action from corresponding Russian Patent Application No.
2021113476, dated May 6, 2022.
Office Action from corresponding Chinese Patent Application No.
201980068786.1, dated Nov. 13, 2023.
Cai Hui, et al., "Research of modified T lymphocyte with chimeric
antigen receptor in tumor immunotherapy", Modern Oncology,
2014, 22, (11); 2730-2734.

* cited by examiner

M:  protein ladder (Thermo, Cat No. 26619)
R: Reducing doncdition (+DTT)
NR: Non-Reducting condition (-DTT)
* Loaded with 2 ug of each protein except mL1CAM-3R-C9 (3 ug)

Plot against mL1CAM and hL1CAM

FIG. 7C

EC50 (µM) and R² values

| Clones | EC50 (µM) | R² |
|---|---|---|
| mL1CAM-3R-H8 | 0.021 | 0.974 |
| mL1CAM-3R-C9 | 0.005 | 0.972 |
| mL1CAM-3R-E1 | 0.050 | 0.990 |
| mL1CAM-3R-E9 | 0.031 | 0.970 |
| hL1CAM-3R-E1 | 0.228 | 0.992 |
| hL1CAM-3R-E9 | 20.87 | 0.985 |
| hL1CAM-3R-H8 | 0.002 | 0.997 |
| hL1CAM-3R-C9 | 6.064 | 1.000 |

| Sensor : AR2G | | | | |
|---|---|---|---|---|
| | Con. | Buffer | Time (sec) | Step |
| Ligand (3R-H8) | 5 ug/ml | 10 mM acetate buffer (pH 5.0) | 300 | Load |
| Analyte (hL1CAM) | 0 ~ 200 nM | 1XPBS + 0.09% Tween | 450 | Association |

3R-H8/hL1CAM

| Ligand/Analyte | KD (M) | kon(1/Ms) | kdis(1/s) | Full X^2 | Full R^2 |
|---|---|---|---|---|---|
| 3R-H8/hL1CAM | 4.14E-09 | 5.77E+04 | 2.39E-04 | 0.34 | 0.99 |

| Sensor : AR2G | | | | |
|---|---|---|---|---|
| | Con. | Buffer | Time (sec) | Step |
| Ligand (3R-H8) | 5 ug/ml | 10 mM acetate buffer (pH 6.0) | 300 | Load |
| Analyte (mL1CAM) | 0 ~ 100 nM | 1XPBS + 0.09% Tween | 100 | Association |

3R-H8/hL1CAM

| Ligand/Analyte | KD (M) | kon(1/Ms) | kdis(1/s) | Full X^2 | Full R^2 |
|---|---|---|---|---|---|
| 3R-H8/mL1CAM | 2.05E-08 | 4.62E+05 | 9.45E-03 | 0.01 | 0.99 | pMT-L1-H8-CAR-004
1833 bp

L1-H8-CAR-001-28BB
1659 bp

L1-H8-CAR-001-28

ANTI-L1CAM ANTIBODY OR ANTIGEN-BINDING FRAGMENT THEREOF AND CHIMERIC ANTIGEN RECEPTOR COMPRISING SAME

TECHNICAL FIELD

The present disclosure was made with the support of the Ministry of Science, ICT and Future Planning of the Republic of Korea, under Project No. 2016M3A9D3021340, which was conducted in the research project named "Research on Multifunctional Fusion T Cell Therapy Using Chimeric Antigen Receptor and B Cells" in the research program entitled "Biomedical Technology Development Project (Next-Generation Bio) Immunity Mechanism Control Technology Development", by the Seoul National University Industry-Academic Cooperation Foundation, under the management of the National Research Foundation of Korea, 1 May 2016 to 31 Jan. 2021.

This application claims priority to and the benefit of Korean Patent Application No. 10-2018-0125538 filed in the Korean Intellectual Property Office on 19 Oct. 2018, the disclosure of which is incorporated herein by reference.

The present disclosure relates to an anti-L1CAM antibody or antigen-binding fragment thereof that specifically binds to L1CAM antigen, a chimeric antigen receptor comprising the same, and uses thereof.

BACKGROUND ART

Ovarian cancer is the most fatal gynecological malignant tumor and the major cause of gynecological tumor-related deaths. Although significant advances have been made in combinative therapies of surgical approach and cytotoxic therapy, most patients with advanced stages at the time of diagnosis eventually undergo recurrence. Therefore, novel treatment methods for ovarian cancer have been urgently required. As the facts are gradually revealed that ovarian cancer may occur due to immunological causes and ovarian cancer may be recognized and attacked by the immune system, various treatment methods based on immunotherapy are being actively studied. A large number of peptide vaccines, dendritic cell vaccines, and adoptive cellular therapies are actually in clinical trials.

In particular, adoptive therapies for hematologic cancer through chimeric antigen receptor (CAR)-expressing T cells (CAR-T) have been recently proven to have therapeutic potentials, and have been marketed. In addition, the newly published research results suggest that CAR-T may exhibit similar effects on even solid cancers. CAR is unique in that it confers cytotoxic effector functions to T cells in an HLA-non-limiting manner, and CAR is very important in that the progression of ovarian cancer correlates with down-regulation of HLA. In fact, ovarian cancer treatments using CAR-T specific to mesothelin, MUC16, and folate receptors, which are known as factors related to ovarian cancer, have been attempted, but the treatment effects thereof are not yet sufficient.

L1-cell adhesion molecule (L1-CAM, L1CAM) is known to be highly expressed in various carcinomas including ovarian cancer, and such high expression of L1CAM is associated with negative clinical treatment results. According to previous studies, as a result of treating human ovarian cancer cells (SKOV3 cell line) directly with monoclonal antibodies specifically binding to L1CAM in vitro and treating human xenograft models in which the cells were transplanted, the growth of tumor cells was inhibited. The present inventors have derived the present disclosure on the basis of the relevance of L1CAM to various carcinomas and the therapeutic potentials at the ovarian cancer and the like.

PRIOR ART DOCUMENT

Non-Patent Documents

Hao Hong. L1 Cell Adhesion Molecule-Specific Chimeric Antigen Receptor-Redirected Human T Cells Exhibit Specific and Efficient Antitumor Activity against Human Ovarian Cancer in Mice. (2016). PLoS ONE 11(1): e0146885

SUMMARY

Technical Problem

The present inventors conducted intensive research efforts to develop an antibody and antigen-binding fragment thereof that binds to L1CAM, and a chimeric antigen receptor including the same. As a result, the present inventors established that developed anti-L1CAM antibodies very specifically bind to human and mouse L1CAM antigen molecules, and chimeric antigen receptors and CAR-T that include the same exhibit high anticancer activity on SKOV3 ovarian cancer cell lines, SH-SY5Y neuroblastoma cell lines, and HeLa cervical cancer cell lines, and thus completed the present disclosure.

Therefore, an aspect of the present disclosure is to provide an anti-L1CAM antibody or antigen-binding fragment thereof that specifically binds to L1CAM antigen.

Another aspect of the present disclosure is to provide a chimeric antigen receptor including an anti-L1CAM antibody or antigen-binding fragment thereof and an effector cell expressing the chimeric antigen receptor.

Still another aspect of the present disclosure is to provide a pharmaceutical composition including the anti-L1CAM antibody or antigen-binding fragment thereof, or an effector cell expressing the chimeric antigen receptor.

Still another aspect of the present disclosure is to provide a method for treating a disease associated with high expression of L1CAM in a subject in need thereof, the method including administering to the subject an effector cell expressing the chimeric antigen receptor.

Technical Solution

Herein, the antibody according to an aspect of the present disclosure is an antibody specifically binding to L1CAM and a modified antibody subjected to affinity maturation.

The anti-L1CAM antibody or antigen-binding fragment thereof of the present disclosure has a specific binding ability to the L1CAM antigen like conventional anti-L1CAM antibodies.

As used herein, the term "antibody" refers to an antibody specific to L1CAM antigen, and encompasses not only the whole antibody form but also antigen-binding fragments of the antibody molecule.

The whole antibody has a structure of two full-length light chains and two full-length heavy chains where each light chain is linked to the heavy chain via disulfide bonds. The term "heavy chain" refers to the larger of the two types of polypeptide chains present in antibody molecules in their naturally occurring conformations, and which normally determines the class to which the antibody belongs. The term "heavy chain" refers to both the full-length heavy chain and a fragment thereof that includes a VH domain, which is a heavy chain variable region of an antibody, comprising an amino acid sequence having a variable region sequence sufficient to impart specificity to an antigen, and CH1, CH2, and CH3 domains, which are three heavy chain constant regions. The heavy chain constant region has gamma (γ), mu (μ), alpha (α), delta (δ), and epsilon (ε) types, and gamma1 γ(γ1), gamma2 (γ2), gamma3 (γ3), gamma4 (γ4), alpha1 (α1), and alpha2 (α2) subclasses.

The term "light chain" refers to the smaller of the two types of polypeptide chains present in antibody molecules in their naturally occurring conformations. The term "light chain" refers to both the full-length light chain and a fragment thereof that include VL domain, which is a light chain variable region of an antibody, comprising an amino acid sequence having a variable region sequence sufficient to impart specificity to an antigen, and CL domain, which is a light chain constant region. The light chain constant regions have kappa and lambda types (Cellular and Molecular Immunology, Wonsiewicz, M. J., Ed., Chapter 45, pp. 41-50, W. B. Saunders Co. Philadelphia, PA (1991); and Nisonoff, A., Introduction to Molecular Immunology, 2nd Ed., Chapter 4, pp. 45-65, sinauer Associates, Inc., Sunderland, MA (1984)).

The term "antigen" or "Ag" refers to a molecule that triggers an immune response. This immune response may involve either antibody production, or the activation of specific immunologically-competent cells, or both.

As used herein, the term "complementarity determining region (CDR)" refers to an amino acid sequence of a hypervariable region of an immunoglobulin heavy or light chain (Kabat et al., Sequences of Proteins of Immunological Interest, 4th Ed., U.S. Department of Health and Human Services, National Institutes of Health (1987)). The heavy chain (CDRH1, CDRH2, and CDRH3) and the light chain (CDRL1, CDRL2, and CDRL3) each include three CDRs. CDRs provide major contact residues in the binding of an antibody to an antigen or epitope.

As used herein, the term "antigen-binding fragment" refers to a fragment that retains an antigen binding function, and includes Fab, F(ab'), F(ab')₂, Fv, and the like. Among the antibody fragments, the fragment antigen binding (Fab) refers to a structure that has variable regions of the heavy and light chains, the constant region of the light chain, and the first constant region ($C_{H1}$) of the heavy chain, and has one antigen-binding site. Fab' is different from Fab in that the former has a hinge region including one or more cysteine residues at the C-terminus of the heavy chain CH1 domain. F(ab')₂ antibody is created by a disulfide bond formed between the cysteine residues in the hinge regions of Fab' fragments. Fv is the minimal antibody fragment having only a heavy chain variable region and a light chain variable region, and recombinant technology for producing an Fv fragment is disclosed in the art. Two-chain Fv is a fragment wherein the heavy chain variable region and the light chain variable region are linked by a non-covalent bond, and the single-chain variable fragment (scFv) is a fragment wherein the heavy chain variable region and the light chain variable region are generally linked by a covalent bond via a peptide linker or are directly linked at the C-terminal, forming a dimer-like structure, like the two-chain Fv. These antibody fragments may be obtained using proteolytic enzymes (e.g., the Fab fragments can be obtained by restriction-cleaving the whole antibody with papain and the F(ab')₂ fragment can be obtained by restriction-cleaving the whole antibody with pepsin), or may be fabricated by genetic recombinant techniques.

The antibody of the present disclosure includes monoclonal antibodies, multi-specific antibodies, human antibodies, humanized antibodies, chimeric antibodies, single-chain Fv (scFv), single-chain antibodies, Fab fragments, F(ab') fragments, disulfide-linked Fv (sdFv), anti-idiotype (anti-Id) antibodies, epitope-binding fragments of the above-mentioned antibodies, and the like, but is not limited thereto.

As used herein, the term "framework" or "FR" refers to a variable domain residue other than a hypervariable region (HVR) residue. The FR of the variable domain is generally composed of four FR domains FR1, FR2, FR3, and FR4. Therefore, the HVR and FR sequences are typically shown in the following order in VH (or VL/Vk):

(a) FRH1(framework region 1 of heavy chain)-CDRH1 (complementarity determining region 1 of heavy chain)-FRH2-CDRH2-FRH3-CDRH3-FRH4; and (b) FRL1(framework region 1 of light chain)-CDRL1 (complementarity determining region 1 of light chain)-FRL2-CDRL2-FRL3-CDRL3-FRL4.

As used herein, the term "specifically bind" or the like means that an antibody or antigen-binding fragment thereof, or other constructs, such as scFv, form a complex with an antigen that is relatively stable under physiological conditions. Specific binding can be at least characterized as an equilibrium dissociation constant of about $1 \times 10^{-6}$ M or less (e.g., a KD smaller than this value indicates tighter binding). Methods of determining whether two molecules specifically bind to each other are well known in the art, and examples thereof include equilibrium dialysis, surface plasmon resonance, and the like.

As used herein, the term "affinity" refers to the total strength of non-covalent interactions between a single binding site of a molecule (e.g., an antibody) and a binding partner thereof (e.g., an antigen). Unless specified otherwise, the term "binding affinity" refers to the intrinsic binding affinity which reflects a 1:1 interaction between the members of a binding pair (e.g., an antibody and an antigen). The affinity between molecule Y and its partner Y may be typically represented by a dissociation constant (Kd). The affinity can be measured by common methods known in the art, including those described in the present disclosure.

As used herein, the term "human antibody" possesses an amino acid sequence which corresponds to an antibody produced by human or a human cell, or an antibody amino acid sequence derived from a non-human source that utilizes human antibody repertoires or other human antibody encoding sequences. Such a definition of the human antibody excludes a humanized antibody comprising non-human antigen binding residues.

As used herein, the term "chimeric antibody" refers to an antibody in which a portion of the heavy chain and/or light chain is derived from a particular source or species while the remainder of the heavy chain and/or light chain is derived from a different source or species.

As used herein, the term "humanized antibody" refers to a chimeric immunoglobulin which comprises the minimal sequence derived from non-human immunoglobulin of non-human (e.g., mouse) antibodies, an immunoglobulin chain or fragment thereof (e.g., Fv, Fab, Fab', F(ab')₂ or other antigen-binding subsequences of the antibody). In most cases, humanized antibodies are human immunoglobulins (recipient antibodies) in which residues from a complementarity-determining region (CDR) of the recipient are replaced by residues from a CDR of a non-human species (donor antibody), such as mouse, rat or rabbit having desired specificity, affinity, and capacity. In some instances, Fv framework region (FR) residues of the human immunoglobulin are replaced by corresponding non-human residues. In addition, humanized antibodies may include residues which are found neither in the recipient antibody nor in the imported CDR or framework sequences. These modifications are made to further improve and optimize antibody performance. In general, the humanized antibody will include substantially all of at least one, and typically two, variable domains, in which all or substantially all of the CDR regions correspond to CDR regions of a non-human immunoglobulin and all or substantially all of the FR regions have sequences of FR regions of a human immunoglobulin sequence. The humanized antibody includes at least a portion of an immunoglobulin constant region (Fc region), typically a constant region (Fc region) of a human immunoglobulin.

The anti-L1CAM antibody or antigen-binding fragment thereof of the present disclosure may include variants of the amino acid sequence within a range capable of specifically recognizing L1CAM, as recognized by a person skilled in the art. For example, in order to improve binding affinity and/or other biological properties of an antibody, modifications may be made to an amino acid sequence of the antibody. Such modifications include, for example, deletions, insertions, and/or substitutions of amino acid sequence residues of the antibody.

Such amino acid variations are made based on relative similarity of amino acid side chain substituents such as hydrophobicity, hydrophilicity, charge, and size. According to analysis on sizes, shapes, and types of amino acid side chain substituents, it can be seen that arginine, lysine, and histidine are all positively charged residues; alanine, glycine, and serine have similar sizes; and phenylalanine, tryptophan, and tyrosine have similar shapes. Thus, based on these considerations, it can be said that arginine, lysine, and histidine; alanine, glycine, and serine; and phenylalanine, tryptophan, and tyrosine are biologically functional equivalents.

In the introduction of variations, the hydropathic index of amino acids may be considered. Each amino acid has been assigned a hydropathic index on the basis of hydrophobicity and charge characteristics thereof: isoleucine (+4.5); valine (+4.2): leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5): aspartate (−3.5); asparagine (−3.5); lysine (−3.9); and arginine (−4.5).

The hydrophobic amino acid indexes are very important in giving interactive biological functions of proteins. It is known in the art that certain amino acids may be substituted by other amino acids having a similar hydropathic index and still result in similar biological activity. In cases where a variation is introduced with reference to the hydrophobic indexes, the substitution is made between amino acids having a difference in the hydrophobic index within preferably ±2, more preferably ±1, and still more preferably ±0.5.

Meanwhile, it is also well known that substitutions between amino acids having similar hydrophilicity values result in proteins with equivalent biological activity. As disclosed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In cases where variations are introduced with reference to the hydrophilicity values, substitutions may be made between amino acids that exhibit a hydrophilicity value difference of preferably within ±2, more preferably within ±1, and even more preferably within ±0.5.

Amino acid exchanges in proteins which do not entirely alter activity of a molecule are known in the art (H. Neurath, R. L. Hill, The Proteins, Academic Press, New York, 1979). The most common occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

In accordance with an aspect of the present disclosure, there is provided an anti-L1CAM antibody or antigen-binding fragment thereof, including a heavy chain variable region (VH) including i), ii), and iii) below and a light chain variable region (VL) including vi), v), and vi) below:

i) complementarity determining region 1 of heavy chain (CDRH1) comprising the following amino acid sequence:

$$X_1YAMX_5$$

wherein, independently of each other,
X1 is D, S, or N; and
X5 is N, H, or S, ii) complementarity determining region 2 of heavy chain (CDRH2) comprising SEQ ID NO: 12, SEQ ID NO: 13, or the following amino acid sequence:

$$AISSX_5GX_7X_8X_9YYADSVKG$$

wherein, independently of each other,
$X_5$ is S or T;
$X_7$ is S or G;
$X_8$ is S or T; and
$X_9$ is I, T, or K, iii) complementarity determining region 3 of heavy chain (CDRH3) comprising any one amino acid sequence selected from SEQ ID NO: 15 to SEQ ID NO: 23, iv) complementarity determining region 1 of light chain (CDRL1) comprising the following amino acid sequence:

$$RASQSIX_7X_8X_9LN$$

wherein, independently of each other,
$X_7$ is S or G;
$X_8$ is R, N, or S; and
$X_9$ is D or Y, v) complementarity determining region 2 of light chain (CDRL2) comprising the following amino acid sequence:

$$AX_2SX_4LQS$$

wherein, independently of each other,
$X_2$ is A or T; and
$X_4$ is S, N, R, or T, and vi) complementarity determining region 3 of light chain (CDRL3) comprising the following amino acid sequence:

$$QQSX_4SX_6PX_8T$$

wherein, independently of each other,
$X_4$ is Y or E;
$X_6$ is T, F, or Y; and
$X_8$ is Y, W, L, or F.

The symbols herein, such as "$X_n$," and "$X_m$", are used to indicate amino acids at positions n and m in the general formulas defined above. In this regard, n and m each are an integer which indicates the position of an amino acid within the sequence as counted from the N-terminal end of said sequence. For example, $X_1$ and $X_5$ indicate the amino acid in position 1 and 5, respectively, from the N-terminal of the sequence.

In an embodiment of the present disclosure, $X_n$ or $X_m$ are independently selected from a group of possible residues that may be $X_n$ or $X_m$ in the general formulas. A person skilled in the art will appreciate that $X_n$ may be selected from any one of the listed groups of possible residues and that this selection is independent from the selection of amino acids in $X_m$, wherein n is different from m. Therefore, any of the listed possible residues in position Xn in the general formulas may be independently combined with any of the listed possible residues at any other variable position (position $X_m$).

As described in detail in the examples below, CDRH1, CDRH2, CDRL1, CDRL2, and CDRL3 of the anti-L1CAM antibody, modified antibody thereof, or antigen-binding fragments thereof that specifically bind to L1CAM, according to the present disclosure, are expressed by i), ii), iv), v), and vi), respectively, and the general formulas were created based on the results of statistical analysis of numerous randomly modified antibodies. The anti-L1CAM antibody and antigen-binding fragment thereof, and modified antibodies thereof that specifically bind to L1CAM were selected by the verification of interactions with L1CAM through repeated selection tests.

In an embodiment of the present disclosure, independently of each other, in CDRH1, $X_1$ is D or S; and $X_5$ is N, H, or S.

In an example of the present disclosure, the amino acid sequence of CDRH1 represented by the general formula corresponds to any one amino acid sequence selected from SEQ ID NOs: 1 to 7.

According to a specific example of the present disclosure, the amino acid sequence of CDRH1 represented by the general formula corresponds to any one amino acid sequence selected from SEQ ID NOs: 1 to 3, and 7, and these correspond to CDRH1 of four types of antibodies finally selected in the present disclosure.

In another embodiment of the present disclosure, independently of each other,
$X_5$ is T or S in the CDRH2;
$X_7$ is S or G in the CDRH2;
$X_8$ is S or T in the CDRH2; and
$X_9$ is I or T in the CDRH2.

In an example of the present disclosure, the amino acid sequence of CDRH2 represented by the general formula corresponds to any one amino acid sequence selected from SEQ ID NOs: 8 to 14.

According to a specific example of the present disclosure, the amino acid sequence of CDRH2 represented by the general formula corresponds to any one amino acid sequence selected from SEQ ID NOs: 8 to 10, and these correspond to CDRH2 of four types of antibodies finally selected in the present disclosure.

According to a specific embodiment of the present disclosure, the amino acid sequence of CDRH3 corresponds to any one amino acid sequence selected from SEQ ID NOs: 15 to 17 and 22, and these correspond to CDRH3 of four types of antibodies finally selected in the present disclosure.

In an embodiment of the present disclosure, the amino acid sequence of CDRL1 corresponds to any one amino acid sequence selected from SEQ ID NOs: 32 to 36.

According to a specific embodiment of the present disclosure, the amino acid sequence of CDRL1 corresponds to any one amino acid sequence selected from SEQ ID NOs: 32 to 34 and 36, and these correspond to CDRL1 of four types of antibodies finally selected in the present disclosure.

In another embodiment of the present disclosure, independently of each other, in CDRH1, X2 is A or T; and X4 is S or N.

In an example of the present disclosure, the amino acid sequence of CDRL2 represented by the general formula corresponds to any one amino acid sequence selected from SEQ ID NOs: 37 to 42.

According to a specific example of the present disclosure, the amino acid sequence of CDRL2 represented by the general formula corresponds to any one amino acid sequence selected from SEQ ID NOs: 37, 38, and 42, and these correspond to CDRL2 of four types of antibodies finally selected in the present disclosure.

In still another embodiment of the present disclosure, independently of each other,
$X_4$ is Y in the CDRL3;
$X_6$ is T or F in the CDRL3; and
$X_8$ is Y or W in the CDRL3.

In an example of the present disclosure, the amino acid sequence of CDRL3 represented by the general formula corresponds to any one amino acid sequence selected from SEQ ID NOs: 43 to 47.

According to a specific example of the present disclosure, the amino acid sequence of CDRL3 represented by the general formula corresponds to the amino acid sequence of SEQ ID NO: 43 or 44, and these correspond to CDRL3 of four types of antibodies finally selected in the present disclosure.

According to still another embodiment of the present disclosure, in the anti-L1CAM antibody or antigen-binding fragment thereof of the present disclosure, the $V_H$ includes framework region 1 of heavy chain (FRH1) comprising any one amino acid sequence selected from SEQ ID NOs: 24 to 26.

According to a specific embodiment of the present disclosure, the $V_H$ includes framework region 1 of heavy chain (FRH1) comprising the amino acid sequence of SEQ ID NO: 24.

In addition, the $V_H$ includes framework region 2 of heavy chain (FRH2) comprising the amino acid sequence of SEQ ID No: 27.

In addition, the $V_H$ includes framework region 3 of heavy chain (FRH3) comprising the amino acid sequence of SEQ ID No: 28 or 29.

In addition, the $V_H$ includes framework region 4 of heavy chain (FRH4) comprising the amino acid sequence of SEQ ID No: 30.

In another embodiment of the present disclosure, the $V_H$ comprises an amino acid sequence of vii) below:

```
vii)
EVQLVESGGGLXaQPGGSLRLSCAASGFTFS[CDRH1]WVRQAPGKGLEW

VS[CDRH2]RFTISRDNSKNTLYLQXbNSLRAEDTAVYYCAK[CDRH3]W

GQGTLVTVSS
``` wherein, independently of each other,

[CDRH1], [CDRH2], and [CDRH3] indicate the amino acid sequences of CDRH1, CDRH2, and CDRH3 defined above, respectively:

$X_a$ is V, L, or A; and $X_b$ is M or I.

In a specific embodiment of the present disclosure, in the sequence vii), $X_a$ is V and $X_b$ is M.

According to an exemplary embodiment of the present disclosure, the amino acid sequence of the $V_H$ corresponds to any one amino acid sequence selected from SEQ ID NOs: 52 to 55.

According to a specific embodiment of the present disclosure, the $V_L$ includes framework region 1 of light chain (FRL1) comprising the amino acid sequence of SEQ ID NO: 48.

In addition, the $V_L$ includes framework region 2 of light chain (FRL2) comprising the amino acid sequence of SEQ ID No: 49.

In addition, the $V_L$ includes framework region 3 of light chain (FRL3) comprising the amino acid sequence of SEQ ID No: 50.

In addition, the $V_L$ includes framework region 4 of light chain (FRL4) comprising the amino acid sequence of SEQ ID No: 51.

In another embodiment of the present disclosure, the $V_L$ comprises an amino acid sequence of viii) below:

```
viii)
DIQMTQSPSSLSASVGDRVTITC[CDRL1]WYQQKPGKAPKLLIY

[CDRL2]GVPSRFSGSGSGTDFTLTISSLQPEDFATYYC[CDRL3]

FGQGTKVEIK
``` wherein, independently of each other, [CDRL1], [CDRL2], and [CDRL3] indicate the amino acid sequences of CDRL1, CDRL2, and CDRL3 defined above, respectively.

According to an example of the present disclosure, the amino acid sequence of $V_L$ corresponds to any one amino acid sequence selected from SEQ ID NOs: 56 to 59.

The anti-L1CAM antibody or antigen-binding fragment thereof of the present disclosure includes an anti-L1CAM antibody or an antigen-binding fragment thereof that comprises a minor modification as compared to the foregoing amino acid sequence, that is, a change which hardly affect the tertiary structure and the functions of the antibody. In some embodiments, the modified anti-L1CAM antibody or antigen-binding fragment thereof may have sequence similarity of at least 90%, 93%, 95%, or 98% even if not identical to the foregoing sequence.

In the present disclosure, a heavy chain variable region and a light chain variable region contained in the antibody or antigen-binding fragment thereof may be linked via a linker comprising an amino acid sequence represented by the general formula $(G_nS_m)_p$ or $(S_mG_n)_p$.

In each case, independently of each other, n is an integer of 1 to 7;

m is an integer of 0 to 7;

the sum of n and m is an integer of 8 or smaller; and p is an integer of 1 to 7.

According to a specific embodiment of the present disclosure, in the linker, n=1 to 5 and m=0 to 5. In a more specific embodiment, n=4 and m=1. In a still more specific embodiment, the linker is $(G_4S)_3$ or $(S_4G)_3$.

In another embodiment, the linker is VDGS, and in still another embodiment, the linker is ASGS.

The light chain variable region and the heavy chain variable region of the antibody or antigen-binding fragment thereof according to the present disclosure may exist, for example, in the following orientations:

light chain variable region-linker-heavy chain variable region; or heavy chain variable region-linker-light chain variable region.

According to a most specific embodiment of the present disclosure, the anti-L1CAM antibody or antigen-binding fragment thereof of the present disclosure comprises the amino acid sequence selected from SEQ ID Nos: 64 to 67, but is not limited thereto.

In accordance with another aspect of the present disclosure, there is provided a fusion protein including an anti-L1CAM antibody or antigen-binding fragment thereof.

In the present disclosure, the fusion protein is prepared for the productivity, purification efficiency, improved biological activity, increased fusion protein stability, improved folding and/or binding to a functional moiety with additional functionality, of the anti-L1CAM antibody or antigen-binding fragment thereof of the present disclosure. The fusion protein may be formed as two or more polypeptide chains connected by a covalent bond through expression thereof as a recombinant protein, or may be implemented in the form of a conjugate in which two or more polypeptide chains are connected by chemical conjugation.

In accordance with still another aspect of the present disclosure, there is provided a chimeric antigen receptor polypeptide including:

(a) an L1CAM binding domain;

(b) a transmembrane domain (TM);

(c) a costimulatory domain; and (d) an intracellular signaling domain (ICD).

As used herein, the term "chimeric antigen receptor (CAR)" refers to an artificially constructed hybrid protein (fusion protein) or polypeptide comprising a target binding domain (e.g., single-chain variable fragment (scFv)) linked to an effector cell-signaling or effector cell-activating domain (e.g., T-cell signaling or T-cell activating domain). In general, chimeric antigen receptors have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CAR the ability to recognize an antigen independent of antigen processing, thus bypassing a major mechanism of tumor escape. Moreover, when expressed in T-cells, CAR advantageously does not dimer with endogenous T-cell receptor (TCR) alpha and beta chains.

The chimeric antigen receptor of the present disclosure includes the foregoing anti-L1CAM antibody or antigen-binding fragment thereof as an extracellular antigen binding domain. Therefore, the chimeric antigen receptor of the present disclosure is expressed as an anti-L1CAM chimeric antigen receptor (anti-L1CAM CAR), anti-L1CAM CAR, or the like.

The terms, such as "L1-CAR", "L1CAM-CAR", and "L1-H8-CAR", used in the example of the present disclosure, are code names of the anti-L1CAM chimeric antigen receptor invented by the present inventors, and refer to a chimeric antigen receptor including an extracellular antigen-binding domain that specifically binds to the foregoing L1CAM.

According to an embodiment of the present disclosure, the chimeric antigen receptor of the present disclosure comprises an L1CAM binding domain including the anti- L1CAM antibody or antigen-binding fragment thereof described in the present disclosure, and thus recognizes the L1CAM antigen and is expressed on the surface of a cell.

The chimeric antigen receptor of the present disclosure is expressed on the surface of a cell, and thus comprises a transmembrane domain. The transmembrane domain may be a transmembrane domain selected from the group consisting of an alpha, beta or zeta chain of a T-cell receptor, CD28, CD3 epsilon, CD45, CD4, CD5, CD8, CD9, CD16, CD22, CD33, CD37, CD64, CD80, CD86, CD134, and CD154, or a combination of all or some sequences thereof, but is not limited thereto.

According to a specific embodiment of the present disclosure, the transmembrane domain is a transmembrane domain of CD8 or CD28, and most specifically, a trans- membrane domain of CD28 encoded by the nucleotide sequence of SEQ ID NO: 78, or a transmembrane domain of CD8 alpha encoded by the nucleotide sequence of SEQ ID NO: 119.

The costimulatory domain of the chimeric antigen recep- tor of the present disclosure is a functional signaling domain obtained from a protein selected from the group consisting of, but is not limited to, ligands specifically binding to MHC class I molecules, TNF receptor proteins, immunoglobulin- like proteins, cytokine receptors, integrins, signaling lym- phocytic activation molecules (SLAMs), activated NK cell receptors, B and T lymphocyte attenuators (BTLAs), Toll- like ligand receptors, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP- 76, PAG/Cbp, CD19a, and CD83.

According to a specific embodiment of the present dis- closure, the costimulatory domain may be a functional signaling domain obtained from a protein selected from the group consisting of CD28, 0X40, 4-1BB (CD137), and ICOS (CD278), more specifically a functional signaling domain of CD28 encoded by the nucleotide sequence of SEQ ID NO: 79, a functional signaling domain of OX40 encoded by the nucleotide sequence of SEQ ID NO: 80, a functional signaling domain of 4-1BB encoded by the nucleotide sequence of SEQ ID NO: 101 or SEQ ID NO: 120, a functional signaling domain of ICOS encoded by the nucleotide sequence of SEQ ID NO: 102, or a combination of all or some sequences thereof.

According to another embodiment of the present disclo- sure, the intracellular signaling domain is a functional sig- naling domain of 4-1BB, CD28, OX40, or CD3 zeta, or a combination thereof. Most specifically, the intracellular sig- naling domain is a functional signaling domain of CD3 zeta.

According to an example of the present disclosure, the intracellular signaling domain is a functional signaling domain of CD3 zeta encoded by the nucleotide sequence of SEQ ID NO: 81, a functional signaling domain of CD3 zeta-iso2M encoded by the nucleotide sequence of SEQ ID NO: 121, or a functional signaling domain of CD3 zeta-iso2 encoded by the nucleotide sequence of SEQ ID NO: 126, but is not limited thereto.

According to an embodiment of the present disclosure, the chimeric antigen receptor optionally further includes a leader sequence (LS). The leader sequence is located at the amino-terminal (N-terminal) of a recombinant polypeptide constituting the chimeric antigen receptor. The leader sequence is optionally cleaved from the antigen binding domain during intracellular processing and localization of the chimeric antigen receptor to the cellular membrane.

In a specific embodiment of the present disclosure, the leader sequence may be a leader sequence of hCD8 alpha, a leader sequence of hGM-CSF receptor alpha-chain, or a leader sequence of 3E8 antibody.

In a more specific embodiment of the present disclosure, the leader sequence is a leader sequence including the amino acid sequences encoded by the nucleotide sequences of SEQ ID NO: 128 to 130.

The L1CAM binding domain of the chimeric antigen receptor of the present disclosure is linked to the transmem- brane domain by a hinge domain (or spacer).

According to another embodiment of the present disclo- sure, the hinge domain is a hinge derived from IgG1, IgG2, IgG4, or IgD, a hinge derived from CD8 or CD28, an extracellular domain (ECD) derived from CD28, or a com- bination thereof.

According to an example of the present disclosure, the hinge domain is an IgD hinge encoded by the nucleotide sequence of SEQ ID NO: 77, an IgG1 hinge encoded by the nucleotide sequence of SEQ ID NO: 85, an IgG1 CH3 hinge encoded by the nucleotide sequence of SEQ ID NO: 86, a hCD8 alpha hinge encoded by the nucleotide sequence of SEQ ID NO: 118, a hinge encoded by the nucleotide sequence of SEQ ID NO: 124, a hCD28 extracellular domain encoded by the nucleotide sequence of SEQ ID NO: 125, or a combination of all or some of these sequences.

In accordance with an aspect of the present disclosure, there is provided a nucleic acid molecule comprising a nucleotide sequence encoding the foregoing anti-L1CAM antibody or antigen-binding fragment thereof.

In accordance with another aspect of the present disclo- sure, there is provided a nucleic acid molecule comprising a nucleotide sequence encoding a fusion protein including the foregoing anti-L1CAM antibody or antigen-binding frag- ment thereof.

In accordance with still another aspect of the present disclosure, there is provided a nucleic acid molecule com- prising a nucleotide sequence encoding the foregoing chi- meric antigen receptor polypeptide.

As used herein, the term "nucleic acid" encompasses DNA (gDNA and cDNA) and RNA molecules, and the nucleotides that are the basic building blocks of the nucleic acid molecule include not only natural nucleotides but also analogues having modified sugar or base moieties (Scheit, Nucleotide Analogs, John Wiley, New York (1980); and Uhlman and Peyman, Chemical Reviews, 90: 543-584 (1990)).

In one embodiment of the present disclosure, the nucleo- tide sequence encoding the chimeric antigen receptor poly- peptide of the present disclosure is sufficient to be a nucleo- tide sequence encoding the amino acid sequence constituting the chimeric antigen receptor molecule, and it would be obvious to a person skilled in the art that such a nucleotide sequence is not limited to any particular nucleotide sequence.

The reason is that even if the nucleotide sequence undergoes mutation, the expression of the mutated nucleotide sequence into a protein may not cause a change in the protein sequence. This is called codon degeneracy. Therefore, the nucleotide sequence includes nucleotide sequences comprising functionally equivalent codons, codons encoding the same amino acid (e.g., the number of codons for arginine or serine is six due to codon degeneracy), or codons encoding biologically equivalent amino acids.

According to a specific embodiment of the present disclosure, the nucleic acid molecule encoding the L1CAM binding domain polypeptide of the chimeric antigen receptor comprises any one nucleotide sequence selected from SEQ ID NOs: 60 to 63.

Considering the foregoing variation having biological equivalent activity, the nucleic acid molecule encoding the chimeric antigen receptor polypeptide of the present disclosure is construed to also include sequences having substantial identity to the sequences described in the sequence listings. The substantial identity means that, when the sequence of the present disclosure and another sequence are aligned to correspond to each other as much as possible and the aligned sequences are analyzed using an algorithm that is commonly used in the art, the sequences have at least 61% homology, more preferably at least 70% homology, still more preferably at least 80% homology, and most preferably at least 90% homology. Methods of the alignment for sequence comparison are known in the art. Various methods and algorithms for the alignment are disclosed in Smith and Waterman, *Adv. Appl. Math.* 2: 482(1981); Needleman and Wunsch, *J. Mol. Bio.* 48: 443(1970); Pearson and Lipman, *Methods in Mol. Biol.* 24: 307-31(1988); Higgins and Sharp, *Gene* 73: 237-44(1988); Higgins and Sharp, *CABIOS* 5: 151-3(1989); Corpet et al., *Nuc. Acids Res.* 16: 10881-90 (1988); Huang et al., *Comp. Appl. BioSci.* 8: 155-65(1992) and Pearson et al., *Meth. Mol. Biol.* 24: 307-31(1994). The NCBI Basic Local Alignment Search Tool (BLAST) (Altschul et al., *J. Mol. Biol.* 215: 403-10(1990)) is accessible from the NBCI (National Center for Biotechnology Information) or the like and, on the Internet, may be used in connection with sequence analysis programs, such as BLASTP, BLASTN, BLASTX, TBLASTN and TBLASTX. BLAST may be accessed through the BLAST webpage of the NCBI's website. The method for comparing sequence homology using such a program is available from the BLAST help page of the NCBI's website.

In accordance with still another aspect of the present disclosure, there is provided a recombinant vector including a nucleic acid molecule encoding the anti-L1CAM antibody or antigen-binding fragment thereof, or the chimeric antigen receptor polypeptide.

As used herein, the term "vector" encompasses a delivery vector and an expression vector.

As used herein, the term "delivery vector" refers to a composition of a material which comprises an isolated nucleic acid and can be used to deliver the isolated nucleic acid into a cell. The delivery vector includes a linear polynucleotide, a polynucleotide linked to an ionic or amphiphilic compound, a plasmid and a virus, but is not limited thereto. More specifically, the delivery vector includes a self-replicating plasmid or virus. The term is also construed to include non-plasmid and non-viral compounds which facilitate transfer of nucleic acids into cells, such as, for example, polylysine compounds, liposomes, etc. Examples of the viral delivery vector include an adenoviral vector, an adeno-associated viral vector, a retroviral vector, and a lentiviral vector, but are not limited thereto.

In an embodiment of the present disclosure, the vector is a lentiviral vector. In a specific embodiment of the present disclosure, the vector further includes a promoter. The promoter may be for example EF-1 promoter, but is not limited thereto.

In another embodiment of the present disclosure, the vector is a retroviral vector. Retroviruses provide a convenient platform for a gene delivery system. A gene selected for gene delivery may be inserted in the retroviral vector and may be packaged within a retroviral particle. Then, the recombinant retrovirus may be delivered to a target host cell in vivo or in vitro. Many retroviral vectors are known in the art, and in a specific embodiment of the present disclosure, the retroviral vector may be a pMT retroviral vector, which is an MLV-based retroviral vector, but is not limited thereto.

The term "expression vector" refers to a vector including a recombinant nucleotide including an expression control sequence operably linked to a nucleotide sequence to be expressed, in order to express a target gene in a host cell. The expression vector comprises a cis-acting element sufficient for expression, and other elements for expression may be provided by a host cell or an in-vitro expression system. Examples of the expression vector include a plasmid vector including a recombinant polynucleotide; a cosmid vector; and a viral vector, such as a bacteriophage vector, an adenoviral vector, a lentiviral vector, a retroviral vector and an adeno-associated viral vector. According to a specific embodiment of the present disclosure, a nucleic acid molecule encoding a switch molecule is operatively linked to a promoter of the vector of the present disclosure. As used herein, the term "operatively linked" refers to a functional linkage between a nucleic acid expression control sequence (e.g., a promoter, a signal sequence, or an array of transcription regulation factor binding sites) and another nucleic acid sequence, by which the control sequence controls the transcription and/or translation of the another nucleic acid sequence.

The recombinant vector system of the present disclosure can be constructed by various methods known in the art, and a specific method thereof is disclosed in Sambrook et al., *Molecular Cloning, A Laboratory Manual*, Cold Spring Harbor Laboratory Press (2001), which is incorporated herein by reference.

The vector of the present disclosure may be constructed as a vector for gene cloning, a vector for gene expression, or a vector for gene delivery. In addition, the vector of the present disclosure may be constructed by using a prokaryotic or eukaryotic cell as a host.

For example, in cases where the vector of the present disclosure is an expression vector and an eukaryotic cell is used as a host cell, a promoter derived from the genome of a mammalian cell (e.g., metallothionein promoter, beta-actin promoter, human hemoglobin promoter, and human muscle creatine promoter) or a promoter derived from mammalian viruses (e.g., adenovirus late promoter, vaccinia virus 7.5 K promoter, SV40 promoter, cytomegalovirus promoter, tk promoter of HSV, mouse mammary tumor virus (MMTV) promoter, LTR promoter of HIV, promoter of Moloney virus, Epstein-Barr virus (EBV), and Rous sarcoma virus (RSV)) may be used, and a polyadenylated sequence may be commonly used as the transcription termination sequence.

The vector of the present disclosure may be fused with the other sequences to facilitate the purification of the polypeptide or protein expressed therefrom. Examples of the fusion sequence include glutathione S-transferase (Pharmacia, USA), maltose binding proteins (NEB, USA), FLAG (IBI, USA), 6× His (hexahistidine; Quiagen, USA), and the like. The expression vector of the present disclosure may include the antibody or antigen-binding fragment thereof of the present disclosure, and a marker gene and/or a reporter gene, which can be used as a selectable marker for evaluating the expression of CAR polypeptide including same. The selectable marker gene includes an antibiotic-resistant gene that is ordinarily used in the art, and examples thereof are resistant genes against ampicillin, gentamycin, carbenicillin, chloramphenicol, streptomycin, kanamycin, geneticin, neomycin, and tetracycline. Examples of the reporter gene include luciferase, beta-galactosidase, chloramphenicol acetyltransferase, or green fluorescent protein genes.

Methods of introducing the recombinant vector of the present disclosure into a cell and expressing the same are well known in the related art. The vector may be easily introduced into a host cell, e.g., a mammalian cell, a bacterial cell, a yeast cell or an insect cell according to methods known in the art. For example, the vector may be delivered into a host cell by physical, chemical or biological means. The physical means includes calcium phosphate coprecipitation, lipofection, particle bombardment, microinjection, electroporation, and the like. The chemical means includes colloidal dispersion systems, such as a macromolecular complex, a nanocapsule, a microsphere, and a bead, and lipid-based systems including an oil-in-water emulsion, a micelle, a mixed micelle, and a liposome. The biological means includes use of a DNA or RNA vector, such as a lentiviral vector or a retroviral vector, as described above.

In accordance with still another aspect of the present disclosure, there is provided an effector cell expressing the chimeric antigen receptor (CAR) polypeptide.

In an embodiment of the present disclosure, the effector cell is selected from the group consisting of dendritic cells, killer dendritic cells, mast cells, natural killer cells, B lymphocytes, T lymphocytes, macrophages, and progenitor cells thereof, but is not limited thereto. The T lymphocytes are selected from the group consisting of inflammatory T lymphocytes, cytotoxic T lymphocytes, regulatory T lymphocytes, or helper T lymphocytes.

In the present disclosure, the effector cell includes a group of autologous cells or allogenic cells. That is to say, the effector cell includes a group of autologous cells or allogenic cells expressing the present L1CAM CAR polypeptide.

As used herein, the term "autologous" refers to any material which is derived from an individual and is to be re-introduced to the same individual. As used herein, the term "allogeneic" refers to any material derived from a different animal of the same species as an individual to which the material is introduced.

According to an embodiment of the present disclosure, the effector cell includes a group of cells transfected or transduced with a vector comprising a nucleic acid molecule encoding the anti-L1CAM CAR polypeptide. The transfection or transduction may be achieved by various means known in the art without limitation.

Accordingly, according to a specific embodiment of the present disclosure, the anti-L1CAM CAR encoding nucleic acid molecule is delivered into an effector cell, e.g., a T lymphocyte or a natural killer cell, and transcribed into mRNA. The anti-L1CAM CAR polypeptide is translated from the mRNA and expressed on the surface of the effector cell.

As validated in the examples of the present disclosure, the effector cell expressing the anti-L1CAM CAR of the present disclosure effectively kills SKOV3 (ovarian cancer cell line), SH-SY5Y (neuroblastoma cell line), and HeLa (cervical cancer cell line), which are cancer cell lines expressing L1CAM on the surface. Therefore, the effector cell expressing the anti-L1CAM CAR of the present disclosure can be advantageously used as an active ingredient of compositions for treatment of various cancers.

In accordance with another aspect of the present disclosure, there is provided a pharmaceutical composition for treatment or diagnosis of cancer or an inflammatory disease, the pharmaceutical composition including the foregoing anti-L1CAM antibody or antigen-binding fragment thereof.

In accordance with still another aspect of the present disclosure, there is provided a pharmaceutical composition for treatment or diagnosis of cancer or an inflammatory disease, the pharmaceutical composition including the foregoing effector cell expressing the chimeric antigen receptor polypeptide.

The pharmaceutical composition is a pharmaceutical composition, for immunotherapy, including the anti-L1CAM antibody or antigen-binding fragment thereof, or the effector cell expressing the chimeric antigen receptor polypeptide.

Here, the "immunotherapy" refers to a treatment of cancer wherein the immune system helps to remove cancer. Immunotherapy is classified into active immunotherapy and passive immunotherapy. The active immunotherapy includes i) cancer vaccine therapy of activating the immune system by injecting cancer cells or substances produced by cancer cells into human body, and ii) immunomodulatory therapy of activating specific leukocytes by administering immunomodulatory agents, such as cytokines (interferons, interleukins, etc.), and growth factors. Passive immunotherapy includes antibody therapy and immune cell therapy binding to specific cancer cells. Specifically, immune cell therapy includes dendritic cell vaccine therapy, chimeric antigen receptor T (CAR-T) cell therapy, natural killer (NK) cell therapy, cytotoxic T lymphocyte (CTL) therapy, adoptive cell transfer, and the like, but is not limited thereto. In the present disclosure, the immunotherapy mainly refers to the foregoing immune cell therapy.

The pharmaceutical composition of the present disclosure includes effector cells expressing an antibody or antigen-binding fragment thereof that binds to the L1CAM antigen of a target cell, or a chimeric antigen receptor including the same, and thus is effective in the diagnosis or treatment of a disease associated with high expression of L1CAM. Examples of the disease associated with high expression of L1CAM are cancer and an inflammatory disease.

Especially, the cancer associated with high expression of L1CAM is a solid cancer, and the solid cancer is selected from the group consisting of gastric cancer, breast cancer, pancreatic cancer, cervical cancer, endometrial carcinoma, gastrointestinal stromal tumor, ovarian cancer, melanoma, gallbladder cancer, hepatocellular carcinoma, cholangiocarcinoma, pancreatic ductal adenocarcinoma, esophageal cancer, renal cell carcinoma, rectal cancer, colon cancer, prostate cancer, small cell lung cancer, non-small cell lung cancer, thyroid cancer, glioma, glioblastoma, neuroblastoma, and astrocytoma.

The inflammatory disease associated with high expression of L1CAM is an inflammatory bowel disease, but is not limited thereto.

The pharmaceutical composition of the present disclosure may include the foregoing CAR-expressing effector cells, for example, a plurality of CAR-expressing effector cells, in combination with one or more pharmaceutically or physiologically acceptable carriers, diluent or excipients. The pharmaceutical composition may include a buffer, such as neutral buffered saline or phosphate buffered saline; a carbohydrate, such as glucose, mannose, sucrose, or dextran, mannitol; a protein; a polypeptide or an amino acid such as glycine; an antioxidant; a chelating agent, such as EDTA or glutathione; an adjuvant (e.g., aluminum hydroxide); and a preservative. In an embodiment of the present disclosure, the pharmaceutical composition is formulated for intravenous administration.

The pharmaceutical composition of the present disclosure may be administered orally or parenterally, and may be attained by for example, intravenous administration, subcutaneous administration, intradermal administration, intramuscular administration, intraperitoneal administration, intratumoral injection, intracerebral administration, intracranial administration, intrapulmonary administration, and rectal administration, but is not limited thereto.

The pharmaceutical composition including the effector cell of the present disclosure is administered to a patient by intradermal or subcutaneous injection. In one embodiment, the pharmaceutical composition of the present disclosure is administered by intravenous injection. In another embodiment, the pharmaceutical composition of the present disclosure is administered directly into a tumor, lymph nodes, or infected sites.

A subject in need of the present disclosure can receive standard treatment using high-dose chemotherapy after peripheral blood stem cell transplantation. In an embodiment of the present disclosure, a subject in need of the present disclosure may receive expanded CAR T cells of the present disclosure by administration, after or simultaneously with the peripheral blood stem cell transplantation. In another embodiment, the expanded cells are administered before or after surgery.

The appropriate dose for the "immunologically effective amount", "anti-tumor effective amount", "tumor-suppressing effective amount", or "therapeutic amount" of the pharmaceutical composition of the present disclosure is determined by factors, such as a formulating method, a manner of administration, patient's age, body weight, and sex, pathological condition, food, administration time, administration route, excretion rate, and responsiveness, and an ordinarily skilled practitioner can easily determine and prescribe the dose that is effective for the desired treatment or prevention, and the appropriate dose will be determined by clinical trials. As used herein, the term "treatment" refers to a reduction, suppression, amelioration, or eradication of a disease condition. As used herein, the term "anti-tumor" encompasses a decrease in tumor volume, a decrease in the number of tumor cells, a decrease in the number of metastases, an increase in life expectancy, a decrease in tumor cell proliferation, a decrease in tumor cell survival, or ameliorations of various physiological symptoms associated with the cancerous condition.

It may generally be stated that the pharmaceutical composition including T cells described herein may be administered at a dosage of $10^4$ to $10^9$ cells/kg body weight, in some cases, $10^5$ to $10^6$ cells/kg body weight (including all integer values within those ranges). The T cell composition may also be administered multiple times at these doses. The cells may be administered by using infusion techniques that are commonly known in immunotherapy (see, e.g., [Rosenberg et al., New Eng. J. of Med. 319: 1676, 1988]).

The pharmaceutical composition of the present disclosure may also be used in combination with other pharmaceutically active drugs and therapies in addition to the above-described active ingredient. The term "combination" may be expressed as simultaneous or co-administration. The CAR-expressing effector cell described herein and at least one additional therapeutic agent may be administered simultaneously, in the same composition or in separate compositions, or sequentially. For sequential administration, the CAR-expressing cell described herein may be administered first, and the additional agent may be administered second, or the order of administration can be reversed.

Examples of a therapeutic agent that can be used in combination with the pharmaceutical composition of the present disclosure include: one or more chemotherapeutic agents known in the art (e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.); one or more targeted therapies (e.g., bevacizumab, olaparib, etc.); PD-1/PD-L1-specific immune checkpoint inhibitors (e.g., Opdivo, Keytruda, etc.), but are not limited thereto.

In accordance with still another aspect of the present disclosure, there is provided a method for treating cancer or an inflammatory disease in a subject in need thereof, the method including administering to the subject an effector cell expressing the chimeric antigen receptor.

The cancer and inflammatory diseases, which are the target diseases of the treatment method of the present disclosure, are the same as those defined with respect to the target diseases of the treatment of the pharmaceutical composition.

In one embodiment of the present disclosure, the subject is a mammal or a human.

Since the method for treatment of cancer or an inflammatory disease of the present disclosure commonly uses the foregoing effector cell expressing the chimeric antigen receptor as an active ingredient, the description of overlapping contents therebetween is omitted in order to avoid excessive complexity of the present specification.

Advantageous Effects

The present disclosure provides an anti-L1CAM antibody or antigen binding fragment thereof that specifically binds to L1CAM antigen, a chimeric antigen receptor including the same, and uses thereof. The anti-L1CAM antibody or antigen binding fragment thereof of the present disclosure has excellent specificity and affinity to L1CAM, and thus can be used in the treatment and diagnosis of various types of cancers and inflammatory diseases associated with high expression of L1CAM. In particular, when a chimeric antigen receptor including the anti-L1CAM antibody of the present disclosure is expressed in effector cells, e.g., T lymphocytes, such expression can be advantageously used as an immunotherapy method for various types of cancers and inflammatory diseases associated with L1CAM.

BRIEF DESCRIPTION OF THE DRAWINGS

FIGS. 7A, 7B and 7C show affinity to mL1CAM and hL1CAM antigens in four types of anti-L1CAM scFv antibodies of the present disclosure according to the soluble ELISA results in FIG. 5.

DETAILED DESCRIPTION

Hereinafter, the present disclosure will be described in more detail with reference to examples. These examples are provided only for the purpose of illustrating the present disclosure in more detail, and therefore, according to the purpose of the present disclosure, it would be apparent to a person skilled in the art that these examples are not construed to limit the scope of the present disclosure.

EXAMPLES

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Example 1: Selection of scFv Antibodies for L1CAM Antigen

1.1. Human Synthetic scFv Phage Display Antibody Library Panning

Figure 1:
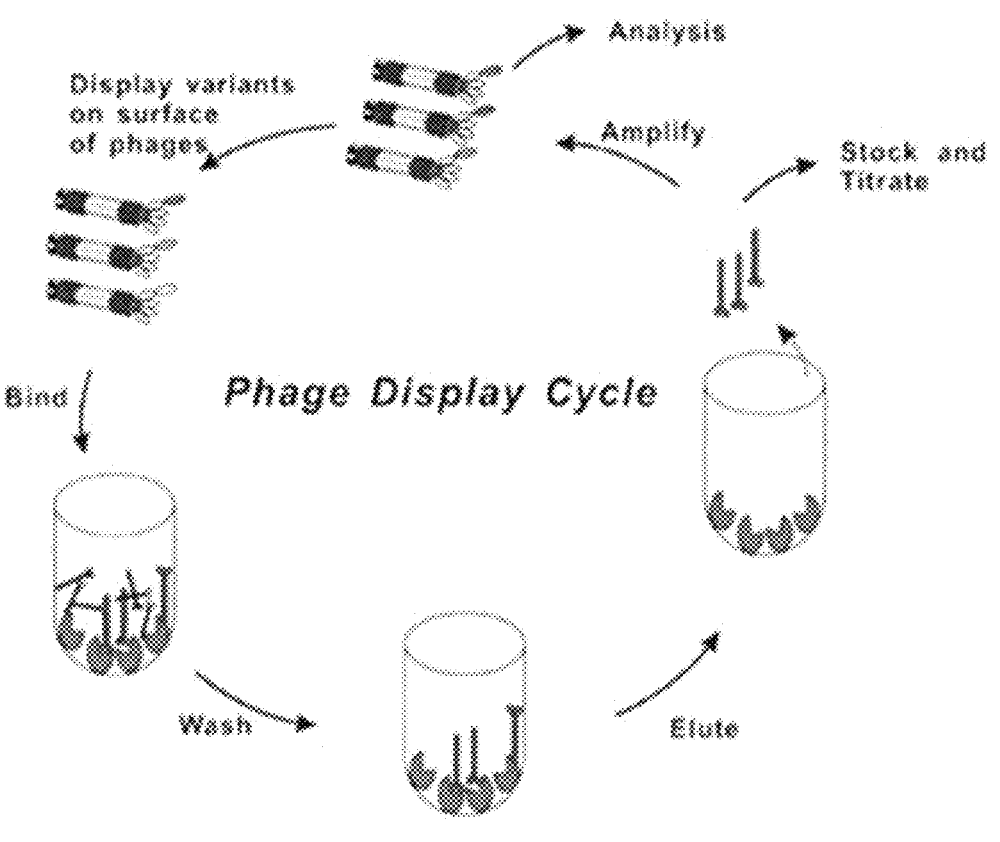
FIG. 1 schematically shows a phage display library panning procedure.
Figure 2:
FIG. 2 shows graphs depicting the degree of enrichment of phages to the antigen mL1CAM according to the phage panning round (top: phage output titer, bottom: elution titer ratio).
Figure 2:
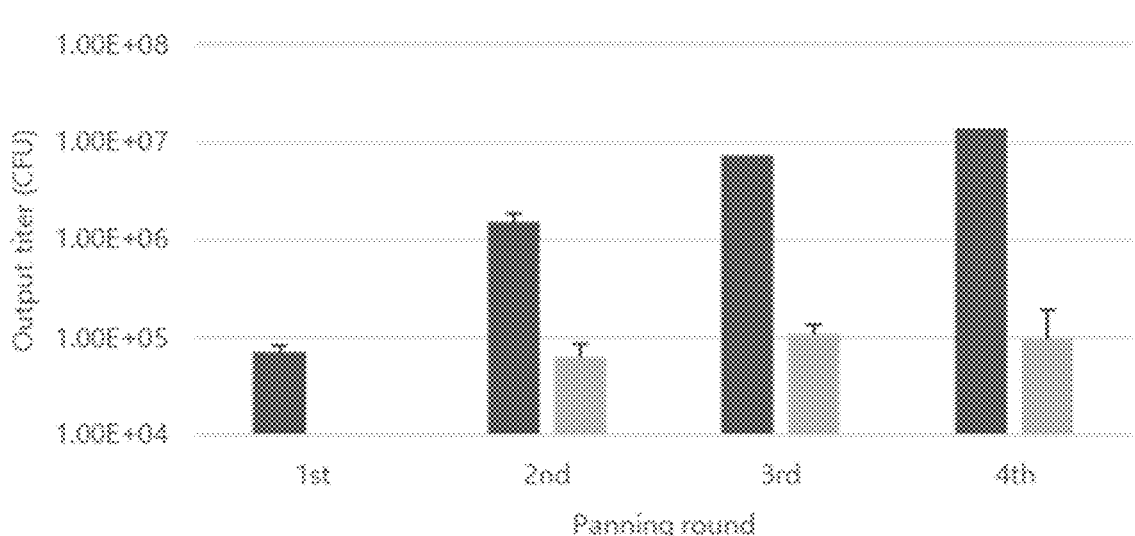
Figure 2:
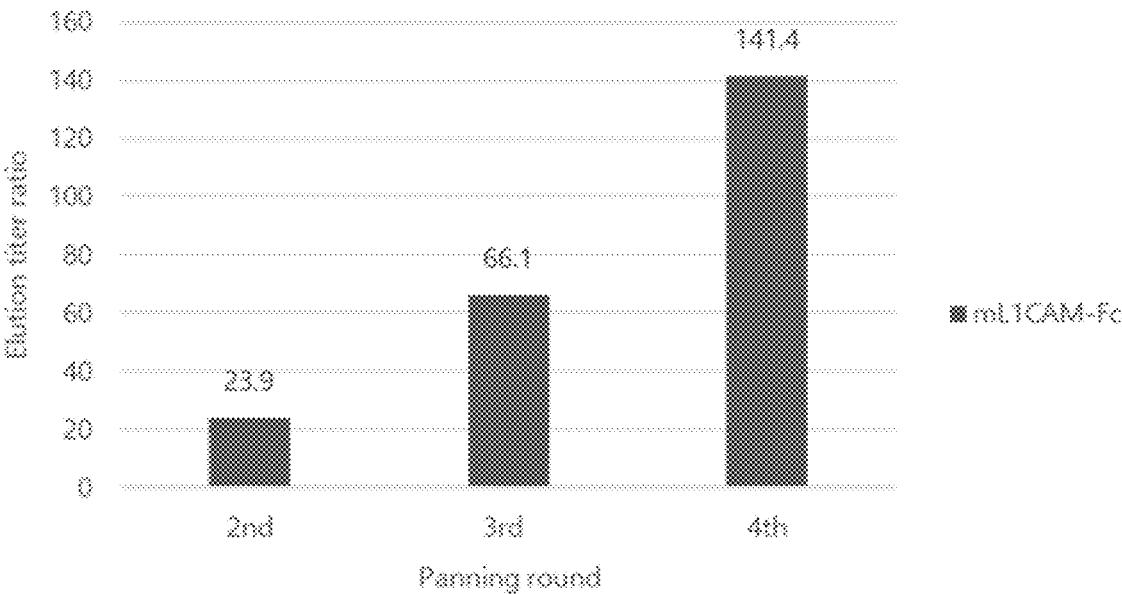

To select anti-mL1CAM scFv antibodies binding to mouse L1CAM (mL1CAM) antigen, phage panning for the antigen mL1CAM protein was performed up to 4 rounds by using the human synthetic scFv phage display library (KscFv-1, KBIO HEALTH) (FIG. 1). The antigen mL1CAM protein (R&D system, Cat No. 5674-NC) was added to immunotubes, incubated at 4° C. overnight, and then blocked by incubation with PBS (MPBS) comprising 5% skim milk at room temperature for 1 hour. MPBS was added to KscFv-1, followed by incubation at room temperature for 1 hour, thereby preparing blocked phages. The blocked phages were added to immunotubes coated with the antigen mL1CAM protein, followed by incubation at 37° C. for 90 minutes. After the phages were washed with PBS comprising 0.05% Tween20, 100 mM trimethylamine was added to harvest (elution) phages adhering to the immunotubes. The harvested phages were neutralized by addition of 1 M Tris-HCl, and then TG1 *E. coli* (Lucigen, Cat No. 60502-2) cultured in the mid-log phase ($OD_{600}$=0.5-1.0) was added, followed by incubation at 37° C. for 1 hour. After incubation, cell pellets were collected, and inoculated on TB medium plates comprising ampicillin and 2% glucose. The cultured colonies were collected, and then stored at −80° C. after the addition of 50% glycerol. Since the antigen mL1CAM protein (R&D system, Cat No. 5674-NC) was fused with the Fc domain, Fc control panning for Fc depletion was also performed in the panning step, and the enrichment of phages was monitored through the elution titer ratio by comparing respective output titer values at each round. The elution titer ratio is the value obtained by dividing the phage output titer value (antigen mL1CAM) by the Fc control output titer value (no antigen mL1CAM). As shown in FIG. 2, mL1CAM-Fc showed a large difference in output titer from Fc control from the 2nd round of phage panning. The enrichment was initiated from the 2nd round of phage panning, and for the antigen mL1CAM, mL1CAM-Fc showed a difference by about 23.9 times compared to the control in the second round of phage panning, a difference by 66.1 times in the third round of phage panning, and a difference by 141.4 times in the fourth round of phage panning.

1.2 Phage ELISA Screening

To select clones specifically adhering to the antigen mL1CAM protein among the phages obtained by phage panning, monoclonal phage ELISA was performed on 95 clones obtained in the 2nd, 3rd, and 4th rounds of panning.

Figure 3A:
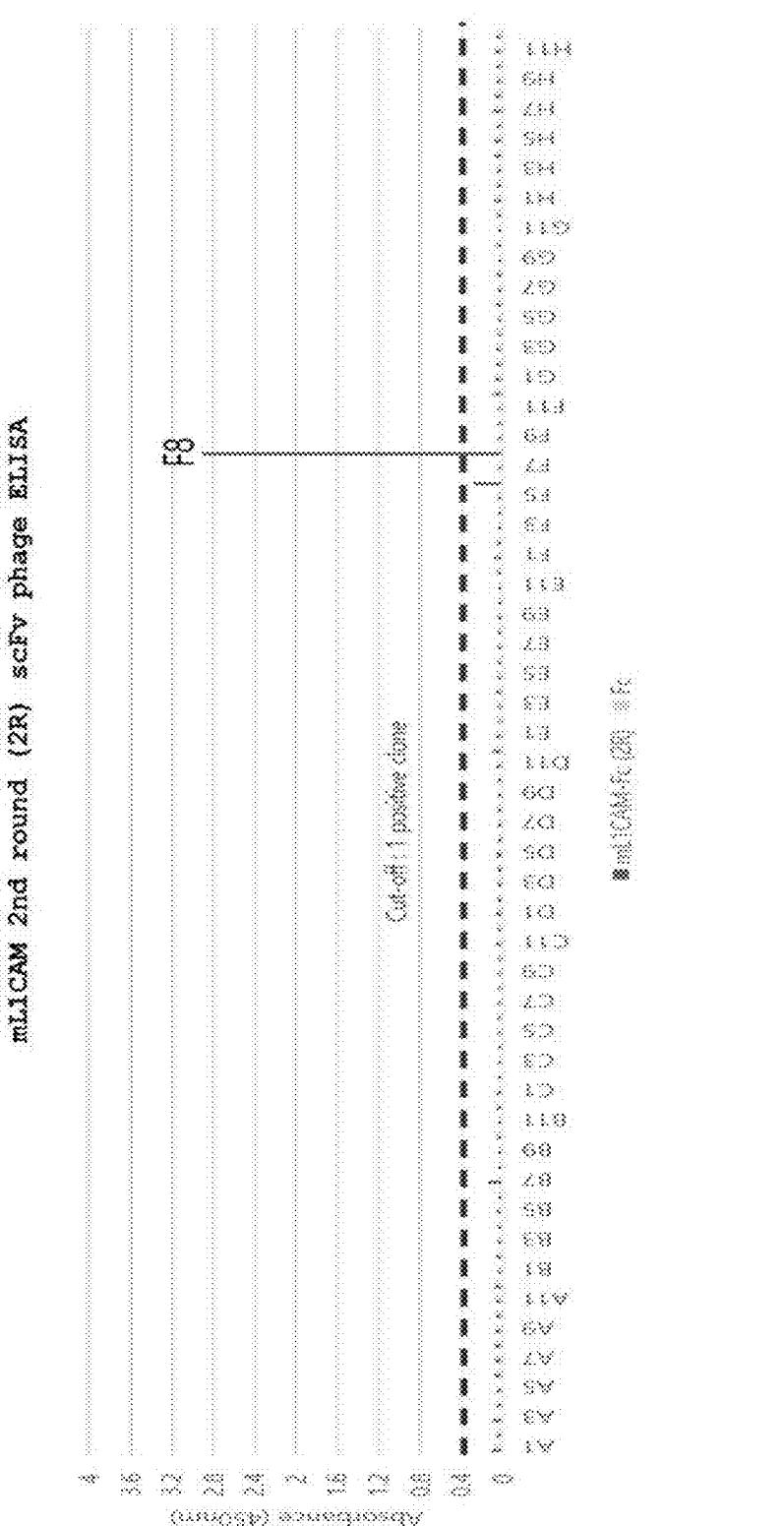
FIGS. 3A, 3B and 3C show the results of performing monoclonal phage ELISA to select phage clones specifically binding to the antigen mL1CAM for each phage panning round
Figure 3B:
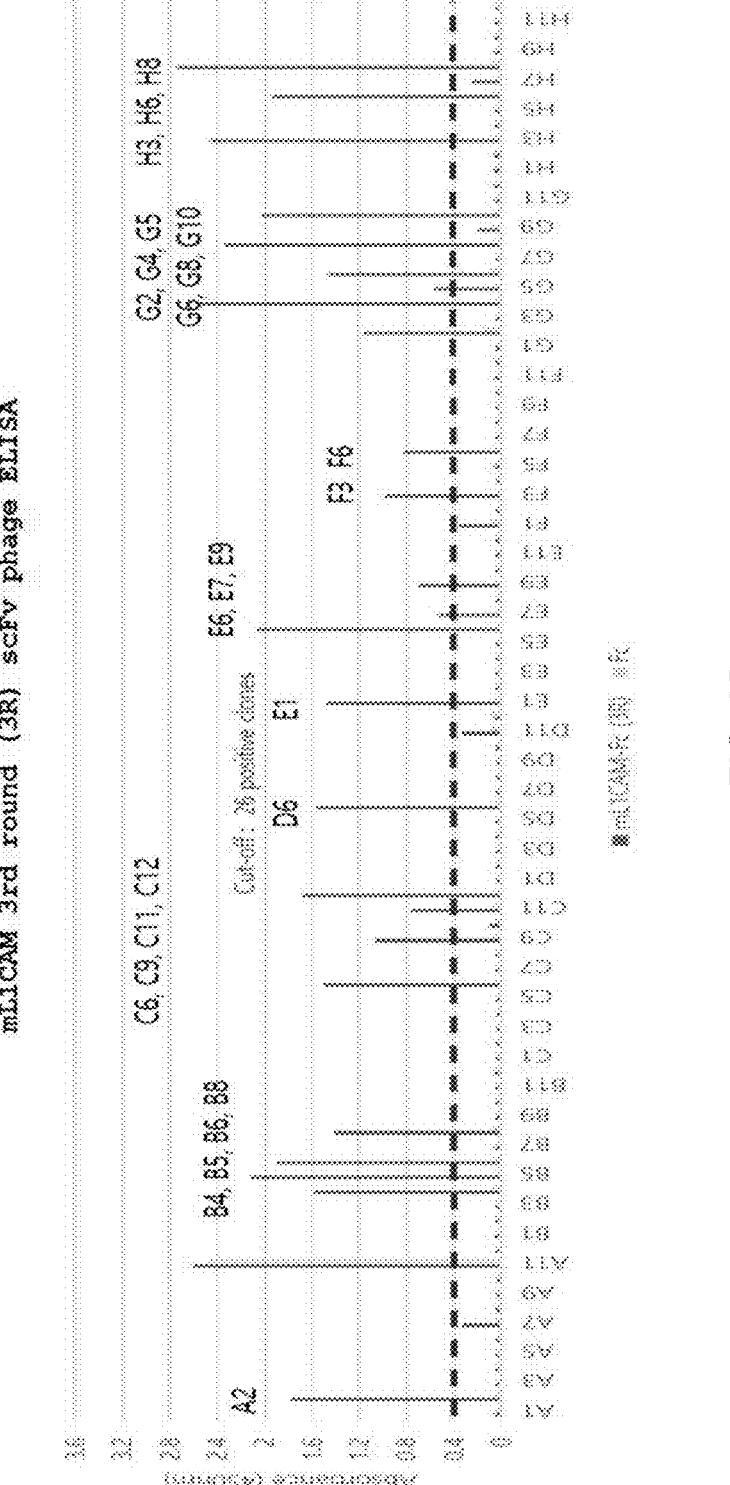
Figure 3C:
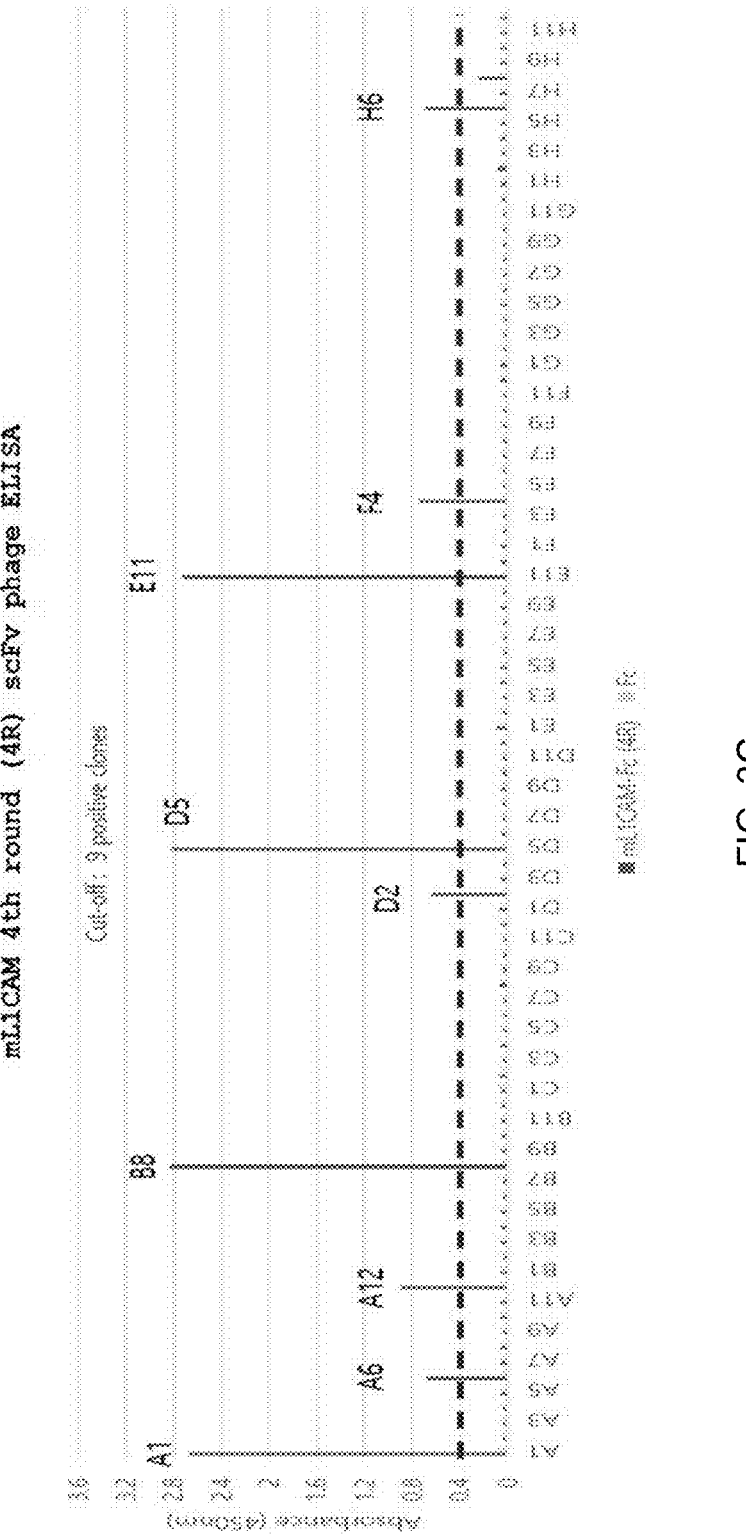

Specifically, the antigen mL1CAM protein was added to 96-well plates, incubated at 4° C. overnight, and then blocked with 2% MPBS at 37° C. for 2 hours. Since the antigen mL1CAM protein was fused with the Fc domain, Fc as an Fc control was also added to the 96-well plates, incubated at 4° C. overnight, and blocked with 2% MPBS at 37° C. for 2 hours. Then, the phages (up to $10^{11}$ cfu) were added to the 96-well plates. After incubation at room temperature for 90 minutes, HRP-anti-M13 (Sino Biological, Cat No. 11973-MM05) was diluted in PBS to 1:5000, and added to 96-well plates. After incubation at room temperature for 1 hour, TMB substrate (Sigma, Cat No. T0440) and 2N H2504 (Merck, Cat No. 100731) were sequentially added, and the absorbance (OD) at 450 nm was measured. As a result, when the absorbance (A450 nm) cut-off for the antigen mL1CAM was set to at least 0.4 for selection, one clone in the 2nd round, a total of 26 clones in the 3rd round, and a total of 9 clones in the 4th round specifically bound (positive) to the antigen mL1CAM in ELISA (FIG. 3).

Figure 4:
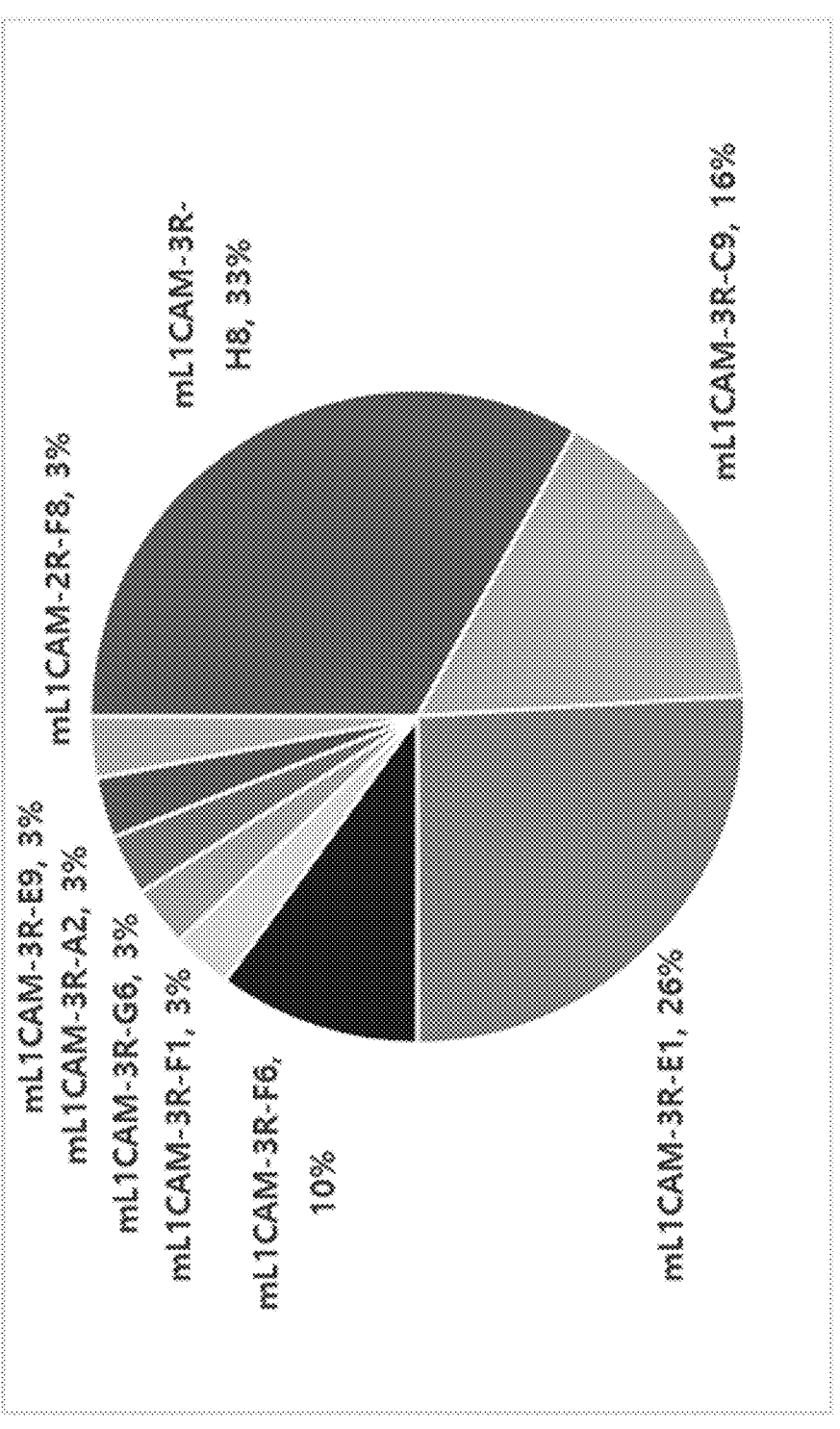
FIG. 4 shows the selection frequency of nine types of scFv clones selected in the present disclosure.

1.3 Sequencing of Unique scFv Clones for mL1CAM Antigen of the Present Disclosure 36 types of scFv clones for the antigen mL1CAM, which showed a positive response in the monoclonal phage ELISA, were sequenced, and the sequences were grouped by alignment through Kabat numbering, and as a result, a total of 9 types of unique anti-mL1CAM scFv clones were obtained (Tables 1 and 2). Considering the selection frequency of the scFv clones obtained for the antigen mL1CAM, the 3rd round clones (mL1CAM-3R-H8, mL1CAM-3R-E1, and mL1CAM-3R-C9) were selected as major clones by accounting for 33%, 26%, and 16%, respectively, and the remaining clones were selected as minor clones by accounting for a range of 3-10% (FIG. 4).

TABLE 1

Amino acid sequences of heavy chain variable regions and linker of 9 types
of anti-mL1CAM scFv clones selected in present disclosure (Kabat)

| ID | FR1_VH | CDR1_VH | FR2_VH | CDR2_VH | FR3_VH | CDR3_VH | FR4_VH | VH_Vk_linker |
|----|--------|---------|--------|---------|--------|---------|--------|--------------|
| 1 | EVQLVESGGG LVQPGGSLRL SCAASGFTFS | DYAMN | WVRQAPG KGLEWVS | AISSTGSTIYY ADSVKG | RFTISRDNSKN TLYLQMNSLRA EDTAVYYCAK | QSTYFYS YFDV | WGQGTL VTVSS | GGGGSGGG GSGGGGS |
| 2 | EVQLVESGGG LVQPGGSLRL SCAASGFTFS | SYAMH | WVRQAPG KGLEWVS | AISSSGGSTY YADSVKG | RFTISRDNSKN TLYLQMNSLRA EDTAVYYCAK | DEGSGLG AFDI | WGQGTL VTVSS | GGGGSGGG GSGGGGS |
| 3 | EVQLVESGGG LVQPGGSLRL SCAASGFTFS | SYAMS | WVRQAPG KGLEWVS | AISSSGSSTYY ADSVKG | RFTISRDNSKN TLYLQMNSLRA EDTAVYYCAK | DESTGLG AFDY | WGQGTL VTVSS | GGGGSGGG GSGGGGS |
| 4 | EVQLVESGGG LVQPGGSLRL SCAASGFTFS | SYAMH | WVRQAPG KGLEWVS | AISSSGSSKYY ADSVKG | RFTISRDNSKN TLYLQINSLRA EDTAVYYCAK | DESYGW LYAFDL | WGQGTL VTVSS | GGGGSGGG GSGGGGS |
| 5 | EVQLVESGGG LVQPGGSLRL SCAASGFTFS | SYAMS | WVRQAPG KGLEWVS | AISSSGGSTY YADSVKG | RFTISRDNSKN TLYLQMNSLRA EDTAVYYCAK | VLELWEG LDY | WGQGTL VTVSS | GGGGSGGG GSGGGGS |
| 6 | EVQLVESGGG LLQPGGSLRL SCAASGFTFS | NYAMH | WVRQAPG KGLEWVS | AIYQSGGDTY YADSVKG | RFTISRDNSKN TLYLQMNSLRA EDTAVYYCAK | VRGTYYG SYLDY | WGQGTL VTVSS | GGGGSGGG GSGGGGS |
| 7 | EVQLVESGGG LVQPGGSLRL SCAASGFTFS | SYAMN | WVRQAPG KGLEWVS | RISSSGTTFYA DSVKG | RFTISRDNSKN TLYLQMNSLRA EDTAVYYCAK | VEEGRYV QAFDY | WGQGTL VTVSS | GGGGSGGG GSGGGGS |
| 8 | EVQLVESGGG LVQPGGSLRL SCAASGFTFS | DYAMH | WVRQAPG KGLEWVS | AISSSGGSTY YADSVKG | RFTISRDNSKN TLYLQMNSLRA EDTAVYYCAK | HGGTWW GRAFDY | WGQGTL VTVSS | GGGGSGGG GSGGGGS |
| 9 | EVQLVESGGG LAQPGGSLRL SCAASGFTFS | SYAMS | WVRQAPG KGLEWVS | AISSSGGTKY YADSVKG | RFTISRDNSKN TLYLQMNSLRA EDTAVYYCAK | HGSYAFV FDY | WGQGTL VTVSS | GGGGSGGG GSGGGGS |

1: mL1CAM-3R-H8_: mL1CAM-3R-E6_: mL1CAM-3R-G10_: mL1CAM-3R-B5_: mL1CAM-3R-H3_: mL1CAM-3R-G5_: mL1CAM-3R-C12_: mL1CAM-3R-G8_: mL1CAM-3R-G4_: mL1CAM-4R-D5_
2: mL1CAM-3R-C9_: mL1CAM-3R-B8_: mL1CAM-3R-B4_: mL1CAM-3R-B6_: mL1CAM-3R-D6_
3: mL1CAM-3R-E1_: mL1CAM-3R-C6_: mL1CAM-3R-C11_: mL1CAM-3R-H6_: mL1CAM-3R-F3_: mL1CAM-4R-E11_: mL1CAM-4R-F4_: mL1CAM-4R-H6_
4: mL1CAM-3R-F6_: mL1CAM-3R-G2_: mL1CAM-3R-E7_
5: mL1CAM-3R-F1_
6: mL1CAM-3R-G6_
7: mL1CAM-3R-A2_
8: mL1CAM-3R-E9_
9: mL1CAM-2R-F8_

The clone IDs expressed in bold mean the clone IDs representing respective groups.

TABLE 2

Amino acid sequences of light chain variable regions of 9 types of anti-mL1CAM scFv clones selected in present disclosure (Kabat)

| ID | FR1_Vk | CDR1_Vk | FR2_Vk | CDR2_Vk | FR3_Vk | CDR3_Vk | FR4_Vk | Frequency |
|---|---|---|---|---|---|---|---|---|
| 1 | DIQMTQSPSSLSA SVGDRVTITC | RASQSISR DLN | WYQQKPGK APKLLIY | AASSL QS | GVPSRFSGSG SGTDFTLTISSL QPEDFATYYCL | QQSYS TPYT | FGQGT KVEIK | 10 |
| 2 | DIQMTQSPSSLSA SVGDRVTITC | RASQSISR YLN | WYQQKPGK APKLLIY | AASNL QS | GVPSRFSGSG SGTDFTLTISSL QPEDFATYYC | QQSYS FPWT | FGQGT KVEIK | 5 |
| 3 | DIQMTQSPSSLSA SVGDRVTITC | RASQSISN YLN | WYQQKPGK APKLLIY | AASNL QS | GVPSRFSGSG SGTDFTLTISSL QPEDFATYYC | QQSYS FPWT | FGQGT KVEIK | 8 |
| 4 | DIQMTQSPSSLSA SVGDRVTITC | RASQSISN YLN | WYQQKPGK APKLLIY | AASRL QS | GVPSRFSGSG SGTDFTLTISSL QPEDFATYYC | QQSYS FPLT | FGQGT KVEIK | 3 |
| 5 | DIQMTQSPSSLSA SVGDRVTITC | RASQSISS YLN | WYQQKPGK APKLLIY | AASRL QS | GVPSRFSGSG SGTDFTLTISSL QPEDFATYYC | QQSES FPYT | FGQGT KVEIK | 1 |
| 6 | DIQMTQSPSSLSA SVGDRVTITC | RASQSISR YLN | WYQQKPGK APKLLIY | AASTL QS | GVPSRFSGSG SGTDFTLTISSL QPEDFATYYC | QQSYS YPFT | FGQGT KVEIK | 1 |
| 7 | DIQMTQSPSSLSA SVGDRVTITC | RASQSISN YLN | WYQQKPGK APKLLIY | ATSRL QS | GVPSRFSGSG SGTDFTLTISSL QPEDFATYYC | QQSYS FPWT | FGQGT KVEIK | 1 |
| 8 | DIQMTQSPSSLSA SVGDRVTITC | RASQSIGS YLN | WYQQKPGK APKLLIY | ATSSL QS | GVPSRFSGSG SGTDFTLTISSL QPEDFATYYC | QQSYS TPYT | FGQGT KVEIK | 1 |
| 9 | DIQMTQSPSSLSA SVGDRVTITC | RASQSISN YLN | WYQQKPGK APKLLIY | AASSL QS | GVPSRFSGSG SGTDFTLTISSL QPEDFATYYC | QQSYS FPWT | FGQGT KVEIK | 1 |

1: mL1CAM-3R-H8_: mL1CAM-3R-E6_: mL1CAM-3R-G10_: mL1CAM-3R-B5_: mL1CAM-3R-H3_: mL1CAM-3R-G5_: mL1CAM-3R-C12_: mL1CAM-3R-G8_: mL1CAM-3R-G4_: mL1CAM-4R-D5_
2: mL1CAM-3R-C9_: mL1CAM-3R-B8_: mL1CAM-3R-B4_: mL1CAM-3R-B6_: mL1CAM-3R-D6_
3: mL1CAM-3R-E1_: mL1CAM-3R-C6_: mL1CAM-3R-C11_: mL1CAM-3R-H6_: mL1CAM-3R-F3_: mL1CAM-4R-E11_: mL1CAM-4R-F4_: mL1CAM-4R-H6_
4: mL1CAM-3R-F6_: mL1CAM-3R-G2_: mL1CAM-3R-E7_
5: mL1CAM-3R-F1_
6: mL1CAM-3R-G6_
7: mL1CAM-3R-A2_
8: mL1CAM-3R-E9_
9: mL1CAM-2R-F8_

The clone IDs expressed in bold mean the clone IDs representing respective groups.

1.4. Discovery of scFv Antibodies Cross-Reactive to Human L1CAM (hL1CAM) and Mouse L1CAM (mL1CAM)

Figure 5:
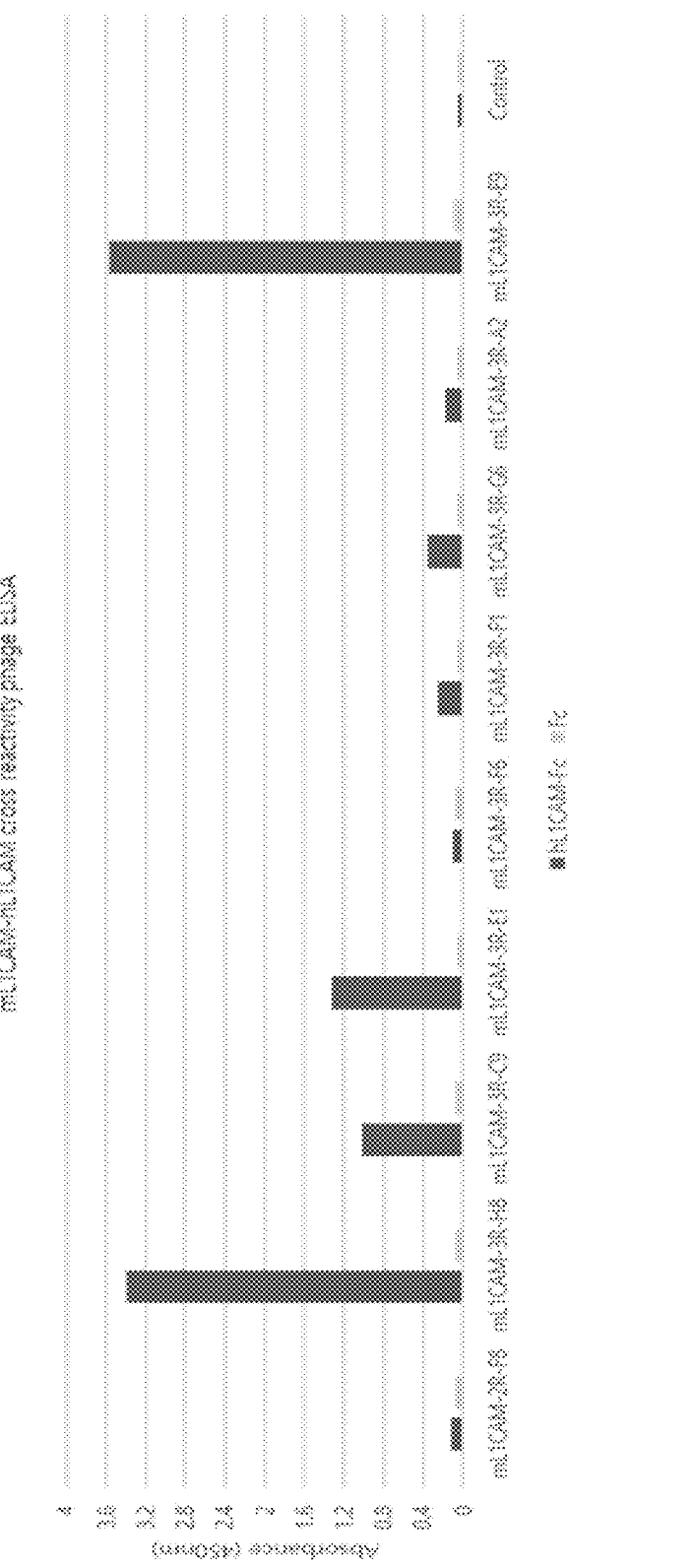
FIG. 5 shows the results of performing monoclonal clone phage ELISA for hL1CAM on nine types of unique anti-mL1CAM scFv clones cross-reactive to mouse L1CAM, which were selected in the present disclosure, in order to discover antibodies cross-reactive to human L1CAM and mouse L1CAM.

To discover antibodies cross-reactive to human L1CAM (hL1CAM, R&D system, Cat No. 777-NC) and mouse L1CAM, monoclonal phage ELISA was performed on a total of 9 types of unique anti-mL1CAM scFv clones for the antigen hL1CAM. As a result, when the absorbance (A450 nm) cut-off for the antigen hL1CAM was set to at least 0.4 for selection, a total of four clones (mL1CAM-3R-H8, mL1CAM-3R-C9, mL1CAM-3R-E1, and mL1CAM-3R-E9) were cross-reactive to the antigen hL1CAM (FIG. 5 and Tables 3 and 4).

TABLE 3

Amino acid sequences of heavy chain variable regions and linker of four types of anti-L1CAM scFv clones finally selected in the present disclosure (Kabat)

| ID | FR1_VH | CDR1_VH | FR2_VH | CDR2_VH | FR3_VH | CDR3_VH | FR4_VH | VH_Vk_linker |
|---|---|---|---|---|---|---|---|---|
| 1 | EVQLVESGGGLV QPGGSLRLSCAA SGFTFS | DYAMN | WVRQAPGK GLEWVS | AISSTGSTIYYA DSVKG | RFTISRDNSKNT LYLQMNSLRAE DTAVYYCAK | QSTYFYSY FDV | WGQGTL VTVSS | GGGGS GGGGS GGGGS |

TABLE 3-continued

| | Amino acid sequences of heavy chain variable regions and linker of four types of anti-L1CAM scFv clones finally selected in the present disclosure (Kabat) | | | | | | | |
|---|---|---|---|---|---|---|---|---|
| ID | FR1_VH | CDR1_VH | FR2_VH | CDR2_VH | FR3_VH | CDR3_VH | FR4_VH | VH_Vk_linker |
| 2 | EVQLVESGGGLV QPGGSLRLSCAA SGFTFS | SYAMH | WVRQAPGK GLEWVS | AISSSGGSTYY ADSVKG | RFTISRDNSKNT LYLQMNSLRAE DTAVYYCAK | DEGSGLG AFDI | WGQGTL VTVSS | GGGGS GGGGS GGGGS |
| 3 | EVQLVESGGGLV QPGGSLRLSCAA SGFTFS | SYAMS | WVRQAPGK GLEWVS | AISSSGGSTYY ADSVKG | RFTISRDNSKNT LYLQMNSLRAE DTAVYYCAK | DESTGLG AFDY | WGQGTL VTVSS | GGGGS GGGGS GGGGS |
| 8 | EVQLVESGGGLV QPGGSLRLSCAA SGFTFS | DYAMH | WVRQAPGK GLEWVS | AISSSGGSTYY ADSVKG | RFTISRDNSKNT LYLQMNSLRAE DTAVYYCAK | HGGTWW GRAFDY | WGQGTL VTVSS | GGGGS GGGGS GGGGS |

1: mL1CAM-3R-H8_: mL1CAM-3R-E6_: mL1CAM-3R-G10_: mL1CAM-3R-B5_: mL1CAM-3R-H3_: mL1CAM-3R-G5_: mL1CAM-3R-C12_: mL1CAM-3R-G8_: mL1CAM-3R-G4_: mL1CAM-4R-D5_
2: mL1CAM-3R-C9_: mL1CAM-3R-B8_: mL1CAM-3R-B4_: mL1CAM-3R-B6_: mL1CAM-3R-D6_
3: mL1CAM-3R-E1_: mL1CAM-3R-C6_: mL1CAM-3R-C11_: mL1CAM-3R-H6_: mL1CAM-3R-F3_: mL1CAM-4R-E11_: mL1CAM-4R-F4_: mL1CAM-4R-H6_
8: mL1CAM-3R-E9_

The clone IDs expressed in bold mean the clone IDs representing respective groups.

TABLE 4

| | Amino acid sequences of light chain variable regions of four types of anti-L1CAM scFv clones finally selected in the present disclosure (Kabat) | | | | | | | |
|---|---|---|---|---|---|---|---|---|
| ID | FR1_Vk | CDR1_Vk | FR2_Vk | CDR2_Vk | FR3_Vk | CDR3_Vk | FR4_Vk | Frequency |
| 1 | DIQMTQSPSSLSA SVGDRVTITC | RASQSISR DLN | WYQQKPGKA PKLLIY | AASSL QS | GVPSRFSGSGS GTDFTLTISSLQP EDFATYYC | QQSYST PYT | FGGGTK VEIK | 10 |
| 2 | DIQMTQSPSSLSA SVGDRVTITC | RASQSISR YLN | WYQQKPGKA PKLLIY | AASNL QS | GVPSRFSGSGS GTDFTLTISSLQP EDFATYYC | QQSYSF PWT | FGGGTK VEIK | 5 |
| 3 | DIQMTQSPSSLSA SVGDRVTITC | RASQSISN YLN | WYQQKPGKA PKLLIY | AASNL QS | GVPSRFSGSGS GTDFTLTISSLQP EDFATYYC | QQSYSF PWT | FGGGTK VEIK | 8 |
| 8 | DIQMTQSPSSLSA SVGDRVTITC | RASQSIGS YLN | WYQQKPGKA PKLLIY | ATSSL QS | GVPSRFSGSGS GTDFTLTISSLQP EDFATYYC | QQSYST PYT | FGGGTK VEIK | 1 |

1: mL1CAM-3R-H8_: mL1CAM-3R-E6_: mL1CAM-3R-G10_: mL1CAM-3R-B5_: mL1CAM-3R-H3_: mL1CAM-3R-G5_: mL1CAM-3R-C12_: mL1CAM-3R-G8_: mL1CAM-3R-G4_: mL1CAM-4R-D5_
2: mL1CAM-3R-C9_: mL1CAM-3R-B8_: mL1CAM-3R-B4_: mL1CAM-3R-B6_: mL1CAM-3R-D6_
3: mL1CAM-3R-E1_: mL1CAM-3R-C6_: mL1CAM-3R-C11_: mL1CAM-3R-H6_: mL1CAM-3R-F3_: mL1CAM-4R-E11_: mL1CAM-4R-F4_: mL1CAM-4R-H6_
8: mL1CAM-3R-E9_

The clone IDs expressed in bold mean the clone IDs representing respective groups.

Figure 6:
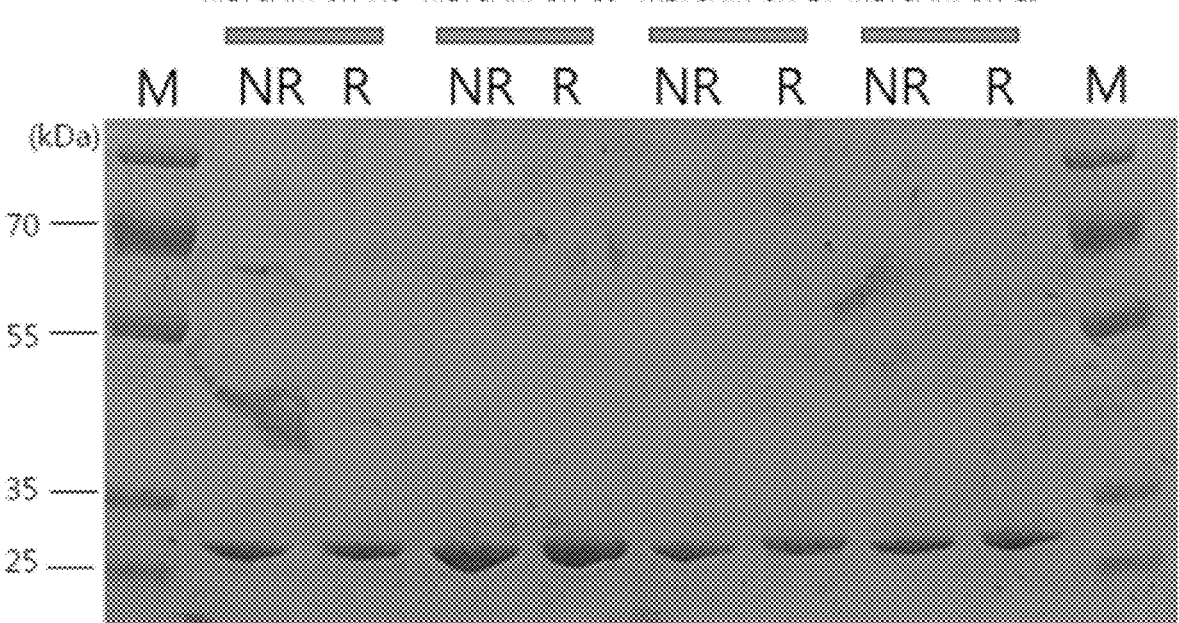
FIG. 6 shows SDS-PAGE analysis results of purified anti-mL1CAM scFv clones.

1.5. *E. coli* Expression and Purification of Four Types of Unique scFv Clones Cross-Reactive to Human L1CAM and Mouse L1CAM A total of four types of unique anti-mL1CAM scFv clones obtained through cross-reactivity evaluation and monoclonal phage ELISA were cloned into *E. coli* expression vectors (pKFAB, KBIO HEALTH), induced to be expressed through 0.5 µM IPTG in 200 mL of TB media, and incubated at 30° C. overnight. The soluble proteins were obtained through periplasmic protein extraction, and then purified through affinity chromatography using a strep tag II column. The expression of each purified clone was confirmed through SDS-PAGE analysis (FIG. 6).

1.6. Affinity Analysis

The affinity of each clone binding to the L1CAM protein was compared and analyzed through soluble ELISA using the anti-L1CAM scFv (4 types) antibody proteins that were selected and purified.

Figure 7A:
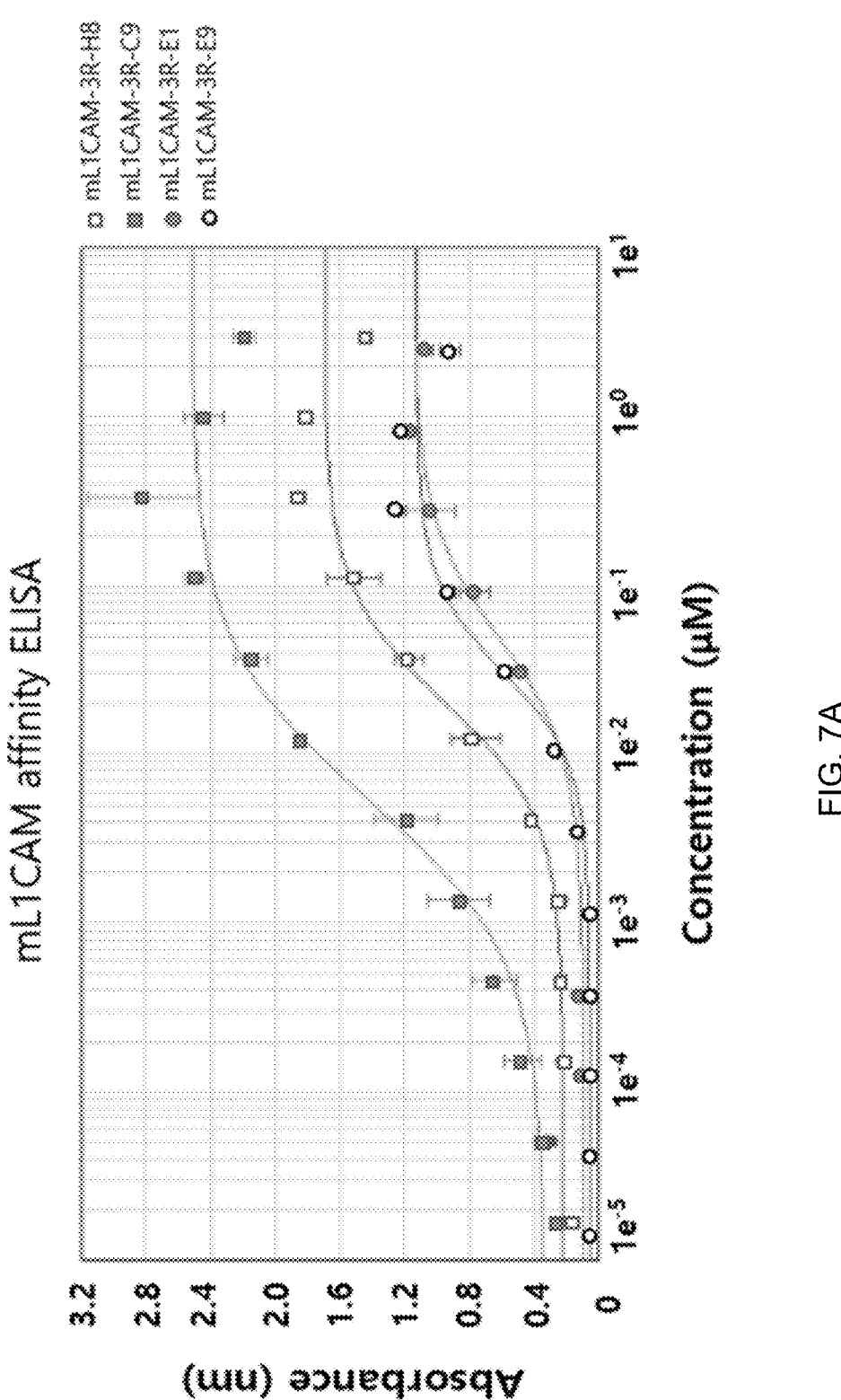
Figure 7B:
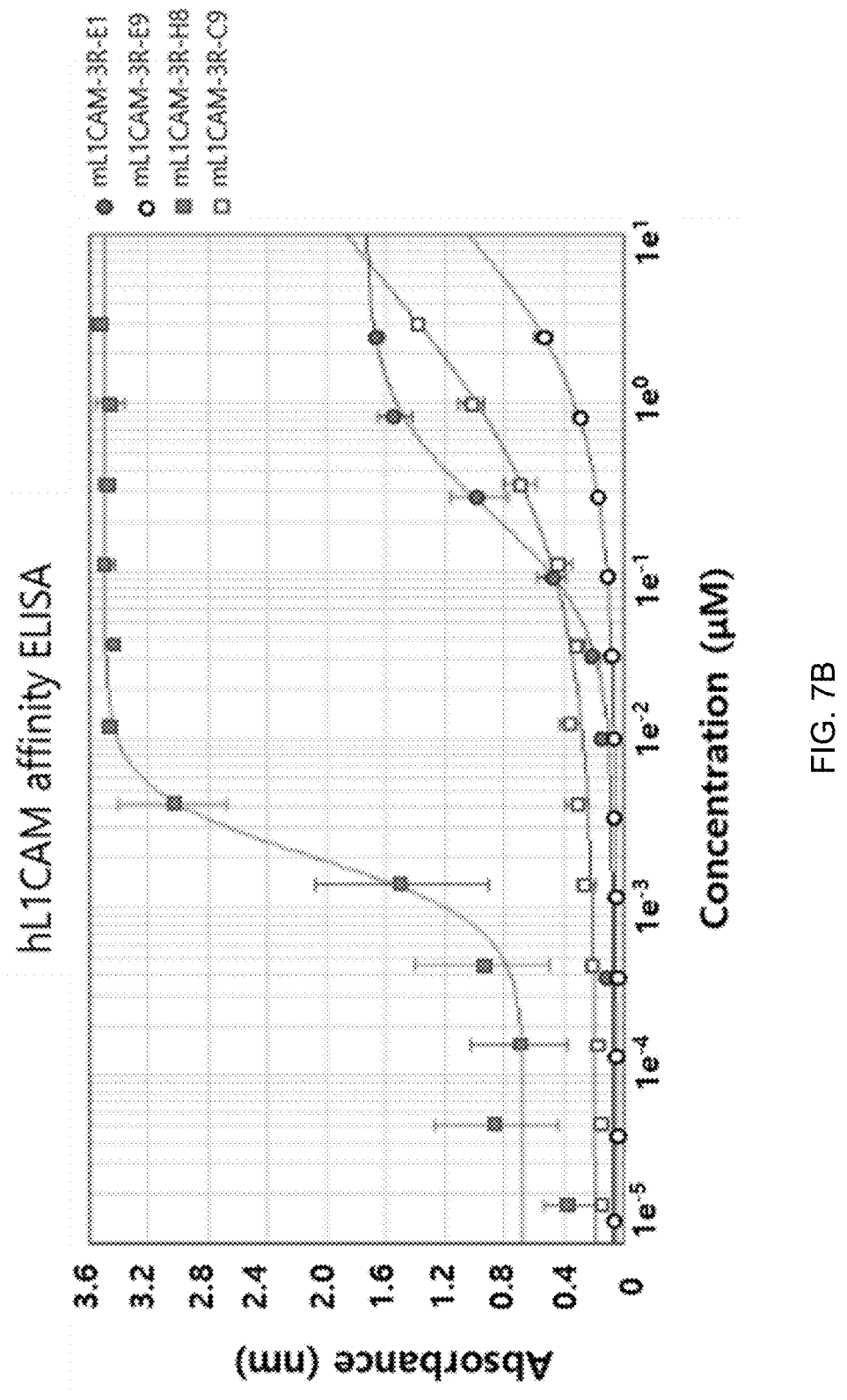

Specifically, the antigen mL1CAM protein or antigen hL1CAM protein was added to 96-well plates, incubated at 4° C. overnight, and then blocked with 2% MPBS at room temperature for 1 hour. Then, the purified anti-L1CAM scFv antibody protein was added. After incubation at room temperature for 90 minutes, HRP-anti-StrepMAB (IBA, Cat No. 2-1509-001) was diluted in 2% MPBS to 1:5000 and added. After incubation at room temperature for 1 hour, TMB substrate (Sigma, Cat No. T0440) and 2N $H_2SO_4$ (Merck, Cat No. 100731) were sequentially added, and the absorbance (OD) at 450 nm was measured. As a result, each clone bound to the antigen mL1CAM with an affinity ranging from 5 nM (mL1CAM-3R-C9) to 50 nM (mL1CAM-3R-E1). As a result of comparing and analyzing affinity for the hL1CAM protein, each clone bound to the antigen hL1CAM with an affinity ranging from 2 nM (mL1CAM-3R-H8) to 20.87 μM (mL1CAM-3R-E9) (FIGS. 7A to 7C). When the binding affinity of four types of cross-reactive clones was synthetically compared for each L1CAM, the binding affinity was high in the order of H8>E1>C9>E9.

Figure 7D:
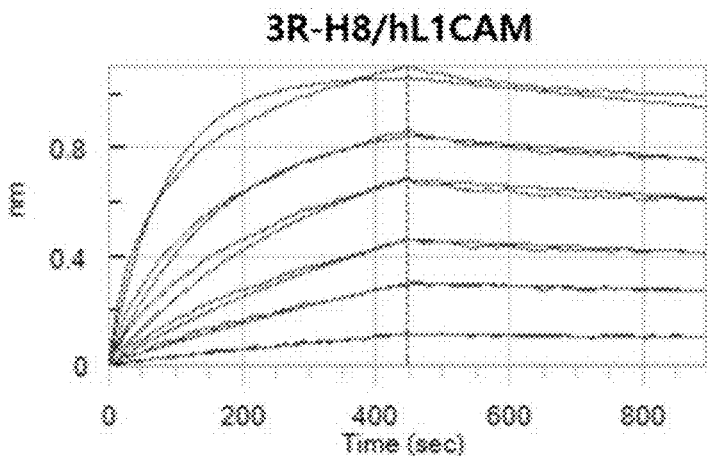
FIGS. 7D and 7E show affinity to mL1CAM and hL1CAM antigens in four types of anti-L1CAM scFv antibodies of the present disclosure according to the octet system results.
Figure 7E:
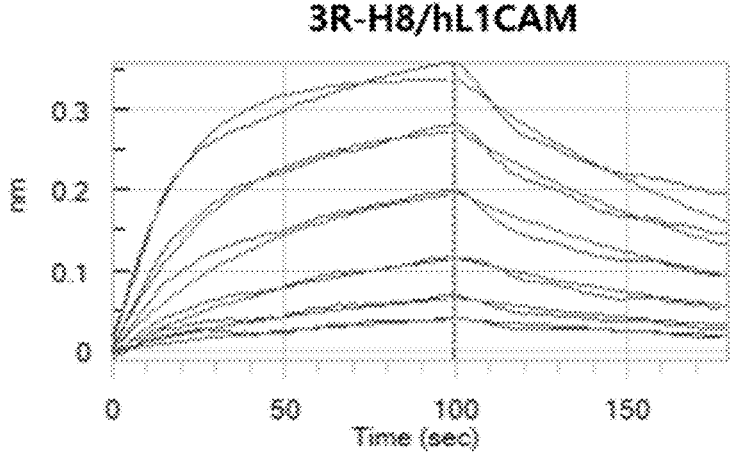

The clone 3R-H8 showing the highest binding affinity among four types of anti-L1CAM scFv was subjected to a conversion procedure, thereby securing the whole IgG1 antibody. Through the Octet system (Forte Bio, Model No. QK384) using the purified whole IgG1 antibody, the antigen-antibody affinity was analyzed for the antigen hL1CAM (Sino biological, Cat No. 10140-H08H) protein or mL1CAM (R&D, Cat No. 5674-NC) protein. The result verified that the corresponding antibody had a binding affinity of 4.14E-09 KD(M) with the antigen hL1CAM protein and a binding affinity of 2.05E-08 KD(M) with the antigen mL1CAM (FIGS. 7D to 7E).

Example 2: Fabrication of Anti-L1CAM-CAR Gene-Expressing T Cells and Verification of Activity Thereof 2.1. Obtainment of Anti-L1CAM-CAR Gene 2.1.1. Obtainment of Anti-mL1CAM scFv Antibody Gene The nucleotide sequences of the anti-L1CAM scFv clones were obtained through sequencing using Lac promoter-forward primers from the phagemids comprising the anti-L1CAM scFv clones selected in the present disclosure. (Table 5). Forward and reverse primers were prepared based on the analyzed nucleotide sequences, and PCR products were obtained by amplifying the phagemids as templates by PCR method. The obtained PCR products of the anti-L1CAM scFv antibodies as templates were amplified by PCR using the primer of SEQ ID NO: 68 (Table 6) and the primer of SEQ ID NO: 69 (Table 6). The primer binding to the 5' site of the anti-L1CAM scFv antibody variable heavy chain (VH) has the 12-nucleotide sequence of the leader sequence (LS) of the 3E8 antibody, which is a mouse monoclonal IgG, and the primer binding to the 3' site of the anti-L1CAM scFv antibody variable light chain (VL) has the 12-nucleotide sequence of the IgD hinge. Therefore, the PCR product amplified by the primers has the hinge nucleotide sequence of 3E8 LS-scFv-IgD. The amplified PCR product was used in the next PCR amplification process.

TABLE 5

Nucleotide sequences encoding four types of anti-L1CAM scFv clones finally selected in present disclosure (Kabat)

| ID | Nucleotide sequence |
|---|---|
| 1 | GAAGTACAGTTGGTCGAAAGTGGCGGTGGCCTCGTGCAACCGGGTGGTTCACTGCGTCTGAGC TGCGCCGCCTCGGGTTTTACTTTCTCTGATTATGCAATGAATTGGGTTCGTCAGGCGCCGGGCAA GGGTCTCGAATGGGTTTCAGCAATCTCTTCTACTGGTTCTACTATCTACTATGCCGATTCAGTGAA GGGTCGCTTTACCATTTCCCGTGACAACTCTAAGAATACTCTGTATCTGCAGATGAACTCGCTGCG TGCCGAAGACACGGCCGTCTATTATTGCGCCAAACAGTCTACTTACTTTTACTCTTACTTTGATGTT TGGGGTCAGGGCACTTTAGTGACCGTCTCATCGGGTGGAGGCGGTTCAGGCGGAGGTGGATCC GGCGGTGGCGGATCGGACATTCAAATGACGCAGAGTCCCTCCTCACTGAGTGCTAGCGTGGGC GATCGTGTGACAATTACTTGTCGCGCTAGCCAGTCTATCTCTCGTGATCTGAACTGGTATCAGCAG AAACCGGGCAAGGCGCCAAAATTGCTGATTTACGCAGCATCCTCTCTGCAGTCTGGTGTACCGT CCCGTTTCTCTGGCAGCGGTTCTGGTACGGATTTTACCCTGACCATCTCAAGCCTCCAGCCTGAA GATTTTGCCACCTATTATTGTCAGCAATCTTACTCTACTCCGTACACGTTCGGGCAGGGAACTAAA GTGGAAATTAAA |
| 2 | GAAGTACAGTTGGTCGAAAGTGGCGGTGGCCTCGTGCAACCGGGTGGTTCACTGCGTCTGAGC TGCGCCGCCTCGGGTTTTACTTTCTCTTCTTATGCAATGCACTGGGTTCGTCAGGCGCCGGGCA AGGGTCTCGAATGGGTTTCAGCAATCTCTTCTTCTGGTGGTTCTACTTACTATGCCGATTCAGTGA AGGGTCGCTTTACCATTTCCCGTGACAACTCTAAGAATACTCTGTATCTGCAGATGAACTCGCTGC GTGCCGAAGACACGGCCGTCTATTATTGCGCCAAAGATGAAGGTTCTGGTCTGGGTGCATTTGAT ATCTGGGGTCAGGGCACTTTAGTGACCGTCTCATCGGGTGGAGGCGGTTCAGGCGGAGGTGGA TCCGGCGGTGGCGGATCGGACATTCAAATGACGCAGAGTCCCTCCTCACTGAGTGCTAGCGTG GGCGATCGTGTGACAATTACTTGTCGCGCTAGCCAGTCTATCTCTCGTTACCTGAACTGGTATCA GCAGAAACCGGGCAAGGCGCCAAAATTGCTGATTTACGCAGCATCCAATCTGCAGTCTGGTGTA CCGTCCCGTTTCTCTGGCAGCGGTTCTGGTACGGATTTTACCCTGACCATCTCAAGCCTCCAGC CTGAAGATTTTGCCACCTATTATTGTCAGCAATCTTACTCTTTTCCGTGGACGTTCGGGCAGGGAA CTAAAGTGGAAATTAAA |
| 3 | GAAGTACAGTTGGTCGAAAGTGGCGGTGGCCTCGTGCAACCGGGTGGTTCACTGCGTCTGAGC TGCGCCGCCTCGGGTTTTACTTTCTCTTCTTATGCAATGTCTTGGGTTCGTCAGGCGCCGGGCAA GGGTCTCGAATGGGTTTCAGCAATCTCTTCTTCTGGTTCTTCTACTTACTATGCCGATTCAGTGAA GGGTCGCTTTACCATTTCCCGTGACAACTCTAAGAATACTCTGTATCTGCAGATGAACTCGCTGCG TGCCGAAGACACGGCCGTCTATTATTGCGCCAAAGATGAATCTACTGGTCTGGGTGCATTTGATTA CTGGGGTCAGGGCACTTTAGTGACCGTCTCATCGGGTGGAGGCGGTTCAGGCGGAGGTGGATC CGGCGGTGGCGGATCGGACATTCAAATGACGCAGAGTCCCTCCTCACTGAGTGCTAGCGTGGG CGATCGTGTGACAATTACTTGTCGCGCTAGCCAGTCTATCTCTAATTACCTGAACTGGTATCAGCA GAAACCGGGCAAGGCGCCAAAATTGCTGATTTACGCAGCATCCAATCTGCAGTCTGGTGTACCG TCCCGTTTCTCTGGCAGCGGTTCTGGTACGGATTTTACCCTGACCATCTCAAGCCTCCAGCCTGA AGATTTTGCCACCTATTATTGTCAGCAATCTTACTCTTTTCCGTGGACGTTCGGGCAGGGAACTAA AGTGGAAATTAAA |

TABLE 5-continued

Nucleotide sequences encoding four types of anti-L1CAM scFv clones
finally selected in present disclosure (Kabat)

ID Nucleotide sequence

8   GAAGTACAGTTGGTCGAAAGTGGCGGTGGCCTCGTGCAACCGGGTGGTTCACTGCGTCTGAGC
    TGCGCCGCCTCGGGTTTTACTTTCTCTGATTATGCAATGCACTGGGTTCGTCAGGCGCCGGGCA
    AGGGTCTCGAATGGGTTTCAGCAATCTCTTCTTCTGGTGGTTCTACTTACTATGCCGATTCAGTGA
    AGGGTCGCTTTACCATTTCCCGTGACAACTCTAAGAATACTCTGTATCTGCAGATGAACTCGCTGC
    GTGCCGAAGACACGGCCGTCTATTATTGCGCCAAACATGGTGGTACTTGGTGGGGTCGTGCATT
    CGATTACTGGGGTCAGGGCACTTTAGTGACCGTCTCATCGGGTGGAGGCGGTTCAGGCGGAGG
    TGGATCCGGCGGTGGCGGATCGGACATTCAAATGACGCAGAGTCCCTCCTCACTGAGTGCTAGC
    GTGGGCGATCGTGTGACAATTACTTGTCGCGCTAGCCAGTCTATCGGTTCTTACCTGAACTGGTA
    TCAGCAGAAACCGGGCAAGGCGCCAAAATTGCTGATTTACGCAACTTCCTCTCTGCAGTCTGGT
    GTACCGTCCCGTTTCTCTGGCAGCGGTTCTGGTACGGATTTTACCCTGACCATCTCAAGCCTCCA
    GCCTGAAGATTTTGCCACCTATTATTGTCAGCAATCTTACTCTACTCCGTACACGTTCGGGCAGGG
    AACTAAAGTGGAAATTAAA

TABLE 6

| SEQ ID NO | Primer name | Nucleotide sequence |
|---|---|---|
| 68 | 3E8 VH_LS + L1 ScFv(F) | GGTGTCCACTCCGAAGTACAGTTGGTC |
| 69 | L1 ScFv + hIgD hinge(R) | ACCTGGCCAGCGTTTAATTTCCACTTT |
| 70 | Mlu 1 + 3E8 VH(F) | ACGCGTATGGAATGGAGCTGGGTC |
| 71 | 3E8 VH + L1 ScFv(R) | CAACTGTACTTCGGAGTGGACACCTGT |
| 72 | L1 ScFv + hIgD hinge(F) | GTGGAAATTAAACGCTGGCCAGGTTCT |
| 73 | Xho I + CD3zeta(R) | CCGCTCGAGTTAGCGAGGGGGCAGGGC |
| 74 | T7(F) | TATACGACTCACTATAGGG |
| 75 | SP6(R) | ATTTAGGTGACACTATAG |

2.1.2. Obtainment of 3E8 Antibody Leader Sequence Gene

Figure 8:
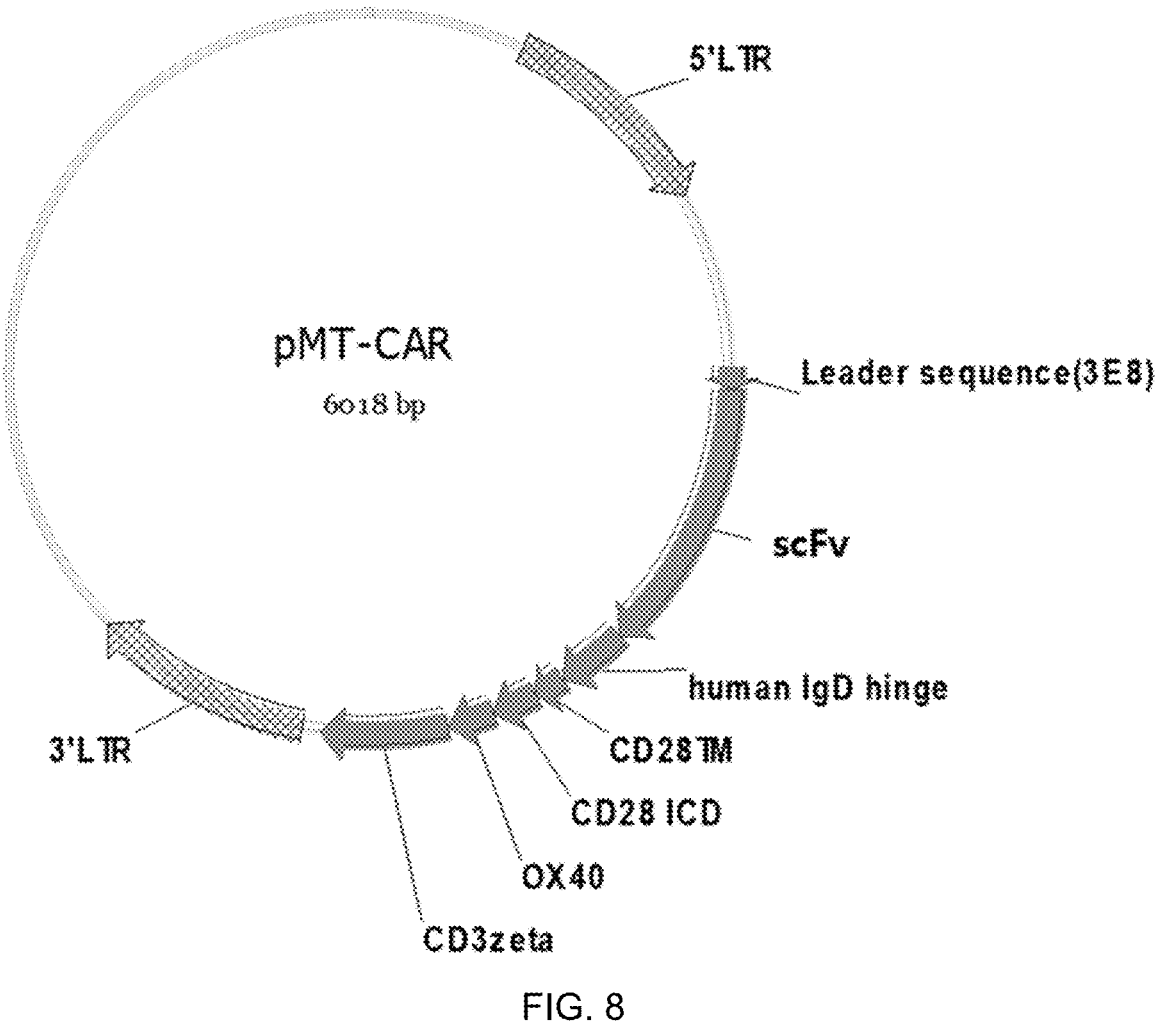
FIG. 8 shows a vector map of the pMT-CART plasmid used to manufacture a CAR-construct comprising the anti-L1CAM scFv selected in the present disclosure.

The pMT-CAR plasmid comprising the 3E8 antibody leader sequence (FIG. 8) as a template was amplified by PCR using the primer of SEQ ID NO: 70 (Table 6) and the primer of SEQ ID NO: 71 (Table 6) before use. The primer binding to the 5' site of the 3E8 leader sequence (LS) has the nucleotide sequence of the Mlu I restriction enzyme, and the primer binding to the 3' site of the 3E8 leader sequence (LS) has the 12-nucleotide sequence of the heavy chain variable region of the anti-L1CAM scFv antibody. Therefore, the amplified PCR product has the nucleotide sequence of Mlu I-3E8 LS-scFv. The amplified PCR product was used in the next PCR amplification process.

2.1.3. Obtainment of Human IgD Hinge Region, Transmembrane Domain, Intracellular Signaling Domain, Costimulatory Domain, and CD3ζ Gene To manufacture the CAR-constructs of the present disclosure, the gene of human IgD hinge region, CD28 trans-membrane domain (TM), intracellular signaling domain (ICD), costimulatory domain OX40, and CD3ζ was obtained by the following methods.

First, the pMT-CAR plasmid (FIG. 8) as a template was amplified by PCR using the primer of SEQ ID NO: 72 (Table 6) and the primer of SEQ ID NO: 73 (Table 6). The primer binding to the 5' site of the human IgD hinge region includes the 12-nucleotide sequence of the anti-L1CAM scFv anti-body light chain variable region, and the primer binding to the 3' site of CD3ζ includes the nucleotide sequence of XhoI restriction enzyme. Therefore, the PCR product amplified by the primers has the nucleotide sequence of scFv-IgD hinge-CD28 TM-ICD-OX40-CD3ζ-Xho I (Table 7). The amplified PCR product was used in the next PCR amplification process.

TABLE 7

Leader sequence, hinge, transmembrane domain (TM), intracellular
domain (ICD), costimulatory domain, and CD3ζ gene sequences used
in construction of CAR constructs of present disclosure

| ID | Nucleotide sequence |
|---|---|
| Mlu I-start codon-3E8 LS | ACGCGTATGGAATGGAGCTGGGTCTTTCTCTTCTTCCTGTCAGTAACTACAGG TGTCCACTCC |

TABLE 7-continued

Leader sequence, hinge, transmembrane domain (TM), intracellular
domain (ICD), costimulatory domain, and CD3ζ gene sequences used
in construction of CAR constructs of present disclosure

| ID | Nucleotide sequence |
|---|---|
| ScFv | (See Table 5) |
| IgD hinge | CGCTGGCCAGGTTCTCCAAAGGCACAGGCCTCCTCCGTGCCCACTGCACAA CCCCAAGCAGAGGGCAGCCTCGCCAAGGCAACCACAGCCCCAGCCACCAC CCGTAACACAGGTAGAGGAGGAGAAGAGAAGAAGAAGGAGAAGGAGAAAGA GGAACAAGAAGAGAGAGAGACAAAGACACCAGGTTGTCCG |
| CD28 TM | TTTTGGGTGCTGGTGGTGGTTGGTGGAGTCCTGGCTTGCTATAGCTTGCTAG TAACAGTGGCCTTTATTATTTTCTGGGTG |
| CD28 ICD | AGGAGTAAGAGGAGCAGGCTCCTGCACAGTGACTACATGAACATGACTCCCC GCCGCCCCGGGCCCACCCGCAAGCATTACCAGCCCTATGCCCCACCACGCG ACTTCGCAGCCTATCGCTCC |
| OX40 | GCCCTGTACCTGCTCCGGAGGGACCAGAGGCTGCCCCCCGATGCCCACAA GCCCCCTGGGGGAGGCAGTTTCCGGACCCCCATCCAAGAGGAGCAGGCCG ACGCCCACTCCACCCTGGCCAAGATC |
| CD3ζ-stop codon-XhoI | AGAGTGAAGTTCAGCAGGAGCGCAGACGCCCCCGCGTACCAGCAGGGCCA GAACCAGCTCTATAACGAGCTCAATCTAGGACGAAGAGAGGAGTACGATGTTT TGGACAAGAGACGTGGCCGGGACCCTGAGATGGGGGGAAAGCCGCAGAGA AGGAAGAACCCTCAGGAAGGCCTGTACAATGAACTGCAGAAAGATAAGATGG CGGAGGCCTACAGTGAGATTGGGATGAAAGGCGAGCGCCGGAGGGGCAAG GGGCACGATGGCCTTTACCAGGGTCTCAGTACAGCCACCAAGGACACCTAC GACGCCCTTCACATGCAGGCCCTGCCCCCTCGCTAACTCGAG |

2.1.4. Preparation of pGemT-L1CAM-CAR Vectors

Mlu I-3E8 LS-scFv, which is the PCR product amplified in 2.1.2, and the 3E8 LS-scFv-IgD hinge, which is the PCR product amplified in 2.1.1, as templates, were amplified by overlap extension PCR (OE-PCR) using the primer of SEQ ID NO: 70 (Table 6) and the primer of SEQ ID NO: 69 (Table 6).

Figure 9:
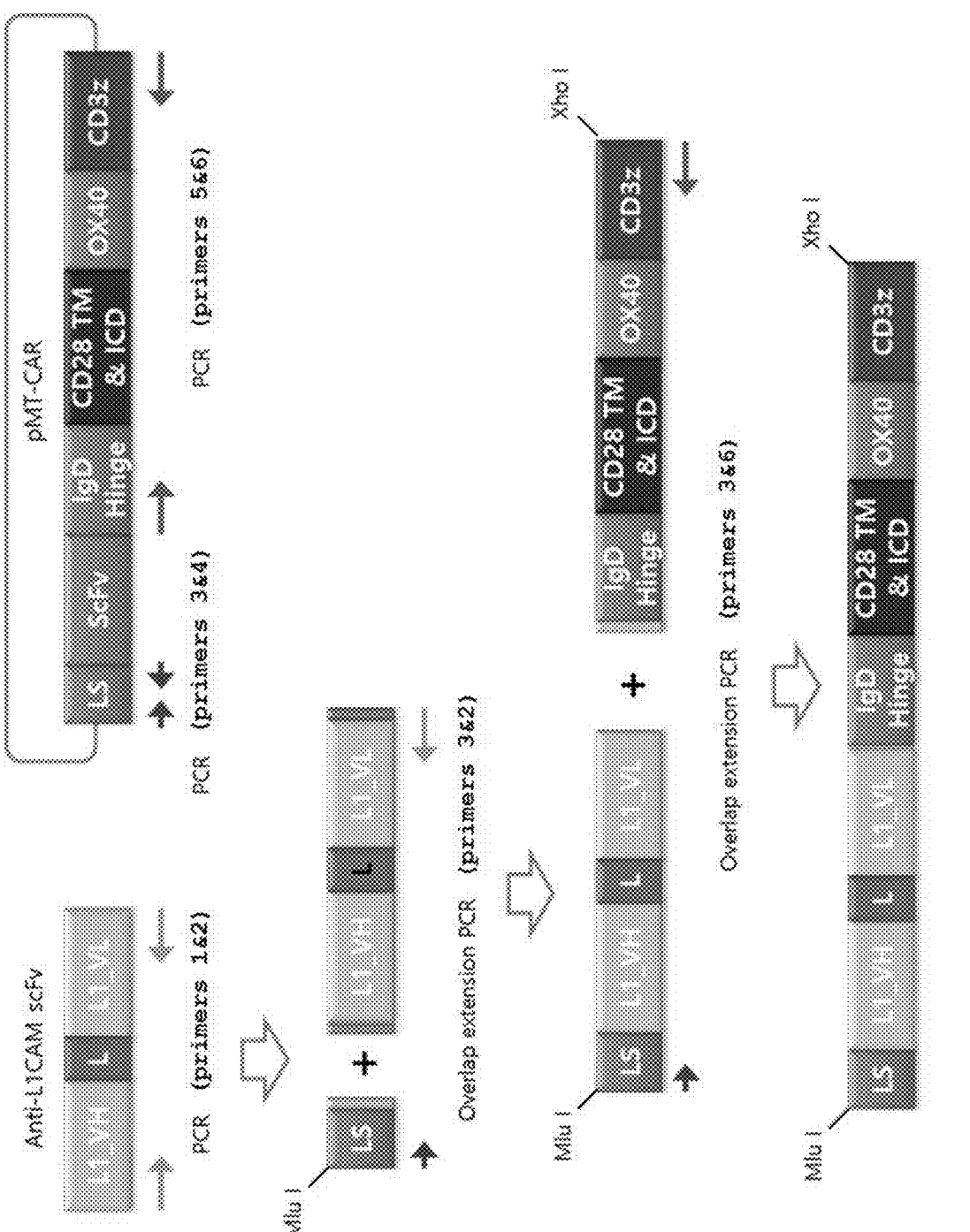
FIG. 9 is a schematic diagram showing a series of PCR amplification procedures in order to manufacture a CAR-construct comprising anti-L1CAM scFv of the present disclosure.
Figure 10A:
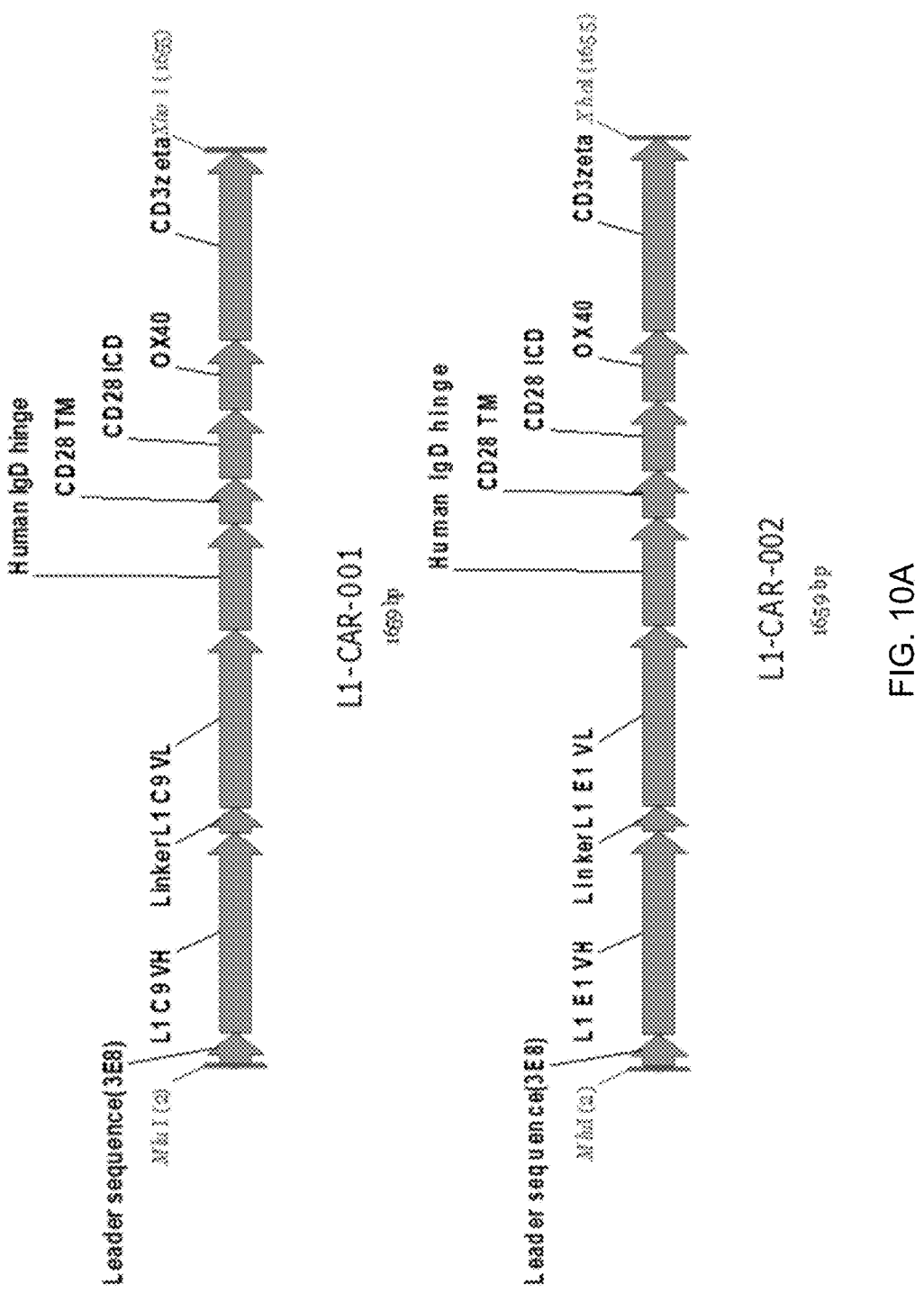
FIGS. 10A and 10B show structures of CAR-constructs comprising anti-L1CAM scFv (L1-CAR-001, L1-CAR-002, L1-CAR-003, and L1-CAR-004) constructed in the example of the present disclosure.
Figure 10B:
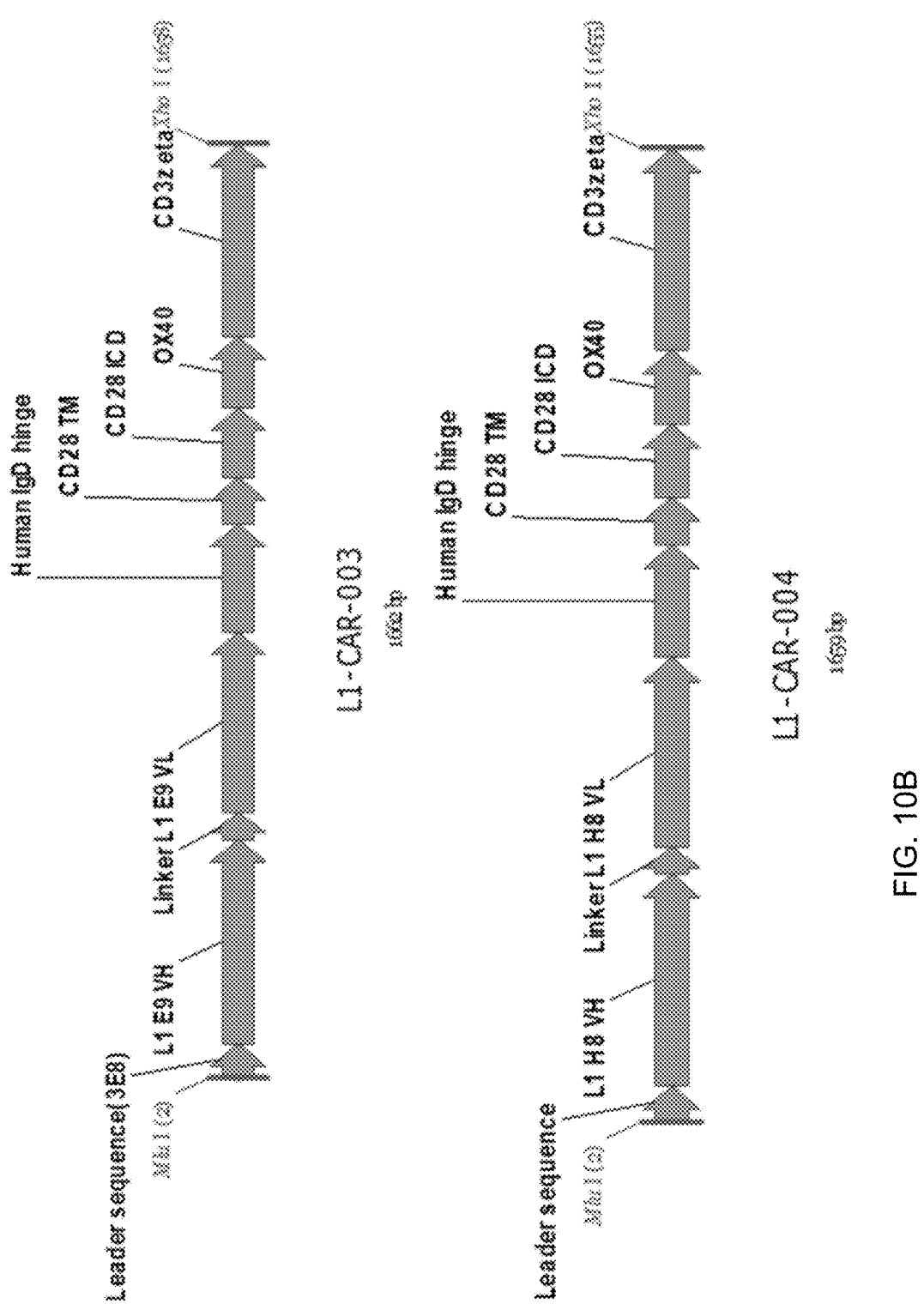

The resulting amplified Mlu I-3E8 LS-scFv-IgD hinge, and scFv-IgD hinge-CD28 TM-ICD-OX40-CD3ζ-Xho I, which is the PCR product amplified in 2.1.3, as templates, were amplified by OE-PCR using the primer of SEQ ID NO: 70 (Table 6) and the primer of SEQ ID NO: 73 (Table 6) (FIG. 9). The resulting amplified PCR product has the nucleotide sequence of Mlu I-3E8 LS-scFv-IgD hinge-CD28 TM-ICD-OX40-CD3ζ-Xho I. The amplified PCR product was ligated to pGemT EASY vector (Promega, WI, USA) having the multiple T sequences at both ends of linear DNA to give the CAR constructs, pGemT-L1-CAR-001, pGemT-L1-CAR-002, pGemT-L1-CAR-003, and pGemT-L1-CAR-004. The obtained CAR constructs were confirmed to be the same as the original sequence through sequencing (FIGS. 10A and 10B). A pair of primers of SEQ ID NOs: 74 and 75 (Table 6) was used for the sequencing.

2.1.5. Preparation of pMIN-L1-CAR Retroviral Vectors

Figure 11A:
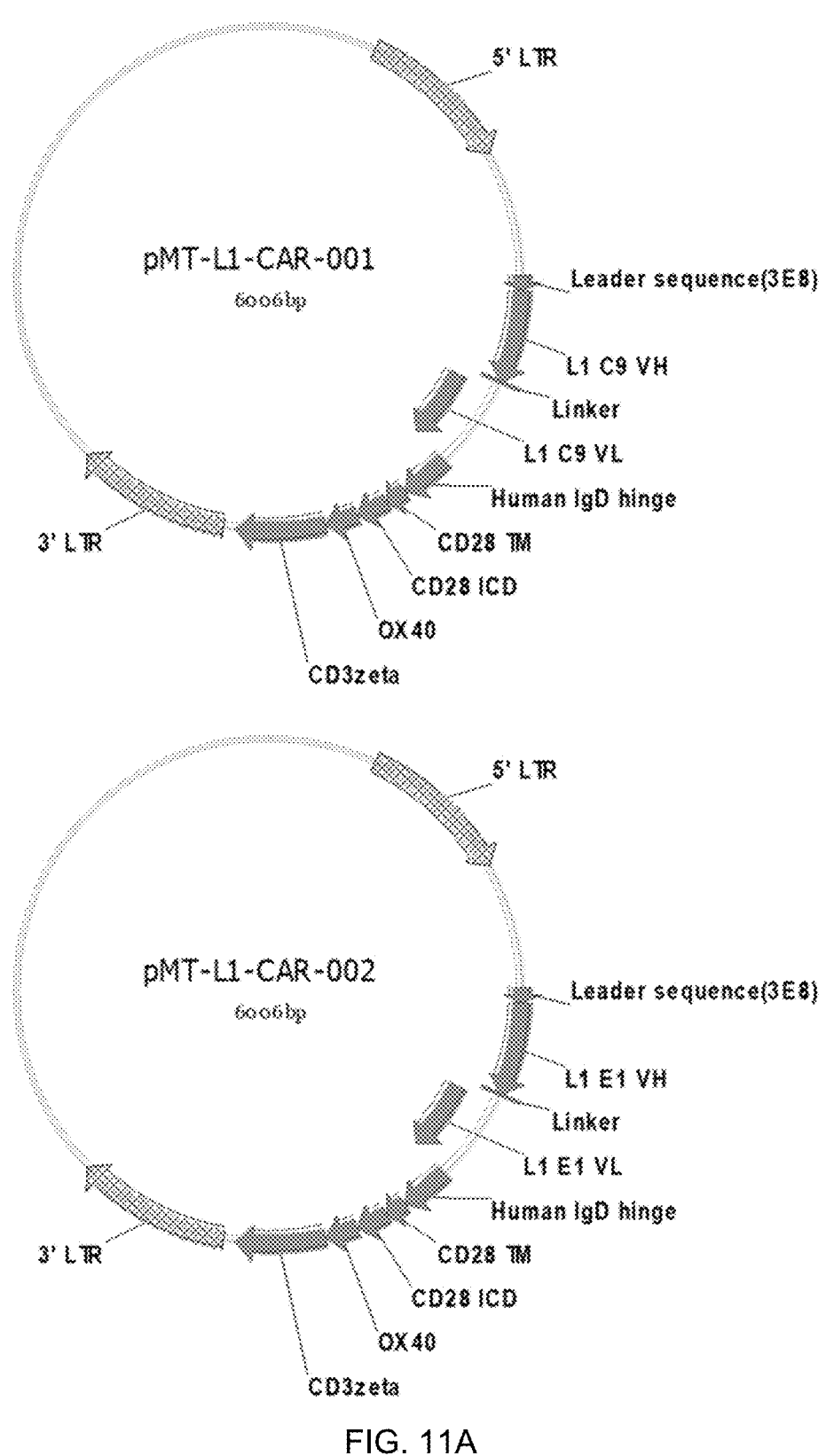
FIGS. 11A and 11B show retroviral vectors into which four types of CAR-constructs comprising anti-L1CAM scFv (L1-CAR-001, L1-CAR-002, L1-CAR-003, and L1-CAR-004) of the present disclosure were introduced.
Figure 11B:
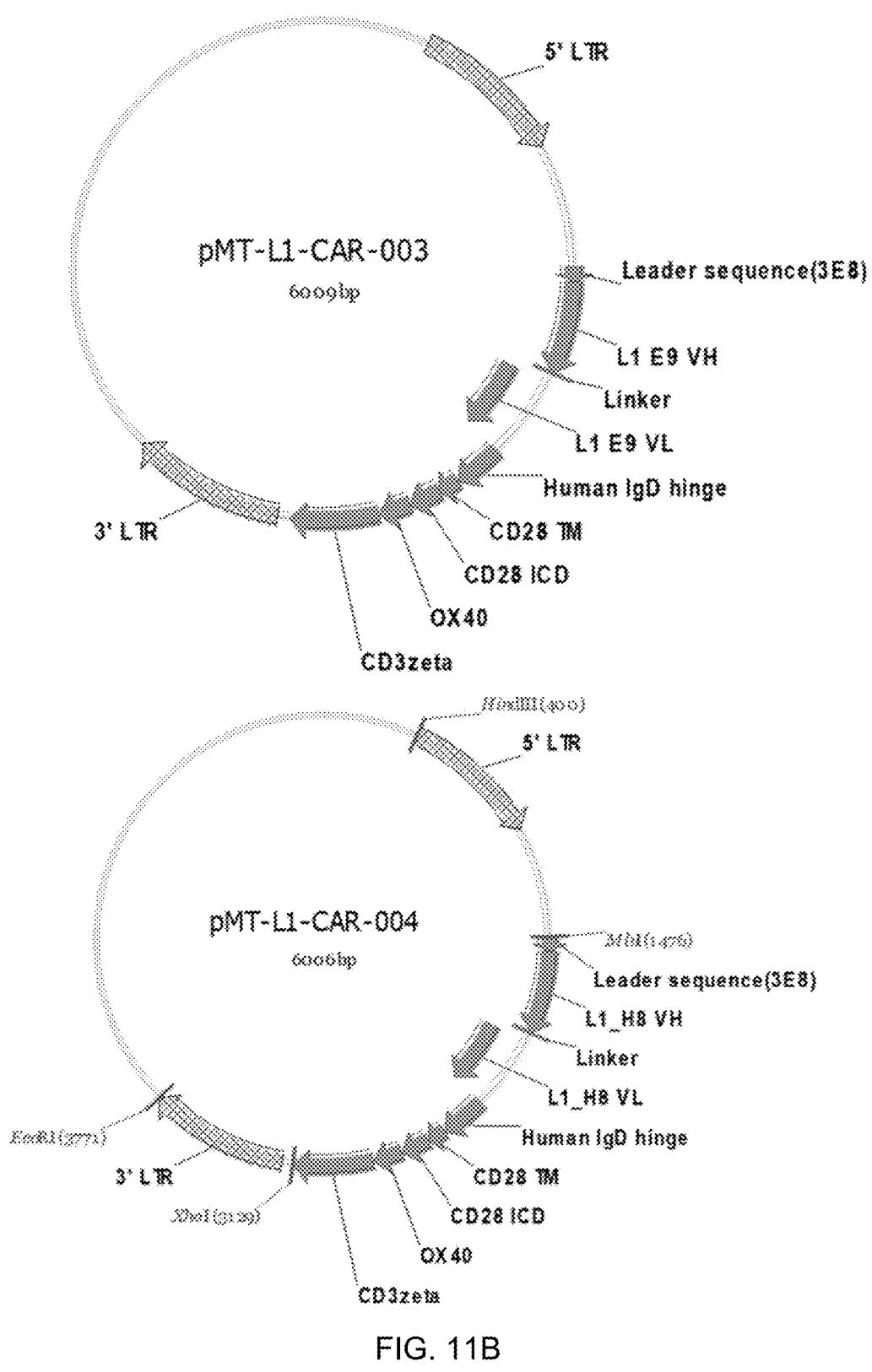

Four types of pGemT-L1-CAR vectors were treated with Mlu I and Xho I restriction enzymes to obtain DNA fragments. The obtained DNA fragments were ligated to the pMT retroviral vectors (U.S. Pat. No. 7,049,143) previously treated with Mlu I and Xho I restriction enzymes to construct four types of pMT-L1-CAR retroviral vectors (FIG. 11). The pMT-L1-CAR retroviral vectors thus constructed include sequences encoding anti-L1-CAR under the control of the MLV LTR promoter.

2.2. Preparation of Anti-L1-CAR Gene-Expressing T Cells

2.2.1. Preparation of Anti-L1-CAR Gene-Expressing Retroviruses (anti-L1-CAR Retroviruses)

The retroviruses for anti-L1-CAR gene delivery were prepared using plasmid DNA transformation (Soneoka Y et al., 1995). The TransiT 293 transformation system (Mirus Bio LLC, Wis., USA) was used and operated according to the manufacturer's protocol. The previous day, pMT-L1-CAR retroviral vectors (pMT-L1-CAR-001, pMT-L1-CAR-002, pMT-L1-CAR-003, and pMT-L1-CAR-004) constructed in 2.1 above, the gag-pol expression vector, and the RD114 env expression vector were transformed into 293T cell lines seeded at $1 \times 10^6$ on 60 mm dishes, and then the cells were cultured for about 48 hours. Upon completion of the culture, the cell cultures were all harvested, and then filtered through a 0.45-μm filter. The four types of anti-L1-CAR retroviruses thus produced were measured for titer by real-time PCR using a retrovirus titer set (TaKaRa, JAPAN), and then stored frozen at −80° C. before use.

2.2.2 Preparation of Anti-L1-CAR Gene-Expressing T Cells

Mononuclear cells were obtained from the blood of a donee by using SepMate™-50 (STEMCELL) and Ficoll-Paque PLUS (GE healthcare, Sweden). The mononuclear cells were dispensed at $1 \times 10^7$ in 100-mm dishes while AIMV medium (Invitrogen) comprising 5% human serum was used as a culture medium, and then the anti-CD3 (OKT3, eBioscience) antibody was added at 50 ng per mL, thereby activating T cells. For the growth of T cells, human IL-2 (R&D) was added to the culture medium at 300 U per mL, and cultured. After 48-hour incubation, the activated T cells were harvested, and used for delivery of four types of anti-L1-CAR retroviruses.

Retronectin (TaKaRa, Japan) prepared at a concentration of 10 µg/mL was added to 6-well plates at 2 mL per well, and then coated on the plates by incubation at room temperature for 2 hours. After the incubation, the residual Retronectin was removed, and then phosphate-buffered saline (PBS) comprising 2.5% bovine serum albumin (BSA) was added at 2 mL per well, and blocked by incubation at room temperature for 30 minutes. After the incubation, the solution used for blocking was removed, and the cells were washed by addition of HBSS comprising 2.5% of 1 M HEPES at 3 mL per well. Anti-L1-CAR retroviruses were diluted to $3\times10^{10}$ copies per well with AIMV media comprising 5% human serum, and 4 mL of the dilution was added, followed by centrifugation under conditions of 2000× g and 32° C. for 2 hours, thereby immobilizing the retroviruses on Retronectin. The same amount of the medium used for retrovirus dilution was added to the wells to be used as a control. After the incubation, the residual retroviruses were removed, and activated T cells were added at $2\times10^6$ per well, followed by incubation at 1000× g for 15 minutes, thereby delivering anti-L1-CAR retroviruses to T cells. To increase the delivery efficiency, the delivery procedure was repeated once more the next day, and thus a total of 2 times of delivery was performed. After 24 hours of delivery, T cells were all harvested, and subcultured in T flasks at $5\times10^5$ cells per mL with AIMV media comprising 300 U/mL of 5% human serum and human IL-2. The cells were subcultured at $5\times10^5$ per mL every 3-4 days, and maintained so as not to exceed $2\times10^6$ per mL.

It was investigated whether anti-L1-CAR was expressed in the activated T cells (anti-L1-CAR-expressing T cells) delivering anti-L1-CAR retroviruses. On days 8 and 20 of the incubation, $1\times10^6$ cells were prepared, and incubated with biotinylated protein L (Genescript, Cat No. M00097) at 4° C. for 45 minutes. After the incubation, the cells were incubated with phycoerythrin-conjugated streptavidin (BD, Cat No. 554061) at 4° C. for 30 minutes, and the expression rate of anti-L1-CAR was checked by flow cytometry. The results verified that although there is a difference depending on the donor, the expression rate of anti-L1-CAR was about 19.9% to 67.2% on day 8 of the incubation and about 34.5% to 94.9% on day 20 of the incubation (Table 8).

TABLE 8

| | | | Expression rates of anti-L1-CAR on surface of anti-L1-CAR-expressing T cells | | | |
|---|---|---|---|---|---|---|
| Donor No | Days of incubation | Control | L1-CAR-001 | L1-CAR-002 | L1-CAR-003 | L1-CAR-004 |
| 30 | 8 Days | 1.1% | 51.6% | 43.1% | 24.7% | 26.3% |
| | 20 Days | 2.0% | 65.7% | 59.7% | 58.4% | 36.2% |
| 32 | 8 Days | 3.4% | 67.2% | 46.8% | 63.7% | 59.7% |
| | 20 Days | 4.6% | 84.6% | 73.1% | 94.9% | 61.9% |
| 34 | 8 Days | 1.3% | 36.6% | 40.1% | 20.9% | 19.9% |
| | 20 Days | 2.0% | 53.9% | 54.9% | 40.8% | 34.5% |

2.3. Verification of Anticancer Activity of Anti-L1-CAR Gene-Expressing T Cells

2.3.1. Verification of Expression Rates of L1CAM in Target Cells

Figure 12:
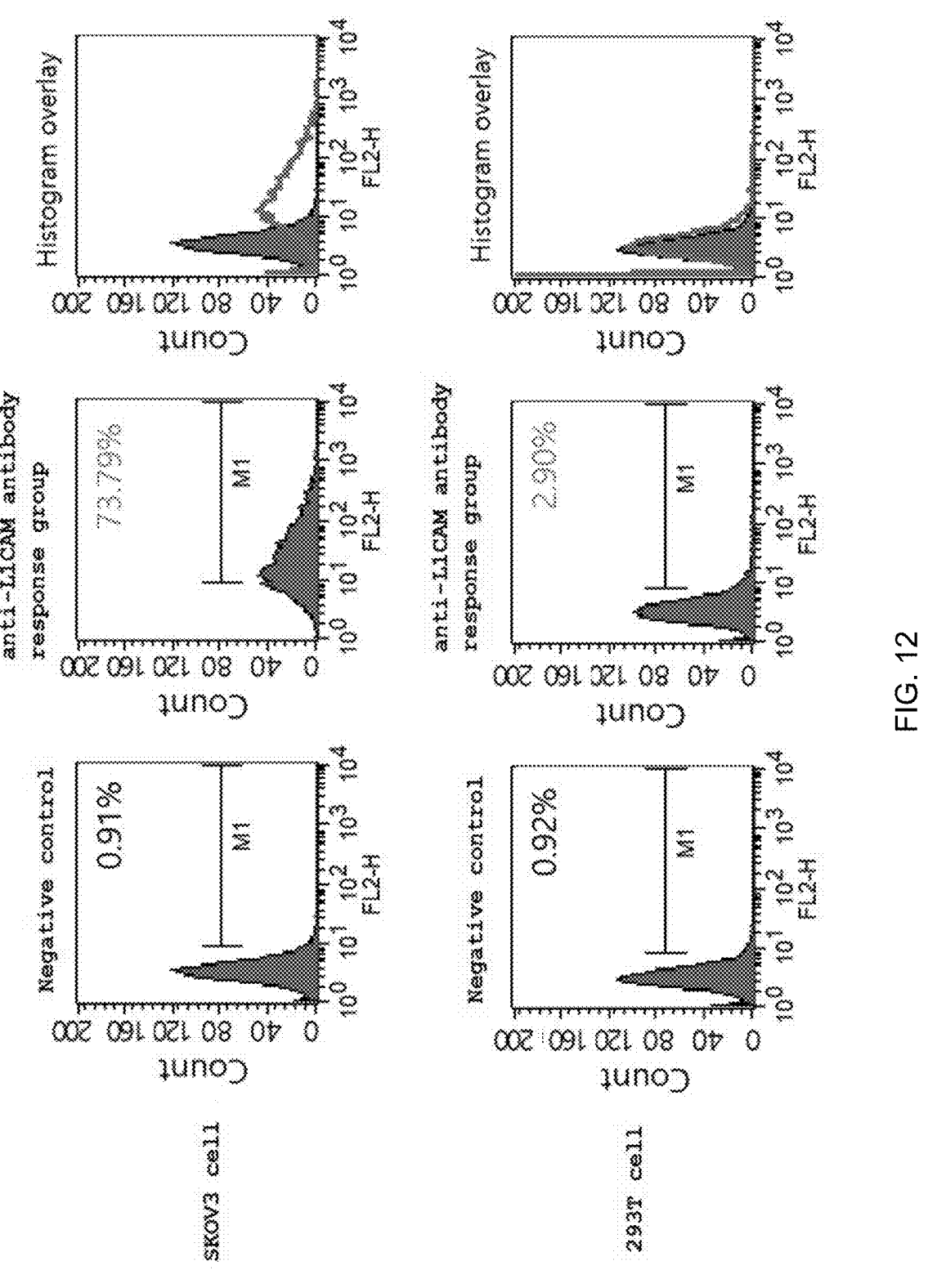
FIG. 12 shows expression rates of L1CAM in SKOV3 cells and 293T cells.

The human ovarian adenocarcinoma cell line SKOV3 is known to highly express L1CAM, which is an antigen in the present disclosure, and thus is a cell line suitable for investigating the anticancer activity of the anti-L1CAM-CAR-expressing T cells of the present disclosure. To check this, the SKOV3 cell line was prepared at $5\times10^5$ cells in 100 µL of PBS, and 0.25 µg of the anti-hCD171-PE (5G3 clone) (eBioscience, Cat No. 12-1719-42) antibody was added, followed by incubation at 4° C. for 30 minutes. After the incubation, the cells were washed twice with PBS, and the expression rate of L1CAM was checked by flow cytometry. The results verified that the L1CAM expression rate was about 74% in SKOV3 cancer cells. Meanwhile, as a result of investigating the expression of L1CAM in the human embryonic kidney cell line 293T by the same method, an expression rate of about 3% was confirmed (FIG. 12).

2.3.2. Verification of Anticancer Activity of L1CAM-Expressing T Cells on Target Cells To investigate the anticancer activity of the anti-L1CAM-CAR (anti-L1-CAR)-expressing T cells (effector cells, E) of the present disclosure on target cells (T), the xCELLigence Real-Time Cell Analysis (RTCA) method was used. According to the xCELLigence RTCA method, the electron flow is displayed numerically as an index value when an electro-conductive solution (e.g., culture media) is included on a plate coated with a gold microelectrode biosensor, and the electron flow is disturbed to result in changed index values when target cells adhere to the plate. Upon the addition of CAR-expressing T cells (CAR-T), the adhering target cells are separated from the plate due to cytotoxicity of the T cells, and the anticancer activity (cytotoxicity) can be checked by analyzing the change in index value. Target cells were prepared at $1\times10^4$ cells in 50 µL of a culture medium, and added to a plate for analysis. After 21 hours, anti-L1-CAR-expressing T cells were prepared at $1\times10^4$, $5\times10^4$, and $1\times10^5$ (E:T ratio=1, 5, and 10) in 50 uL of AIMV media comprising human serum and human IL-2, and added to wells comprising target cells, to check the cell index value in real time for 50 hours. In addition, wells comprising only target cells were prepared, and the anticancer activity of anti-L1-CAR-expressing T cells was calculated as follows.

Figure 13A:
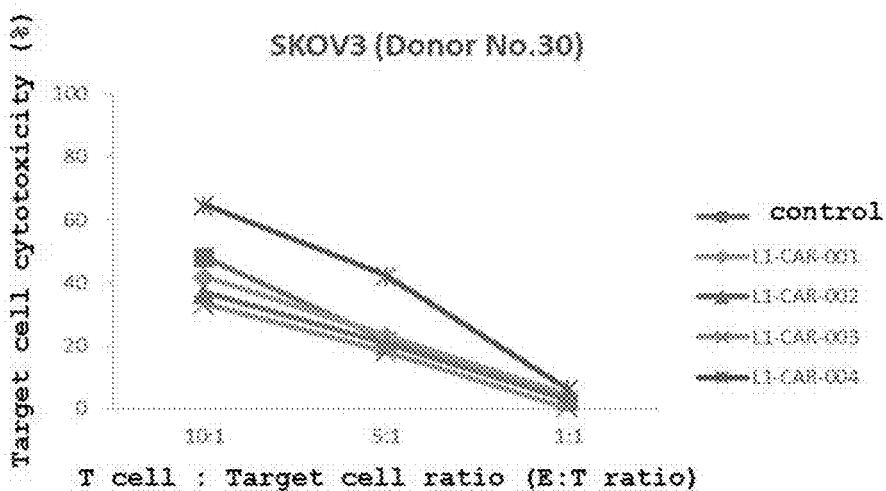
FIGS. 13A and 13B show anticancer activity of the anti-L1CAM-CAR-expressing T cells of the present disclosure on SKOV3 cells (high expression of L1CAM, FIG. 13A) and 293T cells (low expression of L1CAM, FIG. 13B).
Figure 13A:
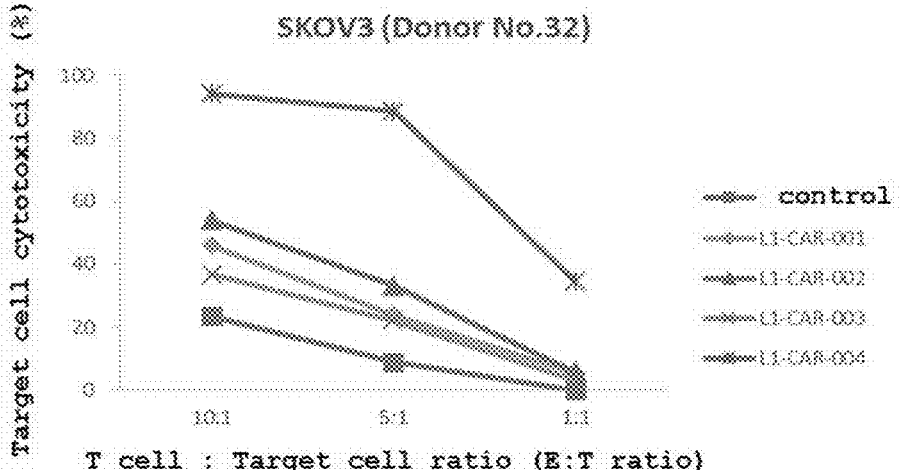
Figure 13A:
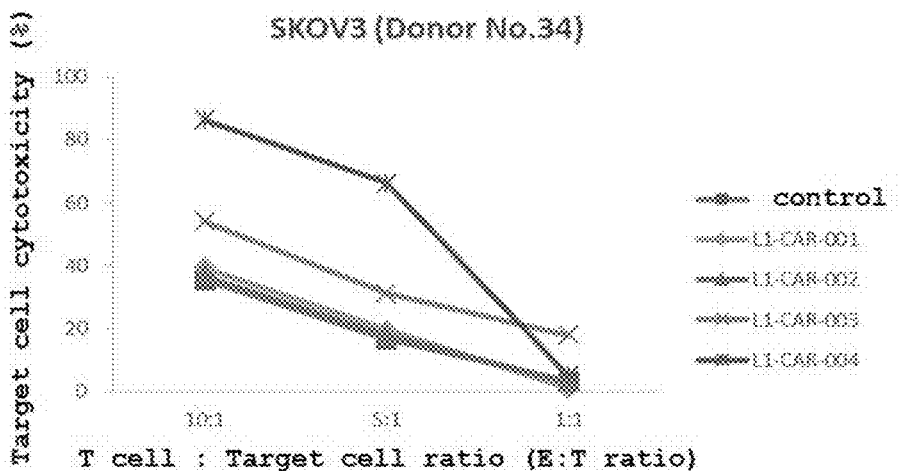
Figure 13B:
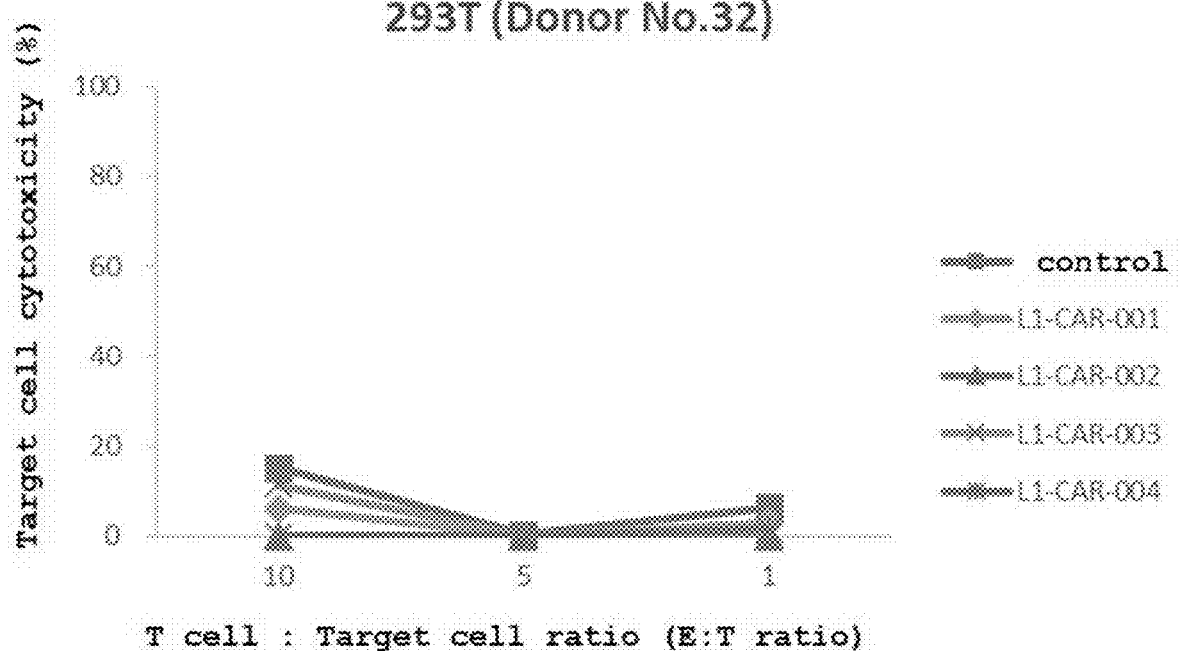

Cytotoxicity (%)={(index value of target cell well)–(index value of target cell and T cell incubation well)}/(index value of target cell well)×100    Equation The results verified that among the four types of anti-L1-CAR-expressing T cells of the present disclosure, L1-CAR-004 showed higher cytotoxicity in SKOV3 cells than CAR-non-expressing T cells (control). Although there is a difference depending on the donor, L1-CAR-001 showed cytotoxicity in SKOV3 cells compared with the control (FIG. 13A). All the four types showed lower cytotoxicity than the control in 293T cells showing a low expression rate of L1CMA (FIG. 13B). Therefore, the anti-L1-CAR-expressing T cells of the present disclosure exhibited anticancer activity in target cancer cells highly expressing L1CAM antigens, and thus can be advantageously used as a cell therapeutic agent for anti-cancer use.

Example 3: Verification of Anti-L1 CAM-CAR Gene-Expressing T Cells in Vivo

Figure 14:
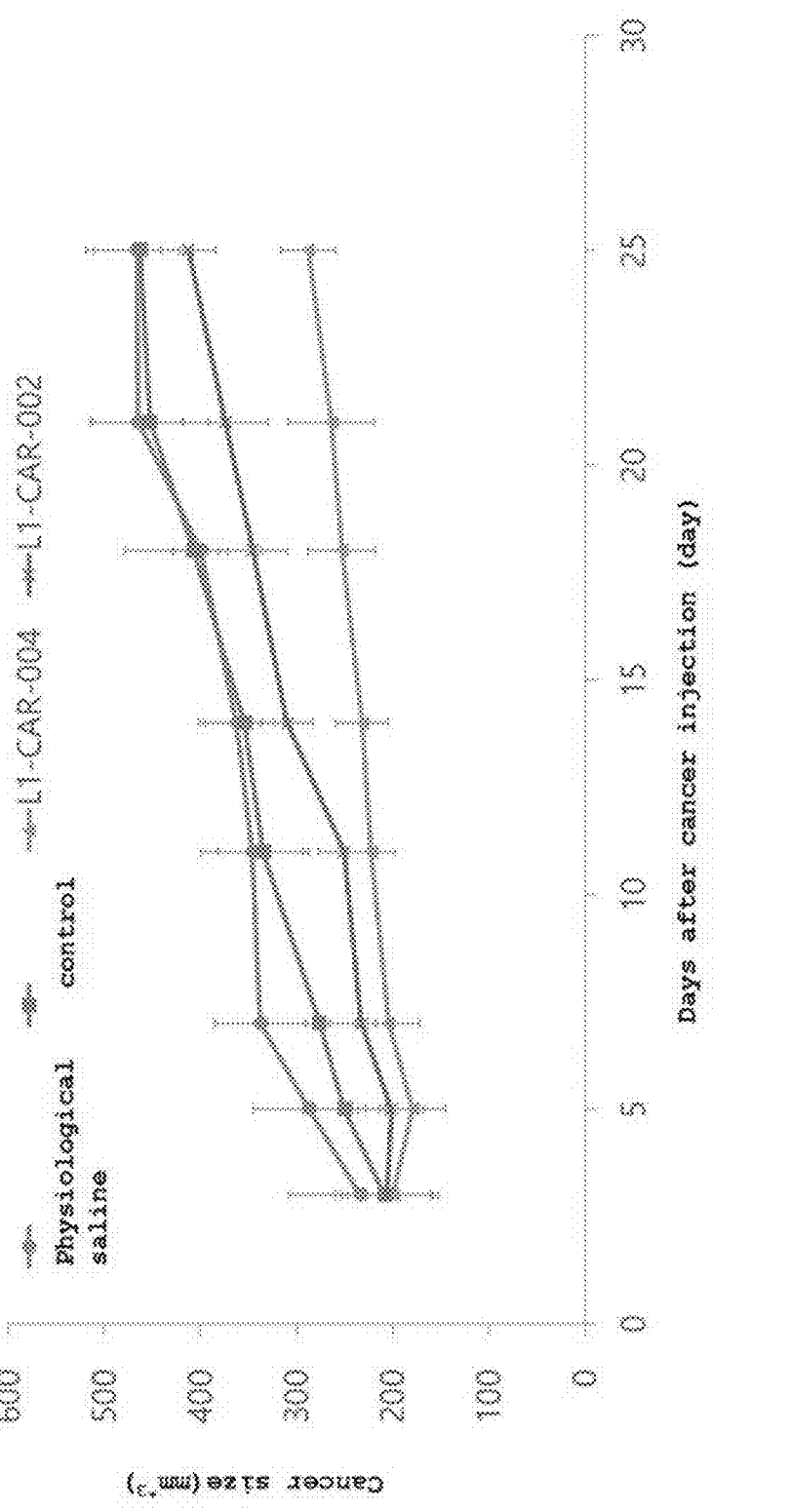
FIG. 14 shows in-vivo anticancer activity of the anti-L1CAM CAR (anti-L1-CAR)-expressing T cells of the present disclosure.

To investigate anticancer activity of anti-L1CAM-CAR gene-expressing T cells in vivo, cancer-induced animal models were used. SKOV3 cancer cells (Target, T) mixed with Matrigel at 1:1 were subcutaneously (SC) administered at $3\times10^6$ to the right flank of NOD/SCID mice (7 weeks old, female) lacking T cells, B cells, and natural killer cells (NK cells), to thereby induce cancer. L1-CAR-002 and L1-CAR- 004, which are two types of anti-L1CAM-CAR-expressing T cells confirmed to have efficacy in vitro, and control T cells were administered to each NOD/SCID mouse 3 days after cancer cell administration, once a day, a total of 3 times. T cells were administered through the tail vein (intravenous, IV) at $2\times10^7$ per dose, and the cancer size was measured up to day 25. The results verified that both two types of anti-L1CAM-CAR-expressing T cells inhibited the cancer growth rate compared with the control T cell administration group (FIG. 14). Through the fact that L1-CAR-004 greatly inhibited the cancer growth rate compared with L1-CAR-002, it was verified that the efficacy of L1-CAR-004 was better in vivo.

Example 4: Fabrication of T Cells Expressing Anti-L1CAM-CAR Genes with Various Spacer Domain Structures and Verification of Activity Thereof 4.1. Obtainment of L1-H8-CAR Genes with Various Spacer Domain Structures 4.1.1. Selection of Anti-mL1CAM scFv Antibody It was verified through the anticancer activity test conducted in Example 3 that the cancer growth rate-inhibitory effect of L1-CAR-004 was best. The nucleotide sequences of polynucleotides encoding the heavy chain and light chain variable regions of the L1CAM-specific antibody of L1-CAR-004 (FIG. 10B) were obtained, and used to prepare the next gene. Hereinafter, pMT-L1-CAR-004 was expressed as pMT-L1-H8-CAR-001.

4.1.2. Obtainment of L1-H8-CAR-002 Gene 4.1.2.1. Obtainment of 3E8 Antibody Leader Sequence (LS) and Anti-mL1CAM scFv Antibody Gene pMT-L1-H8-CAR-001 as a template was amplified by PCR using the primers of SEQ ID NO: 70 (Table 9) and SEQ ID NO: 69 (Table 9). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of L1-H8 scFv has the 12-nucleotide sequence of hIgD, and thus the amplified PCR product has the nucleotide sequence of Mlu I-3E8 LS-L1-H8 scFv-hIgD hinge (Table 10). The amplified PCR product was used in the next PCR amplification process.

TABLE 9

Nucleotide sequence information of used primers

| SEQ ID NO | Primer name | Nucleotide sequence |
|---|---|---|
| 70 | Mlu 1 + 3E8 VH(F) | ACGCGTATGGAATGGAGCTGGGTC |
| 69 | L1 ScFv + hIgD hinge(R) | ACCTGGCCAGCGTTTAATTTCCACTTT |
| 72 | L1 ScFv + hIgD hinge(F) | GTGGAAATTAAACGCTGGCCAGGTTCT |
| 73 | Xho I + CD3zeta(R) | CCGCTCGAGTTAGCGAGGGGGCAGGGC |
| 83 | L1-H8 scFv + IgG1 hinge(R) | AGATTTGGGCTCTTTAATTTCCACTTT |
| 84 | L1-H8 scFv + IgG1 hinge(F) | GTGGAAATTAAAGAGCCCAAATCTTGT |

TABLE 10

LS, L1-H8 scFv, Hinge, CH3, TM, ICD, costimulatory domain, and CD3ζ gene sequences

| ID | Nucleotide sequence |
|---|---|
| Mlu I-start codon-3E8 LS | ACGCGTATGGAATGGAGCTGGGTCTTTCTCTTCTTCCTGTCAGTAACTACAG GTGTCCACTCC |
| L1-H8 scFv (L1CAM-3R-H8) | GAAGTACAGTTGGTCGAAAGTGGCGGTGGCCTCGTGCAACCGGGTGGTTC ACTGCGTCTGAGCTGCGCCGCCTCGGGTTTTACTTTCTCTGATTATGCAATG AATTGGGTTCGTCAGGCGCCGGGCAAGGGTCTCGAATGGGTTTCAGCAATC TCTTCTACTGGTTCTACTATCTACTATGCCGATTCAGTGAAGGGTCGCTTTAC CATTTCCCGTGACAACTCTAAGAATACTCTGTATCTGCAGATGAACTCGCTGC GTGCCGAAGACACGGCCGTCTATTATTGCGCCAAACAGTCTACTTACTTTTA CTCTTACTTTGATGTTTGGGGTCAGGGCACTTTAGTGACCGTCTCATCGGGT GGAGGCGGTTCAGGCGGAGGTGGATCCGGCGGTGGCGGATCGGACATTCA AATGACGCAGAGTCCCTCCTCACTGAGTGCTAGCGTGGGCGATCGTGTGAC AATTACTTGTCGCGCTAGCCAGTCTATCTCTCGTGATCTGAACTGGTATCAGC AGAAACCGGGCAAGGCGCCAAAATTGCTGATTTACGCAGCATCCTCTCTGC AGTCTGGTGTACCGTCCCGTTTCTCTGGCAGCGGTTCTGGTACGGATTTTAC CCTGACCATCTCAAGCCTCCAGCCTGAAGATTTTGCCACCTATTATTGTCAG CAATCTTACTCTACTCCGTACACGTTCGGGCAGGGAACTAAAGTGGAAATTA AA |

TABLE 10-continued

LS, L1-H8 scFv, Hinge, CH3, TM, ICD, costimulatory domain,
and CD3ζ gene sequences

| ID | Nucleotide sequence |
|---|---|
| IgD hinge | CGCTGGCCAGGTTCTCCAAAGGCACAGGCCTCCTCCGTGCCCACTGCACA<br>ACCCCAAGCAGAGGGCAGCCTCGCCAAGGCAACCACAGCCCCAGCCACCA<br>CCCGTAACACAGGTAGAGGAGGAGAAGAGAAGAAGAAGGAGAAGGAGAAA<br>GAGGAACAAGAAGAGAGAGAGACAAAGACACCAGGTTGTCCG |
| IgG1 hinge | GAGCCCAAATCTTGTGACAAAACTCACACATGCCCACCGTGCCCA |
| IgG1 CH3 | GGGCAGCCCCGAGAACCACAGGTGTACACCCTGCCCCCATCCCGGGATGA<br>GCTGACCAAGAACCAGGTCAGCCTGACCTGCCTGGTCAAAGGCTTCTATCC<br>CAGCGACATCGCCGTGGAGTGGGAGAGCAATGGGCAGCCGGAGAACAACT<br>ACAAGACCACGCCTCCCGTGCTGGACTCCGACGGCTCCTTCTTCCTCTACA<br>GCAAGCTCACCGTGGACAAGAGCAGGTGGCAGCAGGGGAACGTCTTCTCA<br>TGCTCCGTGATGCATGAGGCTCTGCACAACCACTACACGCAGAAGAGCCTC<br>TCCCTGTCTCCGGGTAAA |
| CD28 TM | TTTTGGGTGCTGGTGGTGGTTGGTGGAGTCCTGGCTTGCTATAGCTTGCTA<br>GTAACAGTGGCCTTTATTATTTTCTGGGTG |
| CD28 ICD | AGGAGTAAGAGGAGCAGGCTCCTGCACAGTGACTACATGAACATGACTCCC<br>CGCCGCCCCGGGCCCACCCGCAAGCATTACCAGCCCTATGCCCCACCACG<br>CGACTTCGCAGCCTATCGCTCC |
| OX40 | GCCCTGTACCTGCTCCGGAGGGACCAGAGGCTGCCCCCCGATGCCCACAA<br>GCCCCCTGGGGGAGGCAGTTTCCGGACCCCCATCCAAGAGGAGCAGGCC<br>GACGCCCACTCCACCCTGGCCAAGATC |
| CD3ζ-iso1-<br>stop codon-<br>Xho I | AGAGTGAAGTTCAGCAGGAGCGCAGACGCCCCCGCGTACCAGCAGGGCCA<br>GAACCAGCTCTATAACGAGCTCAATCTAGGACGAAGAGAGGAGTACGATGTT<br>TTGGACAAGAGACGTGGCCGGGACCCTGAGATGGGGGGAAAGCCGCAGA<br>GAAGGAAGAACCCTCAGGAAGGCCTGTACAATGAACTGCAGAAAGATAAGA<br>TGGCGGAGGCCTACAGTGAGATTGGGATGAAAGGCGAGCGCCGGAGGGG<br>CAAGGGGCACGATGGCCTTTACCAGGGTCTCAGTACAGCCACCAAGGACAC<br>CTACGACGCCCTTCACATGCAGGCCCTGCCCCCTCGCTAACTCGAG |

Figure 15:
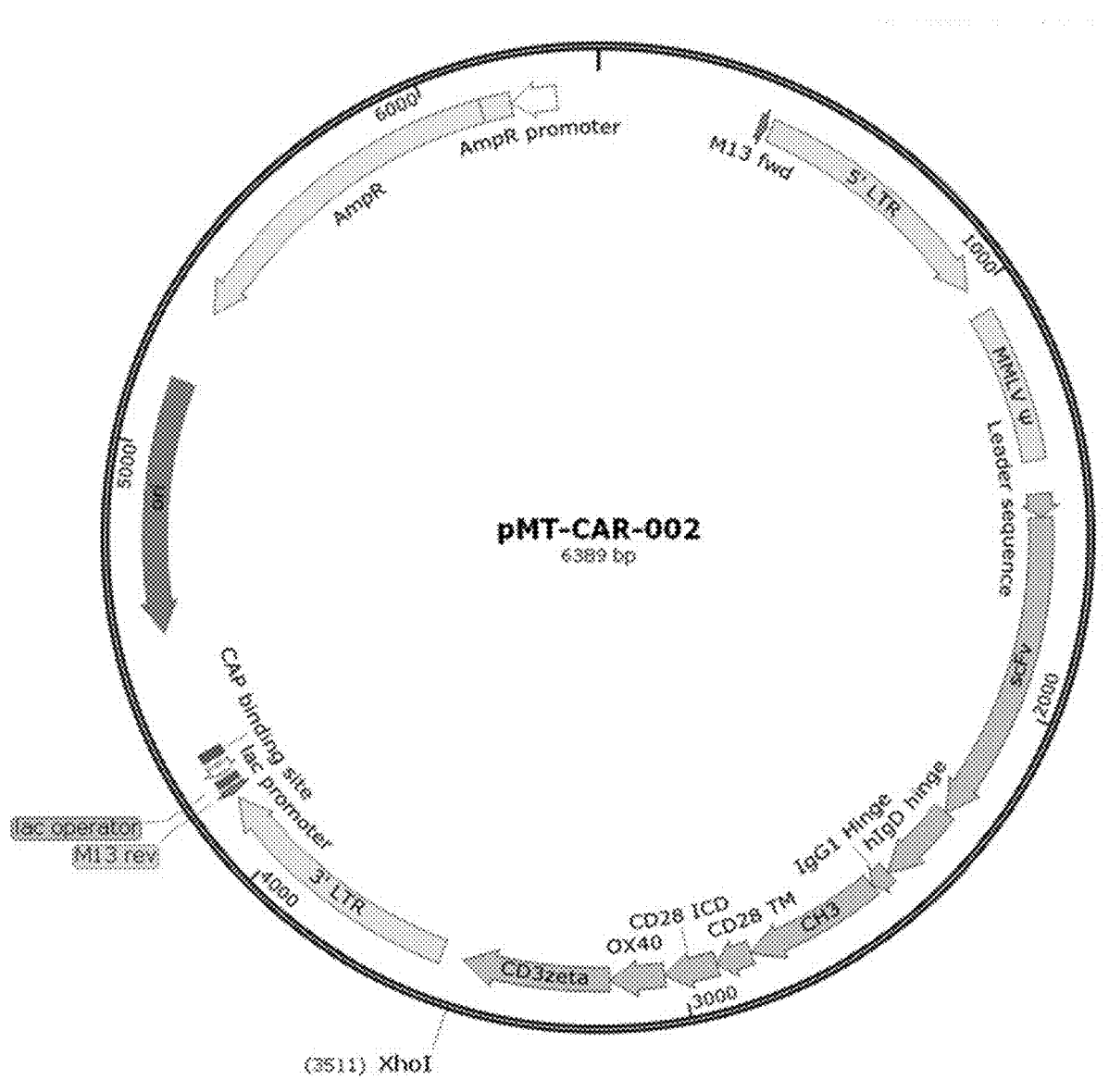
FIG. 15 shows a vector map of the pMT-CAR-002 plasmid used to manufacture a CAR-construct comprising the anti-L1CAM scFv selected in the present disclosure.

4.1.2.2. Obtainment of Hinge, CH3, TM, ICD, Costimulatory Domain, and CD3ζ Gene The pMT-CAR-002 plasmid (FIG. 15), comprising the human IgD hinge and IgG1 hinge, CH3, CD28 TM and ICD, costimulatory domain OX40, and CD3ζ-iso1, as a template was amplified by PCR using the primers of SEQ ID NO: 72 (Table 9) and SEQ ID NO: 73 (Table 9) before use. The primer binding to the 5' end of the hIgD hinge has the 12-nucleotide sequence of the light chain variable region (VL) of L1-H8 scFv antibody, and the primer binding to the 3' end of CD3ζ-iso1 has the nucleotide sequence of Xho I restriction enzyme, and thus the amplified PCR product has the nucleotide sequence of L1-H8 scFv-IgD hinge-IgG1 hinge-CH3-CD28 TM-CD28 ICD-OX40-CD3ζ-iso1-Xho I (Table 10). The amplified PCR product was used in the next PCR amplification process.

Figure 16:
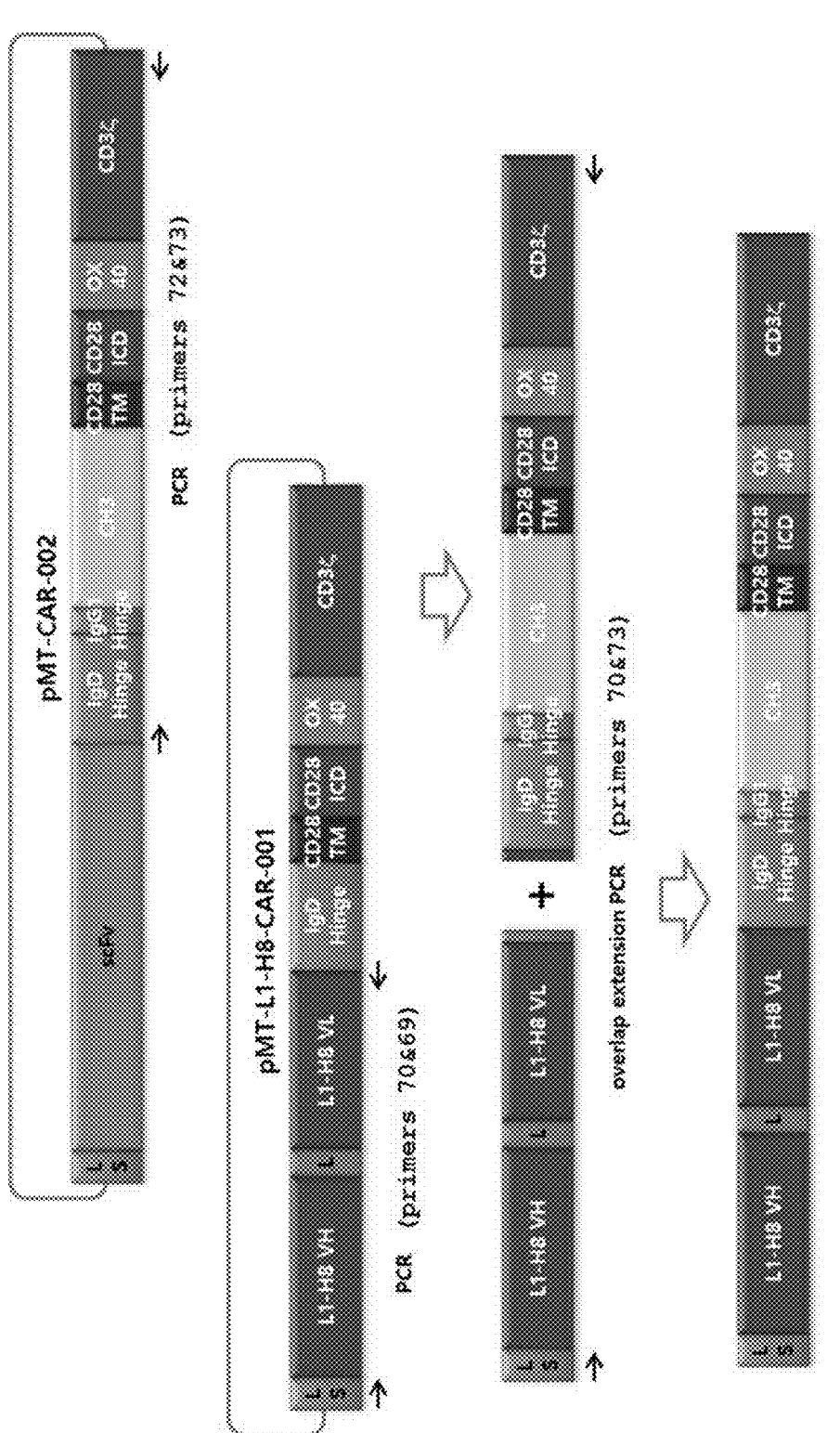
FIG. 16 is a schematic diagram showing a series of PCR amplification procedures in order to manufacture a CAR-construct comprising the anti-L1CAM scFv of the present disclosure.
Figure 17:
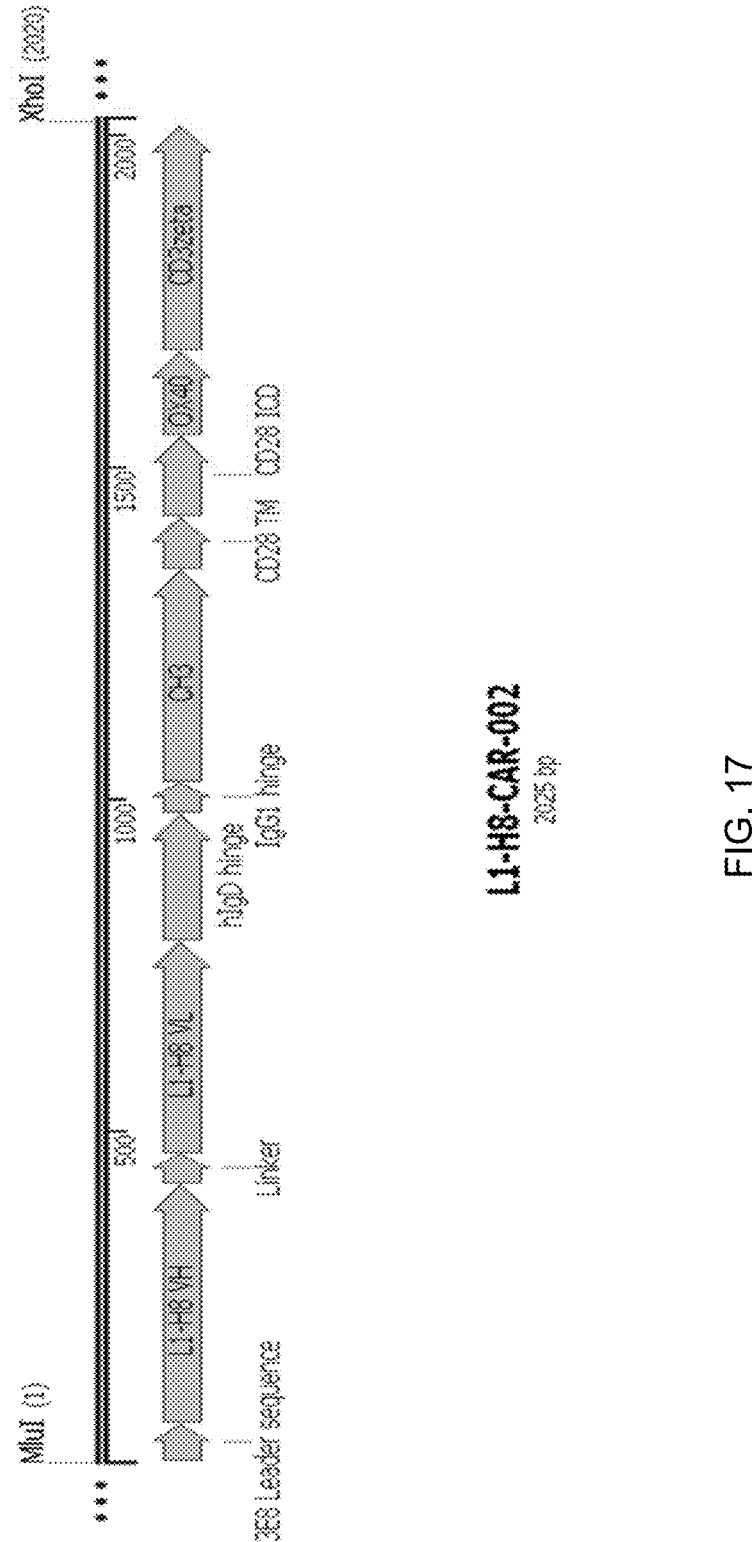
FIG. 17 shows a structure of the CAR-construct comprising anti-L1CAM scFv (L1-H8-CAR-002) constructed in the example of the present disclosure.

4.1.2.3. Obtainment of 3E8 LS, L1-H8 scFv, Hinge, CH3, TM, ICD, Costimulatory Domain, and CD3ζ Gene Mlu I-3E8 LS-L1-H8 scFv-IgD hinge and L1-H8-scFv-IgD hinge-IgG1 hinge-CH3-CD28 TM-CD28 ICD-OX40-CD3ζ-iso1-Xho I, which were the amplified PCR products, as templates, were amplified by the overlap extension PCR (OE-PCR) method using the primers of SEQ ID NO: 70 (Table 9) and SEQ ID NO: 73 (Table 9) (FIG. 16). The amplified PCR product has the nucleotide sequence of Mlu I-3E8-L1-H8 scFv-IgD hinge-IgG1 hinge-CH3-CD28 TM-CD28 ICD-OX40-CD3ζ-iso1-Xho I, and has a structure of L1-H8-CAR-002 (FIG. 17).

4.1.3. Obtainment of L1-H8-CAR-003 Gene

4.1.3.1. Obtainment of 3E8 Antibody Leader Sequence (LS) and Anti-mL1CAM scFv Antibody Gene pMT-L1-H8-CAR-001 as a template was amplified by PCR using the primers of SEQ ID NO: 70 (Table 9) and SEQ ID NO: 69 (Table 9). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of L1-H8 scFv has the 12-nucleotide sequence of hIgD hinge, and thus the amplified PCR product has the nucleotide sequence of Mlu I-3E8 LS-L1-H8 scFv-hIgD hinge (Table 10) The amplified PCR product was used in the next PCR amplification process.

Figure 18:
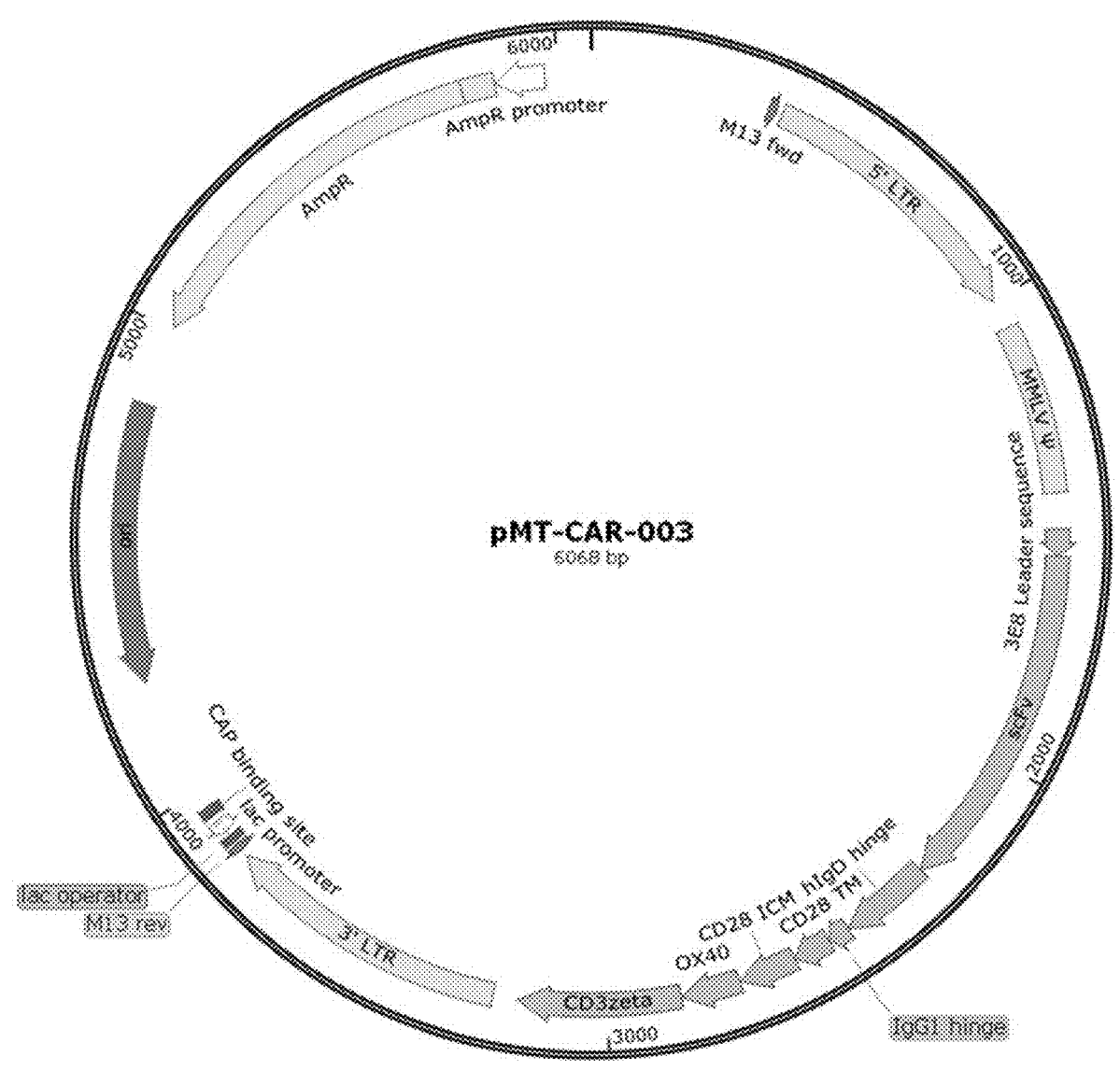
FIG. 18 shows a vector map of the pMT-CART-003 plasmid used to manufacture a CAR-construct comprising the anti-L1CAM scFv selected in the present disclosure.

4.1.3.2. Obtainment of Hinge, CH3, TM, ICD, Costimulatory Domain, and CD3ζ Gene The pMT-CAR-003 plasmid (FIG. 18), comprising human IgD hinge and IgG1 hinge, CD 28 TM and ICD, costimulatory domain OX40, and CD3ζ-iso1, as a template was amplified by PCR using the primers of SEQ ID NO: 72 (Table 9) and SEQ ID NO: 73 (Table 9) before use. The primer binding to the 5' end of the hIgD hinge has the 12-nucleotide sequence of the light chain variable region (VL) of L1-H8 scFv antibody, and the primer binding to the 3' end of CD3ζ-iso1 has the nucleotide sequence of Xho I restriction enzyme, and thus the amplified PCR product has the nucleotide sequence of L1-H8 scFv-IgD hinge-IgG1 hinge-CD28 TM-CD28 ICD-OX40-CD3ζ-iso1-Xho I (Table 10). The amplified PCR product was used in the next PCR amplification process.

Figure 19:
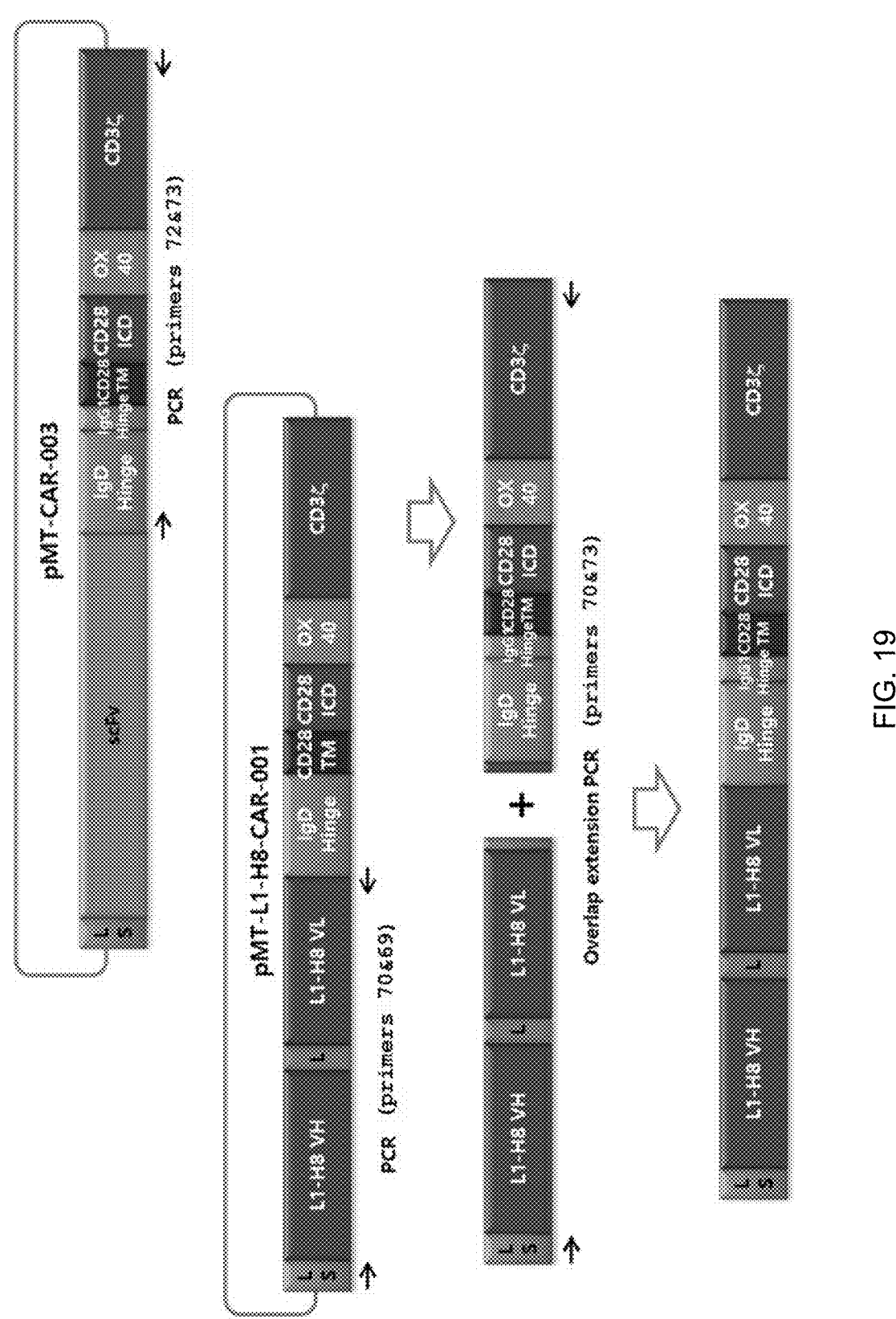
FIG. 19 is a schematic diagram showing a series of PCR amplification procedures in order to manufacture a CAR-construct comprising the anti-L1CAM scFv of the present disclosure.
Figure 20:
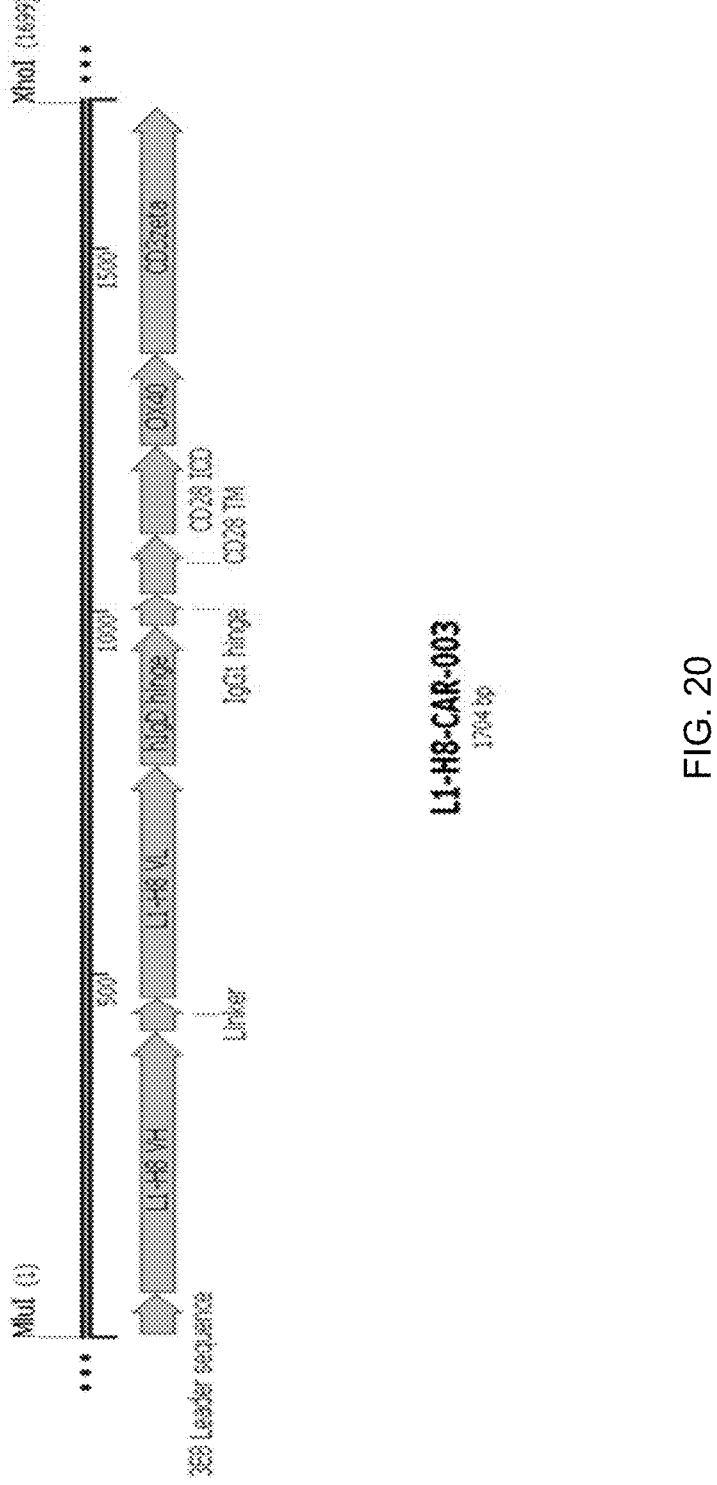
FIG. 20 shows a structure of the CAR-construct comprising anti-L1CAM scFv (L1-H8-CAR-003) constructed in the example of the present disclosure.

4.1.3.3. Obtainment of 3E8 LS, L1-H8 scFv, Hinge, TM, ICD, Costimulatory Domain, and CD3ζ Gene Mlu I-3E8 LS-L1-H8 scFv-IgD hinge and L1-H8-scFv-IgD hinge-IgG1 hinge-CD28 TM-CD28 ICD-OX40-CD3ζ-iso1-Xho I, which were the amplified PCR products, as templates, were amplified by OE-PCR using the primers of SEQ ID NO: 70 (Table 9) and SEQ ID NO: 73 (Table 9) (FIG. 19). The amplified PCR product has the nucleotide sequence of Mlu I-3E8-L1-H8 scFv-IgD hinge-IgG1 hinge-CD28 TM-CD28 ICD-OX40-CDζ3-iso1-Xho I, and has a structure of L1-H8-CAR-003 (FIG. 20).

4.1.4. Obtainment of L1-H8-CAR-004 Gene

4.1.4.1. Obtainment of 3E8 Antibody Leader Sequence (LS) and Anti-mL1CAM scFv Antibody Gene pMT-L1-H8-CAR-001 as a template was amplified by PCR using the primers of SEQ ID NO: 70 (Table 9) and SEQ ID NO: 83 (Table 9). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of L1-H8 scFv has the 12-nucleotide sequence of hIgG1 hinge, and thus the amplified PCR product has the nucleotide sequence of Mlu I-3E8 LS-L1-H8 scFv-hIgG1 hinge (Table 10). The amplified PCR product was used in the next PCR amplification process.

4.1.4.2. Obtainment of Hinge, CH3, TM, ICD, Costimulatory Domain, and CD3ζ Gene The pMT-CAR-002 plasmid (FIG. 15), comprising IgG1 hinge, CH3, CD28 TM and ICD, costimulatory domain OX40, and CD3ζ-iso1, as a template, was amplified by PCR using the primers of SEQ ID NO: 84 (Table 9) and SEQ ID NO: 73 (Table 9). The primer binding to the 5' end of the hIgG1 hinge has the 12-nucleotide sequence of the light chain variable region (VL) of L1-H8 scFv antibody, and the primer binding to the 3' end of CD3ζ-iso1 has the nucleotide sequence of Xho I restriction enzyme, and thus the amplified PCR product has the nucleotide sequence of L1-H8 scFv-IgG1 hinge-CD28 TM-CD28 ICD-OX40-CD3ζ-iso1-Xho I (Table 10). The amplified PCR product was used in the next PCR amplification process.

Figure 21:
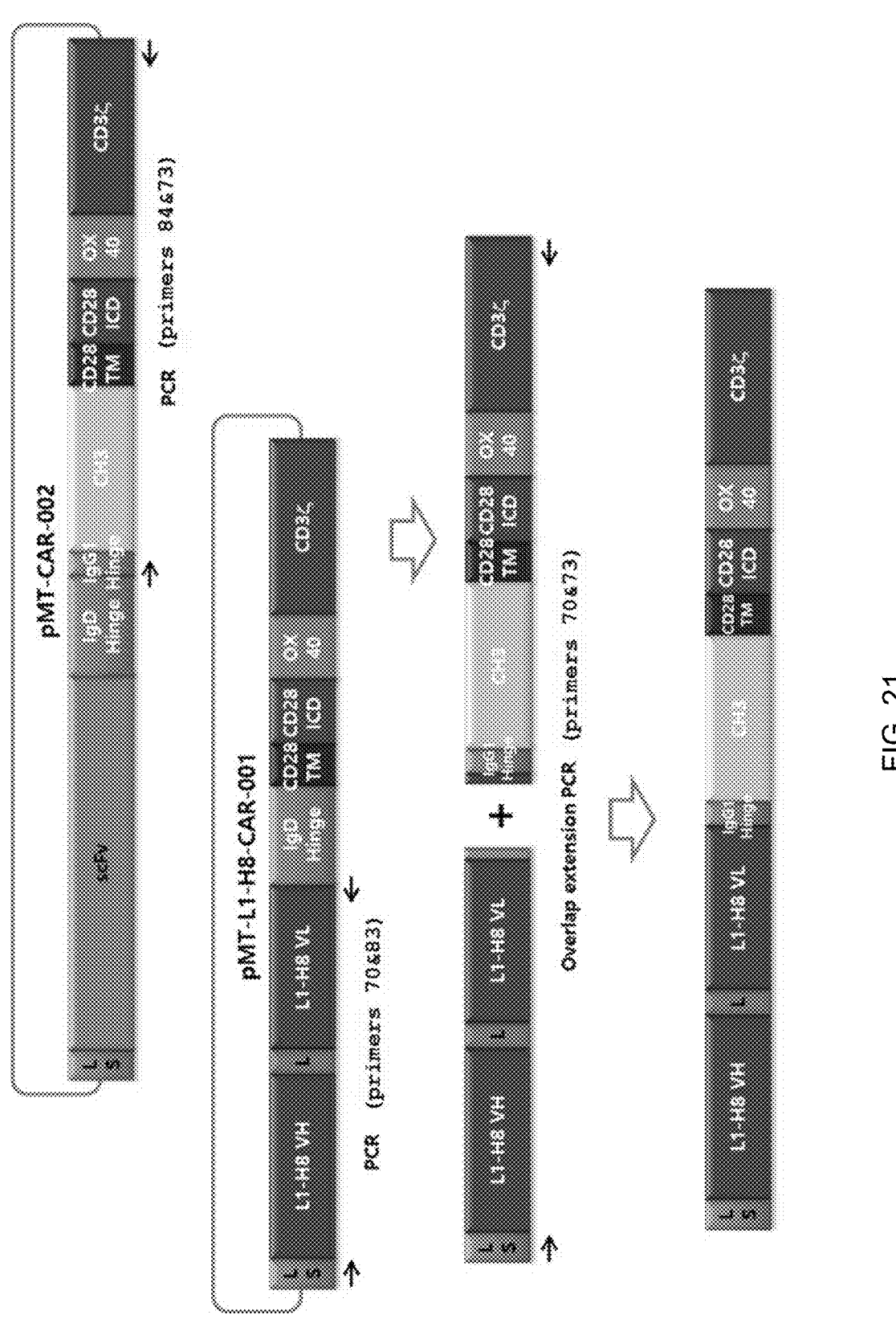
FIG. 21 is a schematic diagram showing a series of PCR amplification procedures in order to manufacture a CAR-construct comprising the anti-L1CAM scFv of the present disclosure.
Figure 22:
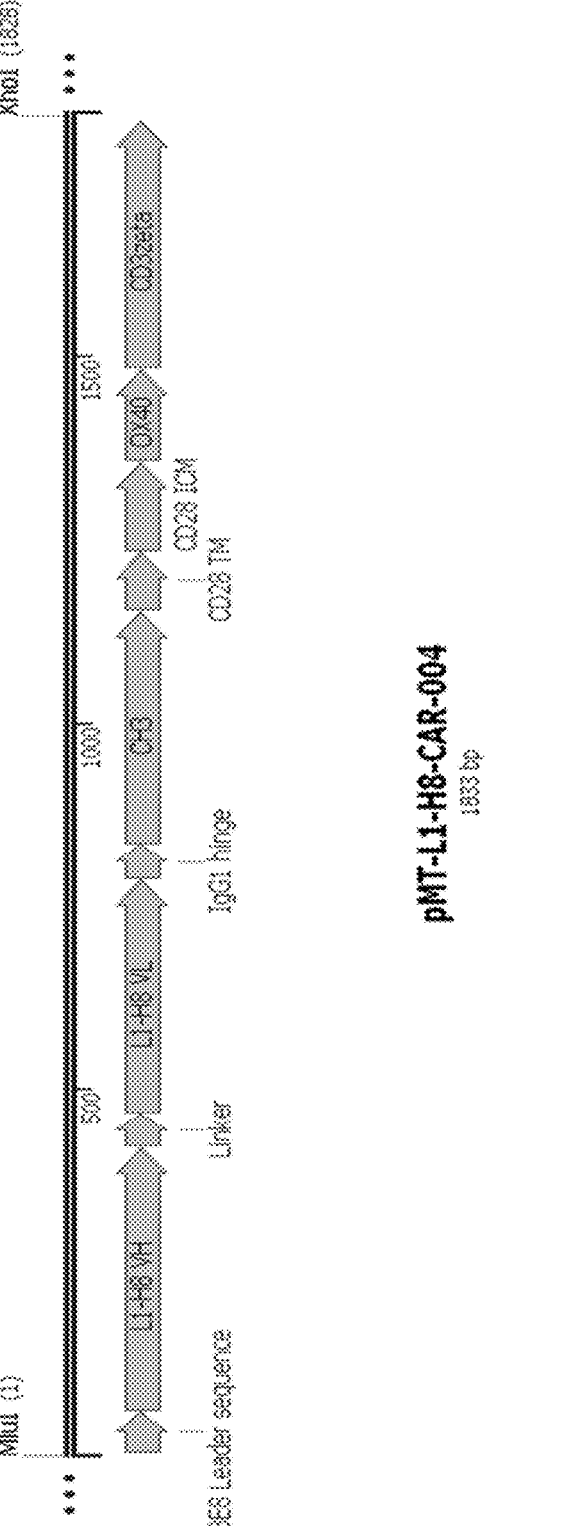
FIG. 22 shows a structure of the CAR-construct comprising anti-L1CAM scFv (L1-H8-CAR-004) constructed in the example of the present disclosure.
Figure 23A:
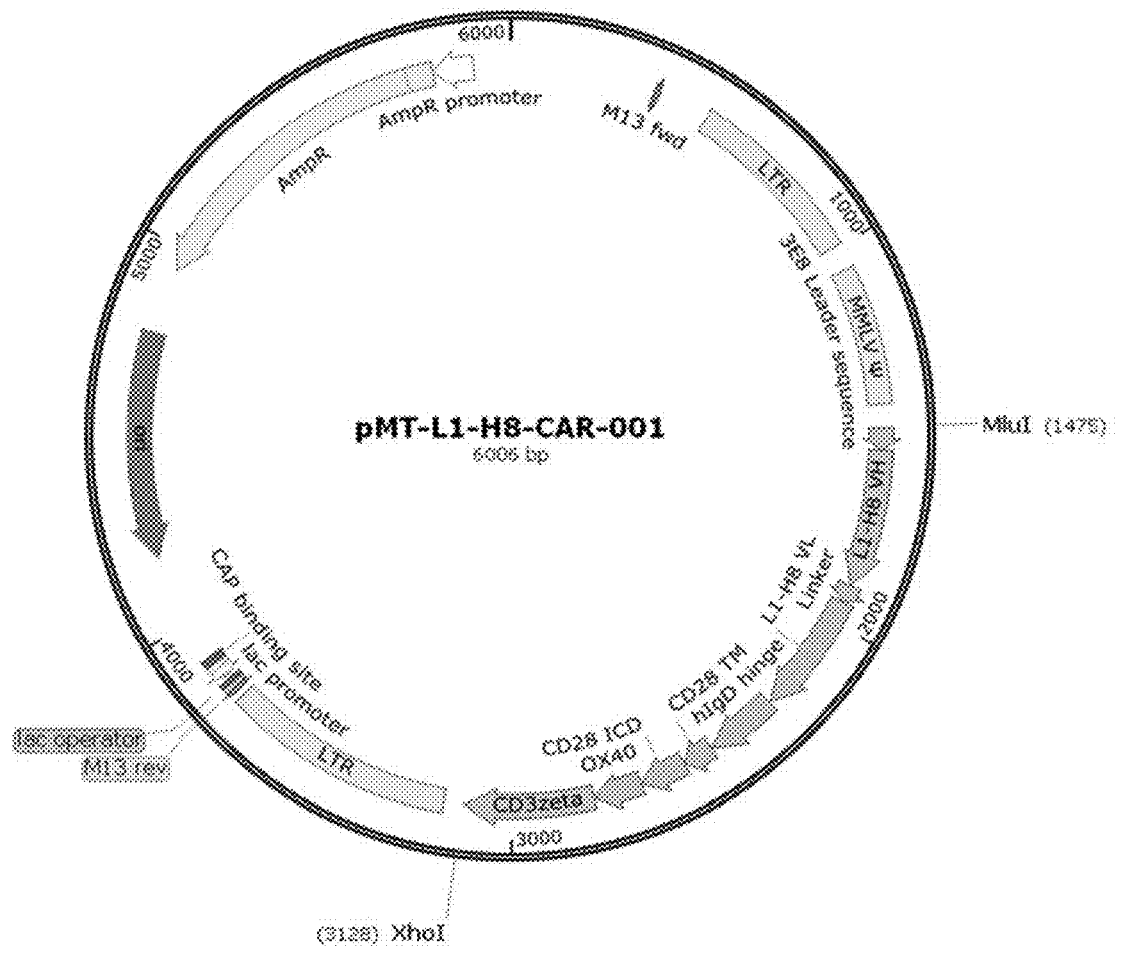
FIGS. 23A, 23B, 23C to 23D show retroviral vectors into which four types of CAR-constructs comprising the anti-L1CAM scFv (L1-H8-CAR-001, L1-H8-CAR-002, L1-H8-CAR-003, and L1-H8-CAR-004) of the present disclosure were introduced.
Figure 23B:
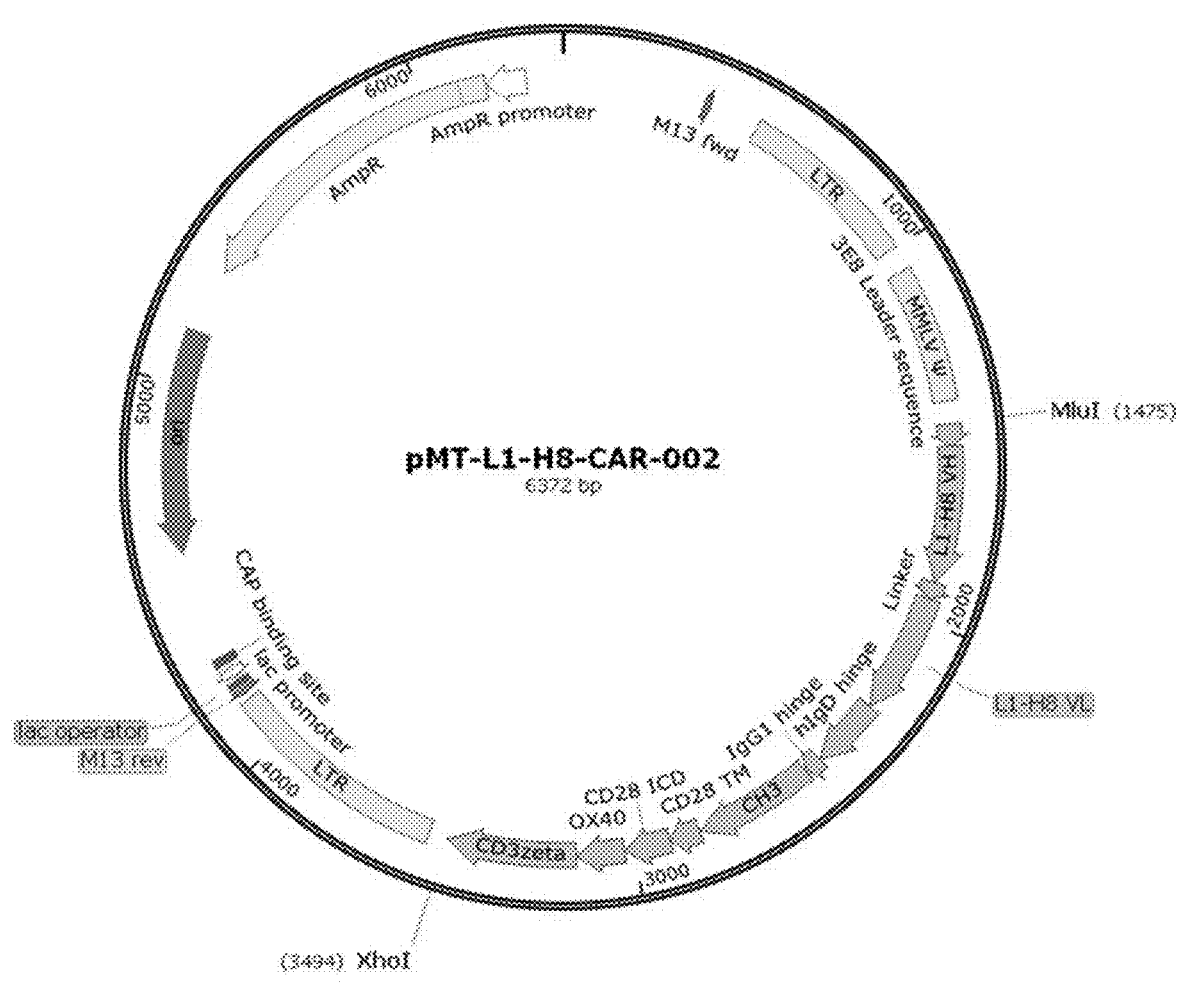
Figure 23C:
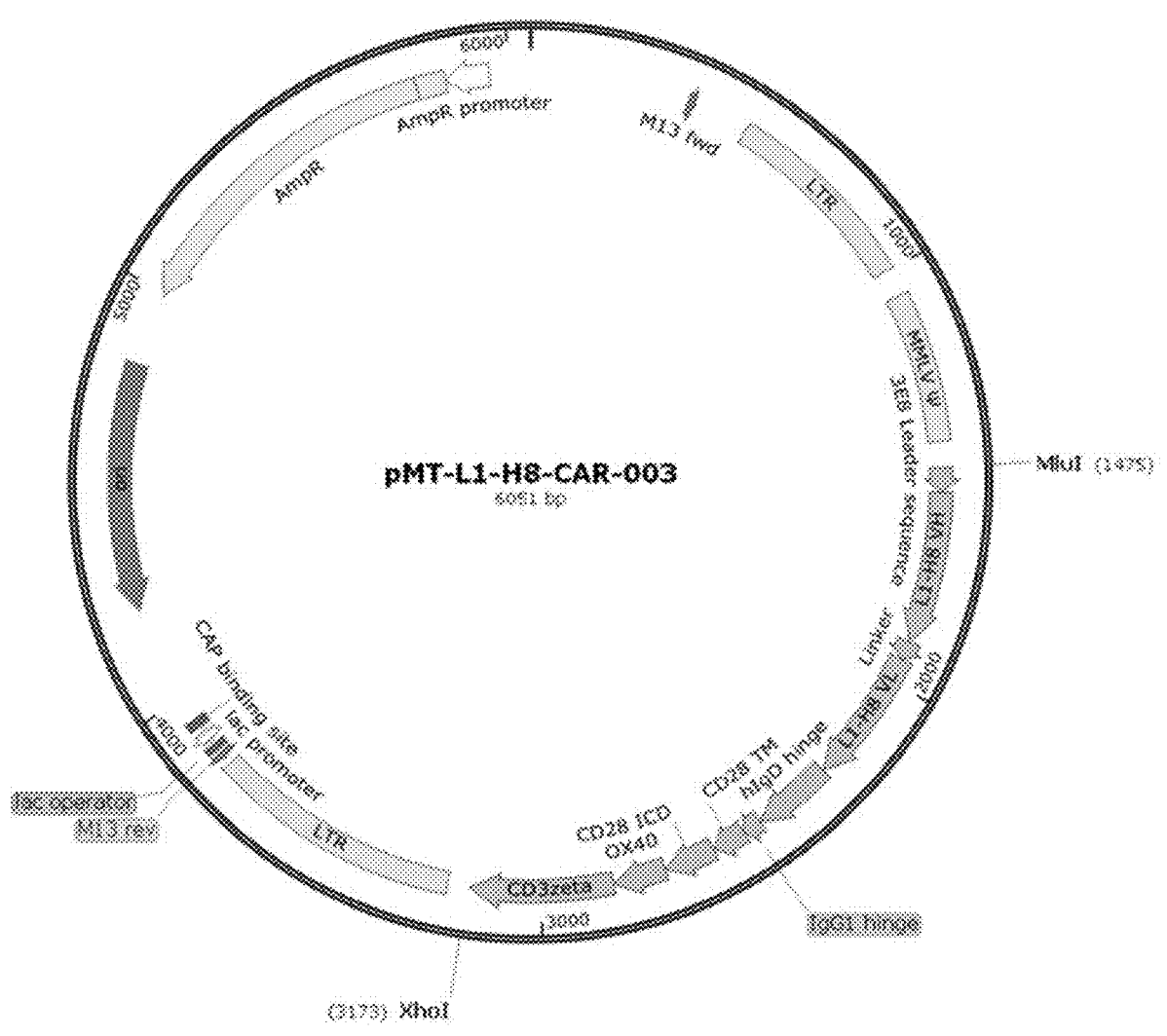
Figure 23D:
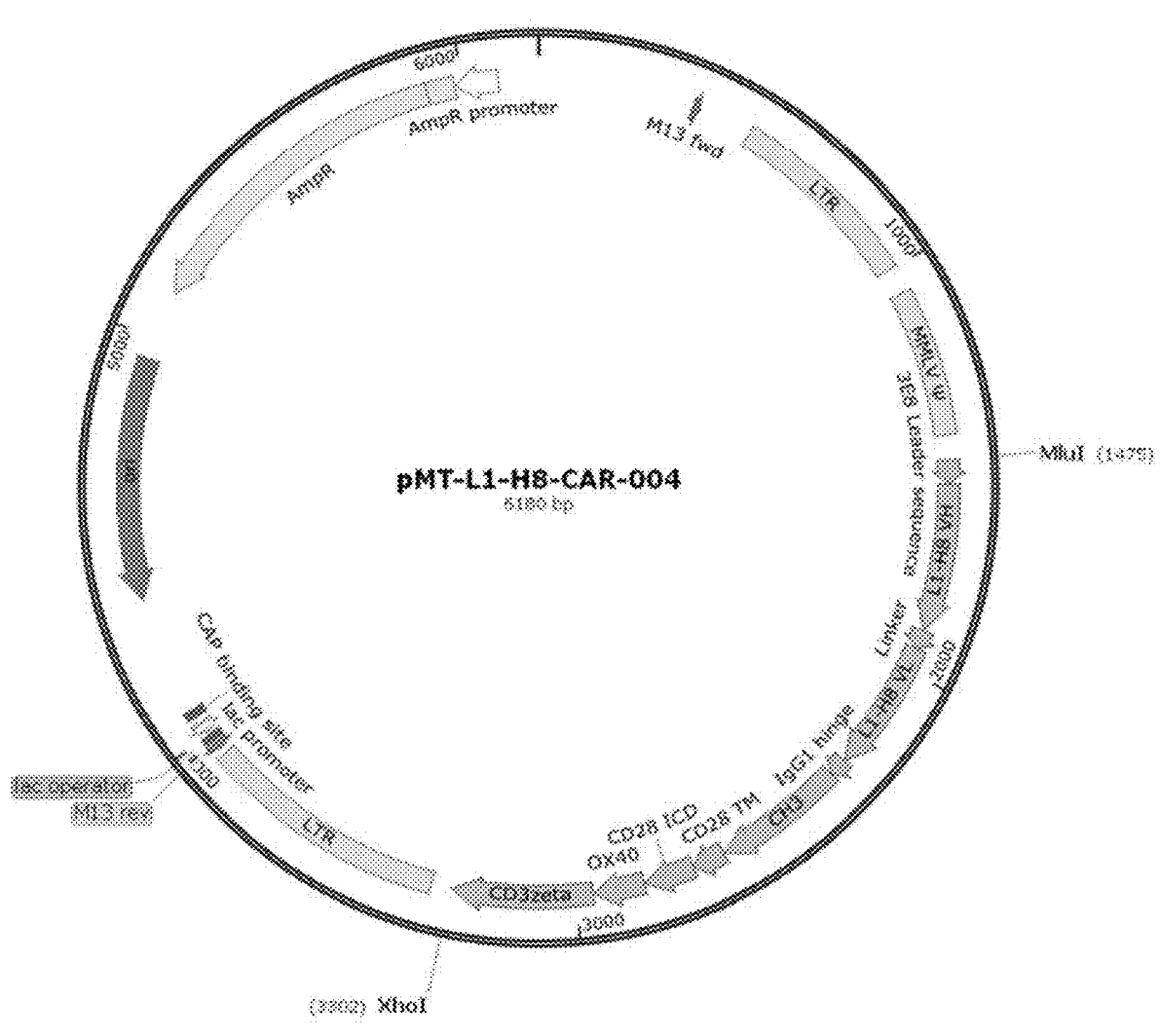

4.1.4.3. Obtainment of 3E8 LS, L1-H8 scFv, Hinge, CH3, TM, ICD, Costimulatory Domain, and CD3ζ Gene Mlu I-3E8 LS-L1-H8 scFv-IgG1 hinge and L1-H8 scFv-IgG1 hinge-CD28 TM-CD28 ICD-OX40-CD3ζ-iso1-Xho I, which were the amplified PCR products, as templates, were amplified by OE-PCR using the primers of SEQ ID NO: 70 (Table 9) and SEQ ID NO: 73 (Table 9) (FIG. 21). The amplified PCR product has the nucleotide sequence of Mlu I-3E8-L1-H8 scFv-IgG1 hinge-CD28 TM-CD28 ICD-OX40-CD3ζ-iso1-Xho I, and has a structure of L1-H8-CAR-004 (FIG. 22).

4.1.5. Preparation of pMT-L1-H8-CAR Retroviral Vectors

Three types of the amplified PCR products were treated with Mlu I and Xho I restriction enzymes to obtain DNA fragments. The obtained DNA fragments were ligated to the pMT retroviral vectors (U.S. Pat. No. 6,451,595) previously treated with Mlu I and Xho I restriction enzymes to prepare three types of pMT-L1-H8-CAR retroviral vectors (FIG. 23). The pMT-L1-H8-CAR retroviral vectors thus prepared include a sequence encoding anti-L1-CAR under the control of the MLV LTR promoter.

4.2. Preparation of Retroviruses Expressing L1-H8-CAR Genes with Various Spacer Domain Structures (L1-H8-CAR Retroviruses)

The retroviruses for L1-H8-CAR gene delivery were prepared using plasmid DNA transformation (Soneoka Y et al., 1995). The TransiT 293 transformation system (Mirus Bio LLC, Wis., USA) was used and operated according to the manufacturer's protocol. The previous day, four types of pMT-L1-H8-CAR retroviral vectors, the gag-pol expression vector, and the RD114 env expression vector were transformed into 293T cell lines seeded at $1 \times 10^6$ on 60 mm dishes, and then the cells were cultured for about 48 hours. Upon completion of the culture, the cell cultures were all harvested, and then filtered through a 0.45-μm filter. The four types of L1-H8-CAR retroviruses thus produced were measured for titer by real-time PCR using a retrovirus titer set (TaKaRa, JAPAN), and then stored frozen at −80° C. before use.

4.3. Preparation of T Cells Expressing L1-H8-CAR Genes with Various Spacer Domain Structures Mononuclear cells were obtained from the blood of a donee using SepMate™-50 (STEMCELL) and Ficoll-Paque PLUS (GE healthcare, Sweden). The mononuclear cells were dispensed at $1 \times 10^7$ in 100-mm dishes while AIMV medium (Invitrogen) comprising 5% human serum was used as a culture medium, and then the anti-CD3 (OKT3, eBioscience) antibody was added at 50 ng per mL, thereby activating T cells. For the growth of T cells, human IL-2 (R&D) was added to the culture medium at 300 U per mL, and cultured. After 48-hour incubation, the activated T cells were harvested, and used for delivery of four types of anti-L1-H8-CAR retroviruses.

Retronectin (TaKaRa, Japan) prepared at a concentration of 10 μg/mL was added to 6-well plates at 2 mL per well, and then coated on the plates by incubation at room temperature for 2 hours. After the incubation, the Retronectin was removed, and then phosphate-buffered saline (PBS) comprising 2.5% human albumin was added at 2 mL per well, and blocked by incubation at room temperature for 30 minutes. After the incubation, the solution used for blocking was removed, and washed by addition of HBSS comprising 2.5% of 1 M HEPES at 3 mL per well. L1-H8-CAR retroviruses were diluted to $3 \times 10^{10}$ copies per well with AIMV media comprising 5% human serum, and 4 mL of the dilution was added, followed by centrifugation under conditions of 2000× g and 32° C. for 2 hours, thereby immobilizing the retroviruses on Retronectin. The same amount of the medium used for retrovirus dilution was added to the wells to be used as a control. After culture, the retroviruses were removed, and activated T cells were added at $2 \times 10^6$ per well, followed by incubation at 1000× g for 15 minutes, thereby delivering L1-H8-CAR retroviruses to T cells. To increase the delivery efficiency, the delivery procedure was repeated once more the next day, and thus a total of 2 times of delivery was performed. After 24 hours of delivery, T cells were all harvested, and subcultured in T flasks at $5\times10^5$ cells per mL with AIMV media comprising 300 U/mL of 5% human serum and human IL-2. The cells were subcultured at $5\times10^5$ per mL every 3-4 days, and maintained so as not to exceed $2\times10^6$ per mL.

It was investigated whether L1-H8-CAR was expressed in the activated T cells (L1-H8-CAR-expressing T cells) delivering L1-H8-CAR retroviruses. At the first and second weeks of culture, $1\times10^6$ cells were prepared, and incubated with FITC-conjugated protein L (ACROBiosystems, Cat No. RPL-PF141) at 4° C. for 30 minutes, and the expression rate of L1-H8-CAR was checked by flow cytometry. The results verified that although there is a difference depending on the donor, the expression rate of L1-H8-CAR was about 16.4% to 52.4% on day 8 of incubation and about 29.6% to 69.2% on day 15 or day 18 of incubation (Table 11).

TABLE 11

Expression rates of L1-H8-CAR on surface of L1-H8-CAR-expressing T cells

| Donor NO. | Days of incubation | Control | L1-H8-CAR-001 | L1-H8-CAR-002 | L1-H8-CAR-003 | L1-H8-CAR-004 |
|---|---|---|---|---|---|---|
| 45 | 8 Days | 1.64% | 33.6% | 40.5% | 34.1% | 16.4% |
| | 18 Days | 0.37% | 52.4% | 64.7% | 54.5% | 30.0% |
| 36 | 8 Days | 1.26% | 33.6% | 44.8% | 42.2% | 21.6% |
| | 15 Days | 1.00% | 50.5% | 69.2% | 63.1% | 29.6% |
| 43 | 8 Days | 1.84% | 42.7% | 52.4% | 50.6% | 27.6% |
| | 15 Days | 0.64% | 52.6% | 60.0% | 63.8% | 33.2% |

4.4. Verification of Anticancer Activity of T Cells Expressing L1-H8-CAR Genes with Various Spacer Domain Structures (In Vitro)

4.4.1. Verification of Expression Rates of L1CAM in Target Cells

Figure 24A:
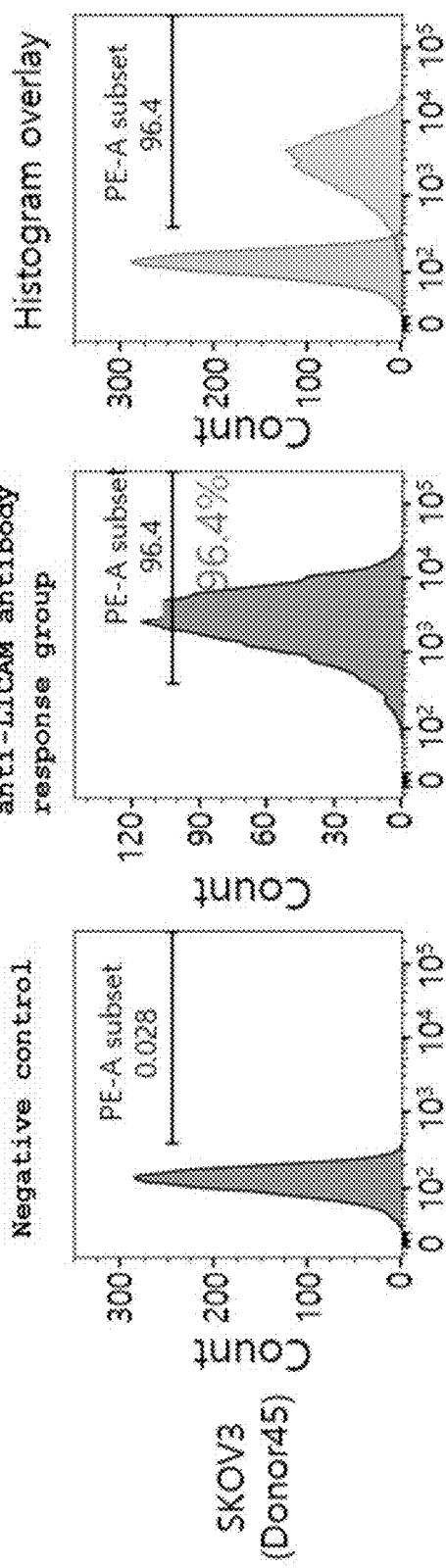
FIGS. 24A, 24B, 24C, 24D, 24E, 24F to 24G show the expression rates of L1CAM in SKOV3 cells, Hela cells, SH-SY5Y cells, and 293T cells.
Figure 24B:
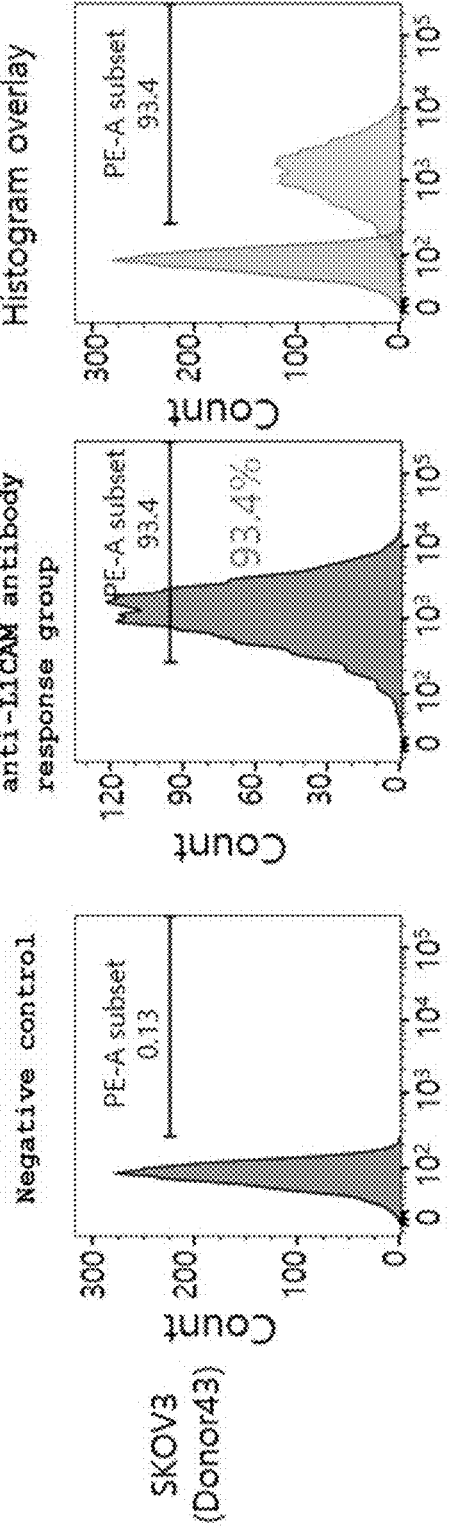
Figure 24C:
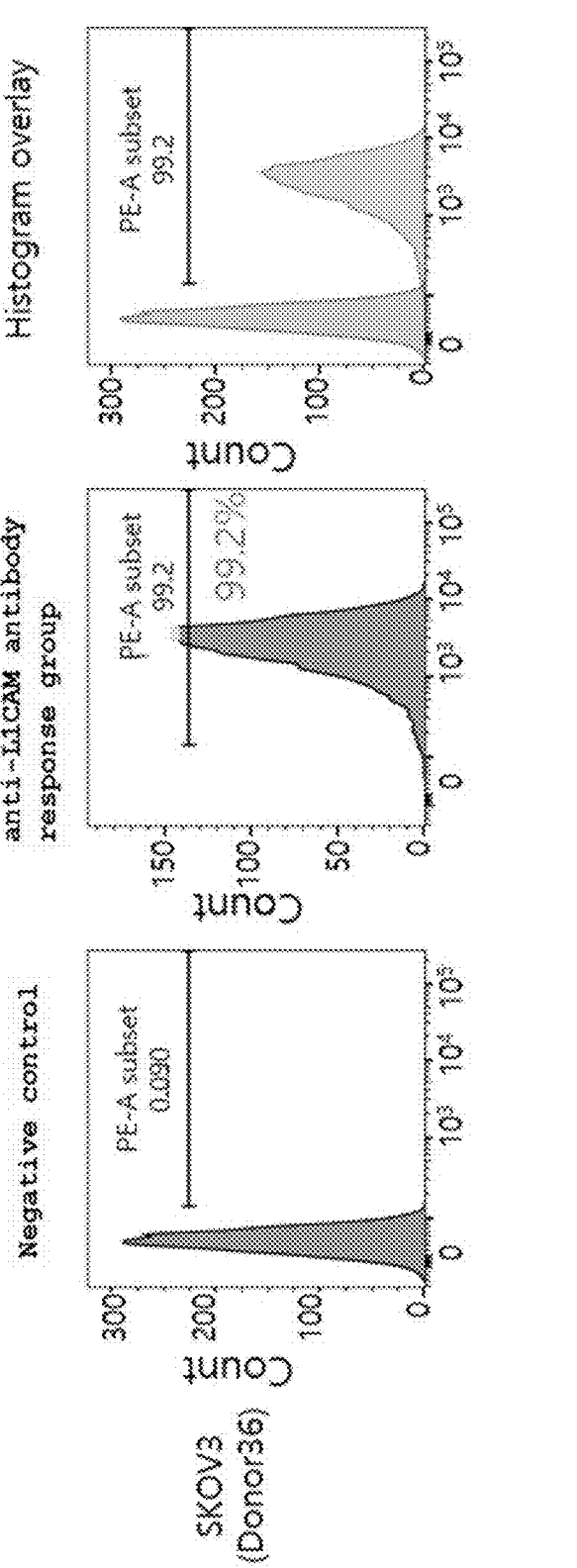
Figure 24D:
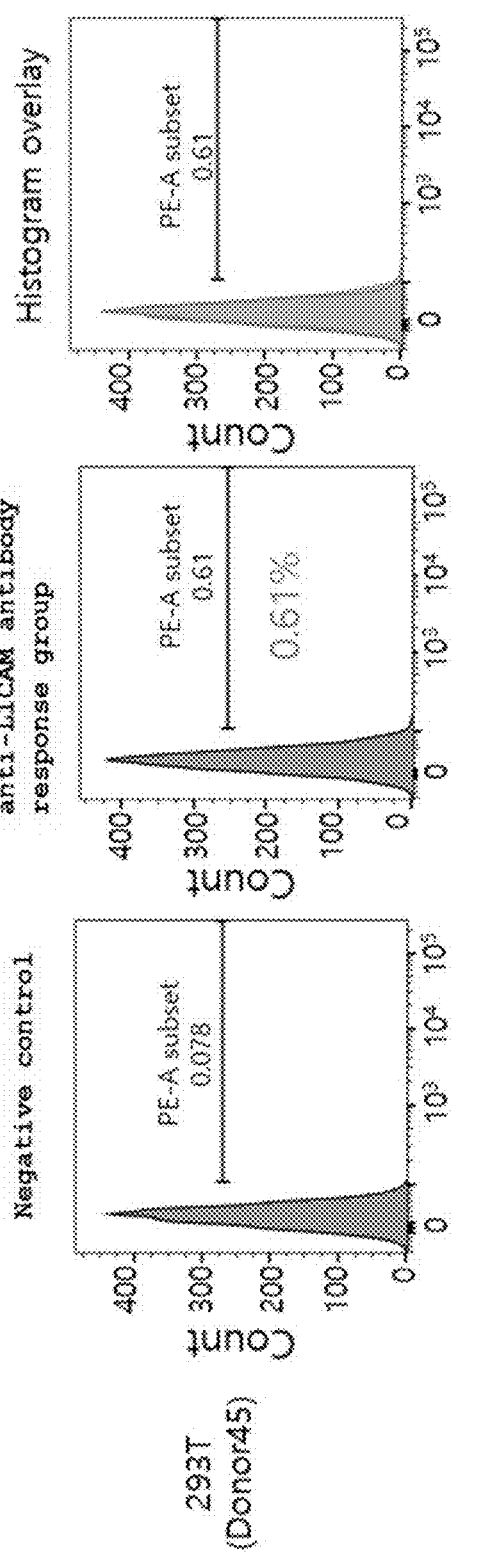
Figure 24E:
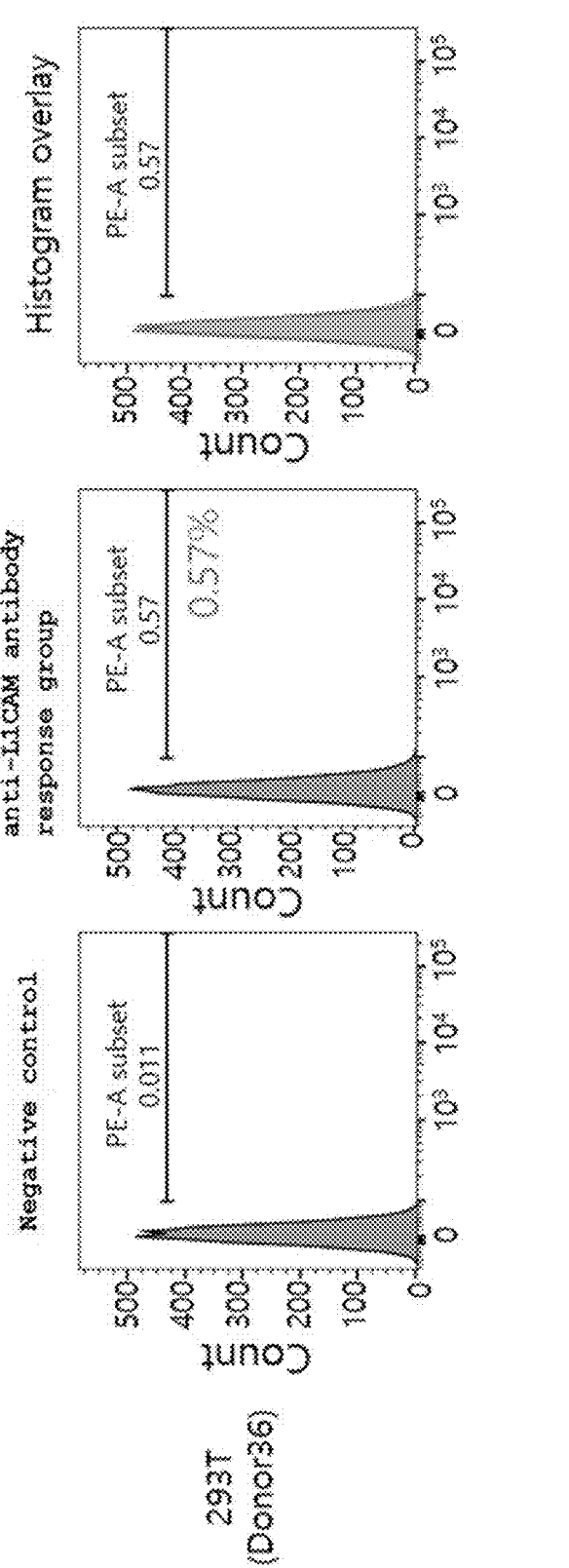
Figure 24F:
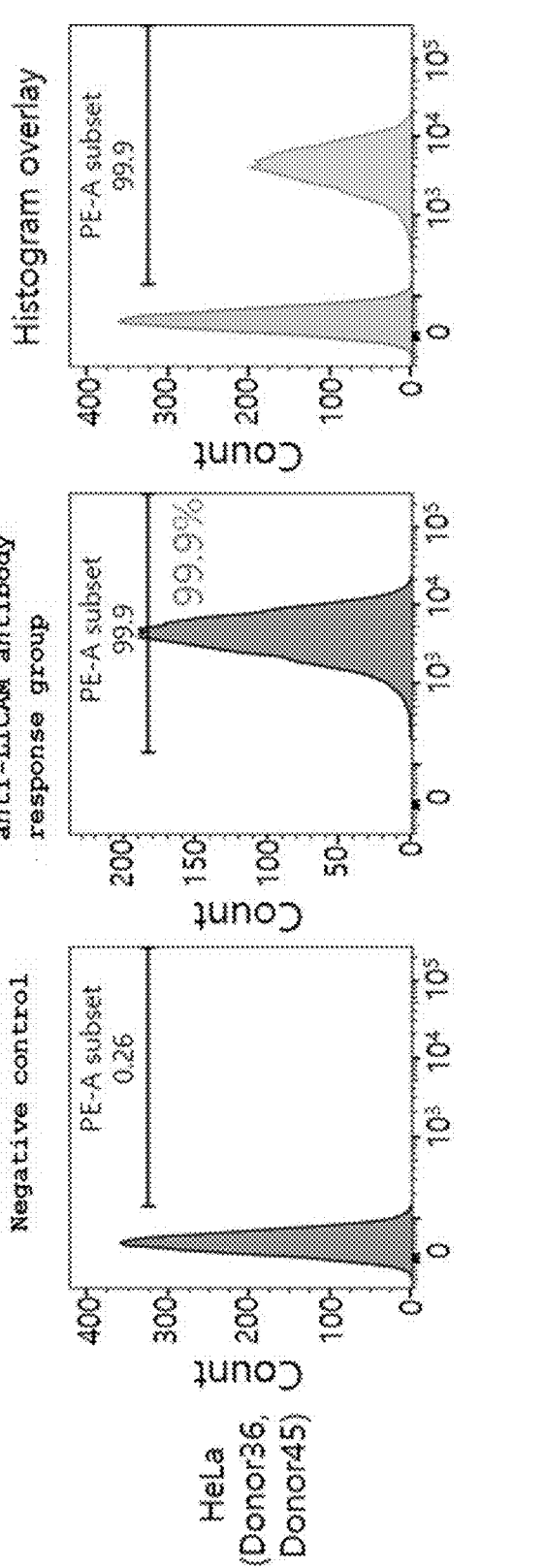
Figure 24G:
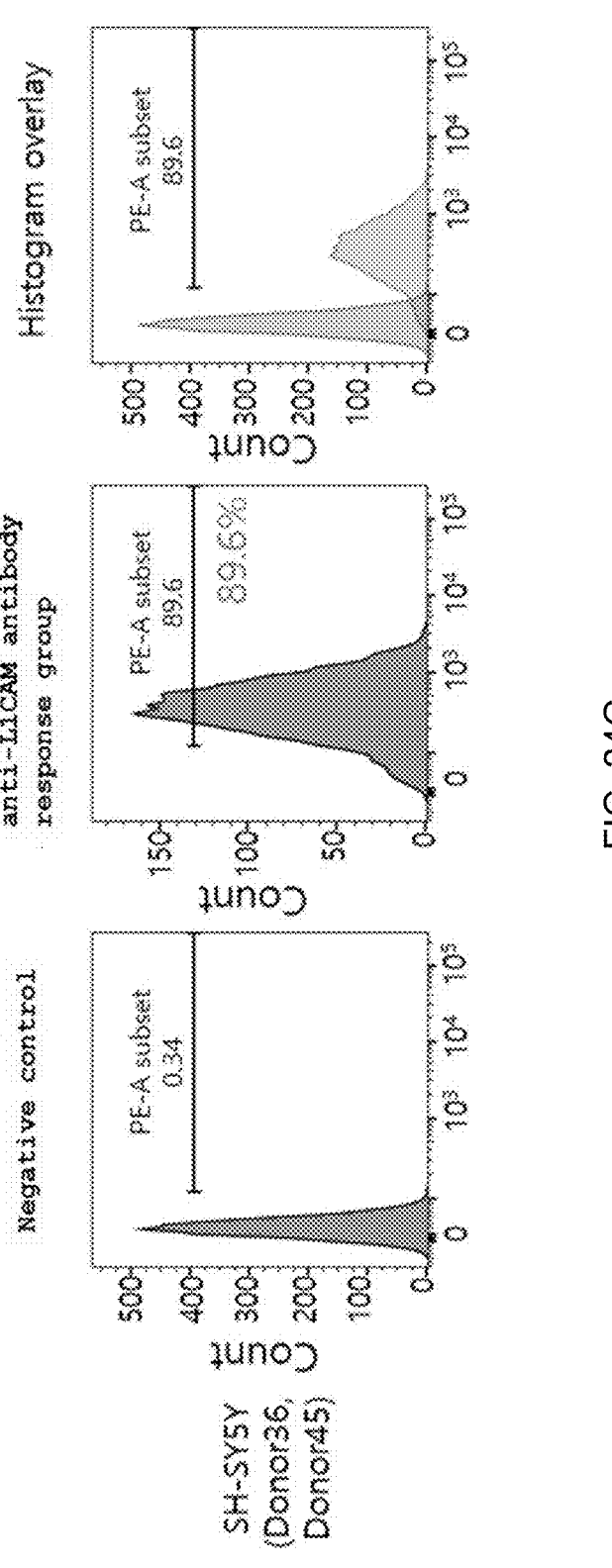

The human ovarian adenocarcinoma cell line SKOV3 is known to highly express L1CAM, and thus is a cell line suitable for investigating the anticancer activity of the anti-L1CAM-CAR-expressing T cells. To check this, the SKOV3 cell line was prepared at $5\times10^5$ cells in 100 μL of PBS, and 0.25 μg of the anti-hCD171-PE (5G3 clone) (eBioscience, Cat No. 12-1719-42) antibody was added, followed by incubation at 4° C. for 30 minutes. After the incubation, the cells were washed with PBS twice, and then the expression of L1CAM was investigated by flow cytometry. The results verified that the L1CAM expression rate was about 93.4 to 99.2% in SKOV3 cancer cells (FIGS. 24A to 24C). As a result of investigating the expression of L1CAM in the human cervical cancer cell line HeLa, the human neuroblastoma cell line SH-SY5Y, and the human embryonic kidney cell line 293T, the expression rate was about 99.9% in HeLa (FIG. 24F), about 89.6% in SH-SY5Y (FIG. 24A), and about 0.57 to 0.61% in 293T (FIGS. 24D and 24E).

4.4.2. Verification of Anticancer Activity of L1CAM-Expressing T Cells on Target Cells (In Vitro)

4.4.2.1. Verification of Anticancer Activity Using xCelligence Assay

To investigate the anticancer activity of the anti-L1CAM-CAR (L1-H8-CAR)-expressing T cells (effector cells, E) on target cells (T), xCELLigence Real-Time Cell Analysis (RTCA) was used. According to the xCELLigence RTCA method, the electron flow is displayed numerically as an index value when an electroconductive solution (e.g., culture media) is included on a plate coated with a gold microelectrode biosensor, and the electron flow is disturbed to result in changed index values when target cells adhere to the plate. Upon the addition of CAR-expressing T cells, the adhering target cells are separated from the plate due to cytotoxicity of the T cells, and the anticancer activity (cytotoxicity) can be checked by analyzing the change in index value. Target cells were prepared at $1\times10^4$ cells in 50 μL of a culture medium, and added to a plate for analysis. After about 21 hours, anti-L1-H8-CAR-expressing T cells were prepared at $1\times10^4$, $5\times10^4$, and $1\times10^5$ (E:T ratio=1, 5, 10) in 50 uL of AIMV media comprising human serum and human IL-2, and added to wells comprising target cells, to check the cell index value in real time for 30 hours. In addition, wells comprising only target cells were prepared, and the anticancer activity of L1-H8-CAR-expressing T cells was calculated as follows.

Figure 25:
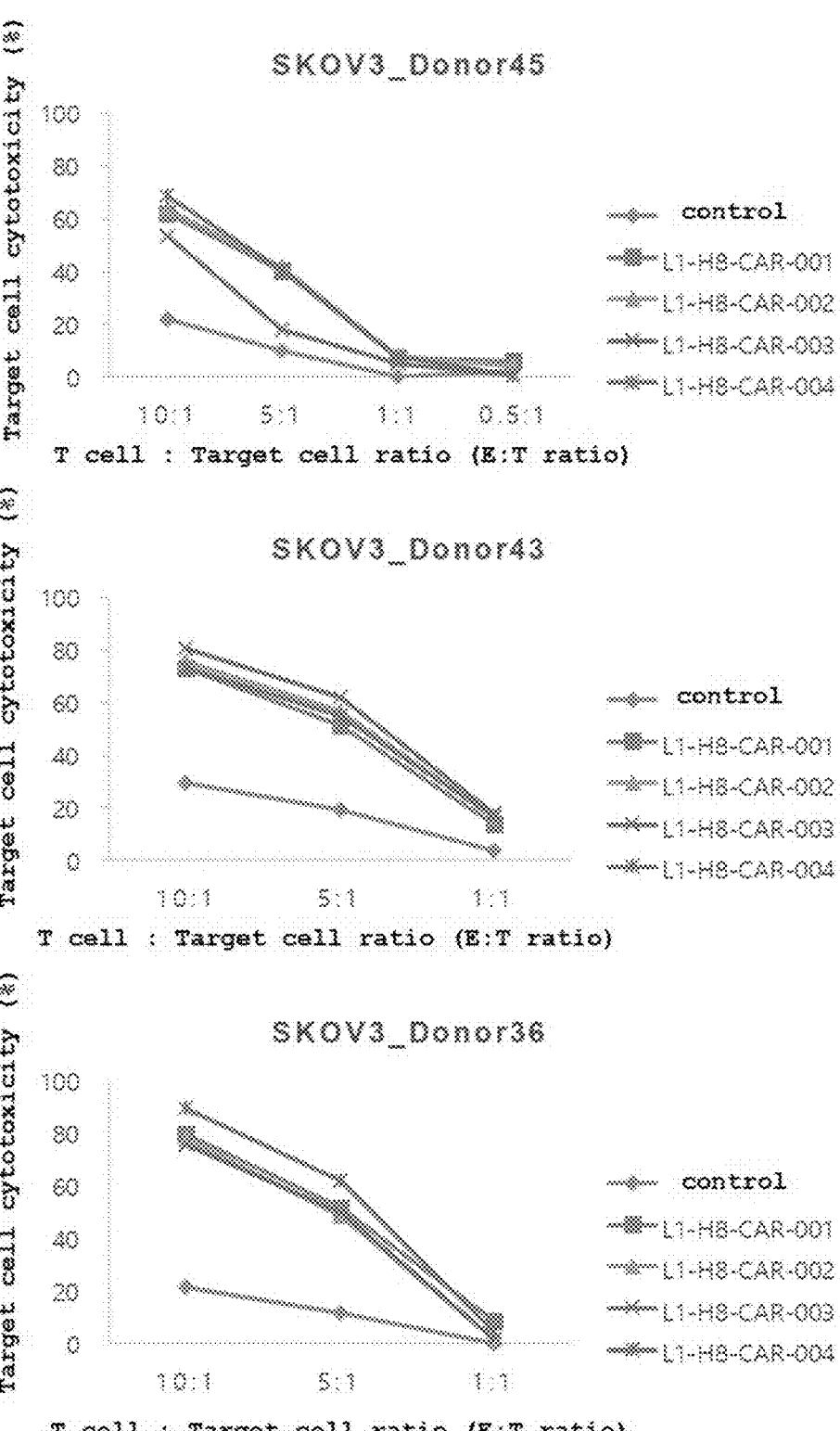
FIG. 25 shows anticancer activity of anti-L1CAM-CAR-expressing T cells of the present disclosure on SKOV3 cells (high expression of L1CAM).

Cytotoxicity (%)={(index value of target cell well)−(index value of target cell and T cell incubation well)}/(index value of target cell well)×100    Equation As a result, four types of T cells expressing L1-H8-CAR-001, -002, -003, and -004 showed high cytotoxicity on SKOV3 cells compared with T cells not expressing 1-H8-CAR (control) (FIG. 25).

Figure 26:
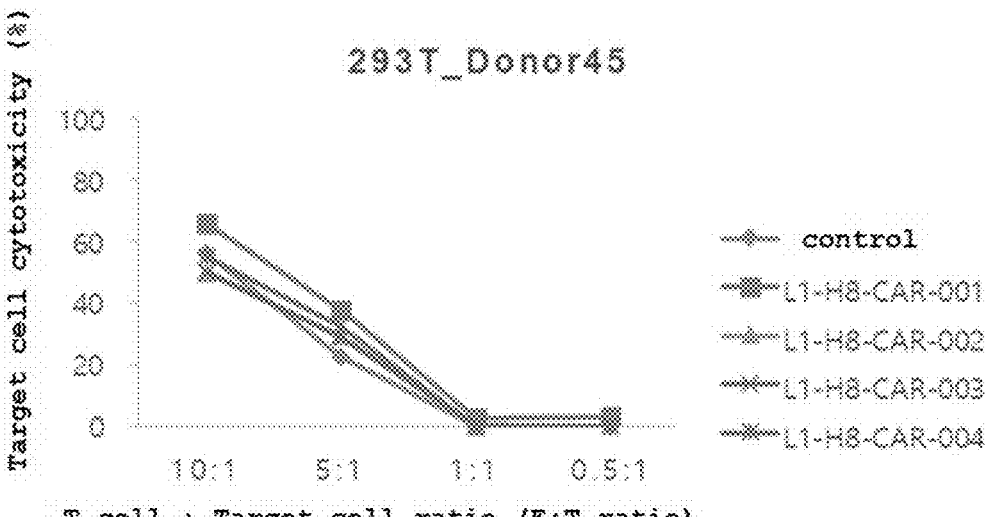
FIG. 26 shows anticancer activity of anti-L1CAM-CAR-expressing T cells of the present disclosure on 293T cells (low expression of L1CAM).
Figure 26:
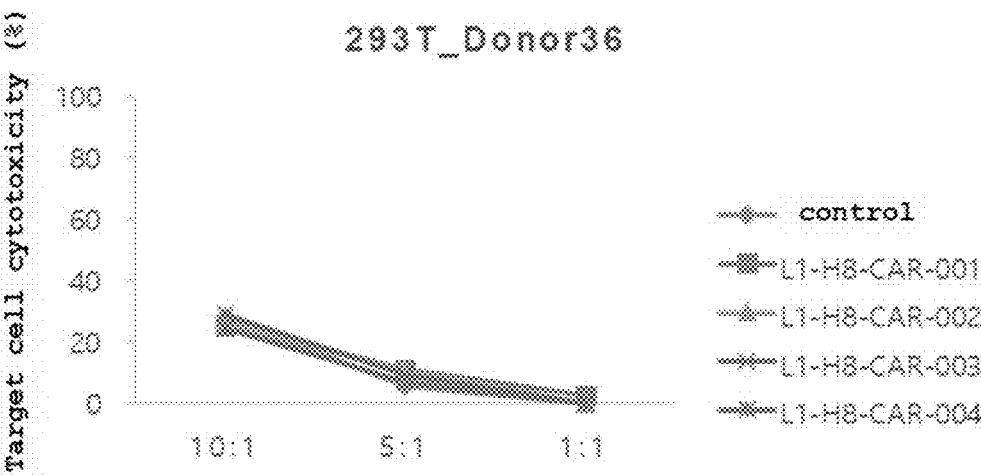

The cytotoxicity on 293T cells were checked by the same method. The target cells were added at $2.5\times10^4$ to 50 uL of culture media, and after about 21 hours, L1-H8-CAR-expressing T cells were prepared at $2.5\times10^4$, $1.25\times10^5$, and $2.5\times10^5$ (E:T ratio=1, 5, and 10) in 50 uL of AIMV media comprising human serum and human IL-2, and added to wells comprising target cells, to check the cell index value in real time for 30 hours. In addition, wells comprising only target cells were prepared, and the anticancer activity of L1-H8-CAR-expressing T cells was calculated in the same manner as in the above tests. As a result, all the four types showed similar cytotoxicity to the control in 293T cells showing a low expression rate of L1CMA (FIG. 26).

4.4.2.2. Verification of Anticancer Activity Using CellTox™ Green Dye

To investigate the anticancer activity of the anti-L1 CAM-CAR (L1-H8-CAR)-expressing T cells (effector cells, E) on target cells (T), CellTox™ Green dye was used. CellTox™ Green dye is a dye that attaches to DNA released from dead cells to exhibit fluorescence, and is used to investigate anticancer activity (cytotoxicity). The target cells were prepared at $1\times10^4$ in 50 uL of culture media, and 0.2 uL of CellTox™ Green dye was added, and the mix was added to 96-well black plates. The L1-H8-CAR-expressing T cells were prepared at $5\times10^3$, $1\times10^4$, $5\times10^4$, and $1\times10^5$ (E:T ratio=0.5, 1, 5, and 10) in 50 uL of AIMV media comprising human serum and human IL-2, and added to wells comprising target cells, followed by incubation in a $CO_2$ incubator at 37° C. for 24 hours. The group added with only L1-H8-CAR-expressing T cells was prepared in the wells comprising the culture media of CellTox™ Green dye and target cells, and the reaction value of the dye, occurring by attachment to DNA released from dead L1-H8-CAR-expressing T cells during the incubation was excluded. The wells comprising only target cells were prepared to correct the low control (spontaneous DNA release) value, and a lysis solution was added to the well comprising only the target cells to correct the high control (maximum DNA release) value. The cytotoxicity on the target cells was calculated by the following method.

$$\text{Cytotoxicity (\%)} = \{(\text{reaction value of Target cells and Effector cells}) - (\text{reaction value of Effector cells})\} - (\text{Low control})/(\text{High control} - \text{Low control}) \times 100 \qquad \text{Equation 2}$$

Figure 27A:
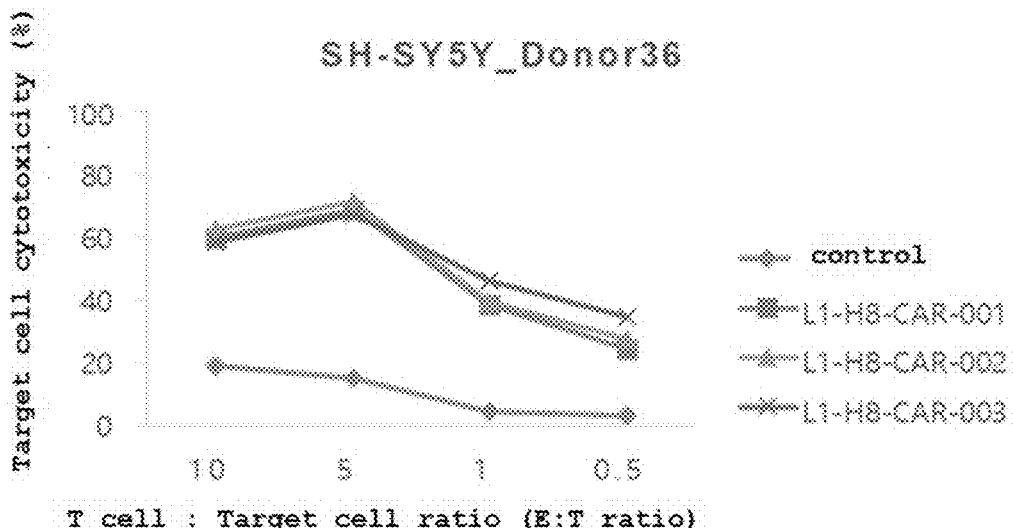
FIGS. 27A and 27B show anticancer activity of anti-L1CAM-CAR-expressing T cells of the present disclosure on SH-SY5Y cells (high expression of L1CAM).
Figure 27A:
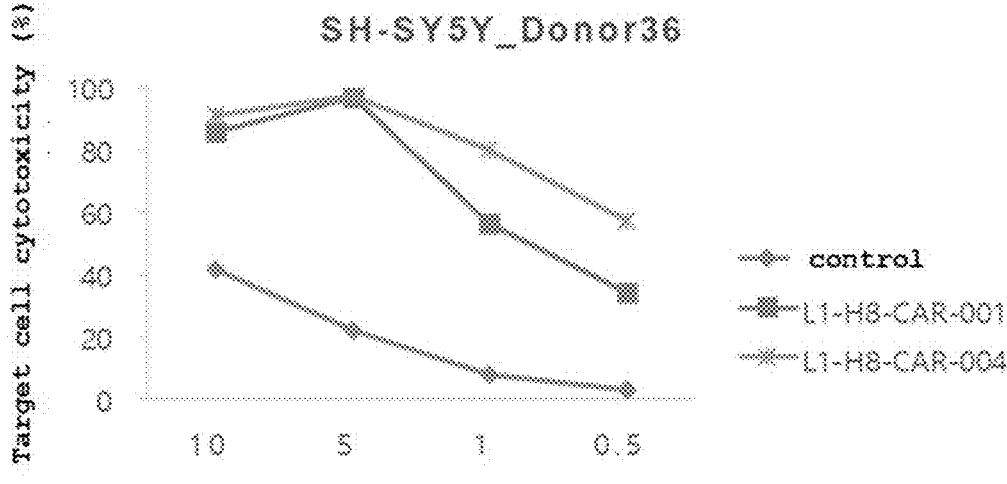
Figure 27B:
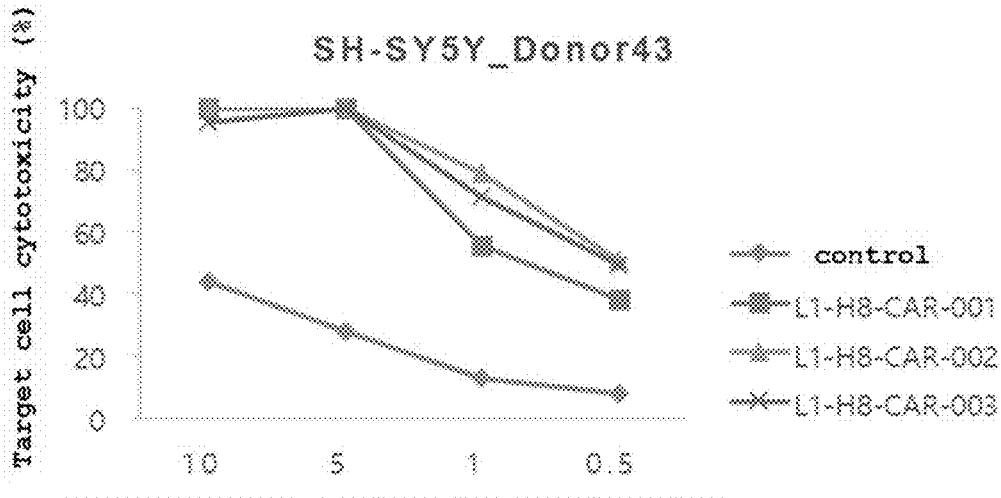
Figure 27B:
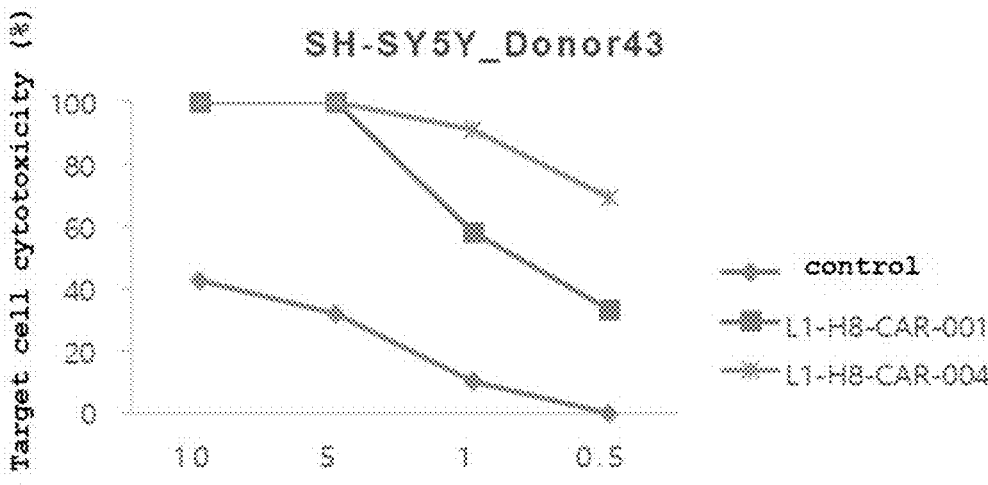

As a result, four types of T cells expressing L1-H8-CAR-001, -002, -003, and -004 showed high cytotoxicity on SH-SY5Y cells compared with T cells not expressing 1-H8-CAR (control) (FIGS. 27A and 27B).

Figure 28A:
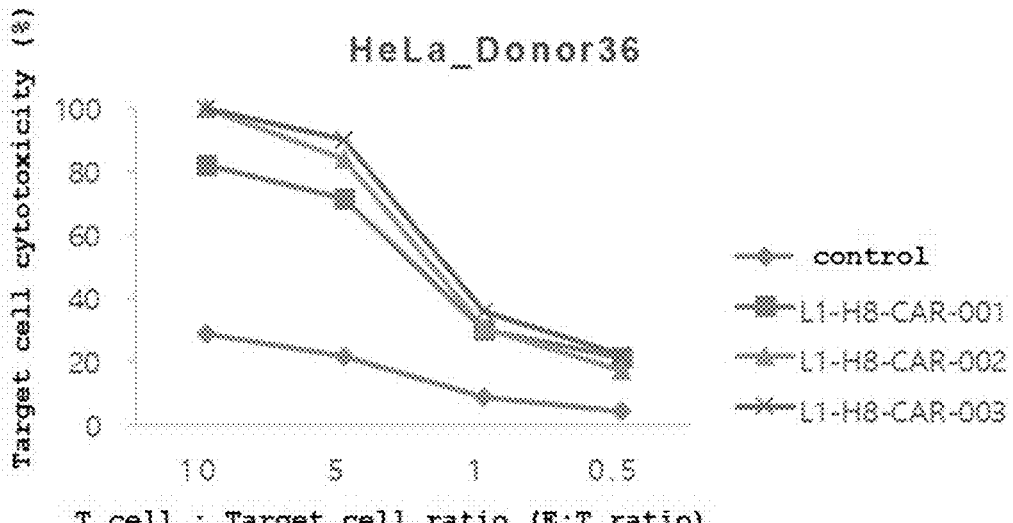
FIGS. 28A and 28B show anticancer activity of anti-L1CAM-CAR-expressing T cells of the present disclosure on HeLa cells (high expression of L1CAM).
Figure 28A:
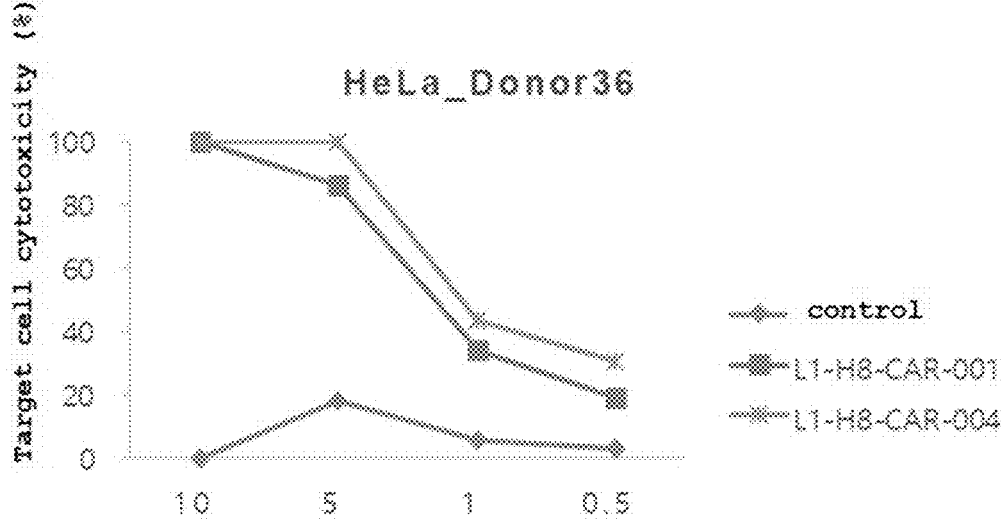
Figure 28B:
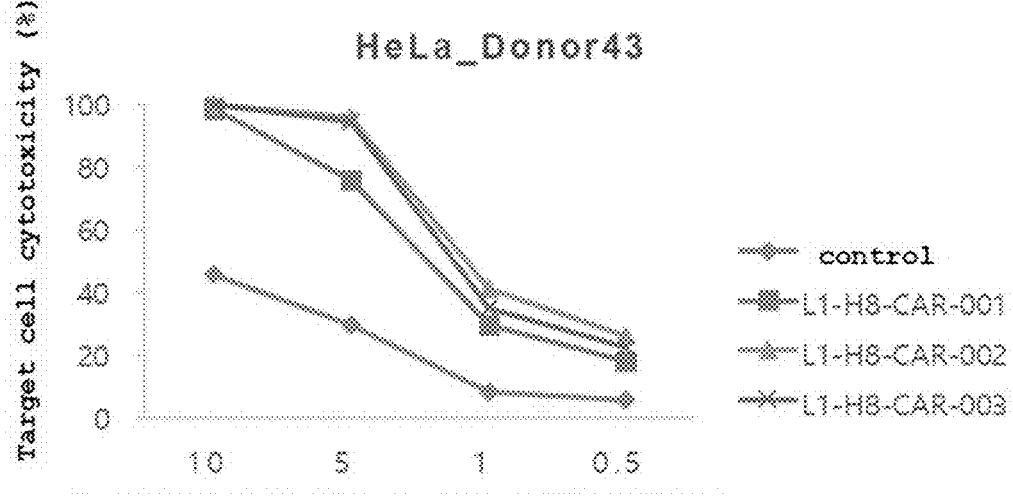
Figure 28B:
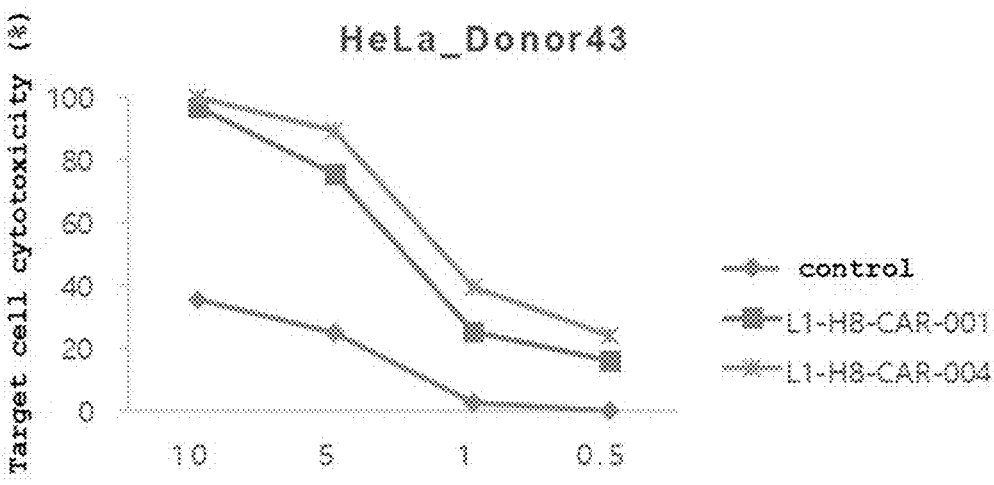

The cytotoxicity on HeLa cells were checked by the same test method. The target cells were prepared at $3.5 \times 10^3$ in 50 uL of culture media, and 0.2 uL of CellTox™ Green dye was added, and the mix was added to 96-well black plates. The L1-H8-CAR-expressing T cells were prepared at $1.75 \times 10^3$, $3.5 \times 10^3$, $1.75 \times 10^4$, and $3.5 \times 10^4$ (E:T ratio=0.5, 1, 5, and 10) in 50 uL of AIMV media comprising human serum and human IL-2, and added to wells comprising target cells, followed by incubation in a $CO_2$ incubator at 37° C. for 24 hours. The cytotoxicity on the target cells was corrected and calculated by the same method. As a result, four types of T cells expressing L1-H8-CAR-001, -002, -003, and -004 showed high cytotoxicity on HeLa cells compared with T cells not expressing 1-H8-CAR (control) (FIGS. 28A and 28B).

4.5. Verification of Anticancer Activity of T Cells Expressing L1-H8-CAR Genes with Various Spacer Domain Structures (In Vitro)

Figure 29:
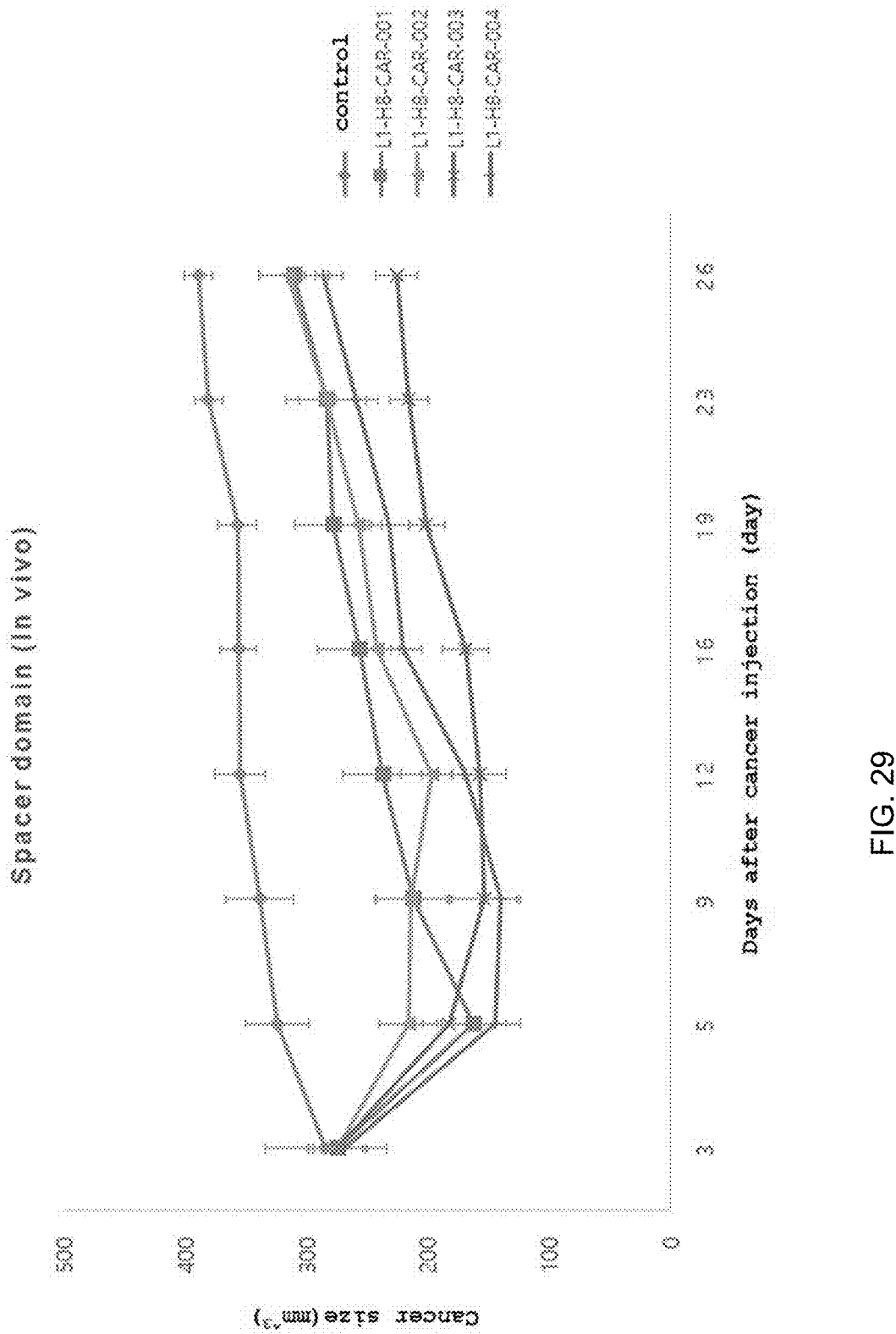
FIG. 29 shows in-vivo anticancer activity of anti-L1CAM-CAR (anti-L1-CAR)-expressing T cells of the present disclosure.

To investigate anticancer activity of anti-L1CAM-CAR (L1CAM-CAR) gene-expressing T cells in vivo, cancer-induced animal models were used. SKOV3 cancer cells (Target, T) mixed with Matrigel at 1:1 were subcutaneously (SC) administered at $3 \times 10^6$ to the right flank of NOD/SCID mice (7 weeks old, female) lacking T cells, B cells, and natural killer cells (NK cells), to thereby induce cancer. Four types of L1-H8-CAR-expressing T cells confirmed to have efficacy in vitro and control T cells were administered to each NOD/SCID mouse 3 days and 5 days after cancer cell administration, once a day, a total of 2 times. T cells were administered through the tail vein (intravenous, IV) at $2 \times 10^7$ per dose, and the cancer size was measured up to day 25. The results verified that both two types of anti-L1CAM-CAR-expressing T cells inhibited the cancer growth rate compared with the control T cell administration group. It was especially verified that the cancer growth inhibitory effect of L1-H8-CAR-003 was the best (FIG. 29).

Example 5: Fabrication of T Cells Expressing Anti-L1CAM-CAR With Various Costimulatory Domain Structures and Verification of Activity Thereof

5.1. Obtainment of L1CMA-CAR Genes with Various Costimulatory Domain Structures

5.1.1. Obtainment of L1-H8-CAR-001-28BB Gene

5.1.1.1. Obtainment of 3E8 Antibody Leader Sequence (LS), L1-H8 scFv, Hinge, TM, and ICD Gene pMT-L1-H8-CAR-001 as a template was amplified by PCR using the primers of SEQ ID NO: 70 (Table 12) and SEQ ID NO: 87 (Table 12). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of CD28 ICD has the 12-nucleotide sequence of 4-1BB, and thus the amplified PCR product has the nucleotide sequence of Mlu I-3E8 LS-L1-H8 scFv-hIgD hinge-CD28 TM-CD28 ICD-4-1BB (Table 13) The amplified PCR product was used in the next PCR amplification process.

TABLE 12

| SEQ ID NO | Primer name | Nucleotide sequence |
|---|---|---|
| | Nucleotide sequence information of used primers | |
| 70 | Mlu 1 + 3E8 VH(F) | ACGCGTATGGAATGGAGCTGGGTC |
| 87 | CD28 ICD + 41BB(R) | TCTGCCCCGTTTGGAGCGATAGGCTGC |
| 88 | CD28 ICD + 41BB(F) | GCCTATCGCTCCAAACGGGGCAGAAAG |
| 73 | Xho I + CD3zeta(R) | CCGCTCGAGTTAGCGAGGGGGCAGGGC |
| 89 | CD28 ICD + ICOS ICD (R) | GGATGAATACTTGGAGCGATAGGCTGC |
| 90 | CD28 ICD + ICOS ICD (F) | GCCTATCGCTCCAAGTATTCATCCAGT |
| 91 | ICOS ICD + CD3zeta(R) | GAACTTCACTCTGGTCACATCTGTGAG |
| 92 | ICOS ICD + CD3zeta(F) | ACAGATGTGACCAGAGTGAAGTTCAGC |
| 93 | CD28 ICD + CD3zeta(R) | GAACTTCACTCTGGAGCGATAGGCTGC |
| 94 | CD28 ICD + CD3zeta(F) | GCCTATCGCTCCAGAGTGAAGTTCAGC |
| 95 | CD28 TM + CX40(R) | CAGGTACAGGGCCACCCAGAAAATAAT |

TABLE 12-continued

| Nucleotide sequence information of used primers | | |
| --- | --- | --- |
| SEQ ID NO | Primer name | Nucleotide sequence |
| 96 | CD28 TM + CX40(F) | ATTTTCTGGGTGGCCCTGTACCTGCTC |
| 97 | CD28 TM + 41BB(R) | TCTGCCCCGTTTCACCCAGAAAATAAT |
| 98 | CD28 TM + 41BB(F) | ATTTTCTGGGTGAAACGGGGCAGAAAG |
| 99 | CD28 TM + ICOS ICD(R) | TGGATGAATACTTCACCCAGAAAATAATA |
| 100 | CD28 TM + ICOS ICD(F) | ATTTTCTGGGTGAAGTATTCATCCAGT |

TABLE 13

| LS, L1-H8 scFv, Hinge, TM, ICD, costimulatory domain, and CD3ζ gene sequences | |
| --- | --- |
| ID | Nucleotide sequence |
| Mlu I-start codon-3E8 LS | ACGCGTATGGAATGGAGCTGGGTCTTTCTCTTCTTCCTGTCAGTAACTAC AGGTGTCCACTCC |
| L1-H8 scFv (L1CAM-3R-H8) | GAAGTACAGTTGGTCGAAAGTGGCGGTGGCCTCGTGCAACCGGGTGGT TCACTGCGTCTGAGCTGCGCCGCCTCGGGTTTTACTTTCTCTGATTATGC AATGAATTGGGTTCGTCAGGCGCCGGGCAAGGGTCTCGAATGGGTTTC AGCAATCTCTTCTACTGGTTCTACTATCTACTATGCCGATTCAGTGAAGGG TCGCTTTACCATTTCCCGTGACAACTCTAAGAATACTCTGTATCTGCAGAT GAACTCGCTGCGTGCCGAAGACACGGCCGTCTATTATTGCGCCAAACAG TCTACTTACTTTTACTCTTACTTTGATGTTTGGGGTCAGGGCACTTTAGTG ACCGTCTCATCGGGTGGAGGCGGTTCAGGCGGAGGTGGATCCGGCGG TGGCGGATCGGACATTCAAATGACGCAGAGTCCCTCCTCACTGAGTGCT AGCGTGGGCGATCGTGTGACAATTACTTGTCGCGCTAGCCAGTCTATCT CTCGTGATCTGAACTGGTATCAGCAGAAACGGGCAAGGCGCCAAAATT GCTGATTTACGCAGCATCCTCTCTGCAGTCTGGTGTACCGTCCCGTTTCT CTGGCAGCGGTTCTGGTACGGATTTTACCCTGACCATCTCAAGCCTCCA GCCTGAAGATTTTGCCACCTATTATTGTCAGCAATCTTACTCTACTCCGTA CACGTTCGGGCAGGGAACTAAAGTGGAAATTAAA |
| IgD hinge | CGCTGGCCAGGTTCTCCAAAGGCACAGGCCTCCTCCGTGCCCACTGCA CAACCCCAAGCAGAGGGCAGCCTCGCCAAGGCAACCACAGCCCCAGC CACCCACCCGTAACACAGGTAGAGGAGGAGAAGAGAAGAAGAAGGAGAA GGAGAAAGAGGAACAAGAAGAGAGAGAGACAAAGACACCAGGTTGTCC G |
| CD28 TM | TTTTGGGTGCTGGTGGTGGTTGGTGGAGTCCTGGCTTGCTATAGCTTGC TAGTAACAGTGGCCTTTATTATTTTCTGGGTG |
| CD28 ICD | AGGAGTAAGAGGAGCAGGCTCCTGCACAGTGACTACATGAACATGACTC CCCGCCGCCCCGGGCCCACCCGCAAGCATTACCAGCCCTATGCCCCAC CACGCGACTTCGCAGCCTATCGCTCC |
| OX40 | GCCCTGTACCTGCTCCGGAGGGACCAGAGGCTGCCCCCCGATGCCCA CAAGCCCCCTGGGGGAGGCAGTTTCCGGACCCCCATCCAAGAGGAGC AGGCCGACGCCCACTCCACCCTGGCCAAGATC |
| 4-1BB | AAACGGGGCAGAAAGAAACTCCTGTATATATTCAAACAACCATTTATGAGA CCAGTACAAACTACTCAAGAGGAAGATGGCTGTAGCTGCCGATTTCCAG AAGAAGAAGAAGGAGGATGTGAACTG |
| ICOS | AAGTATTCATCCAGTGTGCACGACCCTAACGGTGAATACATGTTCATGAG AGCAGTGAACACAGCCAAAAAATCTAGACTCACAGATGTGACC |
| CD3ζ-iso1-stop codon-Xho I | AGAGTGAAGTTCAGCAGGAGCGCAGACGCCCCCGCGTACCAGCAGGG CCAGAACCAGCTCTATAACGAGCTCAATCTAGGACGAAGAGAGGAGTAC GATGTTTTGGACAAGAGACGTGGCCGGGACCCTGAGATGGGGGGAAAG CCGCAGAGAAGGAAGAACCCTCAGGAAGGCCTGTACAATGAACTGCAG AAAGATAAGATGGCGGAGGCCTACAGTGAGATTGGGATGAAAGGCGAG CGCCGGAGGGGCAAGGGGCACGATGGCCTTTACCAGGGTCTCAGTACA GCCACCAAGGACACCTACGACGCCCTTCACATGCAGGCCCTGCCCCCT CGCTAACTCGAG |

5.1.1.2. Obtainment of Costimulatory Domain and CD3ζ Gene

Figure 30:
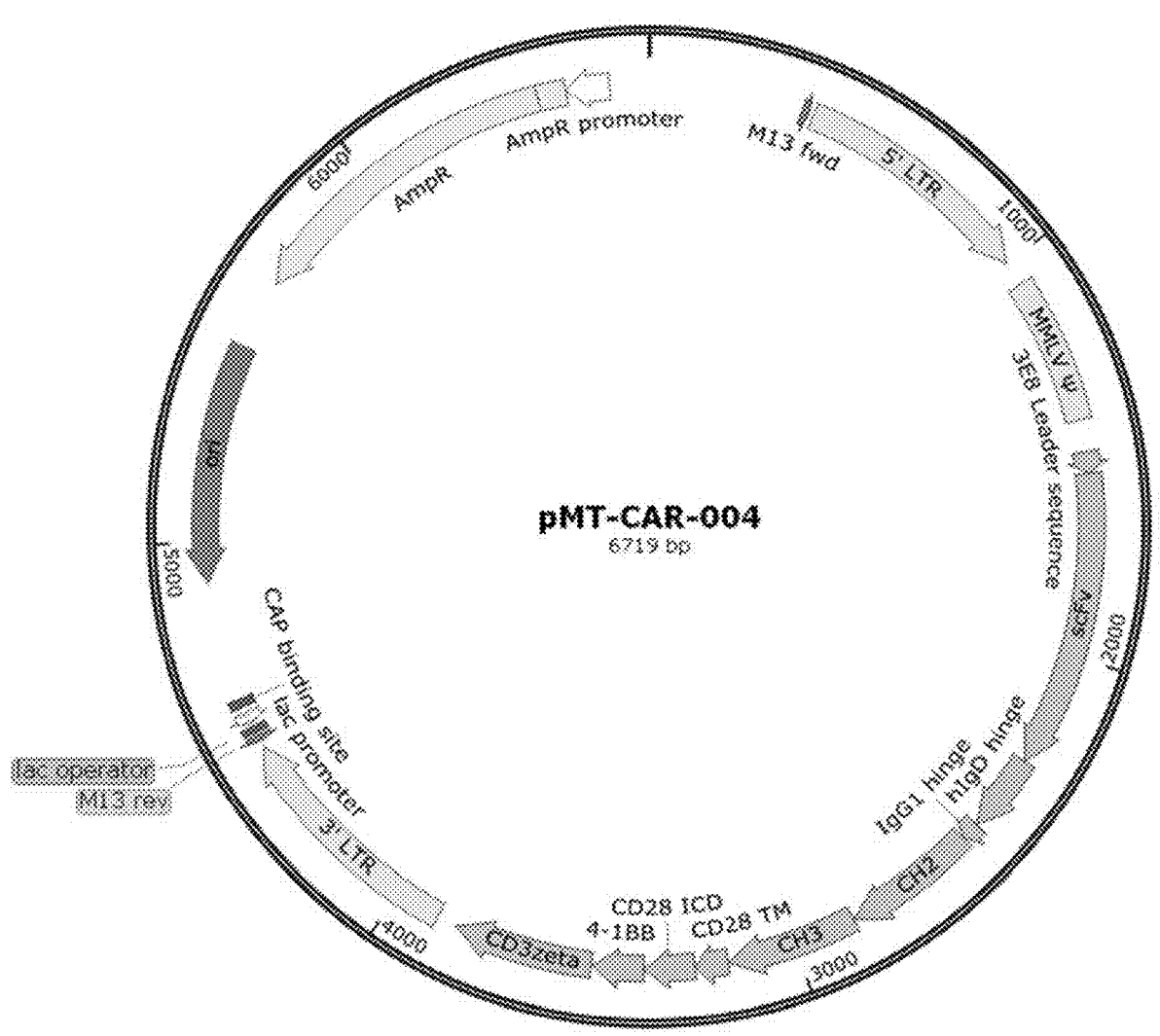
FIG. 30 shows a vector map of the pMT-CART-004 plasmid used to manufacture a CAR-construct comprising the selected anti-L1CAM scFv.

The pMT-CAR-004 plasmid (FIG. 30), comprising the costimulatory domain 4-1BB, and CD3ζ-iso1, as a template, was amplified by PCR using the primers of SEQ ID NO: 88 (Table 12) and SEQ ID NO: 73 (Table 12). The primer binding to the 5' end of 4-1BB has the 12-nucleotide sequence of CD28 ICD, and the primer binding to the 3' end of CD3ζ-iso1 has the nucleotide sequence of Xho I restriction enzyme, and thus the amplified PCR product has the nucleotide sequence of ICD-4-1BB-CD3ζ-iso1-Xho I (Table 13). The amplified PCR product was used in the next PCR amplification process.

Figure 31:
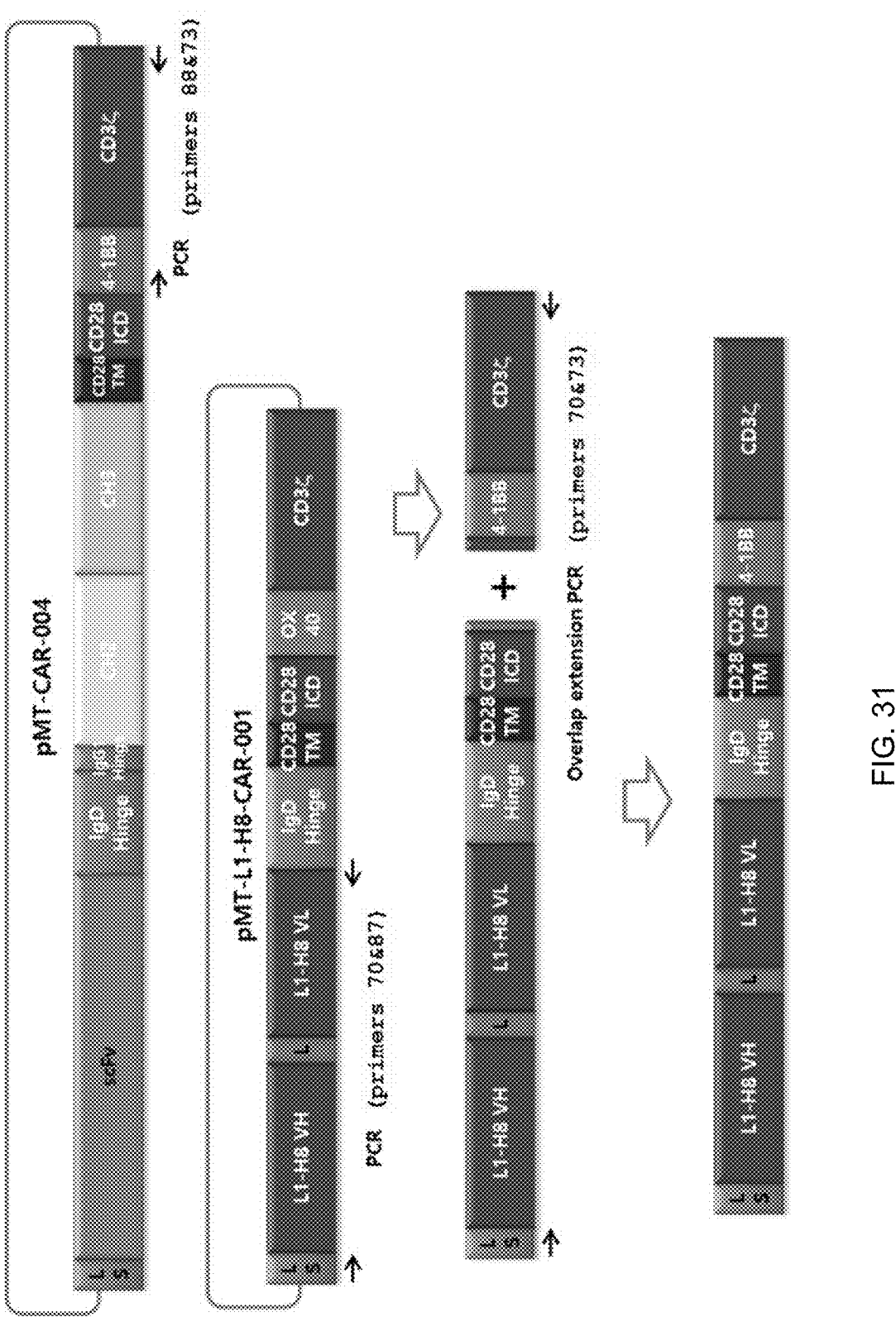
FIG. 31 is a schematic diagram showing a series of PCR amplification procedures in order to manufacture a CAR-construct comprising anti-L1CAM scFv.
Figure 32:
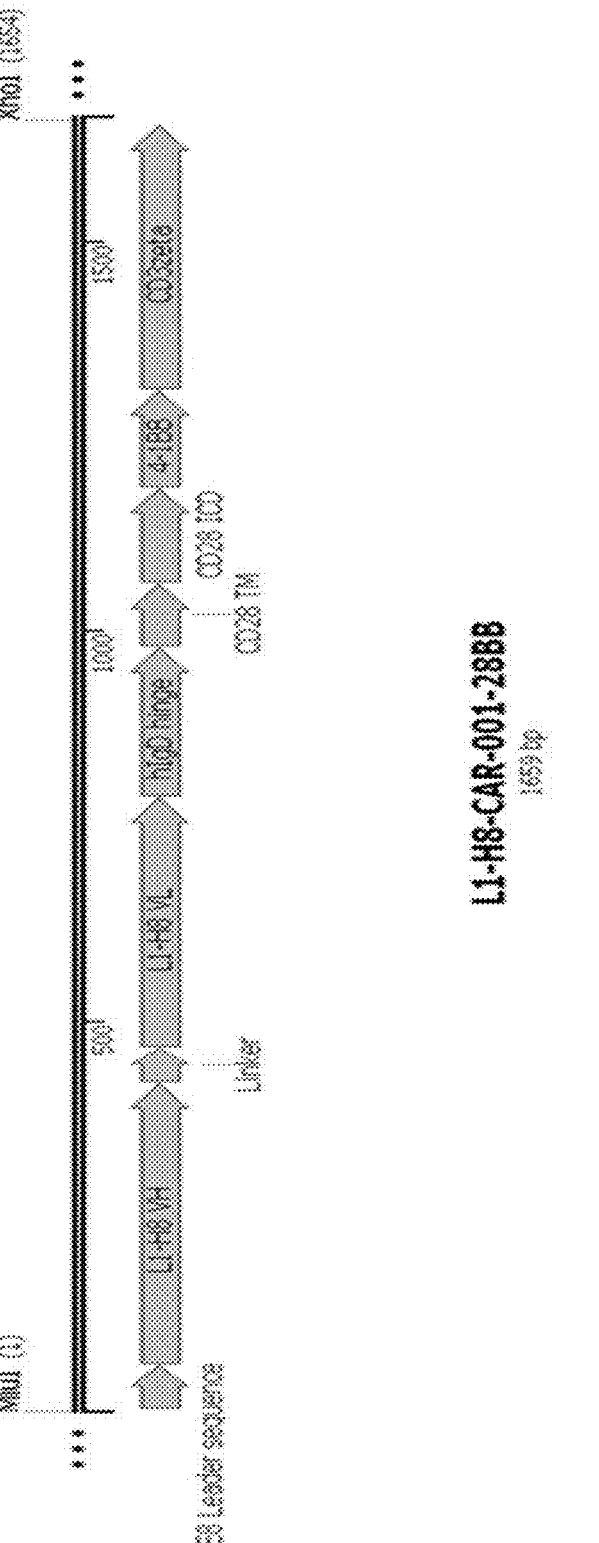
FIG. 32 shows a structure of the CAR-construct comprising anti-L1CAM scFv (L1-H8-CAR-001-28BB) constructed in the example of the present disclosure.

5.1.1.3. Obtainment of 3E8 LS, L1-H8 scFv, Hinge, TM, ICD, Costimulatory Domain, and CD3ζ Gene Mlu I-3E8 LS-L1-H8 scFv-hIgD hinge-CD28 TM-CD28 ICD-4-1BB and CD28 ICD-4-1BB-CD3ζ-iso1-Xho I, which were the amplified PCR products, as templates, were amplified by OE-PCR using the primers of SEQ ID NO: 70 (Table 12) and SEQ ID NO: 73 (Table 12) (FIG. 31). The amplified PCR product has the nucleotide sequence of Mlu I-3E8 LS-L1-H8 scFv-hIgD hinge-CD28 TM-CD28 ICD-4-1BB-CD3ζ-iso1-Xho I, and has a structure of L1-H8-CAR-001-28BB (FIG. 32).

5.1.2. Obtainment of L1-H8-CAR-001-28ICOS Gene

5.1.2.1. Obtainment of 3E8 Antibody Leader Sequence (LS), L1-H8 scFv, Hinge, TM, and ICD Gene pMT-L1-H8-CAR-001 as a template was amplified by PCR using the primers of SEQ ID NO: 70 (Table 12) and SEQ ID NO: 89 (Table 12). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of CD28 ICD has the 12-nucleotide sequence of ICOS, and thus the amplified PCR product has the nucleotide sequence of Mlu I-3E8 LS-L1-H8 scFv-hIgD hinge-CD28 TM-CD28 ICD-ICOS ICD (Table 13) The amplified PCR product was used in the next PCR amplification process.

5.1.2.2. Obtainment of Costimulatory Domain ICOS Gene

Figure 33:
FIG. 33 shows a vector map of the pBHA-ICOS TM+ICD plasmid used to manufacture a CAR-construct comprising the selected anti-L1CAM scFv.

TM and ICD structures of the costimulatory domain ICOS gene were synthesized. The pBHA-ICOS TM+ICD (FIG. 33) secured through gene synthesis as a template was amplified by PCR using the primers of SEQ ID NO: 90 (Table 12) and SEQ ID NO: 91 (Table 12). The primer binding to the 5' end of ICOS ICD has the 12-nucleotide sequence of CD28 ICD, and the primer binding to the 3' end of ICOS ICD has the nucleotide sequence of CD3ζ-iso1, and thus the amplified PCR product has the nucleotide sequence of CD28 ICD-ICOS ICD-CD3ζ-iso1 (Table 13). The amplified PCR product was used in the next PCR amplification process.

5.1.2.3. Obtainment of CD3ζ Gene pMT-L1-H8-CAR-001 as a template was amplified by PCR using the primers of SEQ ID NO: 92 (Table 12) and SEQ ID NO: 73 (Table 12). The primer binding to the 5' end of CD3ζ-iso1 has the 12-nucleotide sequence of ICOS ICD, and the primer binding to the 3' end of CD3ζ-iso1 has the nucleotide sequence of Xho I restriction enzyme, and thus the amplified PCR product has the nucleotide sequence of ICOS ICD-CD3ζ-iso1-Xho I (Table 13). The amplified PCR product was used in the next PCR amplification process.

Figure 34:
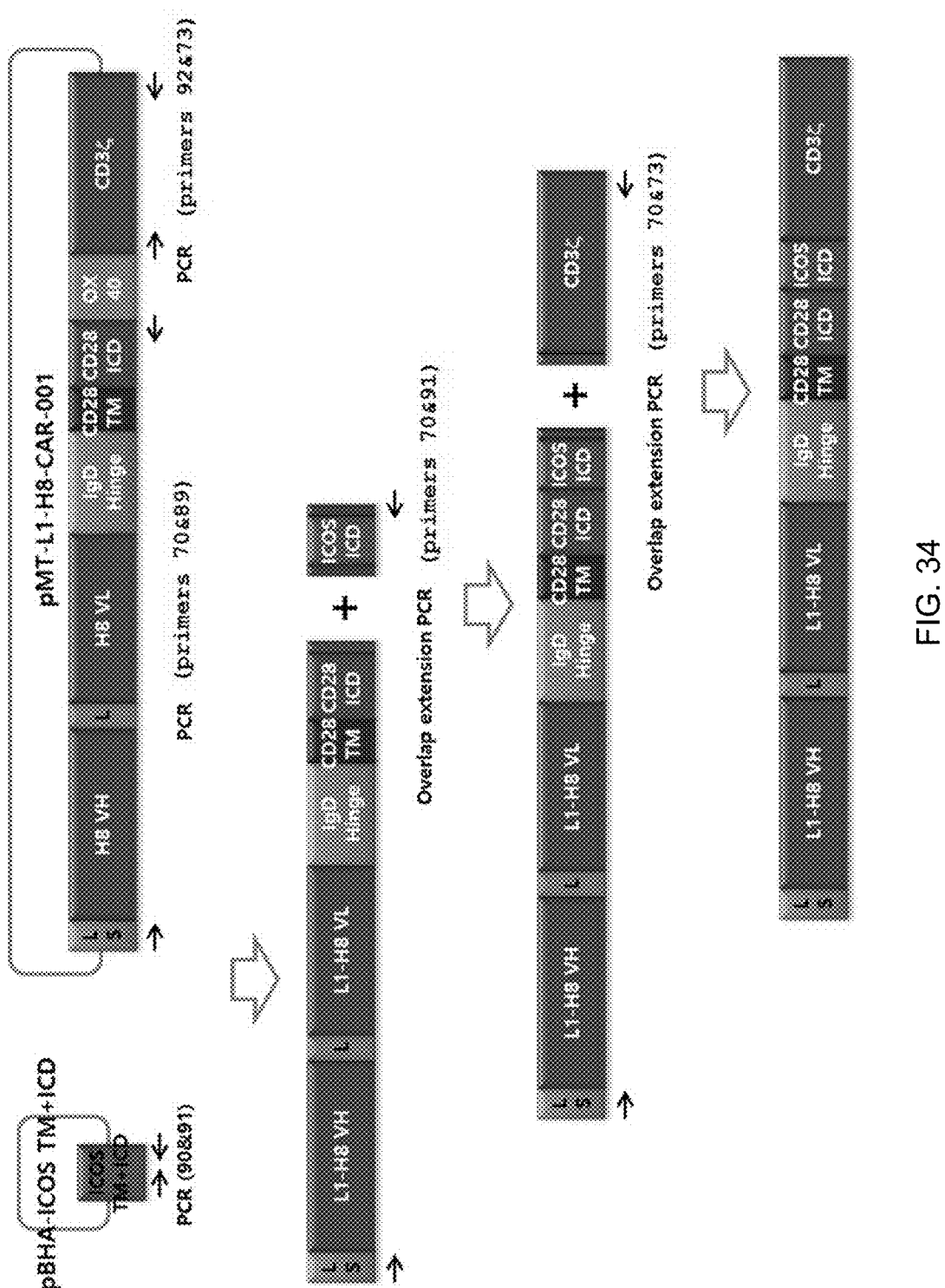
FIG. 34 is a schematic diagram showing a series of PCR amplification procedures in order to manufacture a CAR-construct comprising anti-L1CAM scFv.

5.1.2.4. Obtainment of 3E8 LS, L1-H8 scFv, Hinge, TM, ICD, and Costimulatory Domain Gene Mlu I-3E8 LS-L1-H8 scFv-hIgD hinge-CD28 TM-CD28 ICD-ICOS ICD and CD28 ICD-ICOS ICD-CD3ζ-iso1, which were the amplified PCR products, as templates, were amplified by OE-PCR using the primers of SEQ ID NO: 70 (Table 12) and SEQ ID NO: 91 (Table 12) (FIG. 34). The amplified PCR product has the nucleotide sequence of Mlu I-3E8 LS-L1-H8 scFv-hIgD hinge-CD28 TM-CD28 ICD-ICOS ICD-CD3ζ-iso1 (Table 13). The amplified PCR product was used in the next PCR amplification process.

Figure 35:
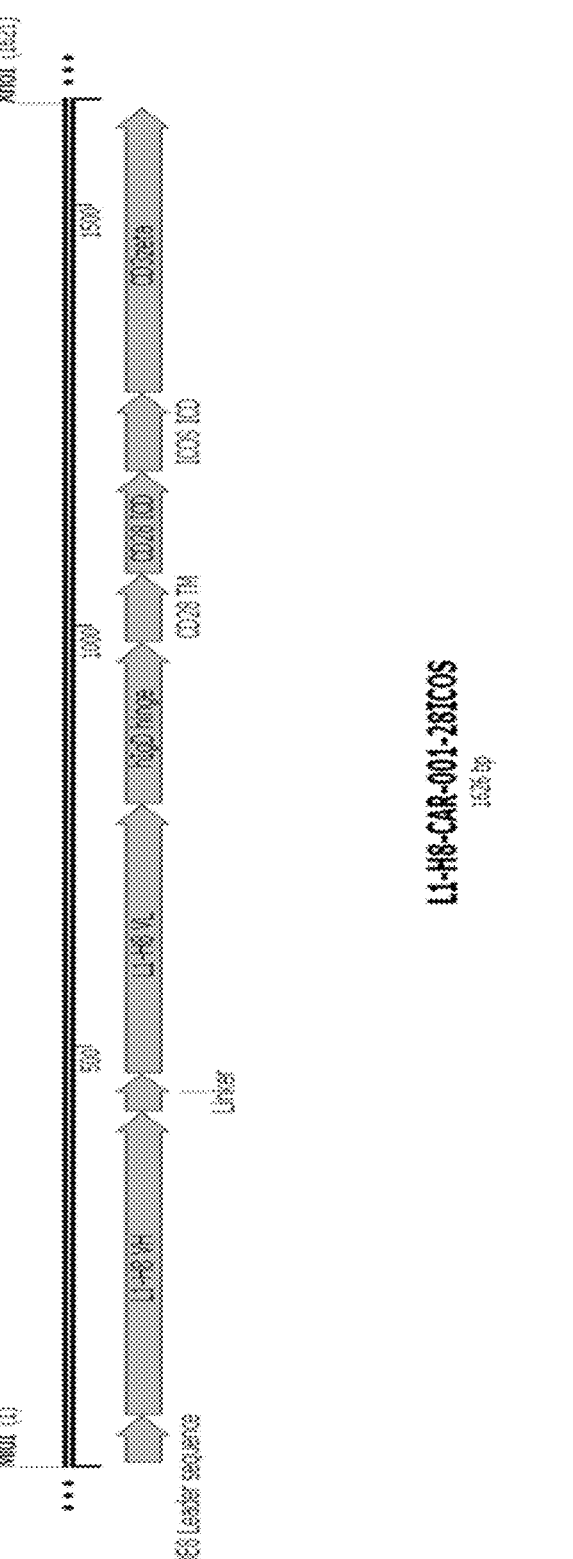
FIG. 35 shows a structure of the CAR-construct comprising anti-L1CAM scFv (L1-H8-CAR-001-28ICOS) constructed in the example of the present disclosure.

5.1.2.5. Obtainment of 3E8 LS, L1-H8 scFv, Hinge, TM, ICD, Costimulatory Domain, and CD3ζ Gene Mlu I-3E8 LS-L1-H8 scFv-hIgD hinge-CD28 TM-CD28 ICD-ICOS ICD-CD3ζ-iso1 and ICOS ICD-CD3ζ-iso1-Xho I, which were the amplified PCR products, as templates, were amplified by OE-PCR using the primers of SEQ ID NO: 70 (Table 12) and SEQ ID NO: 73 (Table 12) (FIG. 34). The amplified PCR product has the nucleotide sequence of Mlu I-3E8 LS-L1-H8 scFv-hIgD hinge-CD28 TM-CD28 ICD-ICOS ICD-CD3ζ-iso1-Xho I and a structure of L1-H8-CAR-001-28ICOS (FIG. 35).

5.1.3. Obtainment of L1-H8-CAR-001-28 Gene

5.1.3.1. Obtainment of 3E8 Antibody Leader Sequence (LS), L1-H8 scFv, Hinge, TM, and ICD Gene pMT-L1-H8-CAR-001 as a template was amplified by PCR using the primers of SEQ ID NO: 70 (Table 12) and SEQ ID NO: 93 (Table 12). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of CD28 ICD has the 12-nucleotide sequence of CD3ζ-iso1, and thus the amplified PCR product has the nucleotide sequence of Mlu I-3E8 LS-L1-H8 scFv-hIgD hinge-CD28 TM-CD28 ICD-CD3ζ-iso1 (Table 13). The amplified PCR product was used in the next PCR amplification process.

5.1.3.2. Obtainment of CD3ζ Gene pMT-L1-H8-CAR-001 as a template was amplified by PCR using the primers of SEQ ID NO: 94 (Table 12) and SEQ ID NO: 73 (Table 12). The primer binding to the 5' end of CD3ζ-iso1 has the 12-nucleotide sequence of CD28 ICD, and the primer binding to the 3' end of CD3ζ-iso1 has the nucleotide sequence of Xho I restriction enzyme, and thus the amplified PCR product has the nucleotide sequence of ICD28 ICD-CD3ζ-iso1-Xho I (Table 13). The amplified PCR product was used in the next PCR amplification process.

Figure 36:
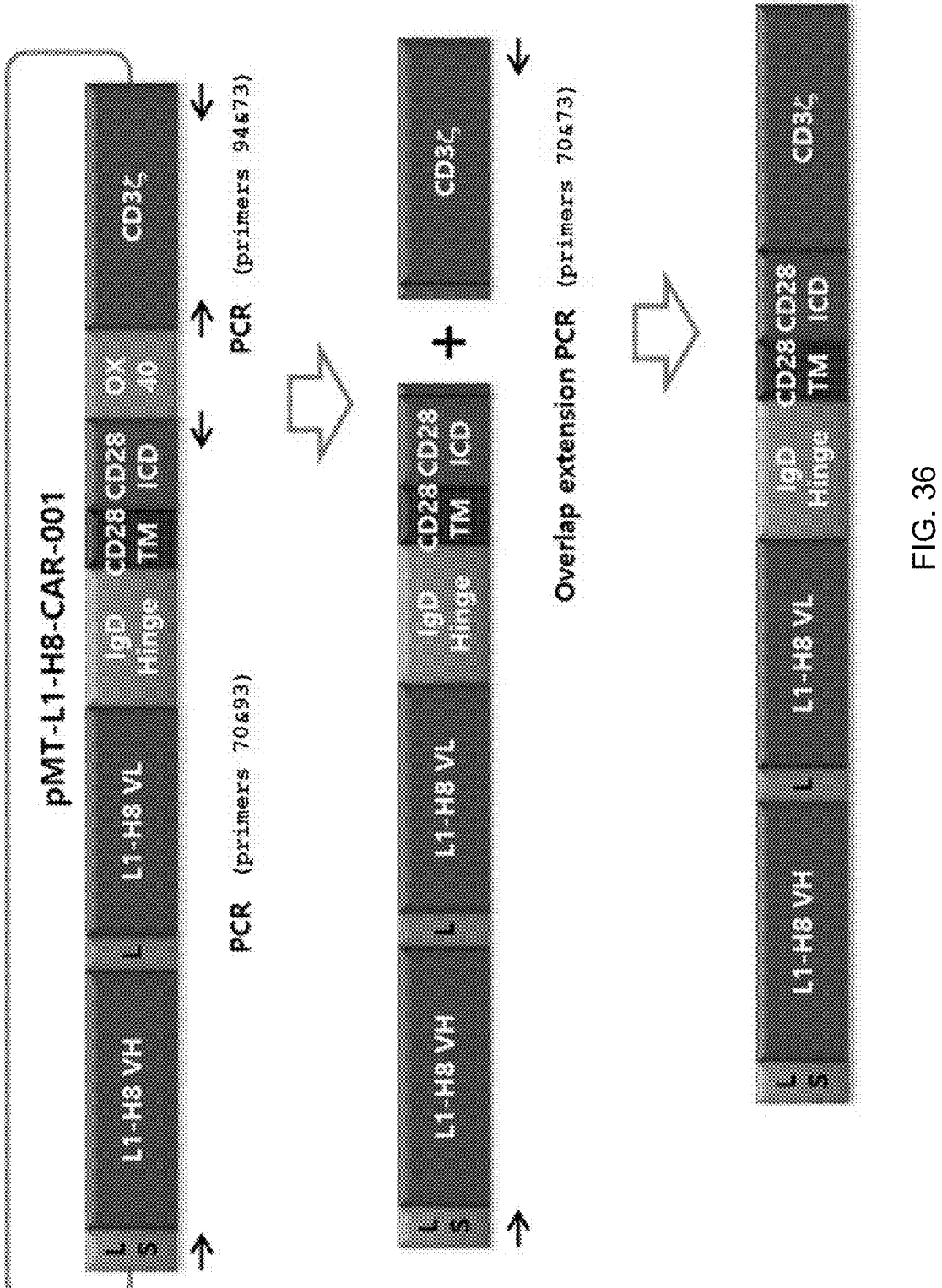
FIG. 36 is a schematic diagram showing a series of PCR amplification procedures in order to manufacture a CAR-construct comprising anti-L1CAM scFv.
Figure 37:
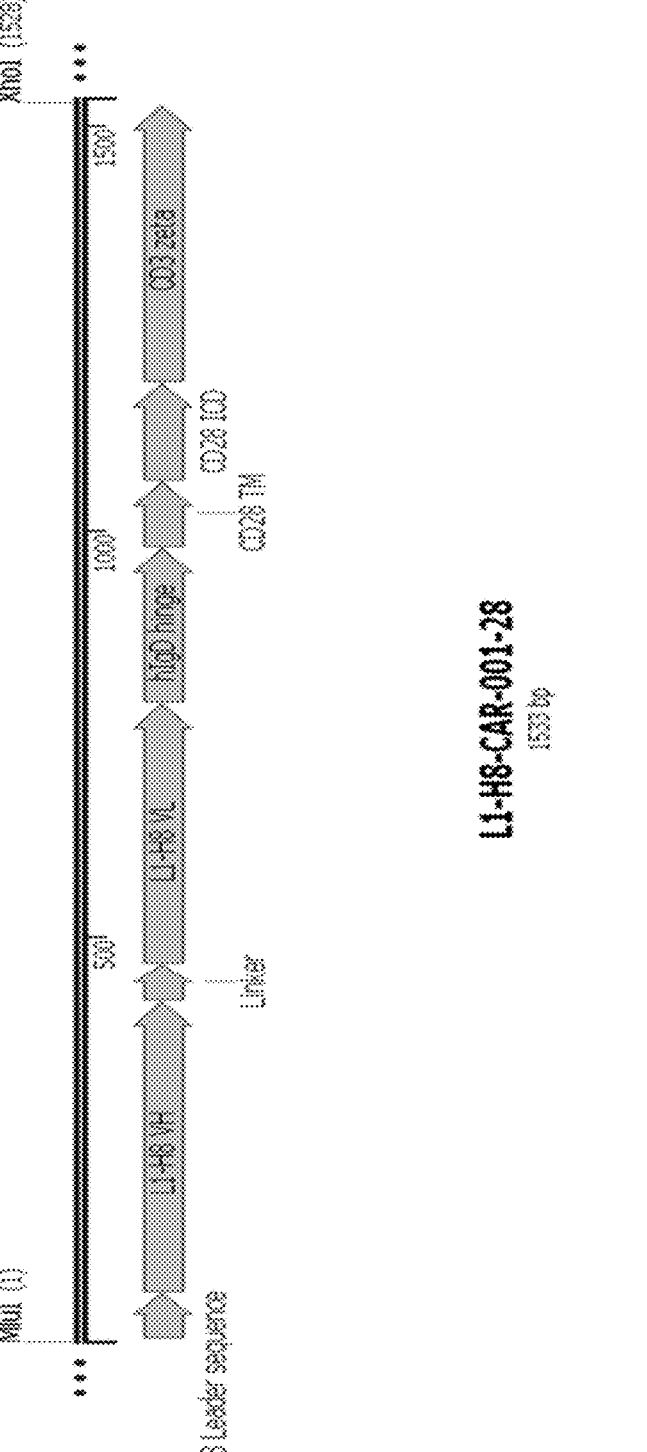
FIG. 37 shows a structure of the CAR-construct comprising anti-L1CAM scFv (L1-H8-CAR-001-28) constructed in the example of the present disclosure.

5.1.3.3. Obtainment of 3E8 LS, L1-H8 scFv, Hinge, TM, ICD, Costimulatory Domain, and CD3ζ Gene Mlu I-3E8 LS-L1-H8 scFv-hIgD hinge-CD28 TM-CD28 ICD-CD3ζ-iso1 and CD28 ICD-CD3ζ-iso1-Xho I, which were the amplified PCR products, as templates, were amplified by OE-PCR using the primers of SEQ ID NO: 70 (Table 12) and SEQ ID NO: 73 (Table 12) (FIG. 36). The amplified PCR product has the nucleotide sequence of Mlu I-3E8 LS-L1-H8 scFv-hIgD hinge-CD28 TM-CD28 ICD-CD3ζ-iso1-Xho I and a structure of L1-H8-CAR-001-28 (FIG. 37).

5.1.4. Obtainment of L1-H8-CAR-001-OX Gene

5.1.4.1. Obtainment of 3E8 Antibody Leader Sequence (LS), L1-H8 scFv, Hinge, and TM Gene pMT-L1-H8-CAR-001 as a template was amplified by PCR using the primers of SEQ ID NO: 70 (Table 12) and SEQ ID NO: 95 (Table 12). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of CD28 TM has the 12-nucleotide sequence of OX40, and thus the amplified PCR product has the nucleotide sequence of Mlu I-3E8 LS-L1-H8 scFv-hIgD hinge-CD28 TM-OX40 (Table 13). The amplified product was used in the next PCR amplification process.

5.1.4.2. Obtainment of Costimulatory Domain and CD3ζ Gene pMT-L1-H8-CAR-001 as a template was amplified by PCR using the primers of SEQ ID NO: 96 (Table 12) and SEQ ID NO: 73 (Table 12). The primer binding to the 5' end of OX40 has the 12-nucleotide sequence of CD28 TM, and the primer binding to the 3' end of CD3ζ-iso1 has the nucleotide sequence of Xho I restriction enzyme, and thus the amplified PCR product has the nucleotide sequence of CD28 TM-OX40-CD3ζ-iso1-Xho I (Table 13). The amplified PCR product was used in the next PCR amplification process.

Figure 38:
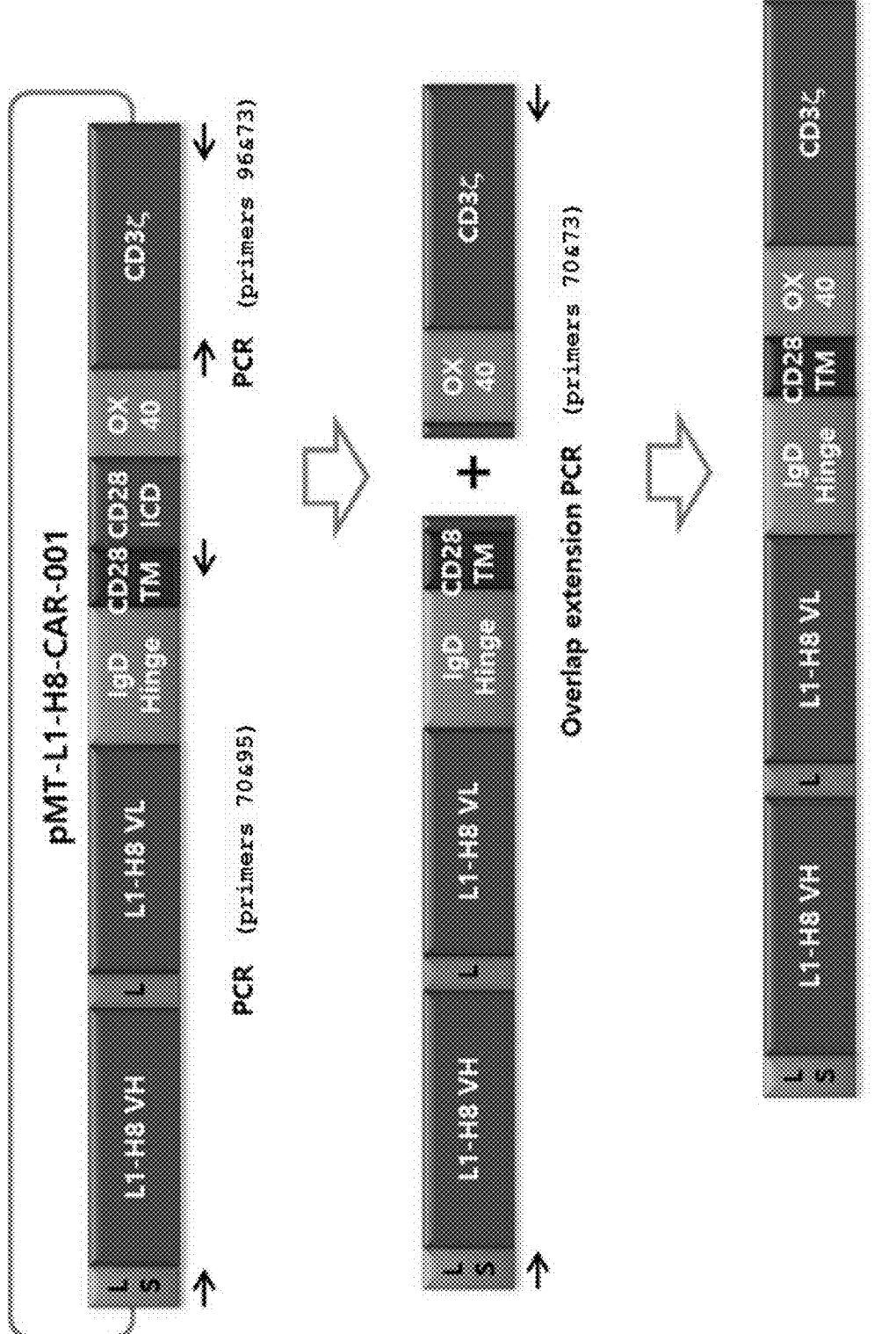
FIG. 38 is a schematic diagram showing a series of PCR amplification procedures in order to manufacture a CAR-construct comprising anti-L1CAM scFv.
Figure 39:
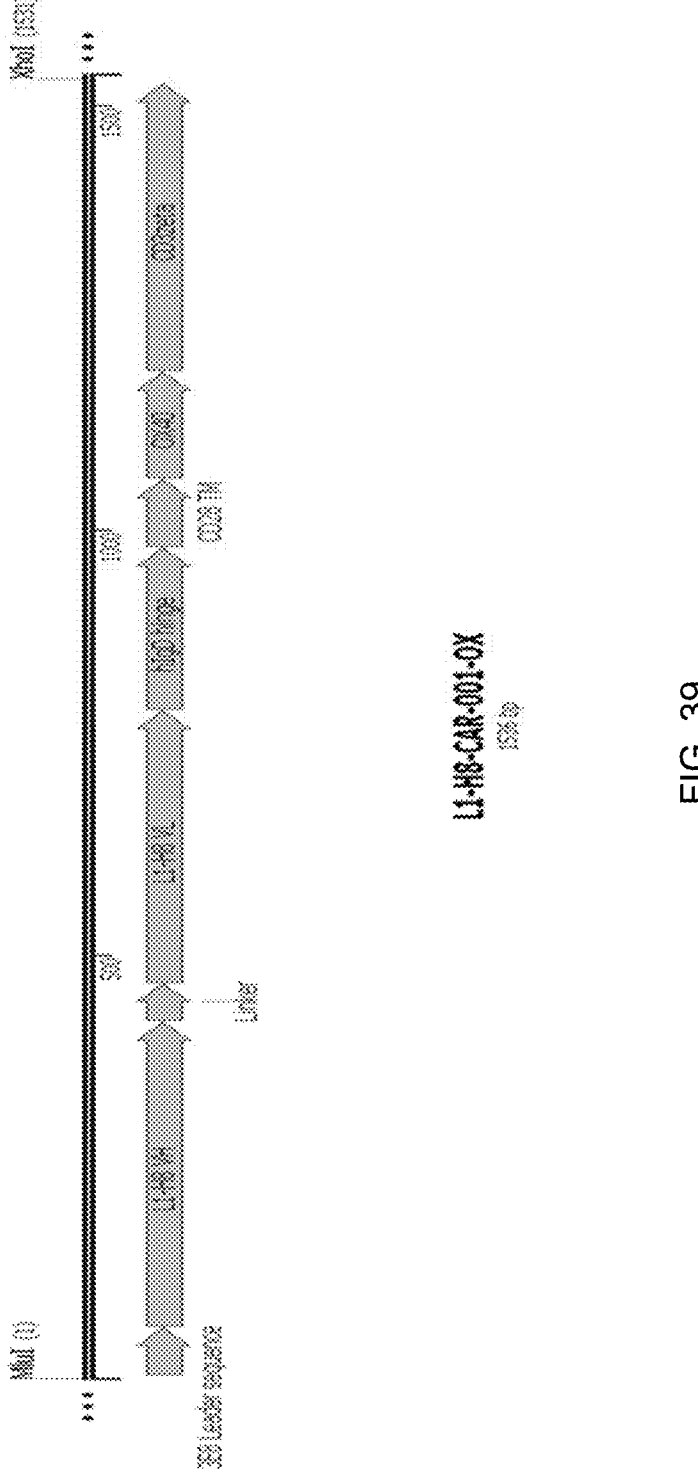
FIG. 39 shows a structure of the CAR-construct comprising anti-L1CAM scFv (L1-H8-CAR-001-OX) constructed in the example of the present disclosure.

5.1.4.3. Obtainment of 3E8 LS, L1-H8 scFv, Hinge, TM, Costimulatory Domain, and CD3ζ Gene Mlu I-3E8 LS-L1-H8 scFv-hIgD hinge-CD28 TM-OX40 and CD28 TM-OX40-CD3ζ-iso1-Xho I, which were the amplified PCR products, as templates, were amplified by OE-PCR using the primers of SEQ ID NO: 70 (Table 12) and SEQ ID NO: 73 (Table 12) (FIG. 38). The amplified PCR product has the nucleotide sequence of Mlu I-3E8 LS-L1-H8 scFv-hIgD hinge-CD28 TM-OX40-CD3ζ-iso1-Xho I and a structure of L1-H8-CAR-001-OX (FIG. 39).

5.1.5. Obtainment of L1-H8-CAR-001-BB Gene

5.1.5.1. Obtainment of 3E8 Antibody Leader Sequence (LS), L1-H8 scFv, Hinge, and TM Gene pMT-L1-H8-CAR-001 as a template was amplified by PCR using the primers of SEQ ID NO: 70 (Table 12) and SEQ ID NO: 97 (Table 12). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of CD28 TM has the 12-nucleotide sequence of 4-1BB, and thus the amplified PCR product has the nucleotide sequence of Mlu I-3E8 LS-L1-H8 scFv-hIgD hinge-CD28 TM-4-1BB (Table 13) The amplified product was used in the next PCR amplification process.

5.1.5.2. Obtainment of Costimulatory Domain and CD3ζ Gene pMT-L1-H8-CAR-004 (FIG. 30) as a template was amplified by PCR using the primers of SEQ ID NO: 98 (Table 12) and SEQ ID NO: 73 (Table 12). The primer binding to the 5' end of 4-1BB has the 12-nucleotide sequence of CD28 TM, and the primer binding to the 3' end of CD3ζ-iso1 has the nucleotide sequence of Xho I restriction enzyme, and thus the amplified PCR product has the nucleotide sequence of CD28 TM-4-1BB-CD3ζ-iso1-Xho I (Table 13). The amplified PCR product was used in the next PCR amplification process.

Figure 40:
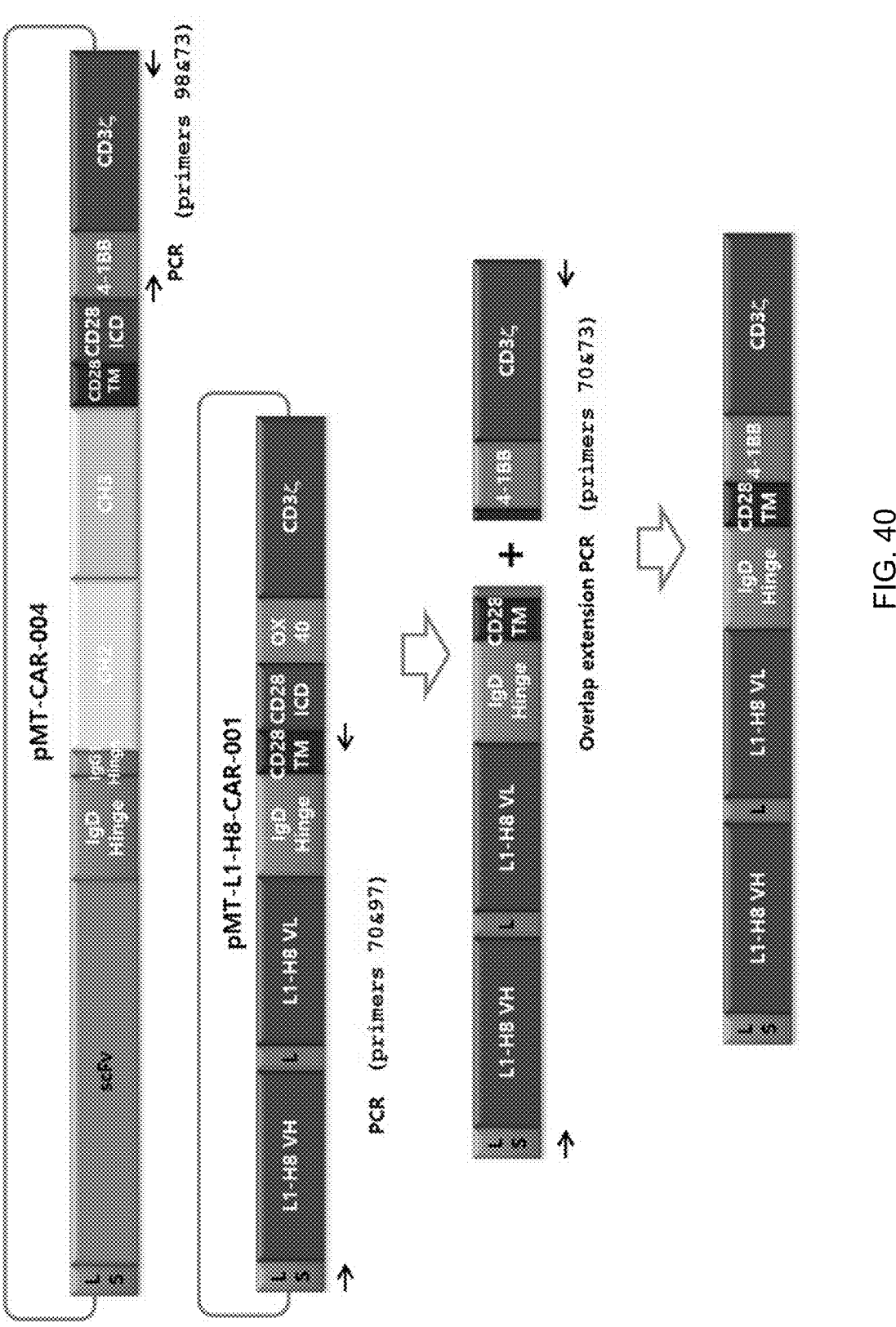
FIG. 40 is a schematic diagram showing a series of PCR amplification procedures in order to manufacture a CAR-construct comprising anti-L1CAM scFv.
Figure 41:
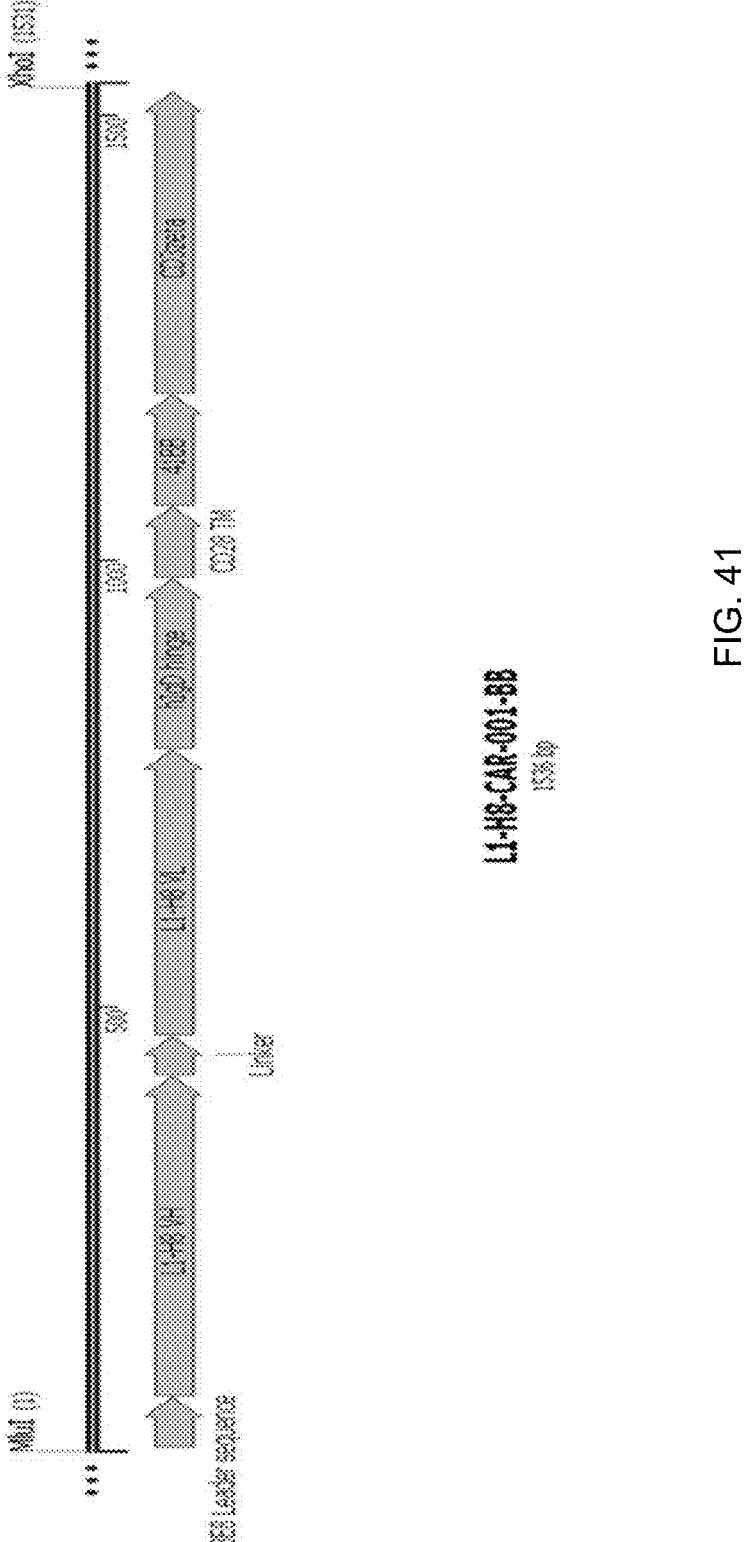
FIG. 41 shows a structure of the CAR-construct comprising anti-L1CAM scFv (L1-H8-CAR-001-BB) constructed in the example of the present disclosure.

5.1.5.3. Obtainment of 3E8 LS, L1-H8 scFv, Hinge, TM, Costimulatory Domain, and CD3ζ Gene Mlu I-3E8 LS-L1-H8 scFv-hIgD hinge-CD28 TM-4-1BB and CD28 TM-4-1BB-CD3ζ-iso1-Xho I, which were the amplified PCR products, as templates, were amplified by OE-PCR using the primers of SEQ ID NO: 70 (Table 12) and SEQ ID NO: 73 (Table 12) (FIG. 40). The amplified PCR product has the nucleotide sequence of Mlu I-3E8 LS-L1-H8 scFv-hIgD hinge-CD28 TM-4-1BB-CD3ζ-iso1-Xho I and a structure of L1-H8-CAR-001-BB (FIG. 41).

5.1.6. Obtainment of L1-H8-CAR-001-ICOS Gene

5.1.6.1. Obtainment of 3E8 Antibody Leader Sequence (LS), L1-H8 scFv, Hinge, and TM Gene pMT-L1-H8-CAR-001 as a template was amplified by PCR using the primers of SEQ ID NO: 70 (Table 12) and SEQ ID NO: 99 (Table 12). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of CD28 TM has the 13-nucleotide sequence of ICOS-ICD, and thus the amplified PCR product has the nucleotide sequence of Mlu I-3E8 LS-L1-H8 scFv-hIgD hinge-CD28 TM-ICOS ICD (Table 13). The amplified product was used in the next PCR amplification process.

5.1.6.2. Obtainment of Costimulatory Domain ICOS Gene

The pBHA-ICOS TM+ICD (FIG. 33) as a template was amplified by PCR using the primers of SEQ ID NO: 100 (Table 12) and SEQ ID NO: 91 (Table 12). The primer binding to the 5' end of ICOS ICD has the 12-nucleotide sequence of CD28 TM, and the primer binding to the 3' end of ICOS ICD has the nucleotide sequence of CD3ζ-iso1, and thus the amplified PCR product has the nucleotide sequence of CD28 TM-ICOS ICD-CD3ζ-iso1 (Table 13). The amplified PCR product was used in the next PCR amplification process.

5.1.6.3. Obtainment of CD3ζ Gene pMT-L1-H8-CAR-001 as a template was amplified by PCR using the primers of SEQ ID NO: 92 (Table 12) and SEQ ID NO: 73 (Table 12). The primer binding to the 5' end of CD3ζ-iso1 has the 12-nucleotide sequence of ICOS ICD, and the primer binding to the 3' end of CD3ζ-iso1 has the nucleotide sequence of Xho I restriction enzyme, and thus the amplified PCR product has the nucleotide sequence of ICOS ICD-CD3ζ-iso1-Xho I (Table 13). The amplified product was used in the next PCR amplification process.

Figure 42:
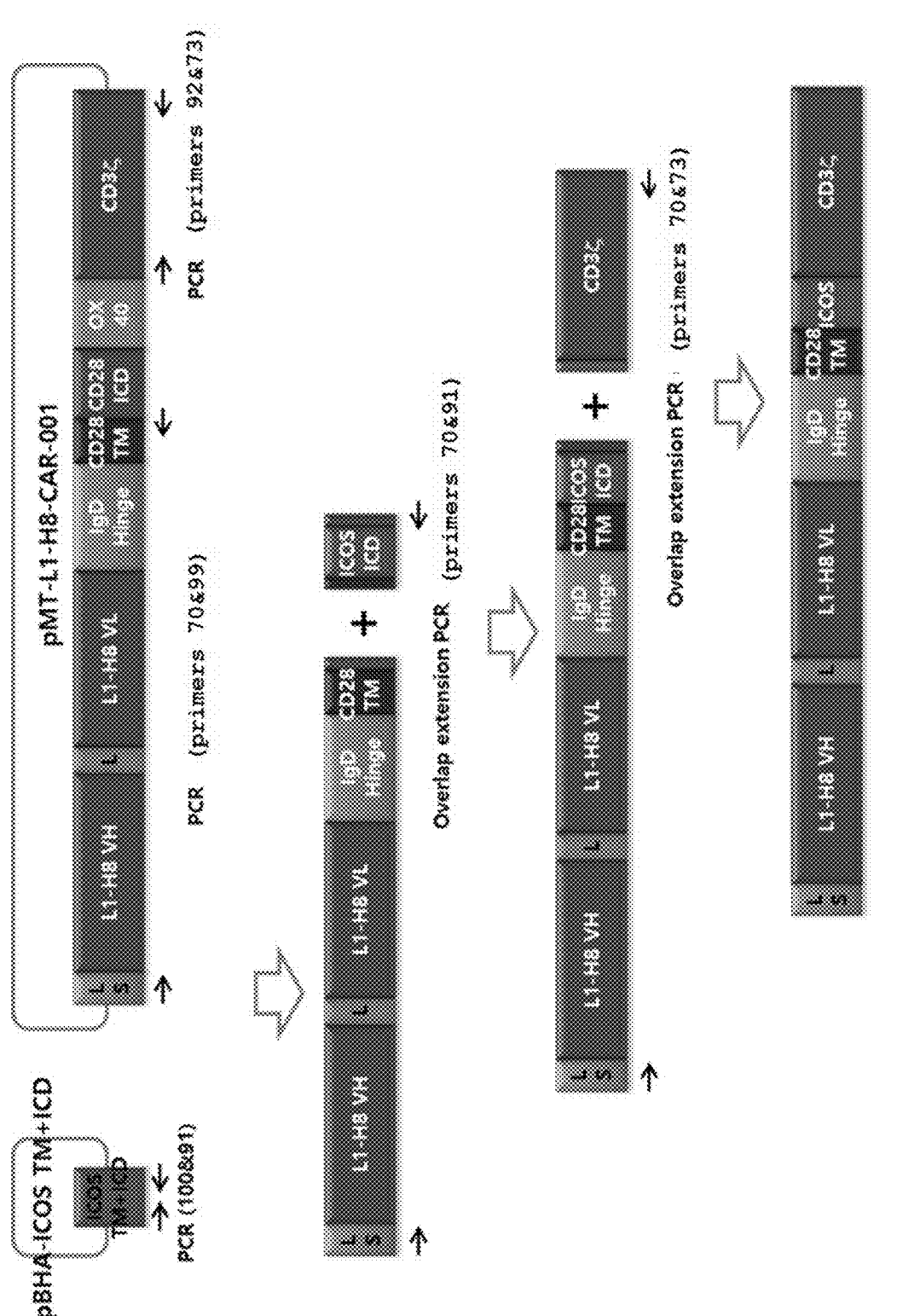
FIG. 42 is a schematic diagram showing a series of PCR amplification procedures in order to manufacture a CAR-construct comprising anti-L1CAM scFv.

5.1.6.4. Obtainment of 3E8 LS, L1-H8 scFv, Hinge, TM, and Costimulatory Domain Gene Mlu I-3E8 LS-L1-H8 scFv-hIgD hinge-CD28 TM-ICOS ICD and CD28 TM-ICOS ICD-CD3ζ-iso1, which were the amplified PCR products, as templates, were amplified by OE-PCR using the primers of SEQ ID NO: 70 (Table 12) and SEQ ID NO: 91 (Table 12) (FIG. 42). The amplified

5.2. Preparation of Retroviruses Expressing L1-H8-CAR Genes with Various Costimulatory Domain Structures Seven types of retroviruses expressing L1-H8-CAR-001 and L1-H8-CAR-001-28BB, -28ICOS, -28, -OX, -BB, and -ICOS were prepared by the same method as in Example 4.2.

5.3. Preparation of T Cells Expressing L1-H8-CAR Genes with Various Costimulatory Domain Structures Seven types of L1-H8-CAR-T were prepared by the same method as in Example 4.3. The results verified that although there is a difference depending on the donor, the expression rate of L1-H8-CAR was about 7.7% to 88.4% on day 7 or day 8 of incubation, about 9.0% to 82.4% on day 11 of incubation, and about 6.7% to 89.8% on day 15 or day 17 of incubation (Table 14).

TABLE 14

| | | | | | | | | | |
|---|---|---|---|---|---|---|---|---|---|
| Expression rates of L1-H8-CAR on surfaces of L1-H8-CAR-expressing T cells | | | | | | | | | |
| Donor NO. | Days of incubation | Control | L1-H8-CAR-001 | L1-H8-CAR-001-28BB | L1-H8-CAR-001-28ICOS | L1-H8-CAR-001-28 | L1-H8-CAR-001-OX | L1-H8-CAR-001-BB | L1-H8-CAR-001-ICOS |
| 39 | 8 Days | 1.14% | 76.8% | 68.7% | 75.4% | 31.9% | 88.4% | 63.6% | 67.4% |
| | 15 Days | 0.96% | 79.0% | 72.4% | 74.6% | 33.3% | 89.8% | 59.3% | 65.6% |
| 37 | 7 Days | 1.87% | 66.1% | 65.2% | 68.8% | 76.7% | 7.7% | 52.7% | 62.5% |
| | 11 Days | 0.39% | 64.8% | 46.4% | 58.6% | 74.0% | 9.0% | 31.8% | 52.6% |
| | 17 Days | 0.41% | 62.4% | 58.3% | 62.5% | 83.2% | 6.7% | 35.2% | 50.5% |
| 40 | 7 Days | 2.21% | 60.0% | 59.8% | 64.3% | 76.3% | 11.3% | 50.5% | 55.3% |
| | 11 Days | 0.90% | 70.7% | 53.2% | 67.1% | 82.4% | 12.2% | 39.9% | 59.2% |
| | 17 Days | 0.32% | 86.3% | 82.4% | 80.6% | 88.5% | 33.9% | 65.5% | 67.4% |

PCR product has the nucleotide sequence of Mlu I-3E8 LS-L1-H8 scFv-hIgD hinge-CD28 TM-ICOS ICD-CD3ζ-iso1 (Table 13). The amplified PCR product was used in the next PCR amplification process.

Figure 43:
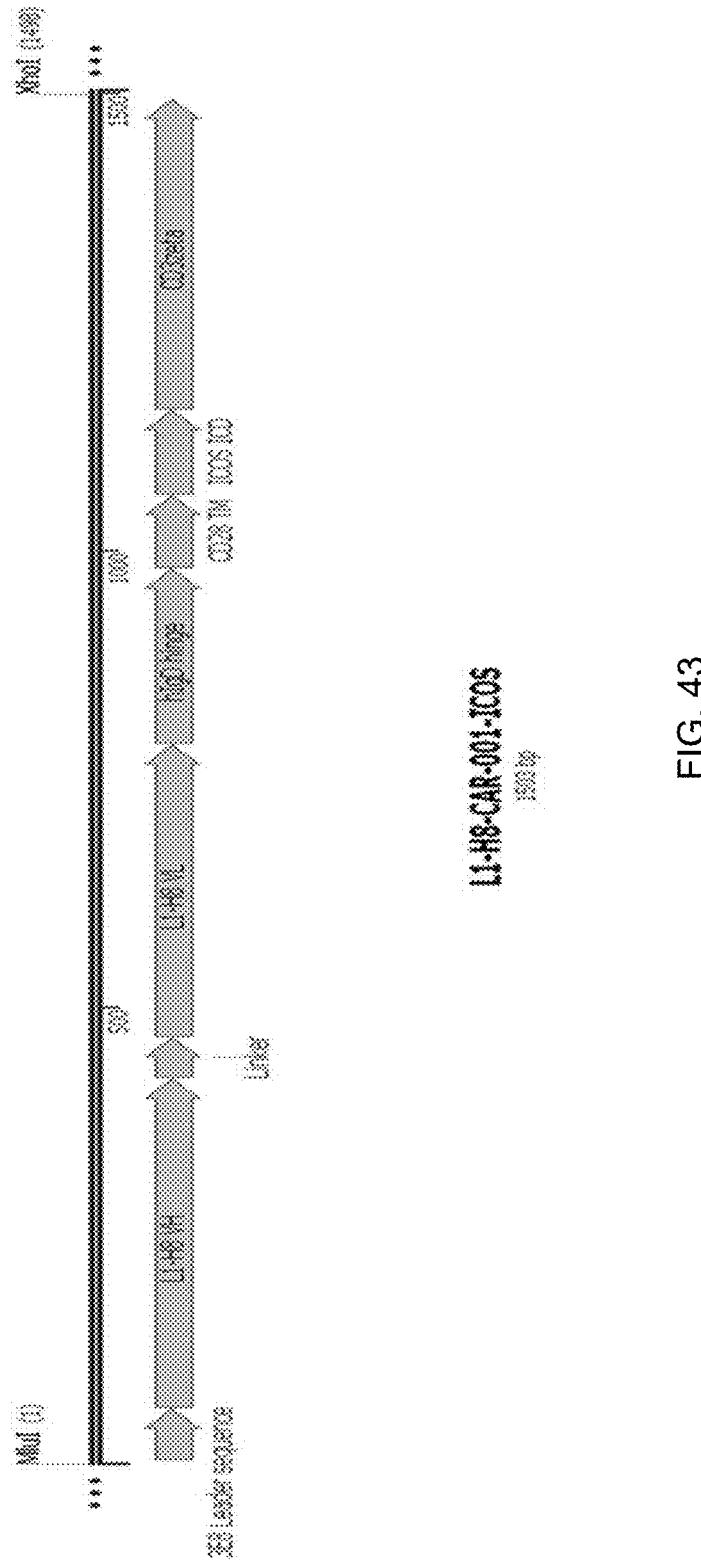
FIG. 43 shows a structure of the CAR-construct comprising anti-L1CAM scFv (L1-H8-CAR-001-ICOS) constructed in the example of the present disclosure.
Figure 44A:
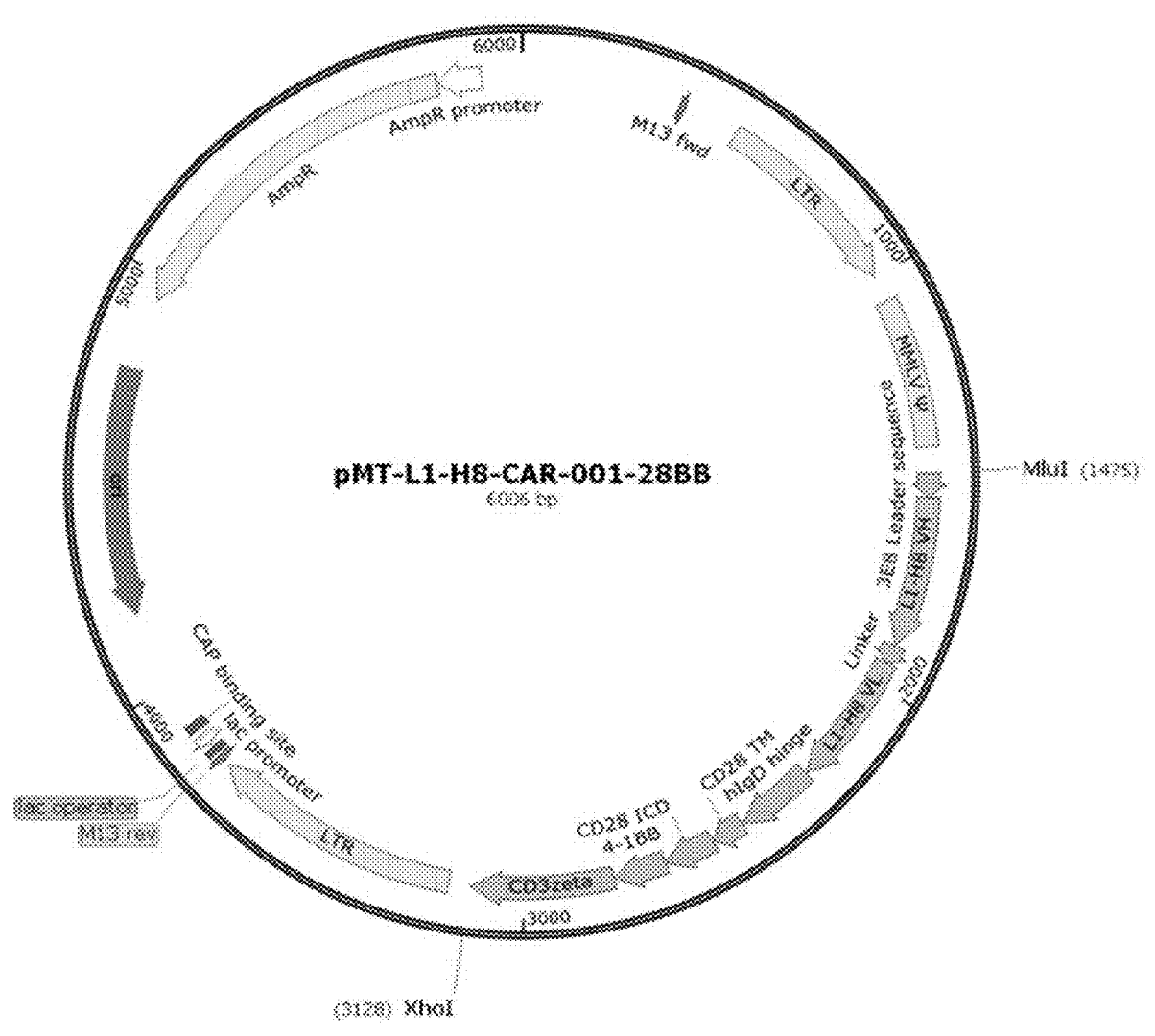
FIGS. 44A, 44B, 44C, 44D, 44E to 44F show retroviral vectors into which six types of CAR-constructs comprising the anti-L1 CAM scFv (L1-H8-CAR-001-28BB, L1-H8-CAR-001-28ICOS, L1-H8-CAR-001-28, L1-H8-CAR-001-OX, L1-H8-CAR-001-BB, and L1-H8-CAR-001-ICOS) of the present disclosure were introduced.
Figure 44B:
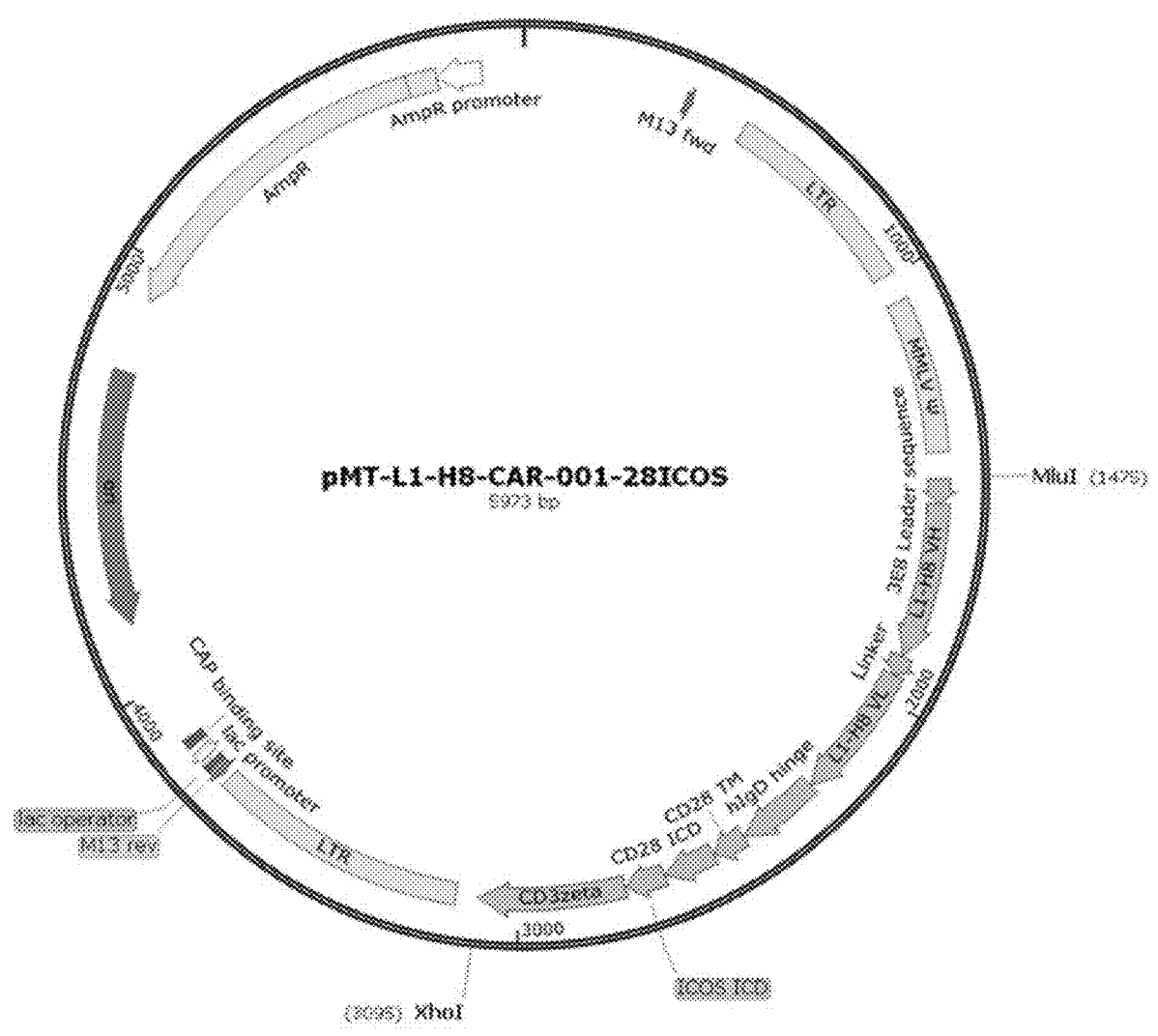
Figure 44C:
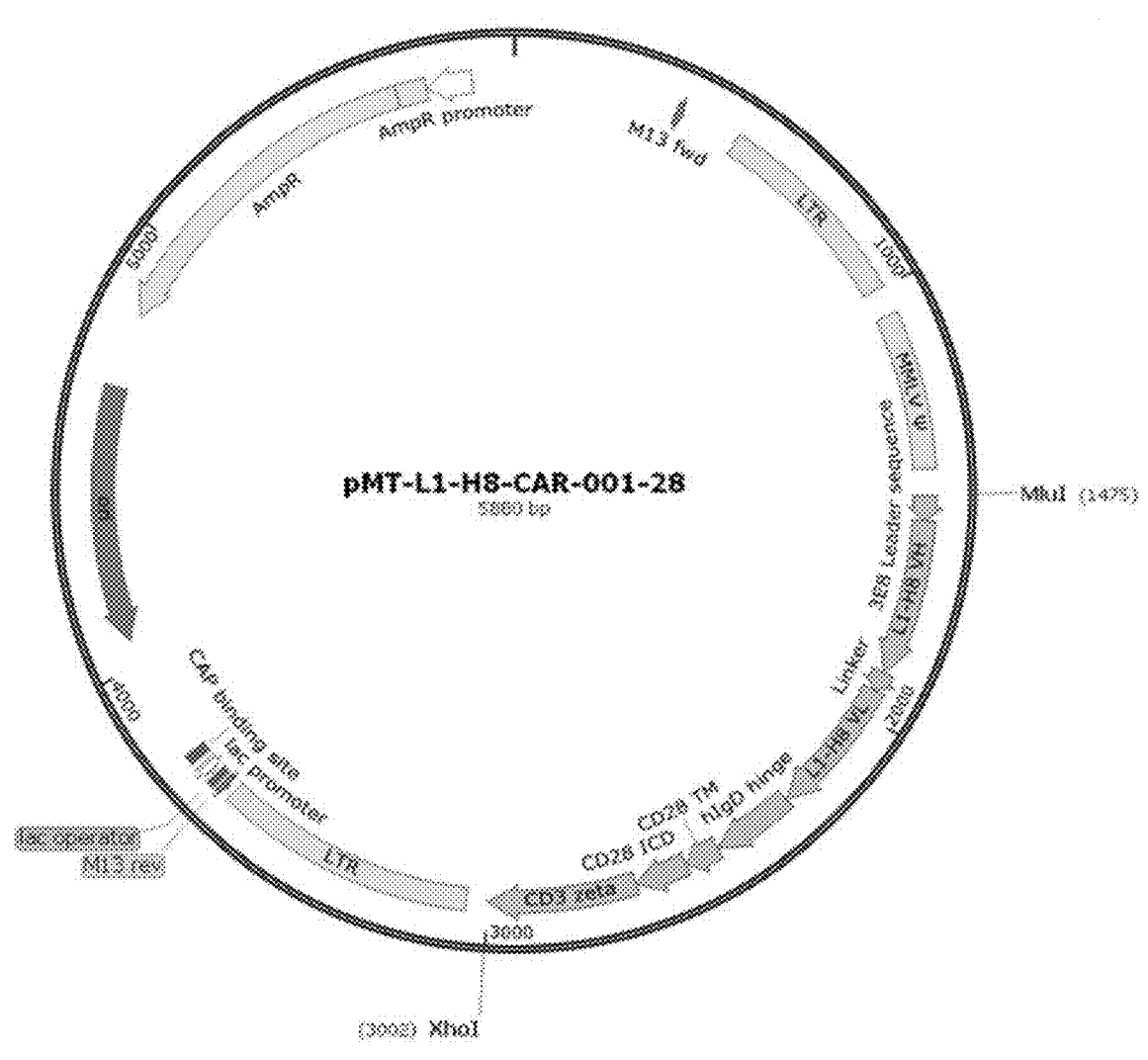
Figure 44D:
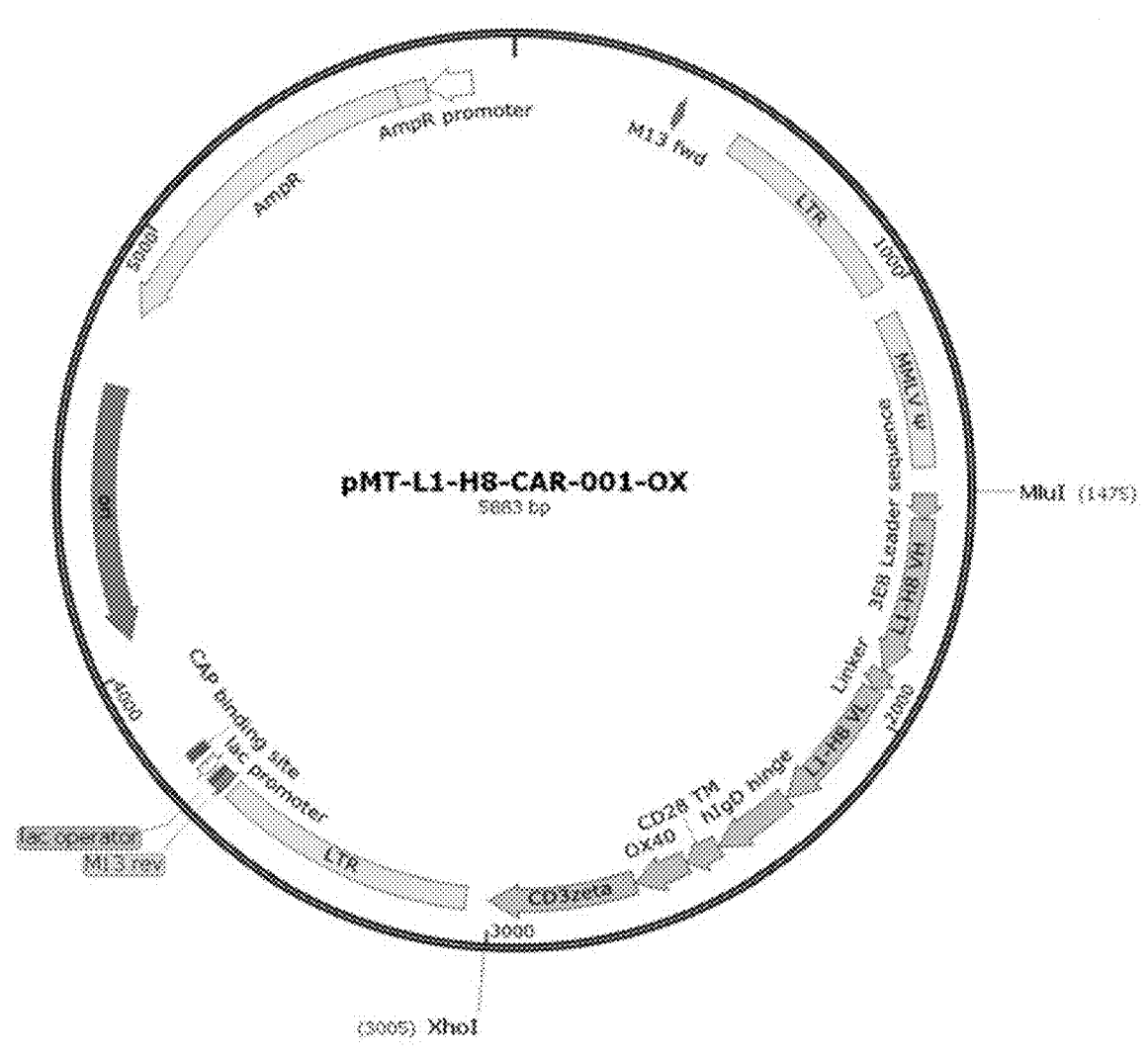
Figure 44E:
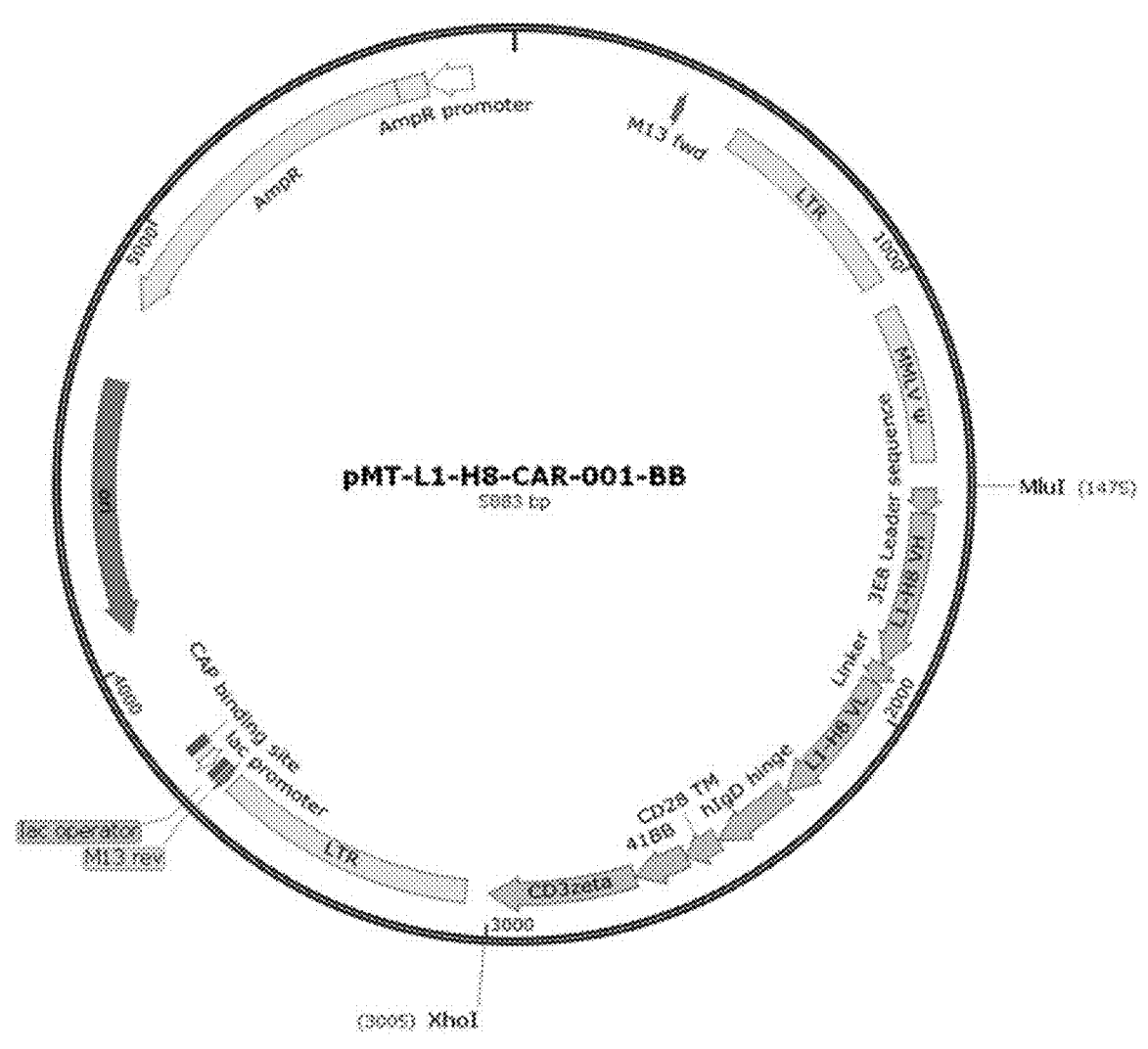
Figure 44F:
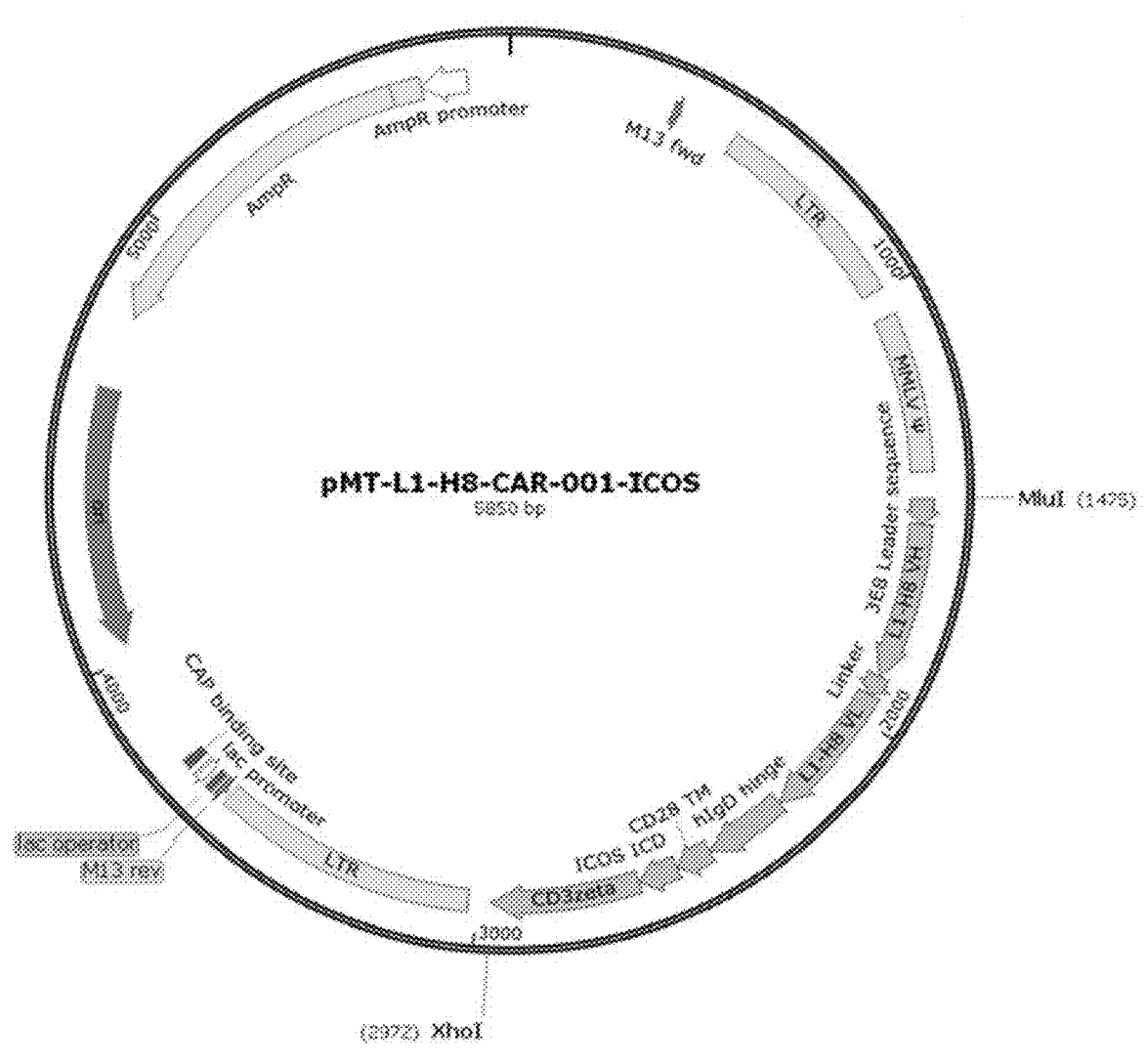

5.1.6.5. Obtainment of 3E8 LS, L1-H8 scFv, Hinge, TM, ICD, Costimulatory Domain, and CD3ζ Gene Mlu I-3E8 LS-L1-H8 scFv-hIgD hinge-CD28 TM-ICOS ICD-CD3ζ-iso1 and ICOS ICD-CD3ζ-iso1-Xho I, which were the amplified PCR products, as templates, were amplified by OE-PCR using the primers of SEQ ID NO: 70 (Table 12) and SEQ ID NO: 73 (Table 12) (FIG. 42). The amplified PCR product has the nucleotide sequence of Mlu I-3E8 LS-L1-H8 scFv-hIgD hinge-CD28 TM-ICOS ICD-CD3ζ-iso1-Xho I and a structure of L1-H8-CAR-001-ICOS (FIG. 43).

5.1.7. Preparation of pMT-L1-H8-CAR Retroviral Vectors

Six types of the amplified PCR products were treated with Mlu I and Xho I restriction enzymes to obtain DNA fragments. The obtained DNA fragments were ligated to the pMT retroviral vectors (U.S. Pat. No. 6,451,595) previously treated with Mlu I and Xho I restriction enzymes to prepare six types of pMT-L1-H8-CAR retroviral vectors (FIG. 44). The pMT-L1-H8-CAR retroviral vectors thus prepared include sequences encoding L1-H8-CAR under the control of the MLV LTR promoter.

5.4. Verification of Anticancer Activity of T Cells Expressing L1-H8-CAR Genes with Various Spacer Domain Structures (In Vitro)

5.4.1. Verification of Expression Rates of L1CAM in Target Cells

Figure 45A:
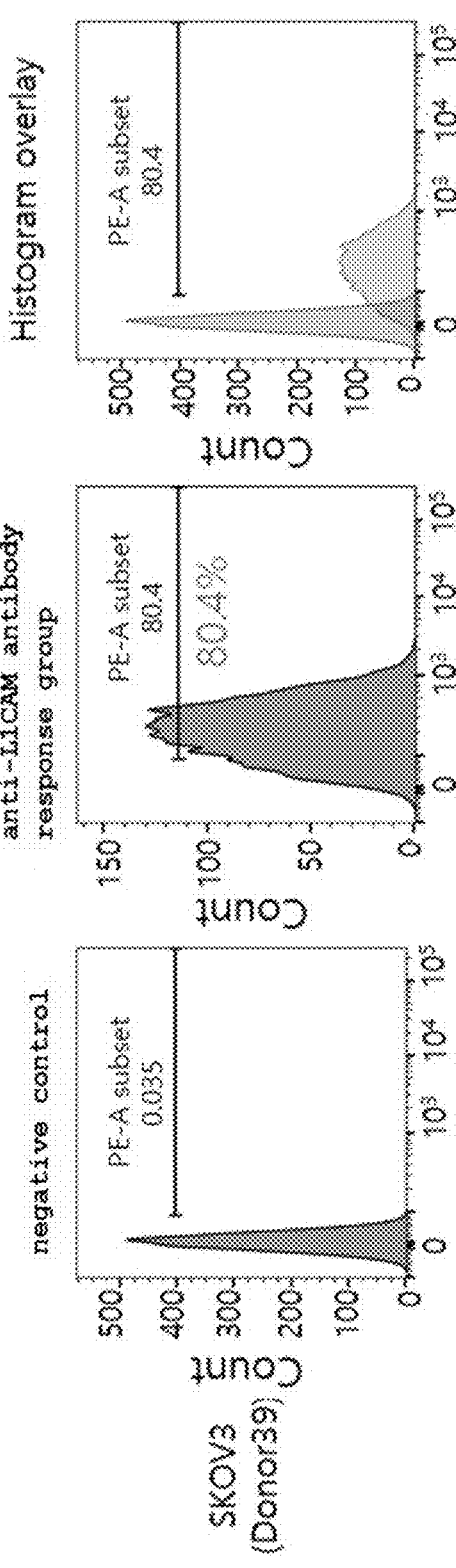
FIGS. 45A, 45B, 45C, 45D, 45E, 45F, 45G, 45H to 45I show the expression rates of L1CAM in SKOV3 cells, SH-SY5Y cells, HeLa cells, and 293T cells.
Figure 45B:
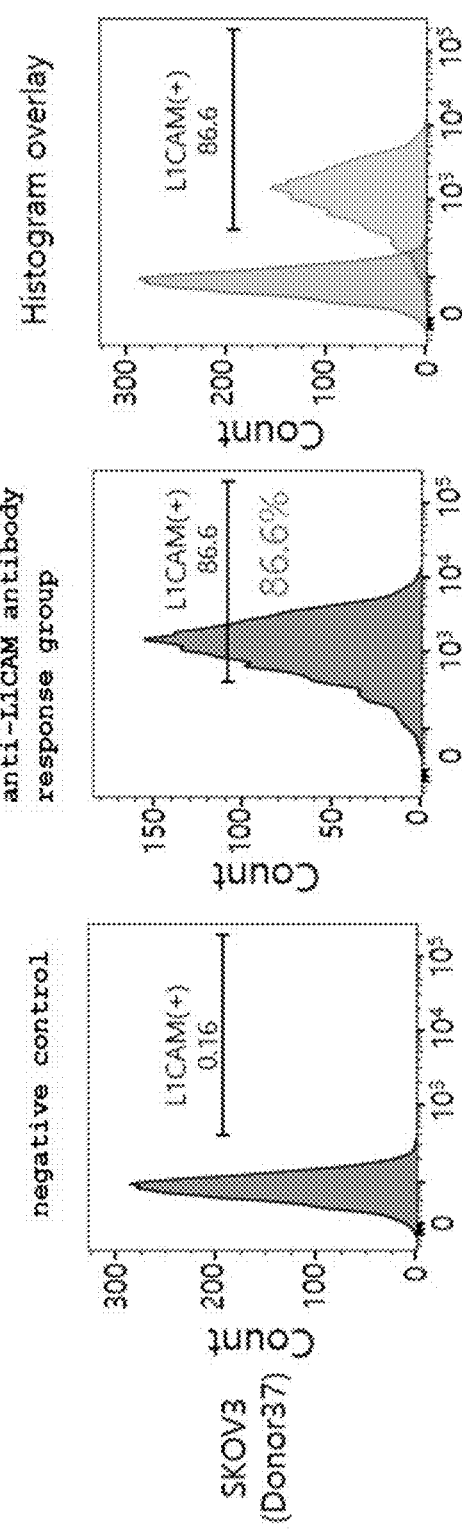
Figure 45C:
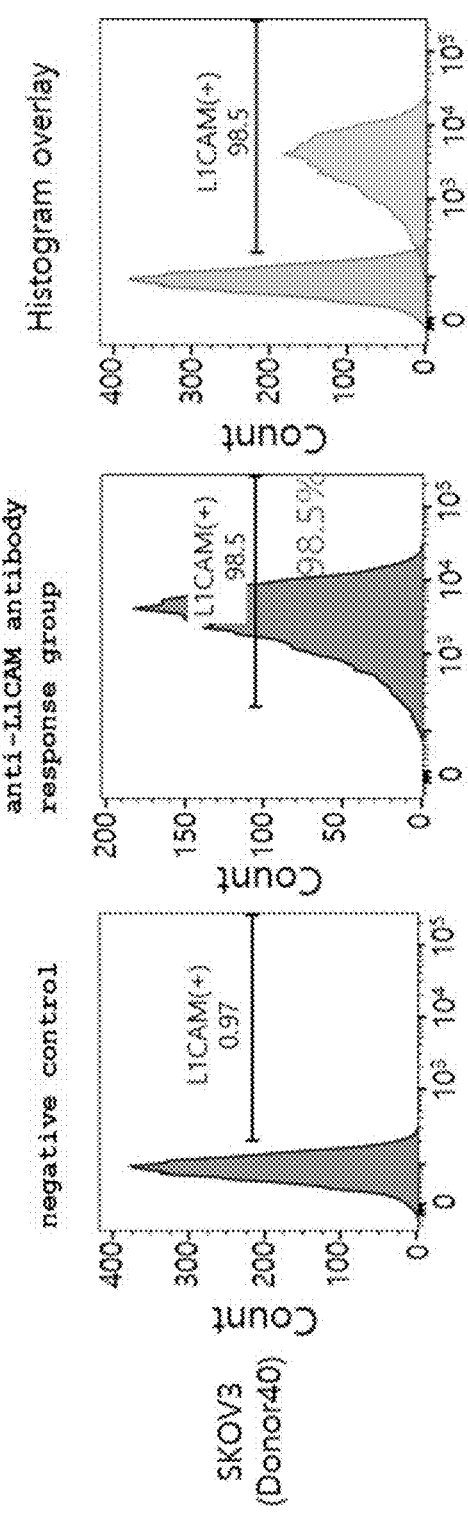
Figure 45D:
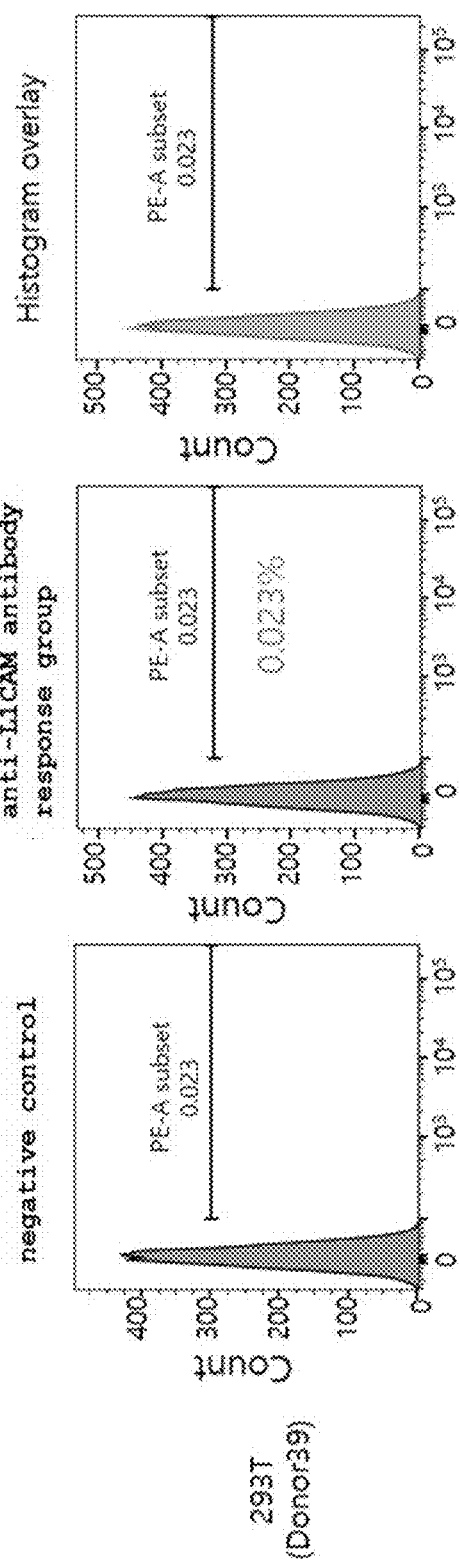
Figure 45E:
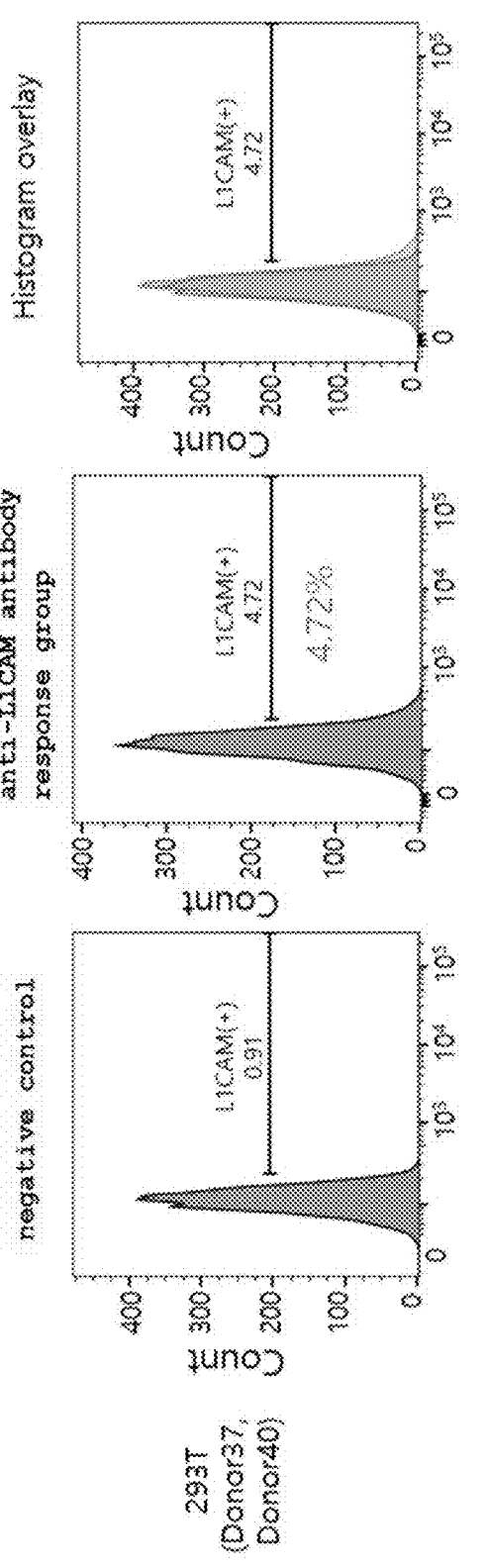
Figure 45F:
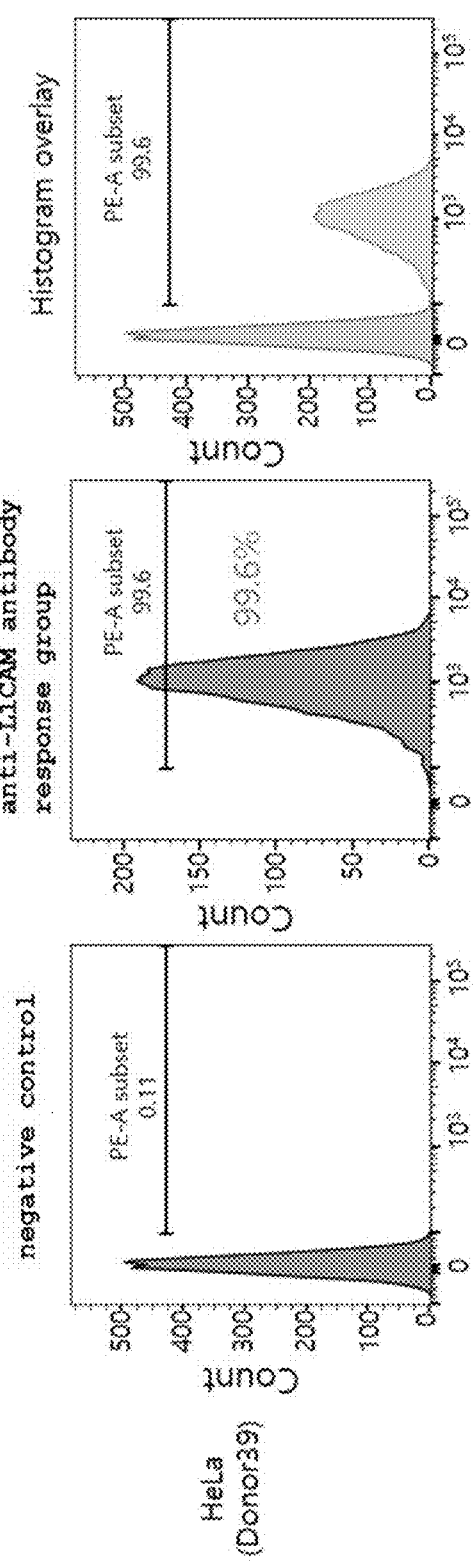
Figure 45G:
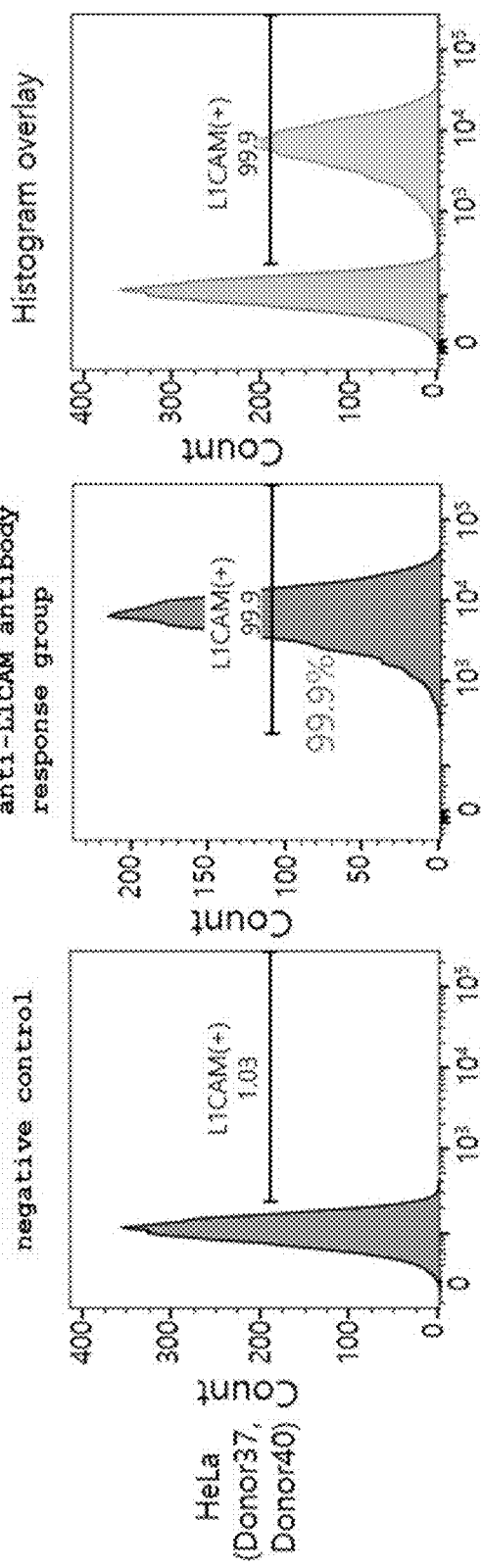
Figure 45H:
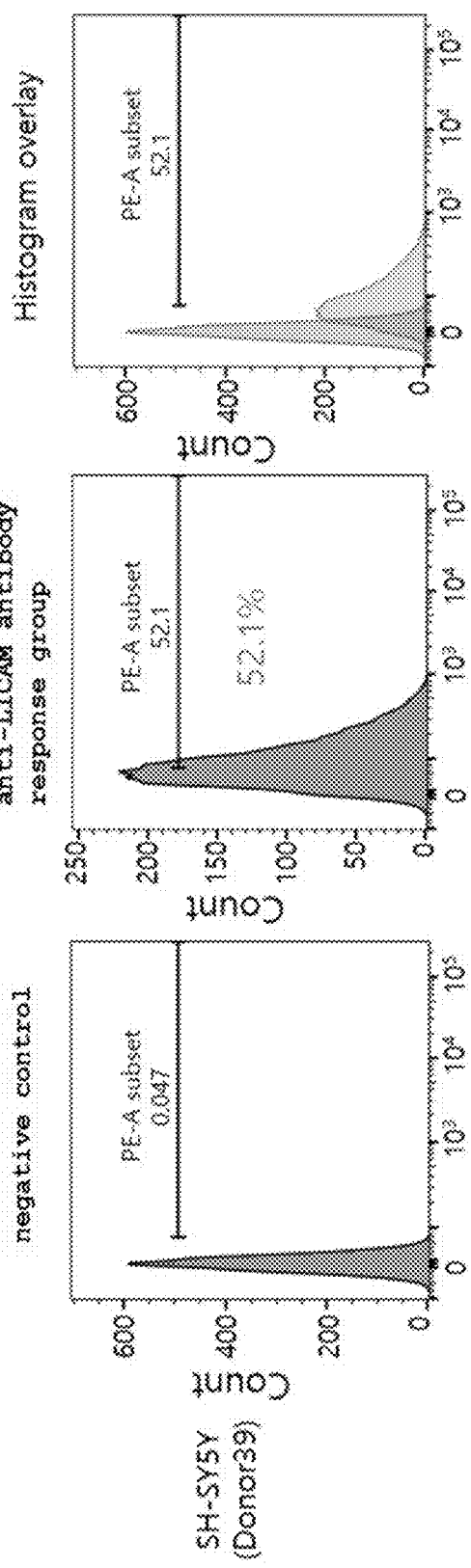
Figure 45I:
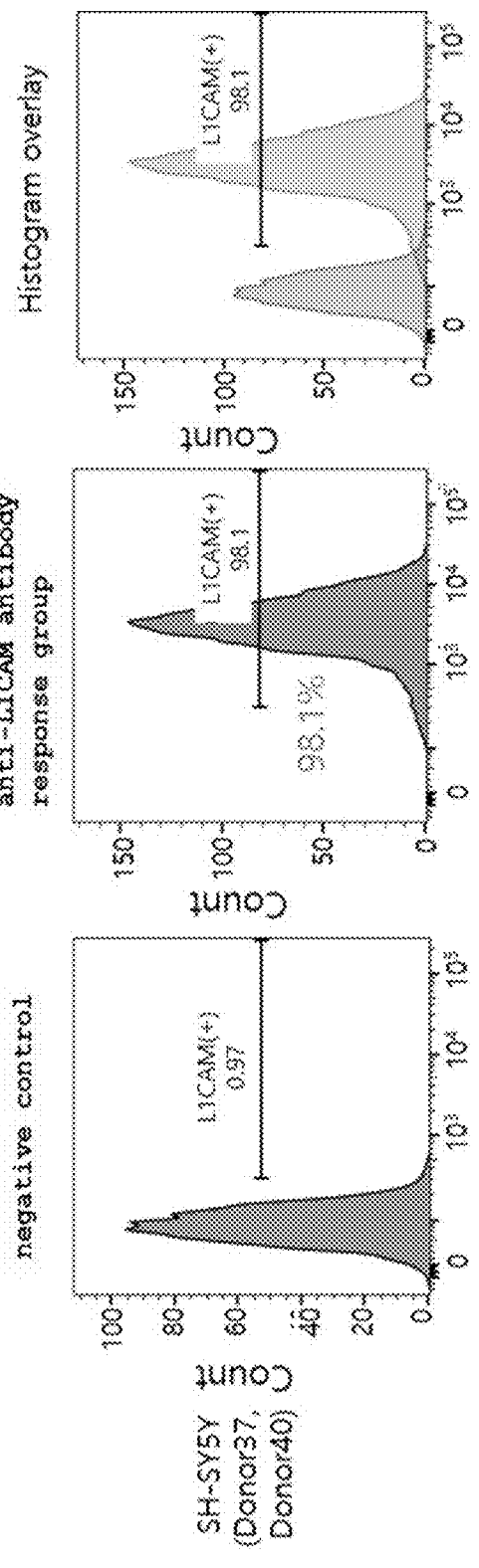

The expression rate of L1CAM in target cells was investigated by the same method as in Example 4.4.1. The results verified that the L1CAM expression rate was about 80.4 to 98.5% in SKOV3 cancer cells (FIGS. 45A to 45C). As a result of investigating the expression of L1CAM in the human cervical cancer cell line HeLa, the human neuroblastoma cell line SH-SY5Y, and the human embryonic kidney cell line 293T by the same method, the expression rate was about 99.6 to 99.9% in HeLa (FIGS. 45F and 45G), about 52.1 to 98.1% in SH-SY5Y (FIGS. 45H and 45I), and about 0.023 to 4.72% in 293T (FIGS. 45D and 45E).

5.4.2. Verification of Anticancer Activity of L1CAM-Expressing T Cells on Target Cells (In Vitro)

5.4.2.1. Verification of Anticancer Activity Using xCelligence Assay

Figure 46:
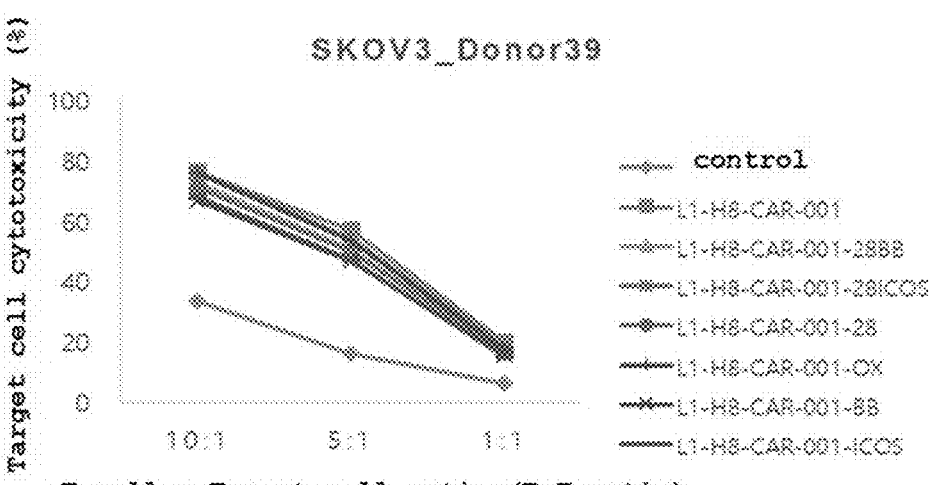
FIG. 46 shows anticancer activity of anti-L1CAM-CAR-expressing T cells of the present disclosure on SKOV3 cells (high expression of L1CAM).
Figure 46:
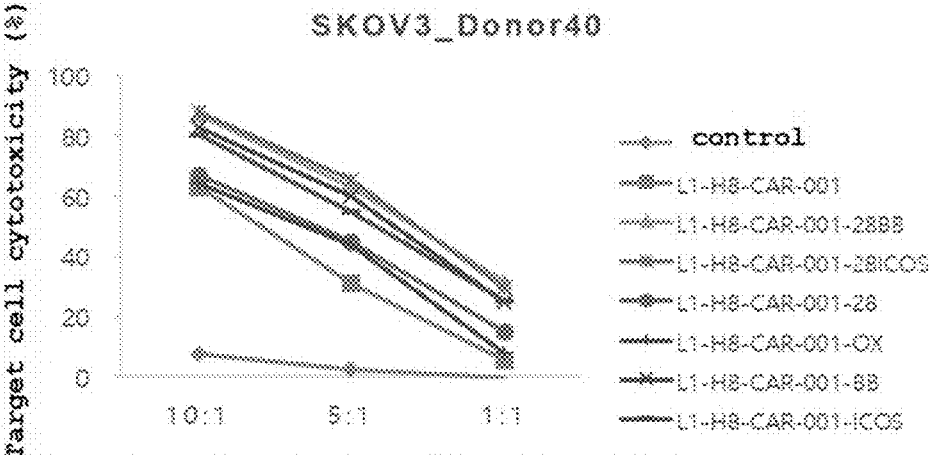
Figure 46:
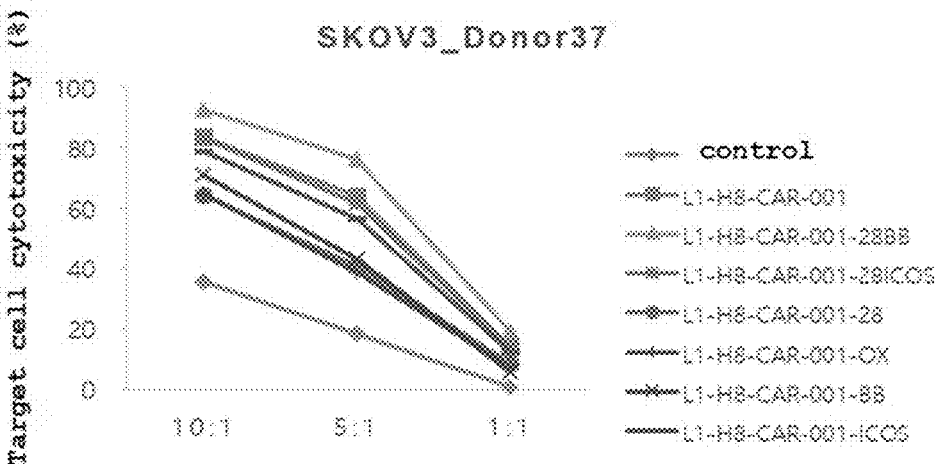

The activity of seven types of L1-H8-CAR on SKOV3 was investigated by the same method as in Example 4.4.2.1. As a result, seven types of T cells expressing L1-H8-CAR-001 and L1-H8-CAR-001-28BB, -28ICOS, -28, -OX, -BB, and -ICOS showed high cytotoxicity on SKOV3 cells compared with T cells not expressing L1-H8-CAR (control) (FIG. 46).

Figure 47:
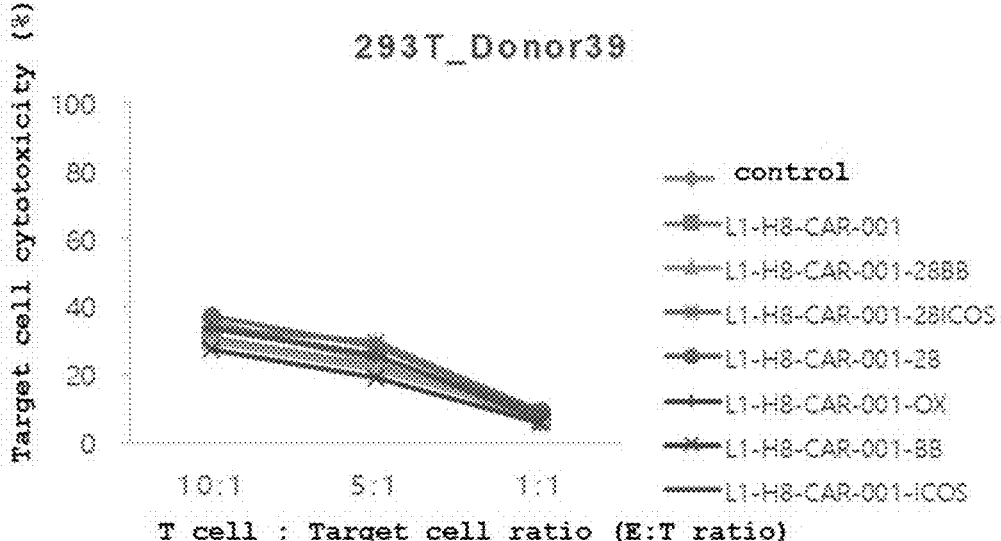
FIG. 47 shows anticancer activity of anti-L1CAM-CAR-expressing T cells of the present disclosure on 293T cells (low expression of L1CAM).
Figure 47:
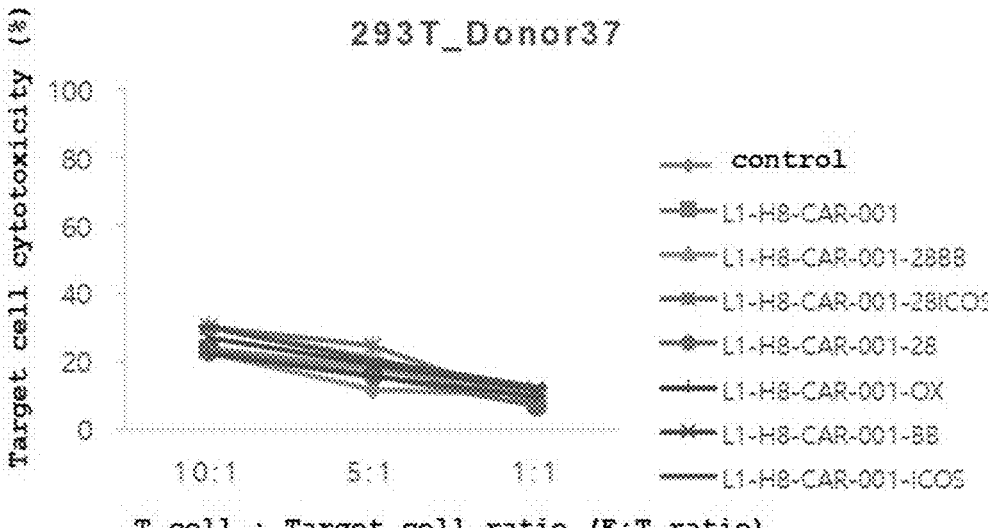

The cytotoxicity on 293T cells were investigated by the same method as in Example 4.4.2.1. As a result, all the seven types showed similar cytotoxicity to the control in 293T cells showing a low expression rate of L1CMA (FIG. 47).

5.4.2.2. Verification of Anticancer Activity Using CellTox™ Green Dye

Figure 48A:
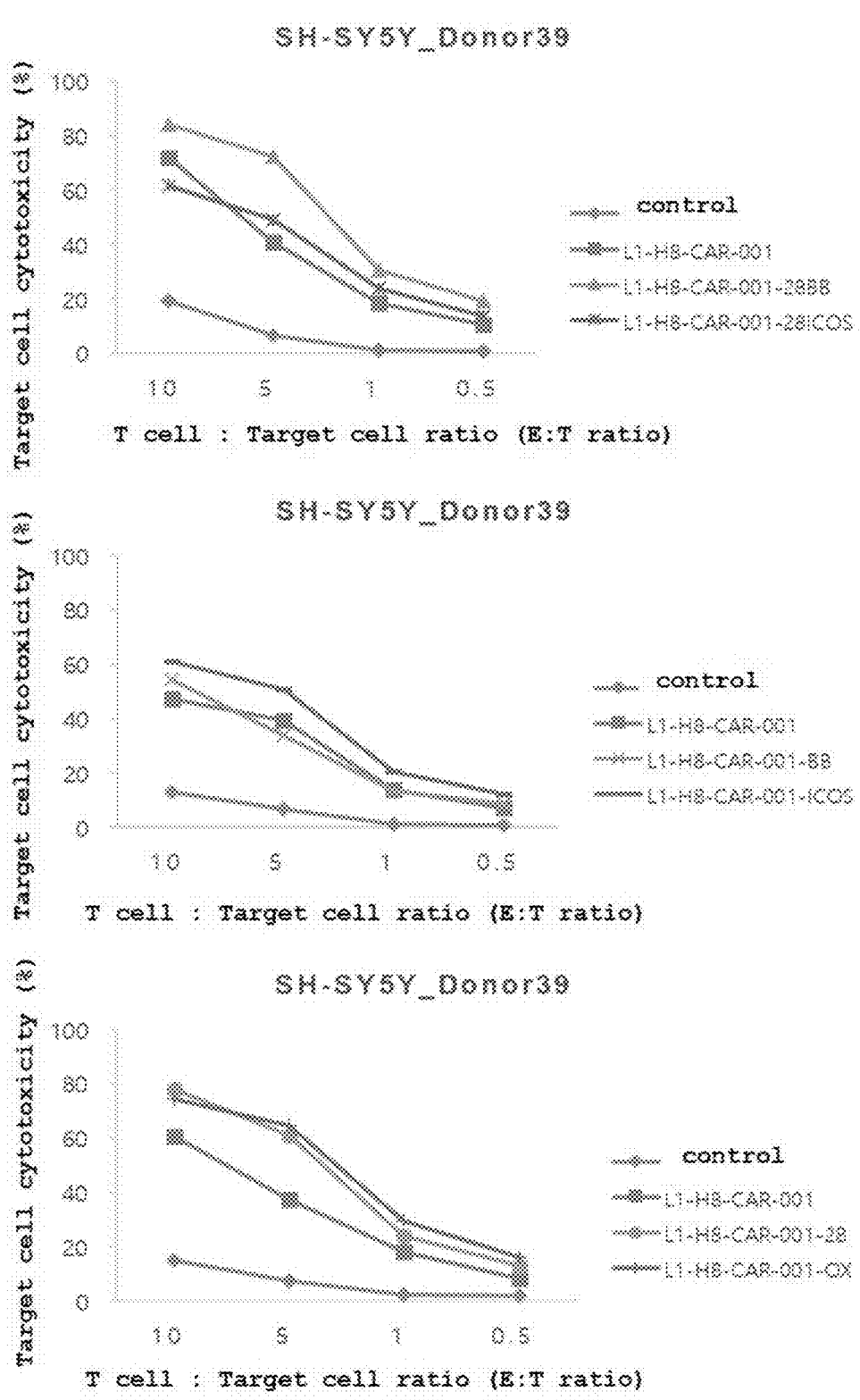
FIGS. 48A, 48B to 48C show anticancer activity of anti-L1CAM-CAR-expressing T cells of the present disclosure on SH-SY5Y cells (high expression of L1CAM).
Figure 48B:
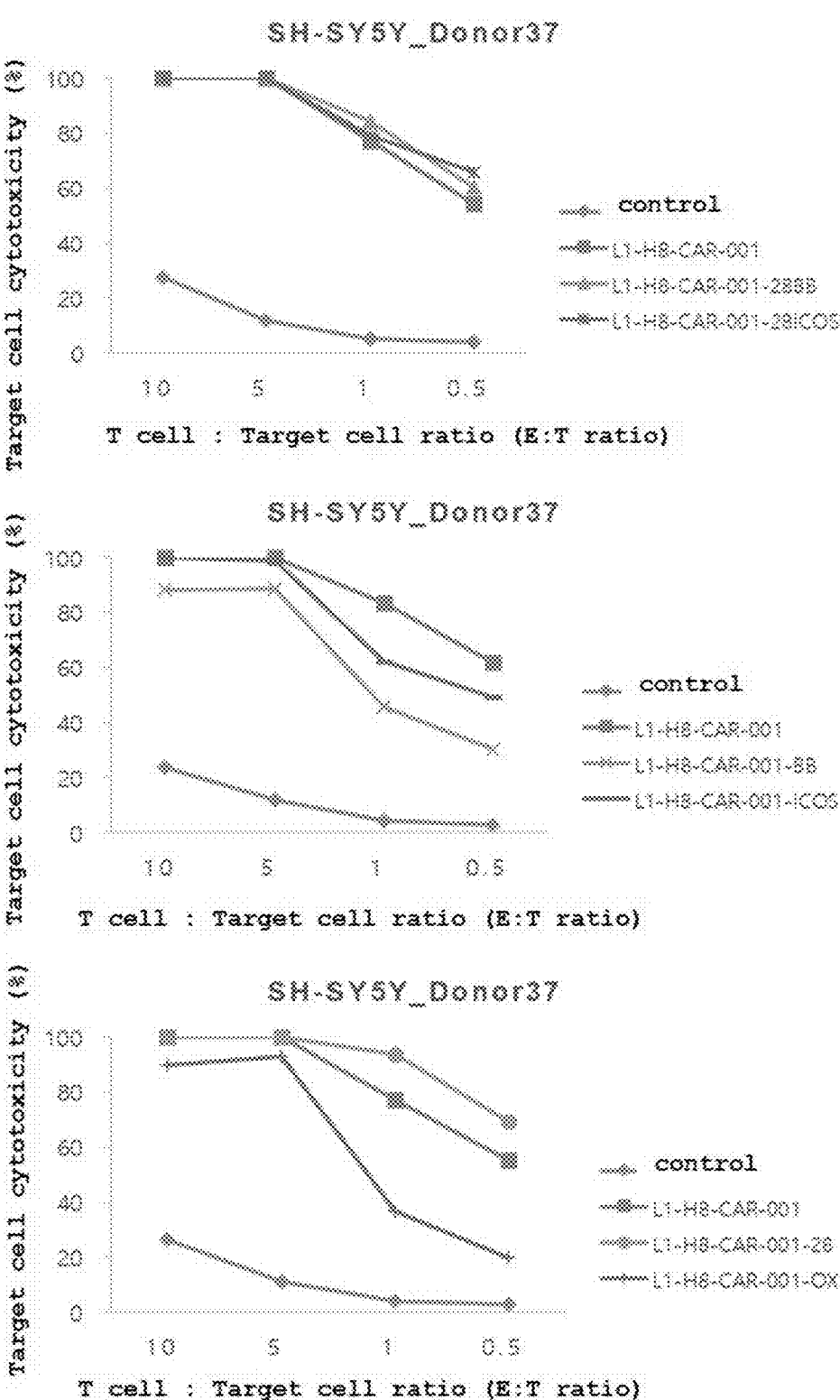
Figure 48C:
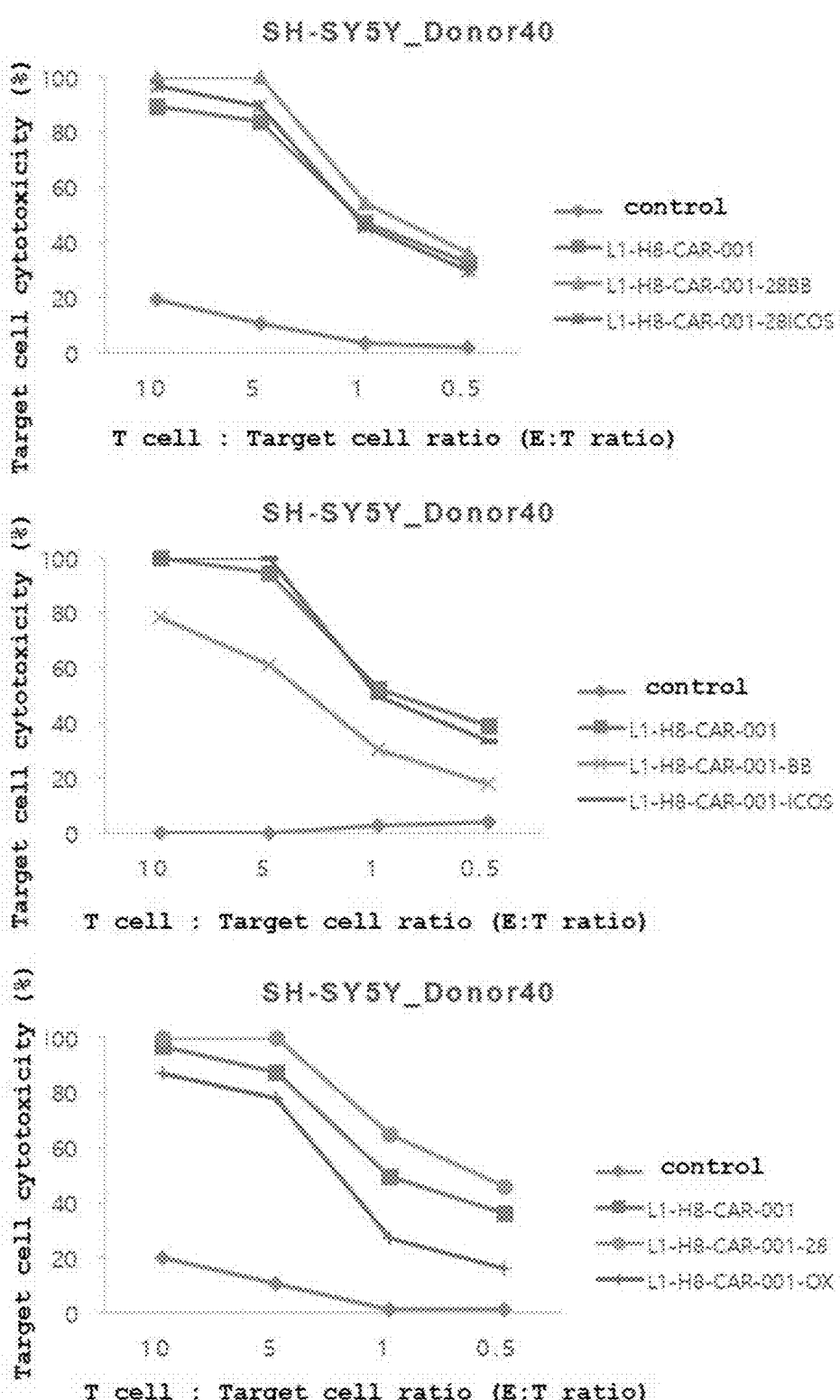

The cytotoxicity on SH-SY5Y cells were investigated by the same method as in Example 4.4.2.2. As a result, seven types of T cells expressing L1-H8-CAR-001 and L1-H8-CAR-001-28BB, -28ICOS, -28, -OX, -BB, and -ICOS showed high cytotoxicity on SH-SY5Y cells compared with T cells not expressing L1-H8-CAR (control) (FIG. 48A to 48C).

Figure 49A:
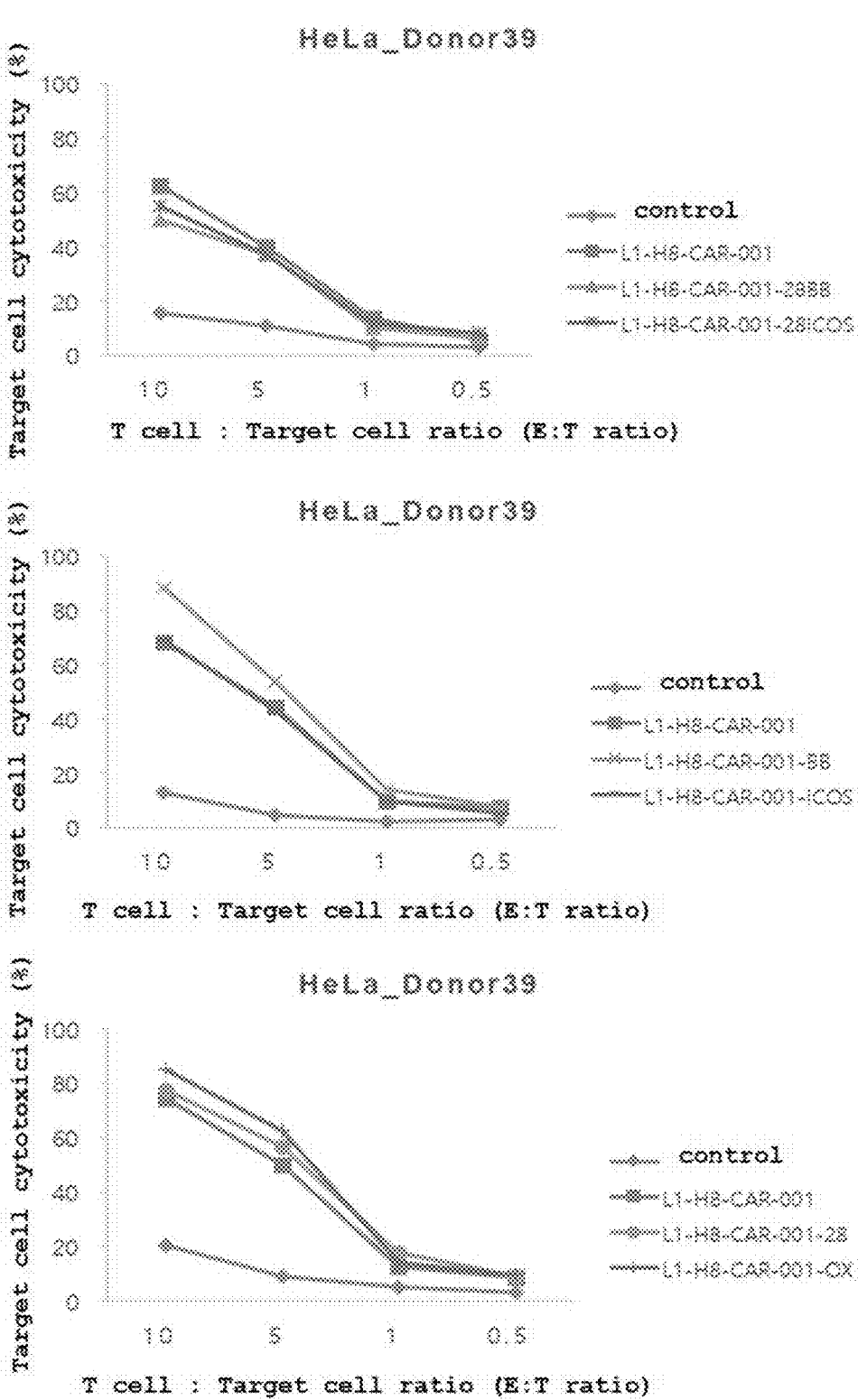
FIGS. 49A, 49B to 49C show anticancer activity of anti-L1CAM-CAR-expressing T cells of the present disclosure on HeLa cells (high expression of L1CAM).
Figure 49B:
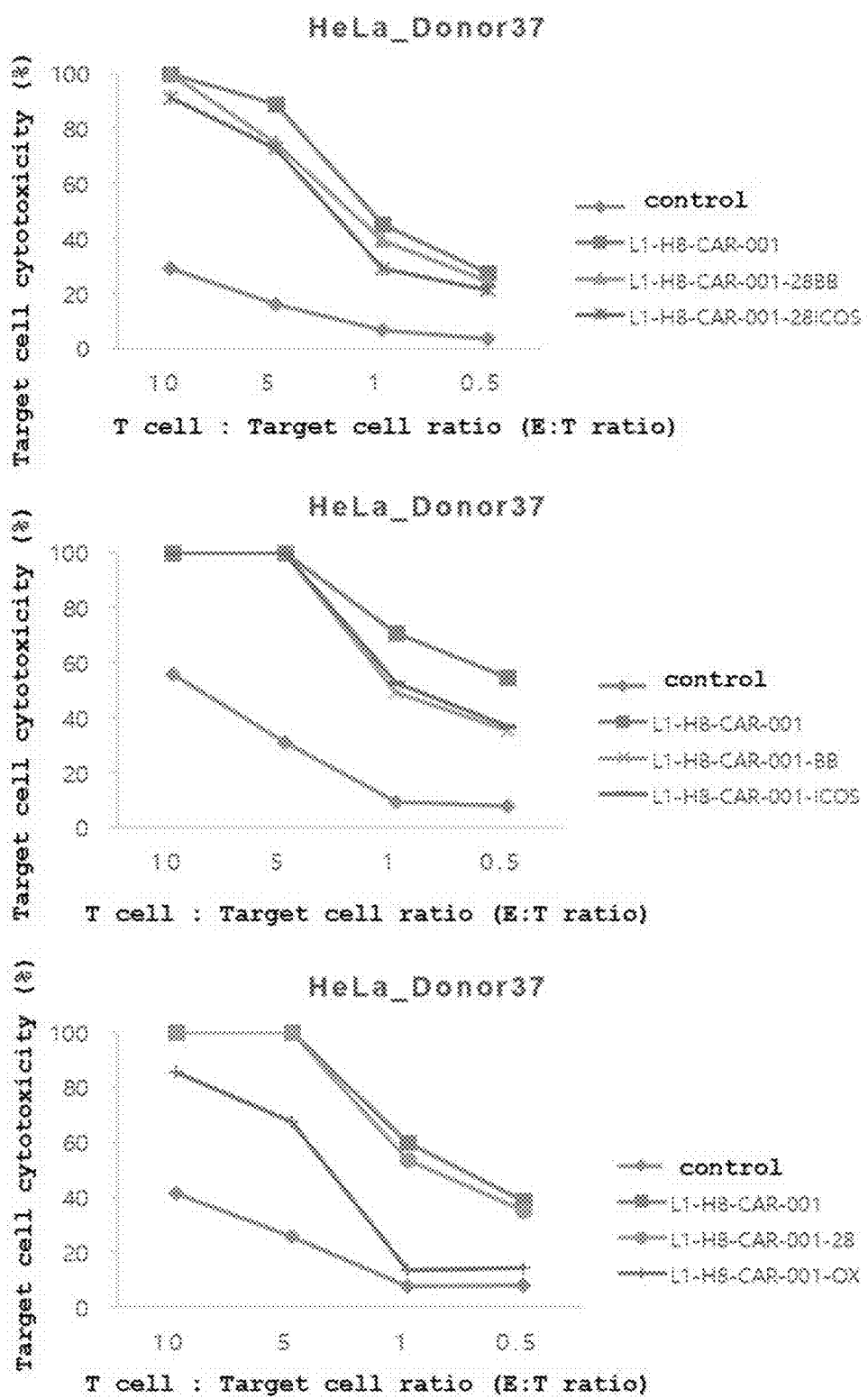
Figure 49C:
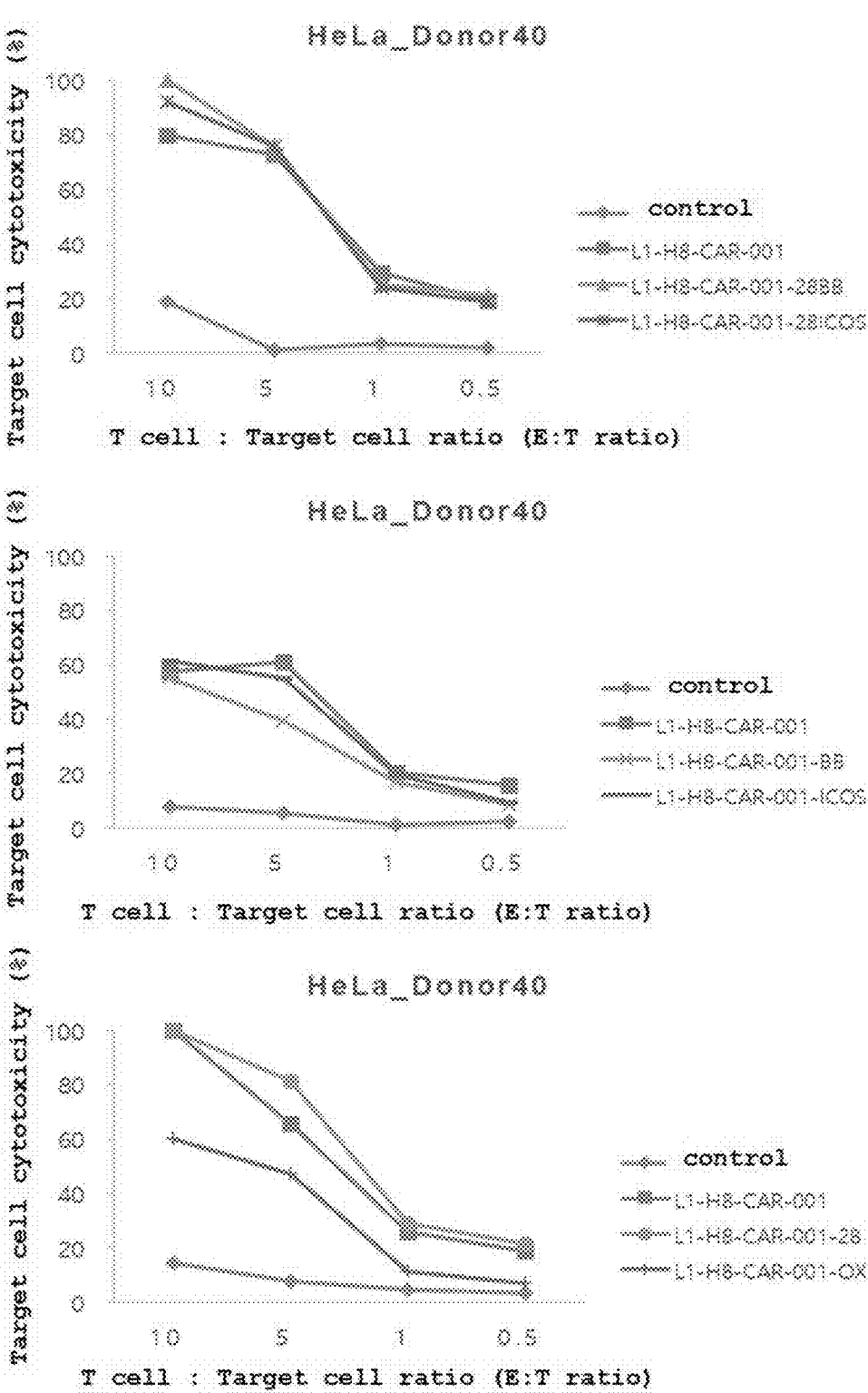

The cytotoxicity on HeLa cells were investigated by the same method as in Example 4.4.2.2. As a result, seven types of T cells expressing L1-H8-CAR-001 and L1-H8-CAR-001-28BB, -28ICOS, -28, -OX, -BB, and -ICOS showed high cytotoxicity on HeLa cells compared with T cells not expressing L1-H8-CAR (control) (FIG. 49A to 49C).

5.5. Verification of Anticancer Activity of T Cells Expressing L1-H8-CAR Genes with Various Spacer Domain Structures (In Vivo)

Figure 50:
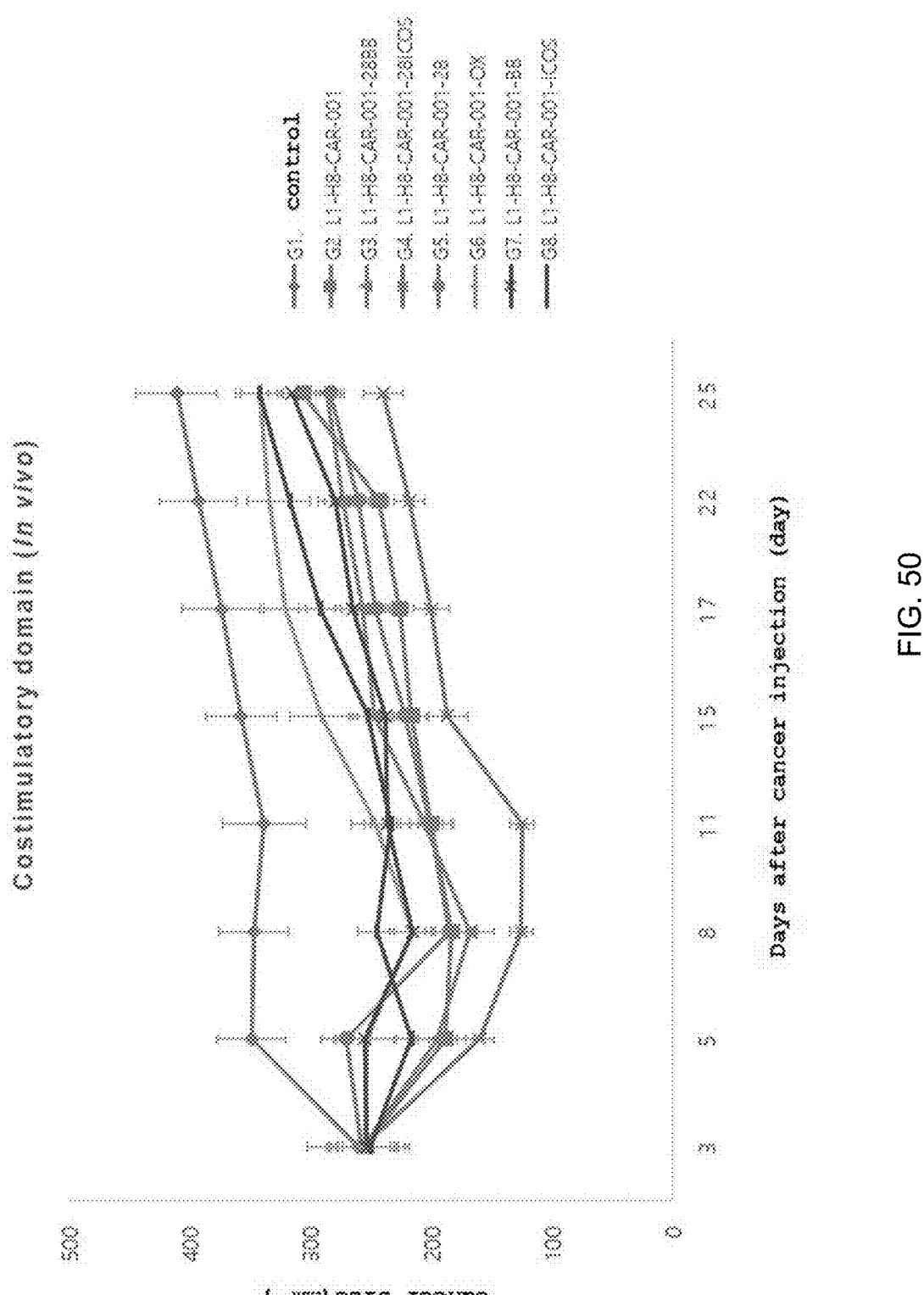
FIG. 50 shows in-vivo anticancer activity of anti-L1CAM-CAR (anti-L1-CAR)-expressing T cells of the present disclosure.

To investigate anticancer activity of anti-L1CAM-CAR (L1-H8-CAR) gene-expressing T cells in vivo, cancer-induced animal models were used. SKOV3 cancer cells (Target, T) mixed with Matrigel at 1:1 were subcutaneously (SC) administered at $3 \times 10^6$ to the right flank of NOD/SCID mice (7 weeks old, female) lacking T cells, B cells, and natural killer cells (NK cells), to thereby induce cancer. Seven types of L1-H8-CAR-expressing T cells confirmed to have efficacy in vitro and control T cells were administered to each NOD/SCID mouse 3 days and 5 days after cancer cell administration, once a day, a total of 2 times. T cells were administered through the tail vein (intravenous, IV) at $2 \times 10^7$ per dose, and the cancer size was measured up to day 25. The results verified that all the seven types of anti-L1CAM-CAR-expressing T cells inhibited the cancer growth rate compared with the control T cell administration group. It was especially verified that the cancer growth inhibitory effect of L1-H8-CAR-001-28ICOS was best (FIG. 50).

Example 6: Fabrication of Anti-L1CAM-CAR-Expressing T Cells With Various Structures and Verification of Activity Thereof

6.1. Obtainment of L1CMA-CAR Genes with Various Structures

6.1.1. Obtainment of L1-H8-CAR-005 Gene

Figure 51:
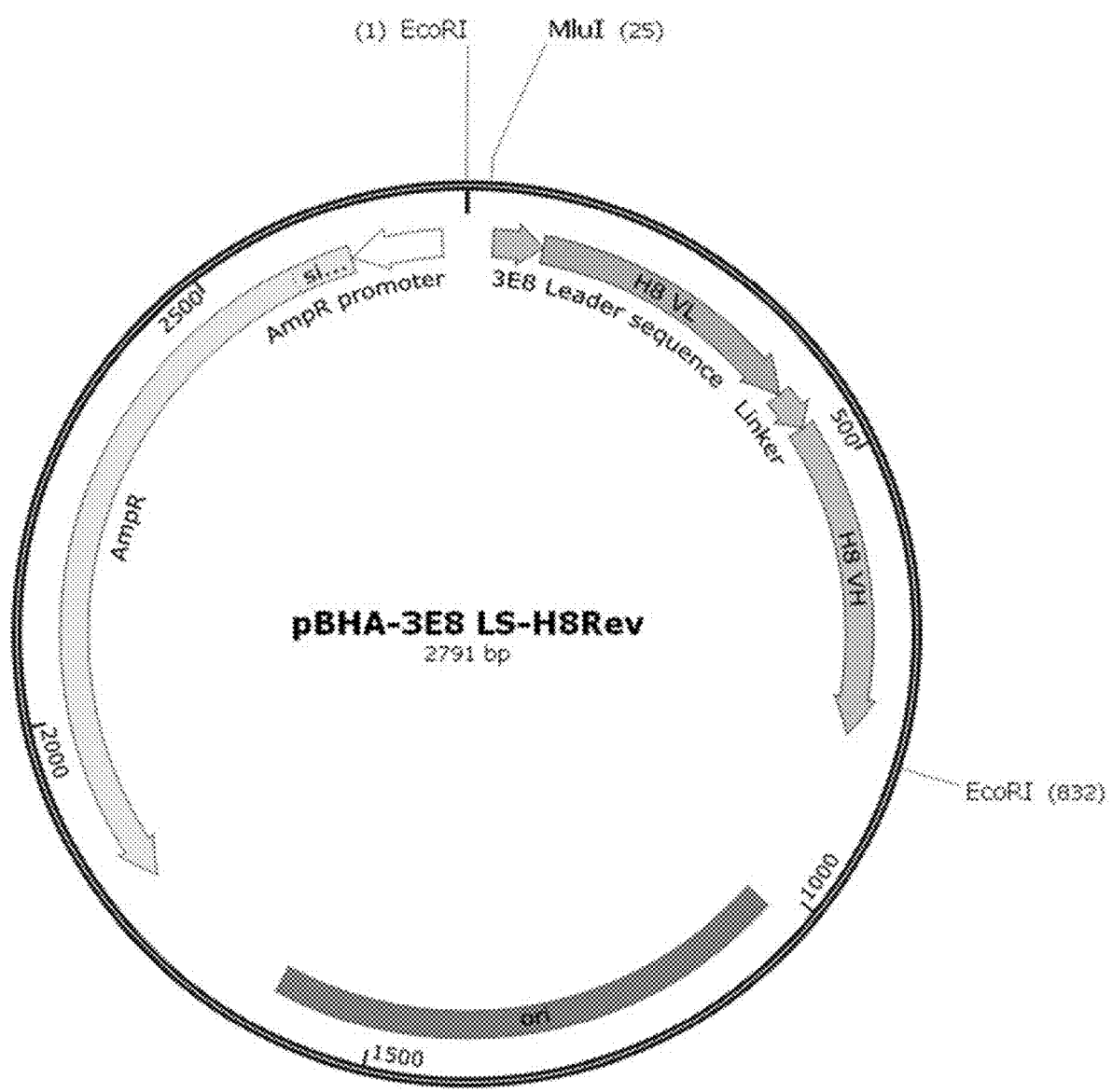
FIG. 51 shows a vector map of the pBHA-3E8LS-H8Rev plasmid used to manufacture a CAR-construct comprising the anti-L1CAM scFv selected in the present disclosure.

6.1.1.1. Obtainment of 3E8 Antibody Leader Sequence (LS) and L1-H8 scFv_Reverse Gene The structure of 3E8 LS, L1-H8 scFv antibody light chain variable region (VL), linker, and L1-H8 scFv antibody heavy chain variable region (VH) was synthesized. The pBHA-3E8-H8Rev (FIG. 51) obtained through gene synthesis as a template was amplified by PCR using the primers of SEQ ID NO: 70 (Table 15) and SEQ ID NO: 103 (Table 15). The primer binding to the 5' end of the 3E8 leader sequence (LS) has the nucleotide sequence of Mlu I restriction enzyme and the 18-nucleotide sequence of the 3E8 leader sequence (LS), and the primer binding to the 3' end of L1-H8 scFv-Reverse has the 12-nucleotide sequence of hIgD hinge, and thus the amplified PCR product has the nucleotide sequence of Mlu I-3E8 LS-L1-H8 scFv-Rev-IgD hinge (Table 16) The amplified product was used in the next PCR amplification process.

TABLE 15

| Nucleotide sequence information of used primers | | |
|---|---|---|
| SEQ ID NO. | Primer name | Nucleotide sequence |
| 70 | Mlu 1 + 3E8 VH(F) | ACGCGTATGGAATGGAGCTGGGTC |
| 103 | L1-H8 HC + IgD hinge(R) | ACCTGGCCAGCGCGATGAGACGGTCAC |
| 104 | L1-H8 HC + IgD hinge(F) | ACCGTCTCATCGCGCTGGCCAGGTTCT |
| 73 | Xho I + CD3zeta(R) | CCGCTCGAGTTAGCGAGGGGGCAGGGC |
| 105 | AS + Mlu I + 2173-CD8a_LS(F) | CGACGCGTATGGCCCTCCCTGTCACCG |
| 106 | 2173-CD8a_LS + C9 ScFv(R) | CAACTGTACTTCGGGCCGAGCGGCGTG |
| 107 | 2173-CD8a_LS + C9 ScFv(F) | GCCGCTCGGCCCGAAGTACAGTTGGTC |
| 108 | C9 ScFv + hCD8a_Hinge(R) | TGGGGTAGTGGTTTTAATTTCCACTTT |
| 109 | C9 ScFv + hCD8a_Hinge(F) | GTGGAAATTAAAACCACTACCCCAGCA |
| 110 | AS + Xho I + 2173-0D3 zeta(R) | CCGCTCGAGTTACCGAGGCGGCAGGGC |
| 111 | AS + Mlu I + GMCSF rec.a LS(F) | CGACGCGTATGCTTCTCCTGGTGACAA |
| 112 | GMCSF rec.a LS + L1-H8 scFv(R) | CAACTGTACTTCTGGGATCAGGAGGAA |
| 113 | GMCSF rec.a LS + L1-H8 scFv(F) | CTCCTGATCCCAGAAGTACAGTTGGTC |

TABLE 15-continued

Nucleotide sequence information of used primers

| SEQ ID NO. | Primer name | Nucleotide sequence |
|---|---|---|
| 114 | L1-H8 scFv + hinge + hCD28(R) | AATTGCGGCCGCTTTAATTTCCACTTT |
| 115 | L1-H8 scFv + hinge + hCD28(F) | GTGGAAATTAAAGCGGCCGCAATTGAA |
| 116 | AS + Xho I + CD3-ζ (R) | CCGCTCGAGTTATTAGCGAGGGGGCAGG |

TABLE 16

LS, L1-H8 scFv, Hinge, TM, ICD, costimulatory domain, and CD3ζ gene sequences

| ID | Nucleotide sequence |
|---|---|
| Mlu I-start codon-3E8 LS | ACGCGTATGGAATGGAGCTGGGTCTTTCTCTTCTTCCTGTCAGTAACTACA GGTGTCCACTCC |
| L1-H8 scFv-Rev (L1CAM-3R-H8Rev) | GACATTCAAATGACGCAGAGTCCCTCCTCACTGAGTGCTAGCGTGGGCG ATCGTGTGACAATTACTTGTCGCGCTAGCCAGTCTATCTCTCGTGATCTGA ACTGGTATCAGCAGAAACCGGGCAAGGCGCCAAAATTGCTGATTTACGCA GCATCCTCTCTGCAGTCTGGTGTACCGTCCCGTTTCTCTGGCAGCGGTTC TGGTACGGATTTTACCCTGACCATCTCAAGCCTCCAGCCTGAAGATTTTGC CACCTATTATTGTCAGCAATCTTACTCTACTCCGTACACGTTCGGGCAGGG AACTAAAGTGGAAATTAAAGGTGGAGGCGGTTCAGGCGGAGGTGGATCC GGCGGTGGCGGATCGGAAGTACAGTTGGTCGAAAGTGGCGGTGGCCTC GTGCAACCGGGTGGTTCACTGCGTCTGAGCTGCGCCGCCTCGGGTTTTA CTTTCTCTGATTATGCAATGAATTGGGTTCGTCAGGCGCCGGGCAAGGGT CTCGAATGGGTTTCAGCAATCTCTTCTACTGGTTCTACTATCTACTATGCCG ATTCAGTGAAGGGTCGCTTTACCATTTCCCGTGACAACTCTAAGAATACTC TGTATCTGCAGATGAACTCGCTGCGTGCCGAAGACACGGCCGTCTATTAT TGCGCCAAACAGTCTACTTACTTTTACTCTTACTTTGATGTTTGGGGTCAG GGCACTTTAGTGACCGTCTCATCG |
| IgD hinge | CGCTGGCCAGGTTCTCCAAAGGCACAGGCCTCCTCCGTGCCCACTGCAC AACCCCAAGCAGAGGGCAGCCTCGCCAAGGCAACCACAGCCCCAGCCA CCACCCGTAACACAGGTAGAGGAGGAGAAGAGAAGAAGGAGGAGAAGGA GAAAGAGGAACAAGAAGAGAGAGAGACAAAGACACCAGGTTGTCCG |
| CD28 TM | TTTTGGGTGCTGGTGGTGGTTGGTGGAGTCCTGGCTTGCTATAGCTTGCT AGTAACAGTGGCCTTTATTATTTTCTGGGTG |
| CD28 ICD | AGGAGTAAGAGGAGCAGGCTCCTGCACAGTGACTACATGAACATGACTCC CCGCCGCCCCGGGCCCACCCGCAAGCATTACCAGCCCTATGCCCCACCA CGCGACTTCGCAGCCTATCGCTCC |
| OX40 | GCCCTGTACCTGCTCCGGAGGGACCAGAGGCTGCCCCCCGATGCCCAC AAGCCCCCTGGGGGAGGCAGTTTCCGGACCCCCATCCAAGAGGAGCAG GCCGACGCCCACTCCACCCTGGCCAAGATC |
| CD3ζ-iso1-stop codon-Xho I | AGAGTGAAGTTCAGCAGGAGCGCAGACGCCCCCGCGTACCAGCAGGGC CAGAACCAGCTCTATAACGAGCTCAATCTAGGACGAAGAGAGGAGTACGA TGTTTTGGACAAGAGACGTGGCCGGGACCCTGAGATGGGGGGGAAAGCC GCAGAGAAGGAAGAACCCTCAGGAAGGCCTGTACAATGAACTGCAGAAA GATAAGATGGCGGAGGCCTACAGTGAGATTGGGATGAAAGGCGAGCGCC GGAGGGGCAAGGGGCACGATGGCCTTTACCAGGGTCTCAGTACAGCCAC CAAGGACACCTACGACGCCCTTCACATGCAGGCCCTGCCCCCTCGCTAA CTCGAG |

6.1.1.2. Obtainment of Hinge, TM, ICD, Costimulatory Domain, and CD3ζ Gene

The pMT-L1-H8-CAR-003 plasmid (FIG. 23), comprising human IgD hinge and IgG1 hinge, CD28 TM and ICD, the costimulatory domain OX40, and CD3ζ-iso1, as a template, was amplified by PCR using the primers of SEQ ID NO: 104 (Table 15) and SEQ ID NO: 73 (Table 15) before use. The primer binding to the 5' end of the hIgD hinge has the 12-nucleotide sequence of the heavy chain variable region (VH) of L1-H8 scFv antibody, and the primer binding to the 3' end of CD3ζ-iso1 has the nucleotide sequence of Xho I restriction enzyme, and thus the amplified PCR product has the nucleotide sequence of L1-H8 scFv-Rev-IgD hinge-IgG1 hinge-CD28 TM-CD28 ICD-OX40-CD3ζ-iso1-Xho I (Table 16). The amplified PCR product was used in the next PCR amplification process.

6.1.1.3. Obtainment of 3E8 LS, L1-H8 scFv-Rev, Hinge, TM, ICD, Costimulatory Domain, and CD3ζ Gene Mlu I-3E8 LS-L1-H8 scFv-Rev-IgD hinge and L1-H8 scFv-Rev-IgD hinge-IgG1 hinge-CD28 TM-CD28 ICD-tide sequence of L1-H8 scFv antibody heavy chain variable region (VH), and thus the amplified PCR product has the nucleotide sequence of Mlu I-hCD8α LS-L1-H8 scFv (Table 17) The amplified product was used in the next PCR amplification process.

TABLE 17

LS, L1-H8 scFv, Hinge, TM, ICD, costimulatory domain, and CD3ζ gene sequences

| ID | Nucleotide sequence |
|---|---|
| Mlu I-start codon-hCD8α LS | ACGCGTATGGAATGGAGCTGGGTCTTTCTCTTCTTCCTGTCAGTAACTAC AGGTGTCCACTCC |
| L1-H8 scFv (L1CAM-3R-H8) | GAAGTACAGTTGGTCGAAAGTGGCGGTGGCCTCGTGCAACCGGGTGGT TCACTGCGTCTGAGCTGCGCCGCCTCGGGTTTTACTTTCTCTGATTATG CAATGAATTGGGTTCGTCAGGCGCCGGGCAAGGGTCTCGAATGGGTTT CAGCAATCTCTTCTACTGGTTCTACTATCTACTATGCCGATTCAGTGAAGG GTCGCTTTACCATTTCCCGTGACAACTCTAAGAATACTCTGTATCTGCAG ATGAACTCGCTGCGTGCCGAAGACACGGCCGTCTATTATTGCGCCAAAC AGTCTACTTACTTTTACTCTTACTTTGATGTTTGGGGTCAGGGCACTTTAG TGACCGTCTCATCGGGTGGAGGCGGTTCAGGCGGAGGTGGATCCGGC GGTGGCGGATCGGACATTCAAATGACGCAGAGTCCCTCCTCACTGAGT GCTAGCGTGGGCGATCGTGTGACAATTACTTGTCGCGCTAGCCAGTCTA TCTCTCGTGATCTGAACTGGTATCAGCAGAAACCGGGCAAGGCGCCAA ATTGCTGATTTACGCAGCATCCTCTCTGCAGTCTGGTGTACCGTCCCGTT TCTCTGGCAGCGGTTCTGGTACGGATTTTACCCTGACCATCTCAAGCCT CCAGCCTGAAGATTTTGCCACCTATTATTGTCAGCAATCTTACTCTACTCC GTACACGTTCGGGCAGGGAACTAAAGTGGAAATTAAA |
| hCD8a hinge | ACCACTACCCCAGCACCGAGGCCACCCACCCCGGCTCCTACCATCGCC TCCCAGCCTCTGTCCCTGCGTCCGGAGGCATGTAGACCCGCAGCTGGT GGGGCCGTGCATACCCGGGGTCTTGACTTCGCCTGCGAT |
| hCD8a TM | ATCTACATTTGGGCCCCTCTGGCTGGTACTTGCGGGGTCCTGCTGCTTT CACTCGTGATCACTCTTTACTGT |
| 4-1BB | AAGCGCGGTCGGAAGAAGCTGCTGTACATCTTTAAGCAACCCTTCATGA GGCCTGTGCAGACTACTCAAGAGGAGGACGGCTGTTCATGCCGGTTCC CAGAGGAGGAGGAAGGCGGCTGCGAACTG |
| CD3ζ-iso2M-stop codon-Xho I | CGCGTGAAATTCAGCCGCAGCGCAGATGCTCCAGCCTACAAGCAGGGG CAGAACCAGCTCTACAACGAACTCAATCTTGGTCGGAGAGAGGAGTACG ACGTGCTGGACAAGCGGAGAGGACGGGACCCAGAAATGGGCGGGAAG CCGCGCAGAAAGAATCCCCAAGAGGGCCTGTACAACGAGCTCCAAAAG GATAAGATGGCAGAAGCCTATAGCGAGATTGGTATGAAAGGGGAACGCA GAAGAGGCAAAGGCCACGACGGACTGTACCAGGGACTCAGCACCGCC ACCAAGGACACCTATGACGCTCTTCACATGCAGGCCCTGCCGCCTCGG TAACTCGAG |

45

Figure 52:
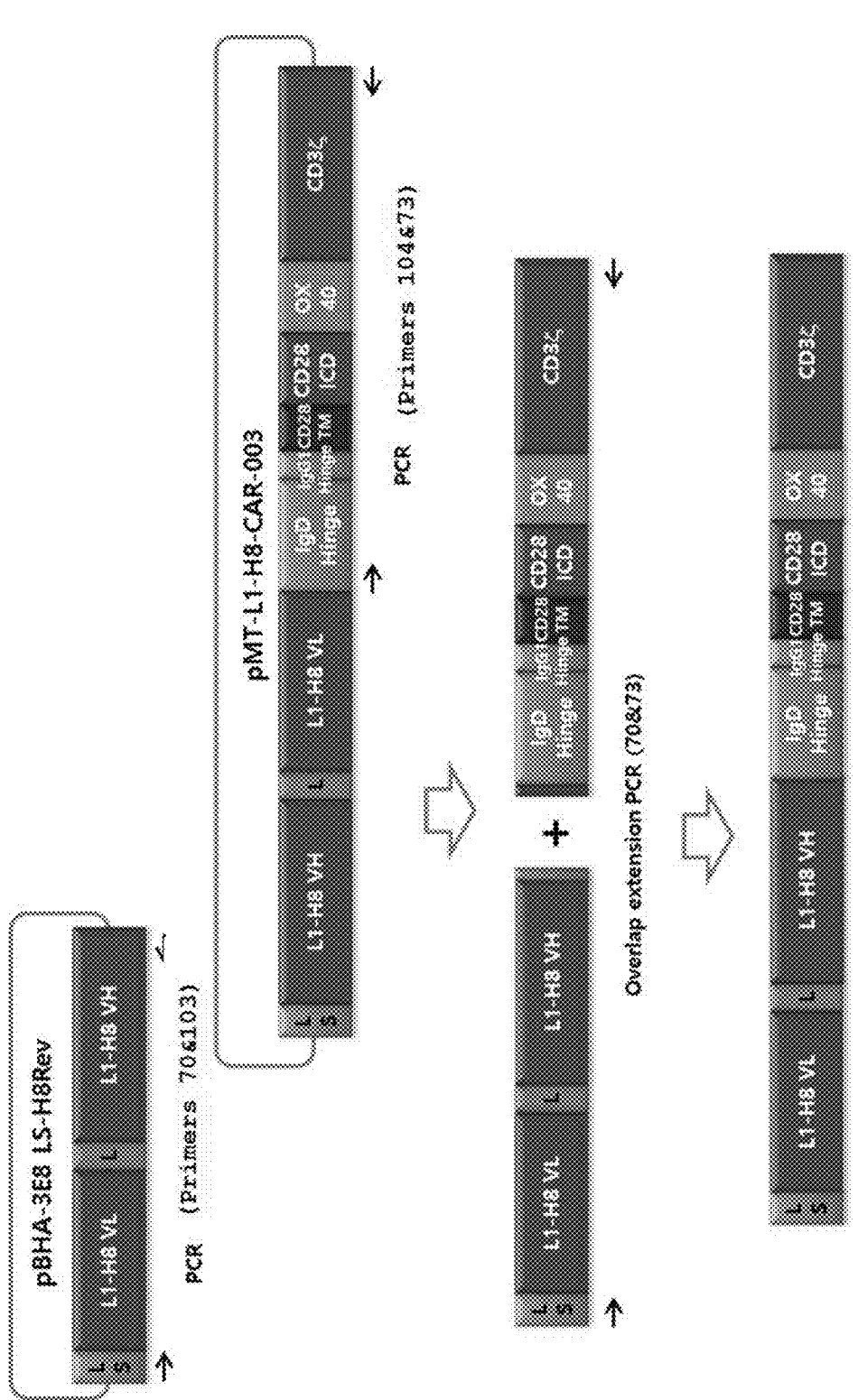
FIG. 52 is a schematic diagram showing a series of PCR amplification procedures in order to manufacture a CAR-construct comprising the anti-L1CAM scFv of the present disclosure.
Figure 53:
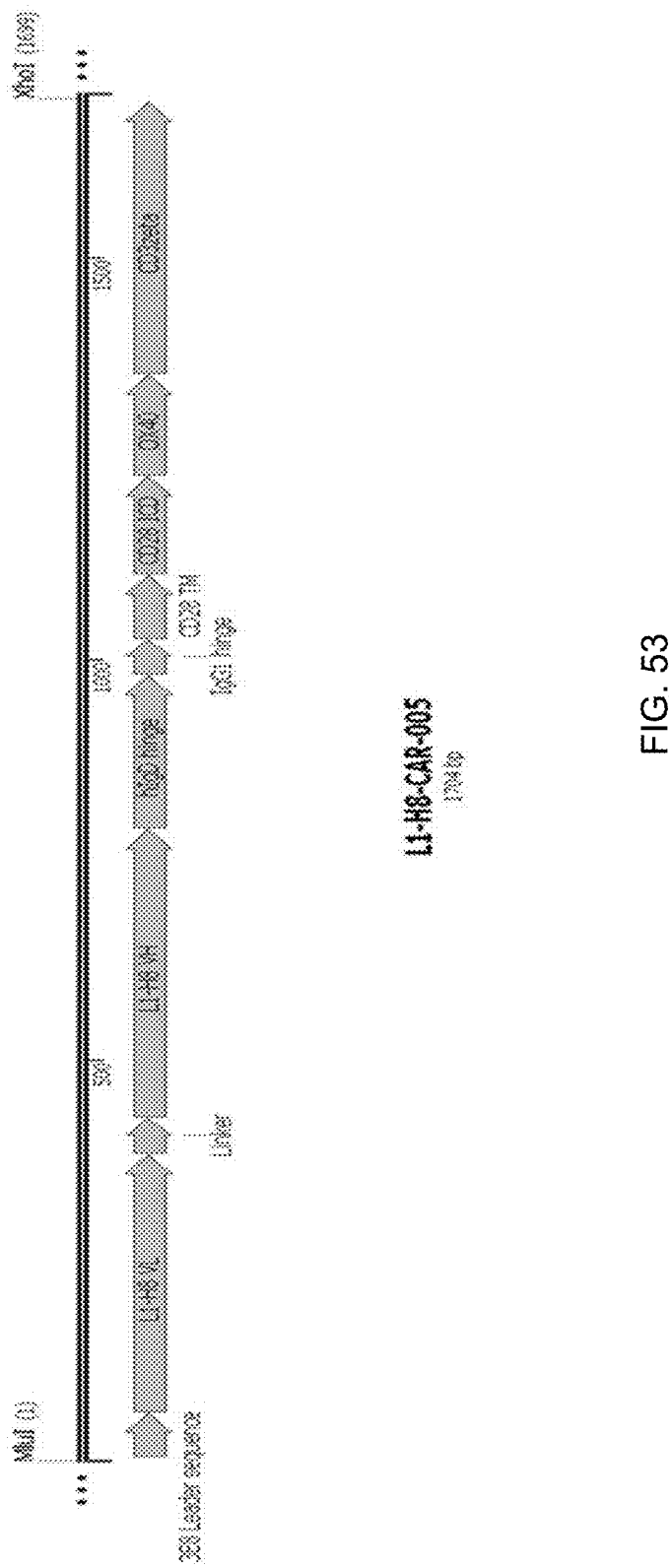
FIG. 53 shows a structure of the CAR-construct comprising anti-L1CAM scFv (L1-H8-CAR-005) constructed in the example of the present disclosure.

OX40-CD3ζ-iso1-Xho I, which were the amplified PCR products, as templates, were amplified by OE-PCR using the primers of SEQ ID NO: 70 (Table 15) and SEQ ID NO: 73 (Table 15) (FIG. 52). The amplified PCR product has the nucleotide sequence of Mlu I-3E8-L1-H8 scFv-Rev-IgD hinge-IgG1 hinge-CD28 TM-CD28 ICD-OX40-CD3ζ-iso1-Xho I, and has a structure of L1-H8-CAR-005 (FIG. 53).

6.1.2. Obtainment of L1-H8-CAR-006 Gene

Figure 54:
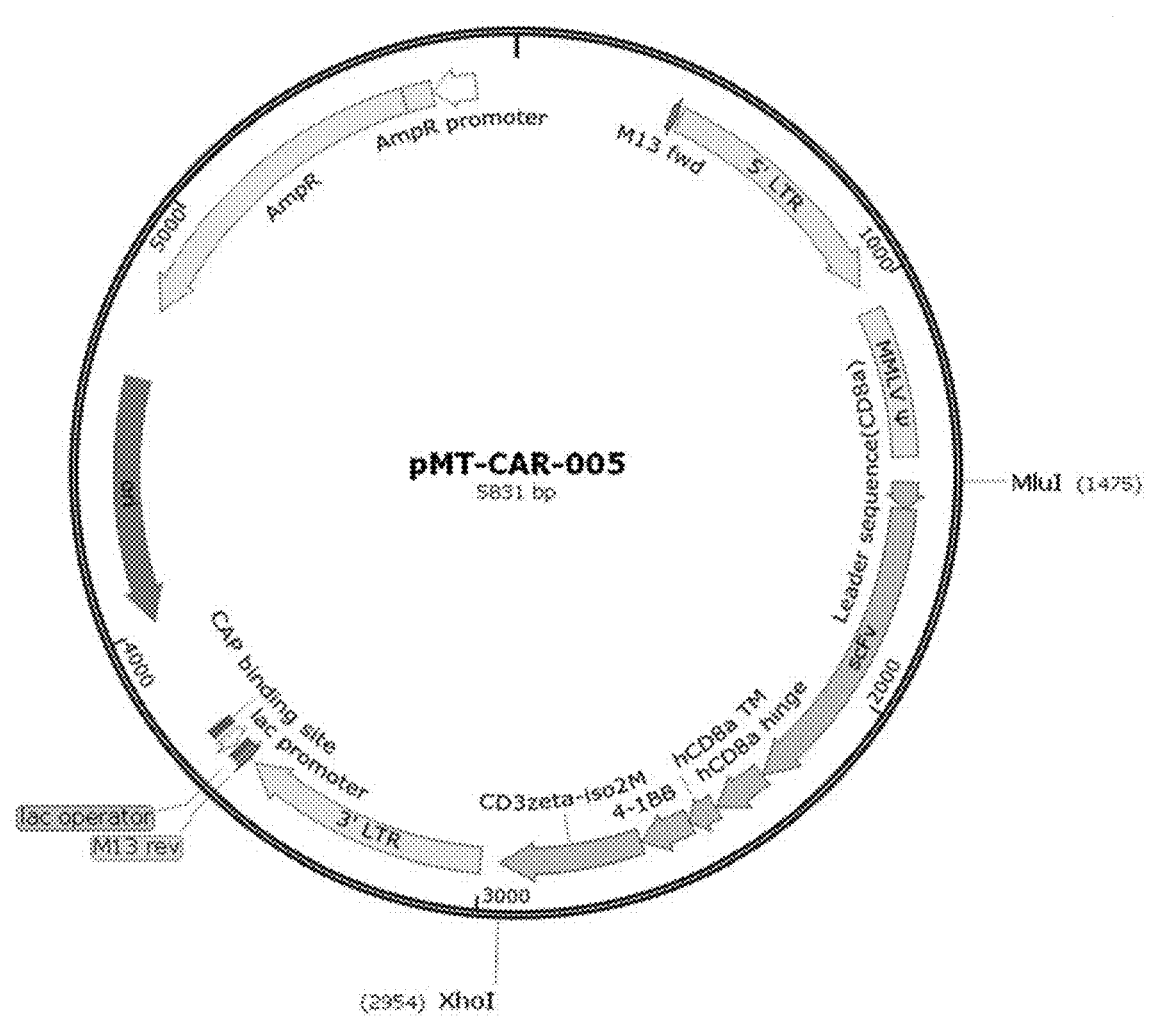
FIG. 54 shows a vector map of the pMT-CART-005 plasmid used to manufacture a CAR-construct comprising the anti-L1CAM scFv selected in the present disclosure.

6.1.2.1. Obtainment of CD8 Alpha Leader Sequence (LS) Gene pMT-CAR-005 (FIG. 54) plasmid, comprising CD8 alpha LS, as a template, was amplified by PCR using the primers of SEQ ID NO: 105 (Table 15) and SEQ ID NO: 106 (Table 15). The primer binding to the 5' end of the CD8 alpha leader sequence (LS) has the nucleotide sequence of Mlu I restriction enzyme and the 18-nucleotide sequence of the CD8 alpha leader sequence (LS), and the primer binding to the 3' end of CD8 alpha leader sequence (LS) has the 12-nucleo-

6.1.2.2. Obtainment of L1-H8 scFv Gene pMT-L1-H8-CAR-001 (FIG. 23) plasmid, comprising L1-H8 scFv, as a template, was amplified by PCR using the primers of SEQ ID NO: 107 (Table 15) and SEQ ID NO: 108 (Table 15) before use. The primer binding to the 5' end of L1-H8 scFv has the 12-nucleotide sequence of CD8 alpha LS, and the primer binding to the 3' end of L1-H8 scFv 3' has the 12-nucleotide sequence of hCD8 alpha Hinge, and thus the amplified PCR product has the nucleotide sequence of hCD8α LS-L1-H8 scFv-hCD8α hinge (Table 17). The amplified PCR product was used in the next PCR amplification process.

6.1.2.3. Obtainment of Hinge, TM, ICD, Costimulatory Domain, and CD3ζ Gene

The pMT-CAR-005 plasmid (FIG. 54), comprising human CD8 alpha hinge, TM, the costimulatory domain 4-1BB, and CD3ζ-iso2M, as a template, was amplified by PCR using the primers of SEQ ID NO: 109 (Table 15) and SEQ ID NO: 110 (Table 5) before use. The primer binding to the 5' end of the hCD8α hinge has the 12-nucleotide sequence of the light chain variable region (VL) of L1-H8 scFv antibody, and the primer binding to the 3' end of CD3ζ-iso2M has the nucleotide sequence of Xho I restriction enzyme, and thus the amplified PCR product has the nucleotide sequence of L1-H8 scFv-hCD8α hinge-hCD8α TM-4-1BB-CD3ζ-iso2M-Xho I (Table 17). The amplified PCR product was used in the next PCR amplification process.

6.1.2.4. Obtainment of CD8α LS and L1-H8 scFv Gene

Figure 55:
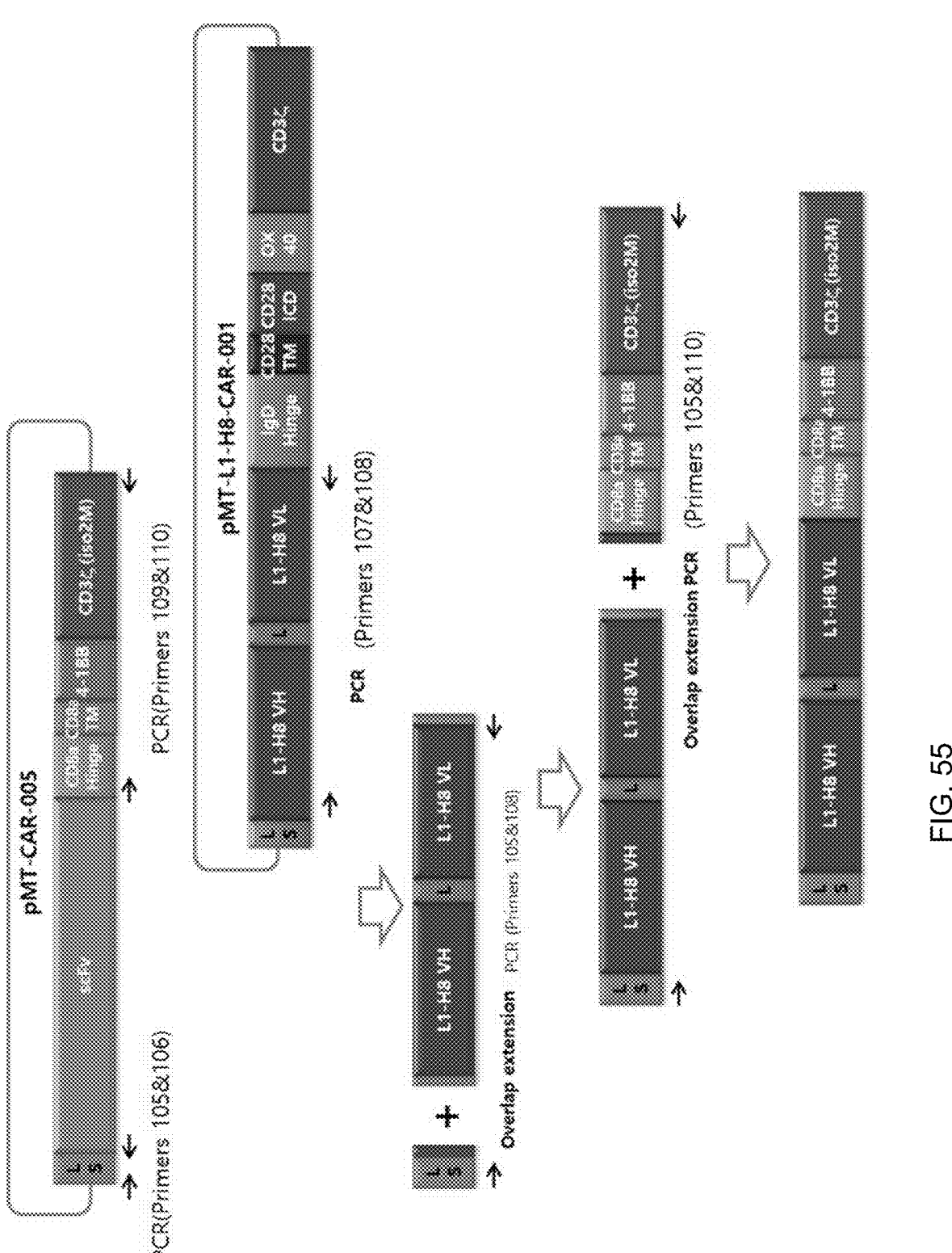
FIG. 55 is a schematic diagram showing a series of PCR amplification procedures in order to manufacture a CAR-construct comprising the anti-L1CAM scFv of the present disclosure.

Mlu I-hCD8α LS-L1-H8 scFv and hCD8α LS-L1-H8 scFv-hCD8α hinge, which were the amplified PCR products, as templates, were amplified by OE-PCR using the primers of SEQ ID NO: 105 (Table 15) and SEQ ID NO: 108 (Table 15) (FIG. 55). The amplified PCR product has the nucleotide sequence of Mlu I-hCD8α LS-L1-H8 scFv-CD28 hinge. The amplified PCR product was used in the next PCR amplification process.

Figure 56:
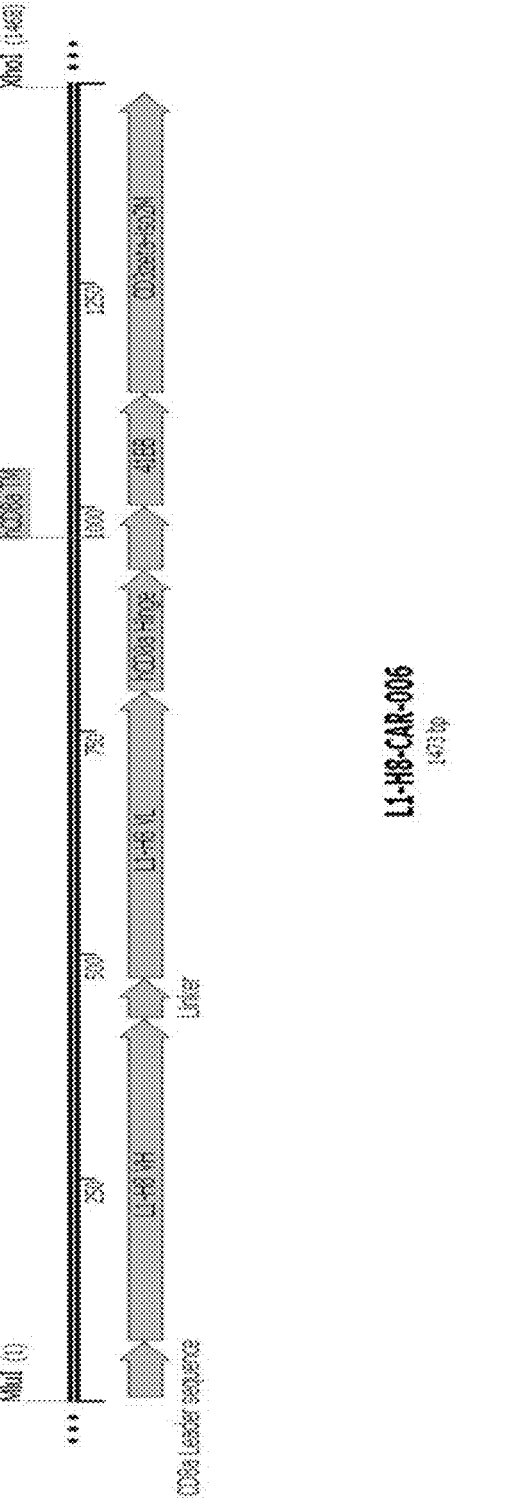
FIG. 56 shows a structure of the CAR-construct comprising anti-L1CAM scFv (L1-H8-CAR-006) constructed in the example of the present disclosure.

6.1.2.5. Obtainment of CD8α LS, L1-H8 scFv, Hinge, TM, ICD, Costimulatory Domain, and CD3ζ Gene Mlu I-hCD8α LS-L1-H8 scFv-hCD8αhinge and L1-H8 scFv-hCD8α hinge-hCD8α TM-4-1BB-CD3ζ-iso2M-Xho I, which were the amplified PCR products, as templates, were amplified by OE-PCR using the primers of SEQ ID NO: 105 (Table 15) and SEQ ID NO: 110 (Table 15) (FIG. 55). The amplified PCR product has the nucleotide sequence of Mlu I-hCD8αLS-L1-H8 scFv-hCD8α hinge-hCD8α TM-4-1BB-CD3ζ-iso2M-Xho I, and has a structure of L1-H8-CAR-006 (FIG. 56).

6.1.3. Obtainment of L1-H8-CAR-007 Gene

6.1.3.1. Obtainment of hGM-CSF Receptor Alpha-Chain Signal Sequence Gene

Figure 57:
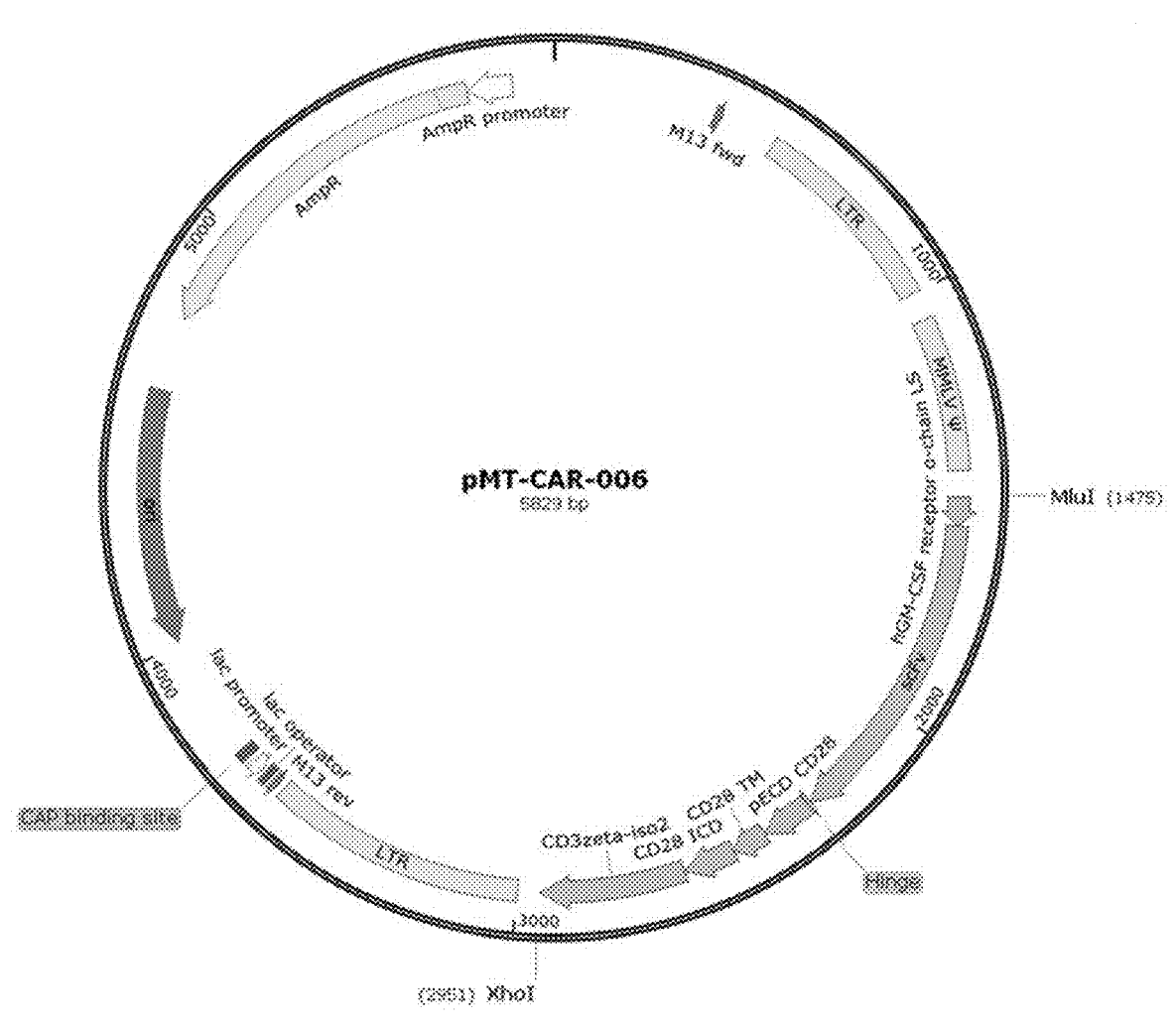
FIG. 57 shows a vector map of the pMT-CART-006 plasmid used to manufacture a CAR-construct comprising the anti-L1CAM scFv selected in the present disclosure.

The pMT-CAR-006 (FIG. 57) plasmid, comprising the hGM-CSF rec.α signal sequence, as a template, was amplified by PCR using the primers of SEQ ID NO: 111 (Table 15) and SEQ ID NO: 112 (Table 15). The primer binding to the 5' end of the hGM-CSF rec.α has the nucleotide sequence of Mlu I restriction enzyme, and the primer binding to the 3' end of hGM-CSF rec.α has the 12-nucleotide sequence of L1-H8 scFv heavy chain variable region (VH), and thus the amplified PCR product has the nucleotide sequence of Mlu I-hGM-CSF rec.α-L1-H8 scFv (Table 18). The amplified product was used in the next PCR amplification process.

TABLE 18

| ID | Nucleotide sequence |
|---|---|
| LS, L1-H8 scFv, Hinge, TM, ICD, costimulatory domain, and CD3 gene sequences | |
| Mlu I-start codon-hGM-CSF rec.a LS | ACGCGTATGGAATGGAGCTGGGTCTTTCTCTTCTTCCTGTCAGTAACTACAG GTGTCCACTCC |
| L1-H8 scFv (L1CAM-3R-H8) | GAAGTACAGTTGGTCGAAAGTGGCGGTGGCCTCGTGCAACCGGGTGGTTC ACTGCCGTCTGAGCTGCGCCGCCTCGGGTTTTACTTTCTCTGATTATGCAATG AATTGGGGTTCGTCAGGCGCCGGGCAAGGGTCTCGAATGGGTTTCAGCAATC TCTTCTACTGGTTCTACTATCTACTATGCCGATTCAGTGAAGGGTCGCTTTAC CATTTCCCGTGACAACTCTAAGAATACTCTGTATCTGCAGATGAACTCGCTGC GTGCCGAAGACACGGCCGTCTATTATTGCGCCAAACAGTCTACTTACTTTTAC TCTTACTTTGATGTTTGGGGTCAGGGCACTTTAGTGACCGTCTCATCGGGTG GAGGCGGTTCAGGCGGAGGTGGATCCGGCGGTGGCGGATCGGACATTCAA ATGACGCAGAGTCCCTCCTCACTGAGTGCTAGCGTGGGCGATCGTGTGACA ATTACTTGTCGCGCTAGCCAGTCTATCTCTCGTGATCTGAACTGGTATCAGCA GAAACCGGGCAAGGCGCCAAAATTGCTGATTTACGCAGCATCCTCTCTGCA GTCTGGTGTACCGTCCCGTTTCTCTGGCAGCGGTTCTGGTACGGATTTTACC CTGACCATCTCAAGCCTCCAGCCTGAAGATTTTGCCACCTATTATTGTCAGCA ATCTTACTCTACTCCGTACACGTTCGGGCAGGGAACTAAAGTGGAAATTAAA |
| hinge | GCGGCCGCA |
| hCD28 pECD | ATTGAAGTTATGTATCCTCCTCCTTACCTAGACAATGAGAAGAGCAATGGAAC CATTATCCATGTGAAAGGGAAACACCTTTGTCCAAGTCCCCTATTTCCCGGAC CTTCTAAGCCC |
| hCD28 TM | TTTTGGGTGCTGGTGGTGGTTGGGGGAGTCCTGGCTTGCTATAGCTTGCTA GTAACAGTGGCCTTTATTATTTTCTGGGTG |
| hCD28 ICD | AGGAGTAAGAGGAGCAGGCTCCTGCACAGTGACTACATGAACATGACTCCC CGCCGCCCCGGGCCCACCCGCAAGCATTACCAGCCCTATGCCCCACCACG CGACTTCGCAGCCTATCGCTCC |
| CD3ζ-iso2-stop codon-Xho I | AGAGTGAAGTTCAGCAGGAGCGCAGACGCCCCCGCGTACCAGCAGGGCCA GAACCAGCTCTATAACGAGCTCAATCTAGGACGAAGAGAGGAGTACGATGTT TTGGACAAGAGACGTGGCCGGGACCCTGAGATGGGGGGAAAGCCGAGAAG GAAGAACCCTCAGGAAGGCCTGTACAATGAACTGCAGAAAGATAAGATGGC GGAGGCCTACAGTGAGATTGGGATGAAAGGCGAGCGCCGGAGGGGCAAGG GGCACGATGGCCTTTACCAGGGTCTCAGTACAGCCACCAAGGACACCTACG ACGCCCTTCACATGCAGGCCCTGCCCCCTCGCTAATAATAACTCGAG |

6.1.3.2. Obtainment of L1-H8 scFv Gene

The pMT-L1-H8-CAR-001 (FIG. 23) plasmid, comprising L1-H8 scFv, as a template, was amplified by PCR using the primers of SEQ ID NO: 113 (Table 15) and SEQ ID NO: 114 (Table 15) before use. The primer binding to the 5' end of L1-H8 scFv has the 12-nucleotide sequence of hGM-CSF rec.α LS, and the primer binding to the 3' end of L1-H8 scFv has the 9-nucleotide sequence of Hinge and the 3-nucleotide sequence of hCD28 pECD, and thus the amplified PCR product has the nucleotide sequence of hGM-CSF rec.α LS-L1-H8 scFv-hinge-hCD28 pECD (Table 18). The amplified PCR product was used in the next PCR amplification process.

6.1.3.3. Obtainment of Hinge, TM, ICD, Costimulatory Domain, and CD3ζ Gene

The pMT-CAR-006 plasmid (FIG. 57), comprising Hinge, hCD28 pECD, TM, ICD, and hCD3ζ-iso2, as a template, was amplified by PCR using the primers of SEQ ID NO: 115 (Table 13) and SEQ ID NO: 116 (Table 13). The primer binding to the 5' end of Hinge has the 12-nucleotide sequence of the light chain variable region (VL) of L1-H8 scFv, and the primer binding to the 3' end of CD3ζ-iso2 has the nucleotide sequence of Xho I restriction enzyme, and thus the amplified PCR product has the nucleotide sequence of L1-H8 scFv-Hinge-hCD28 pECD-hCD28 TM-hCD28 ICD-CD3ζ-iso2-Xho I (Table 16). The amplified product was used in the next PCR amplification process.

Figure 58:
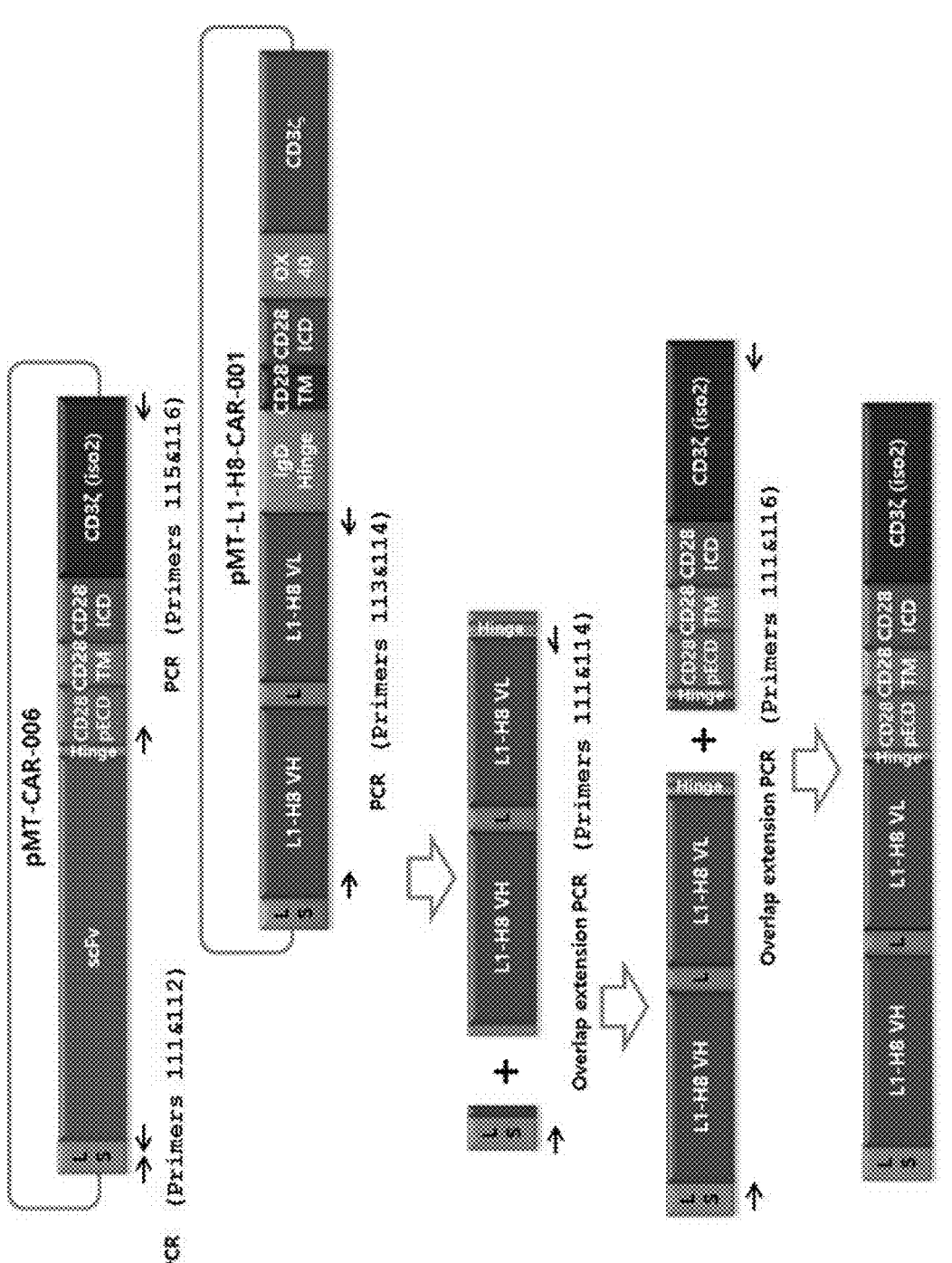
FIG. 58 is a schematic diagram showing a series of PCR amplification procedures in order to manufacture a CAR-construct comprising the anti-L1CAM scFv of the present disclosure.

6.1.3.4. Obtainment of hGM-CSF Receptor Alpha-Chain Signal Sequence and L1-H8 scFv Gene Mlu I-hGM-CSF rec.α-L1-H8 scFv and hGM-CSF rec.α LS-L1-H8 scFv-hinge-hCD28 pECD, which were the amplified PCR products, as templates, were amplified by OE-PCR using the primers of SEQ ID NO: 111 (Table 15) and SEQ ID NO: 114 (Table 15) (FIG. 58). The amplified PCR product has the nucleotide sequence of Mlu I-hGM-CSF rec.α-L1-H8 scFv-hinge-hCD28 pECD. The amplified PCR product was used in the next PCR amplification process.

Figure 59:
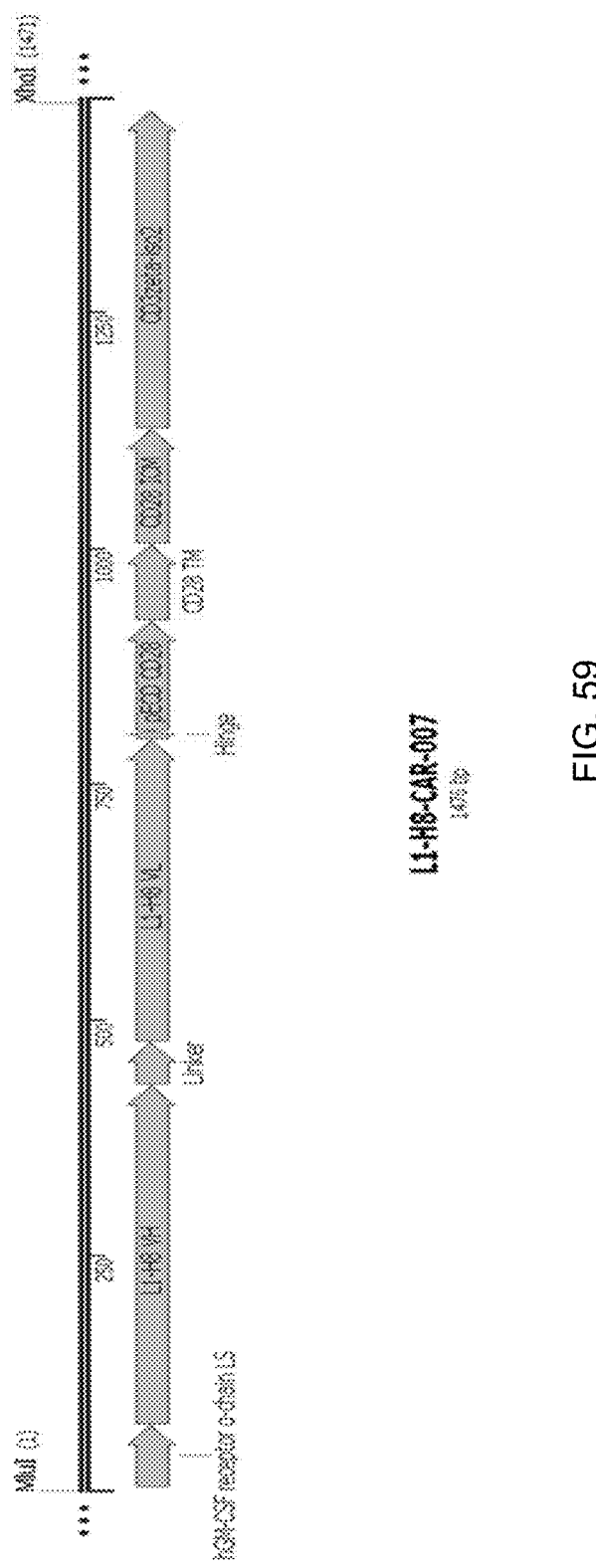
FIG. 59 shows a structure of the CAR-construct comprising anti-L1CAM scFv (L1-H8-CAR-007) constructed in the example of the present disclosure.
Figure 60A:
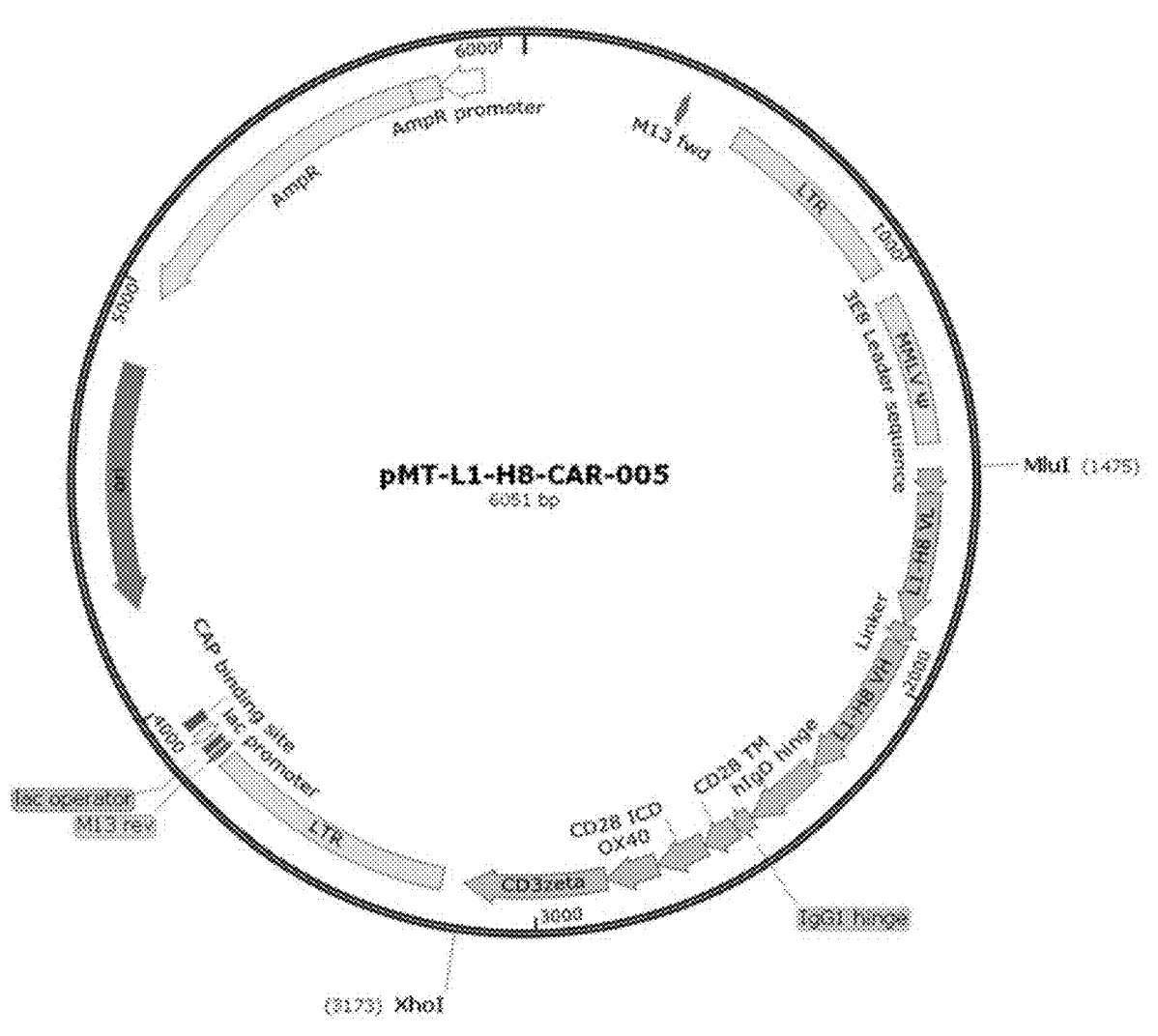
FIGS. 60A, 60B to 60C show retroviral vectors into which three types of CAR-constructs comprising anti-L1CAM scFv (L1-H8-CAR-005, L1-H8-CAR-006, and L1-H8-CAR-007) of the present disclosure were introduced.
Figure 60B:
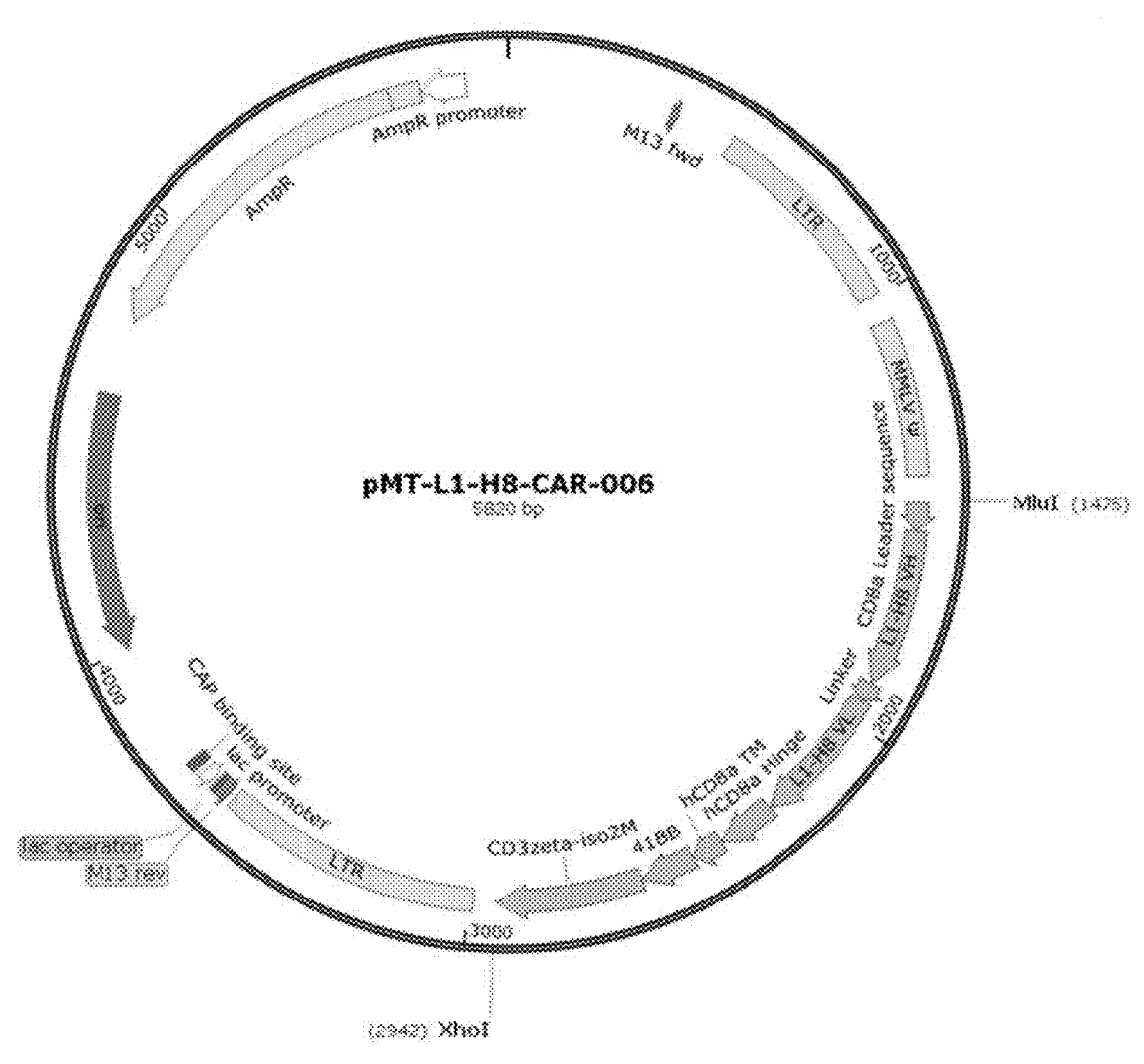
Figure 60C:
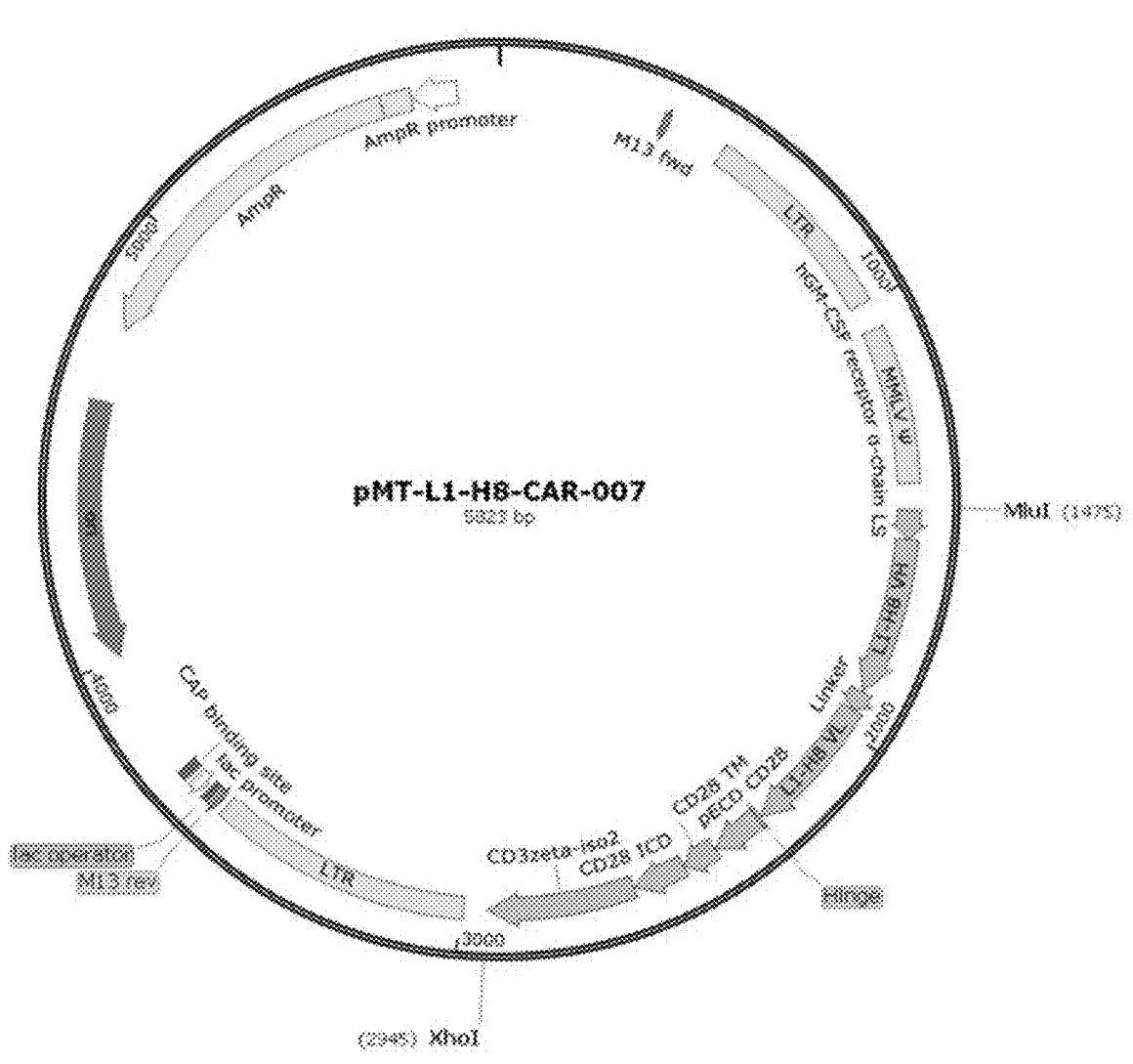
Figure 61A:
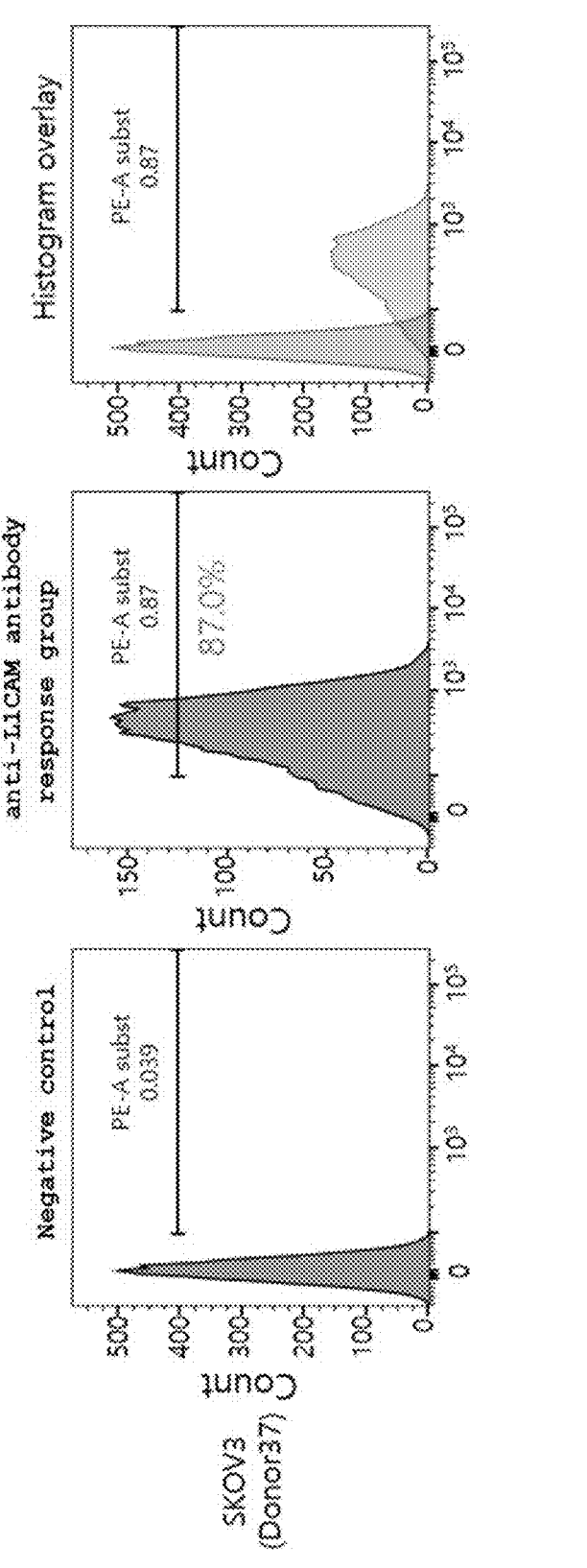
FIGS. 61A, 61B, 61C, 61D, 61E to 61F show the expression rates of L1CAM in SKOV3 cells, SH-SY5Y cells, HeLa cells, and 293T cells.
Figure 61B:
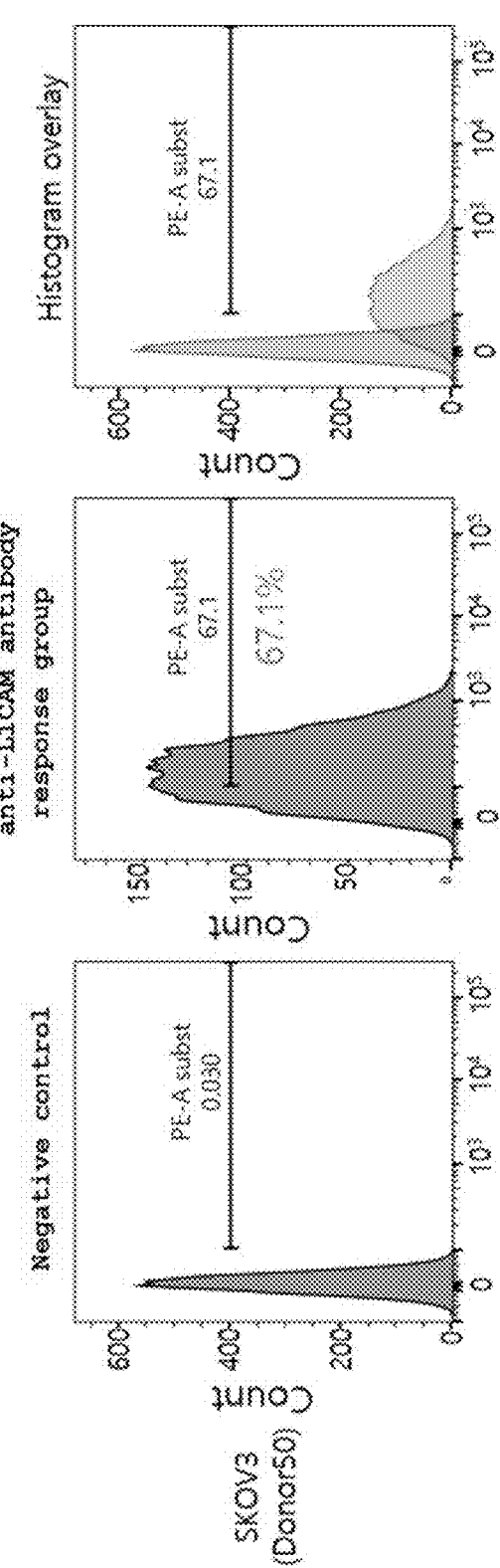
Figure 61C:
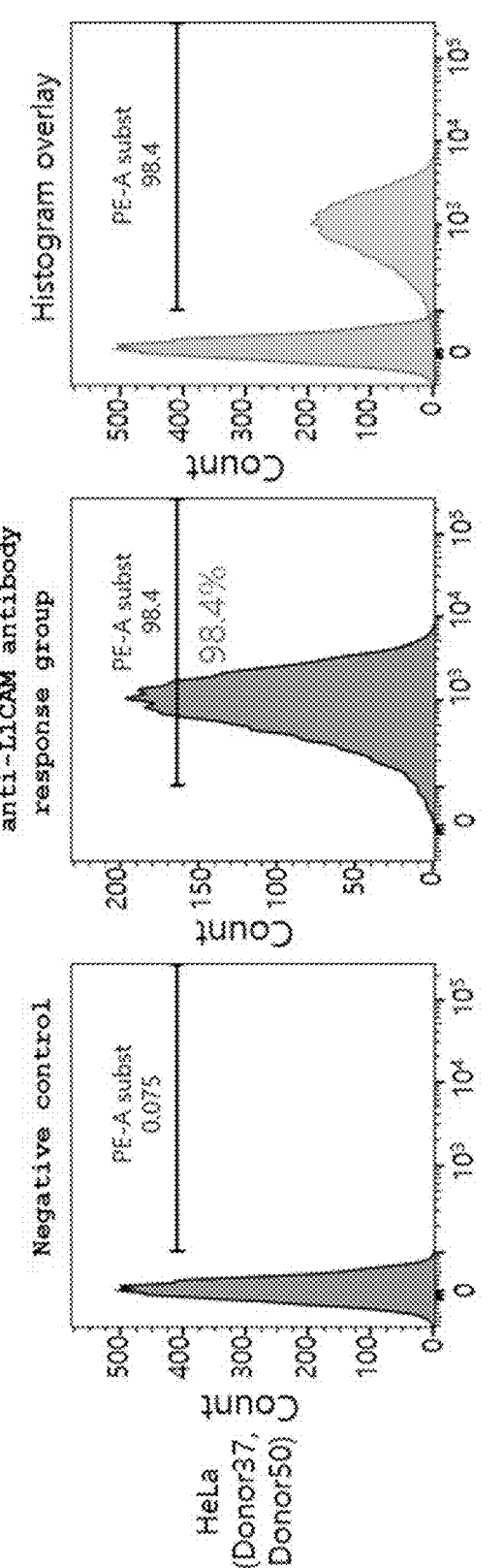
Figure 61D:
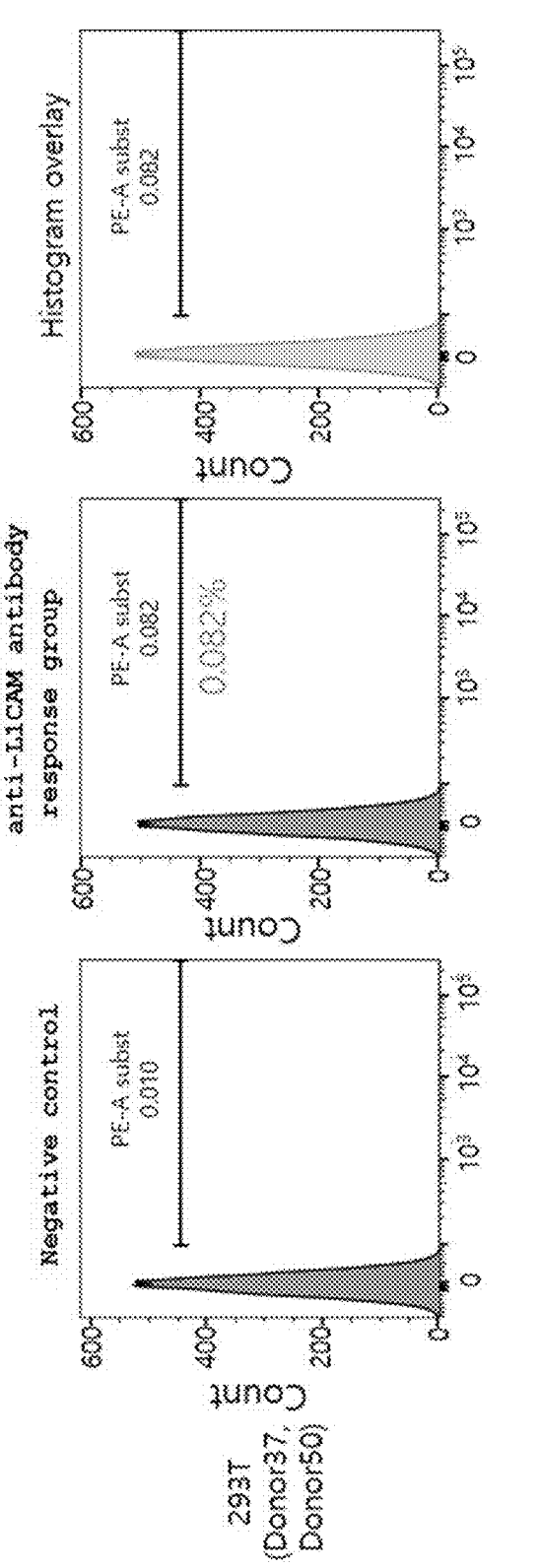
Figure 61E:
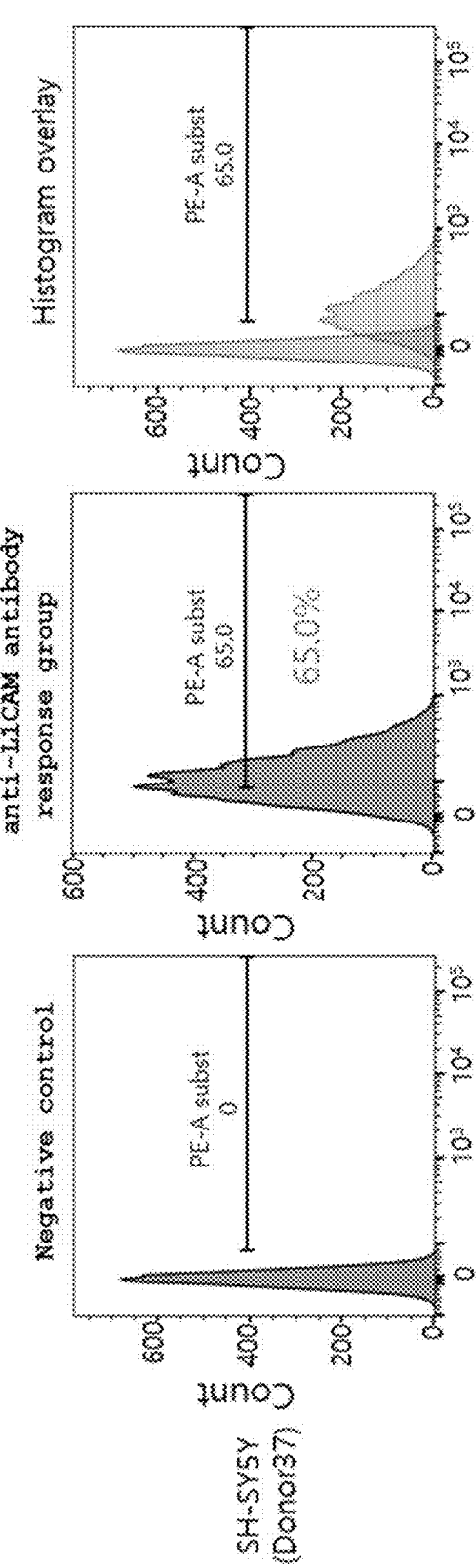
Figure 61F:
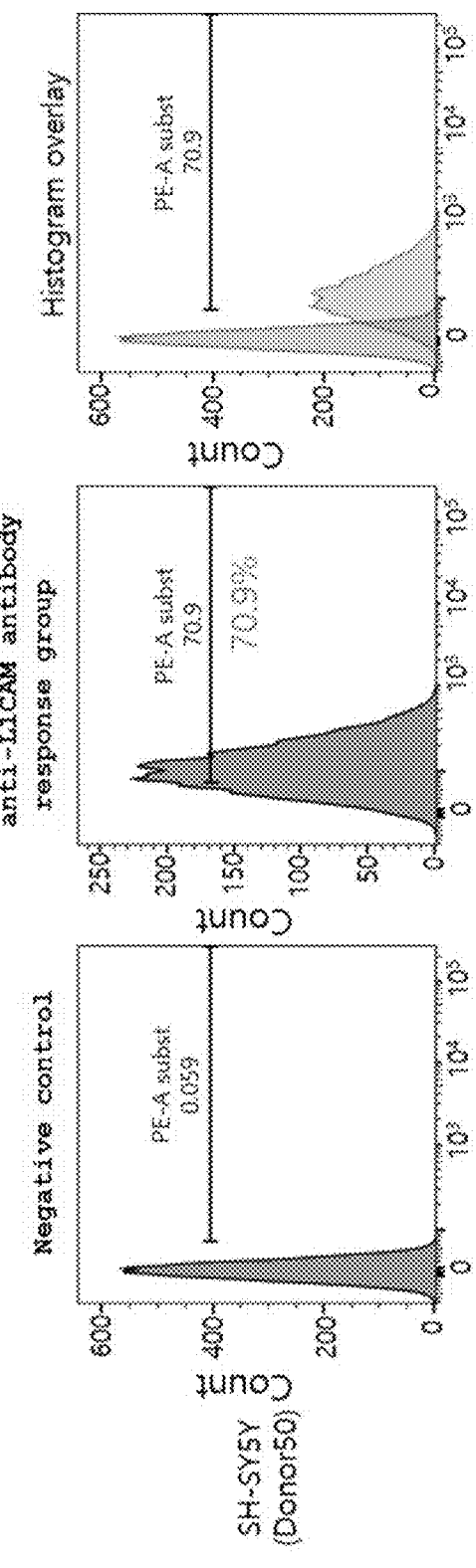

6.1.3.5. Obtainment of hGM-CSF Receptor Alpha-Chain Signal Sequence, L1-H8 scFv, Hinge, TM, ICD, Costimulatory Domain, and CD3ζ Gene Mlu I-hGM-CSF rec.α-L1-H8 scFv-hinge-hCD28 pECD and L1-H8 scFv-Hinge-hCD28 pECD-hCD28 TM-hCD28 ICD-CD3ζ-iso2-Xho I, which were the amplified PCR products, as templates, were amplified by OE-PCR using the primers of SEQ ID NO: 111 (Table 15) and SEQ ID NO: 116 (Table 15) (FIG. 58). The amplified PCR product has the nucleotide sequence of Mlu I-hGM-CSF rec.α-L1-H8 scFv-hinge-hCD28 pECD-hCD28 TM-hCD28 ICD-CD3ζ-iso2-Xho I and the structure of L1-H8-CAR-007 (FIG. 59).

6.1.4. Preparation of pMT-L1-H8-CAR Retroviral Vectors

Three types of the amplified PCR products were treated with Mlu I and Xho I restriction enzymes to obtain DNA fragments. The obtained DNA fragments were ligated to the pMT retroviral vectors (U.S. Pat. No. 6,451,595) previously treated with Mlu I and Xho I restriction enzymes to prepare three types of pMT-L1-H8-CAR retroviral vectors (FIG.

60). The pMT-L1-H8-CAR retroviral vectors thus prepared include a sequence encoding L1-H8-CAR under the control of the MLV LTR promoter.

6.2. Preparation of Retroviruses Expressing L1-H8-CAR Genes with Various Structures (L1-H8-CAR Retroviruses)

Four types of retroviruses expressing L1-H8-CAR-003, -005, -006, and -007 genes were prepared by the same method as in Example 4.2.

6.3. Preparation of T Cells Expressing L1-H8-CAR Genes with Various Structures Four types of L1-H8-CAR-T were prepared by the same method as in Example 4.3. The results verified that although there is a difference depending on the donor, the expression rate of L1-H8-CAR was about 22.1% to 74.1% on day 8 of incubation, about 27.1% to 77.1% on day 11 of incubation, about 24.6% to 76.6% on day 14 of incubation, and about 29.8% to 81.9% on day 16 of incubation (Table 19).

TABLE 19

| | | Expression rates of L1-H8-CAR on surfaces of L1-H8-CAR-expressing T cells | | | | |
|---|---|---|---|---|---|---|
| Donor NO. | Days of culture | Control | L1-H8-CAR-003 | L1-H8-CAR-005 | L1-H8-CAR-006 | L1-H8-CAR-007 |
| 37 | 8 Days | 1.07% | 67.1% | 22.1% | 71.4% | 63.4% |
| | 11 Days | 1.75% | 65.7% | 27.1% | 72.8% | 61.2% |
| | 14 Days | 1.01% | 60.0% | 24.6% | 64.5% | 52.7% |
| | 16 Days | 0.81% | 69.5% | 29.8% | 78.3% | 70.7% |
| 50 | 8 Days | 1.36% | 73.2% | 34.5% | 74.1% | 63.3% |
| | 11 Days | 1.73% | 75.6% | 39.0% | 77.1% | 68.3% |
| | 14 Days | 0.87% | 76.6% | 35.4% | 69.8% | 62.5% |
| | 16 Days | 0.59% | 81.9% | 43.9% | 81.8% | 74.3% |

6.4. Verification of Anticancer Activity of T Cells Expressing L1-H8-CAR Genes with Various Structures (In Vitro)

6.4.1. Verification of Expression Rates of L1CAM in Target Cells

The expression rate of L1CAM in target cells was investigated by the same method as in Example 4.4.1. The results verified that the L1CAM expression rate was about 67.1% to 87.0% in SKOV3 cancer cells. As a result of investigating the expression of L1CAM in the human cervical cancer cell line HeLa, the human neuroblastoma cell line SH-SY5Y, and the human embryonic kidney cell line 293T, the expression rate was about 98.4% in HeLa, about 65.0 to 70.9% in SH-SY5Y, and about 0.082% in 293T (FIGS. 61A to 61F).

6.4.2. Verification of Anticancer Activity of L1CAM-Expressing T Cells on Target Cells (In Vitro)

6.4.2.1. Verification of Anticancer Activity Using xCelligence Assay

The ability of four types of L1-H8-CAR on SKOV3 were investigated by the same method as in Example 4.4.2.1. As a result, four types of T cells expressing L1-H8-CAR-003 and L1-H8-CAR-005, -006, and -007 showed high cytotox-

65

Figure 62:
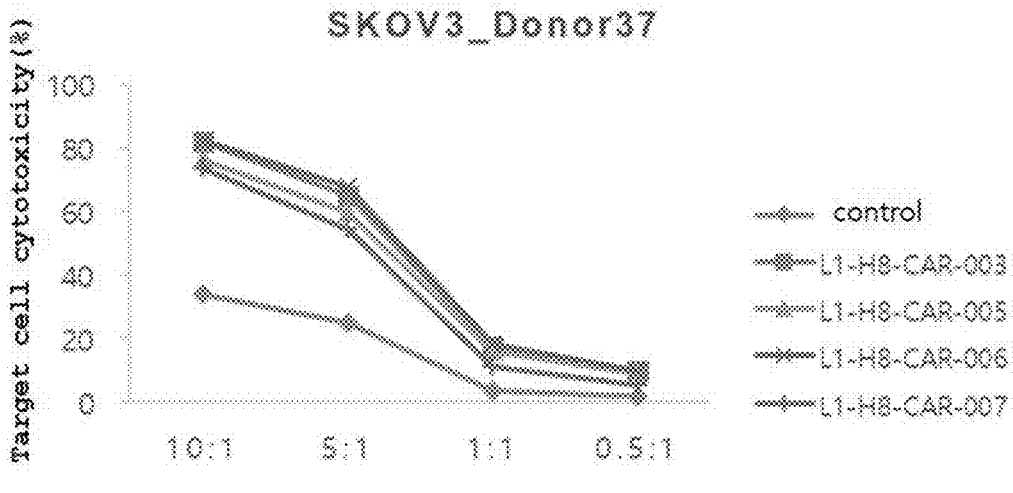
FIG. 62 shows anticancer activity of anti-L1CAM-CAR-expressing T cells of the present disclosure on SKOV3 cells (high expression of L1CAM).
Figure 62:
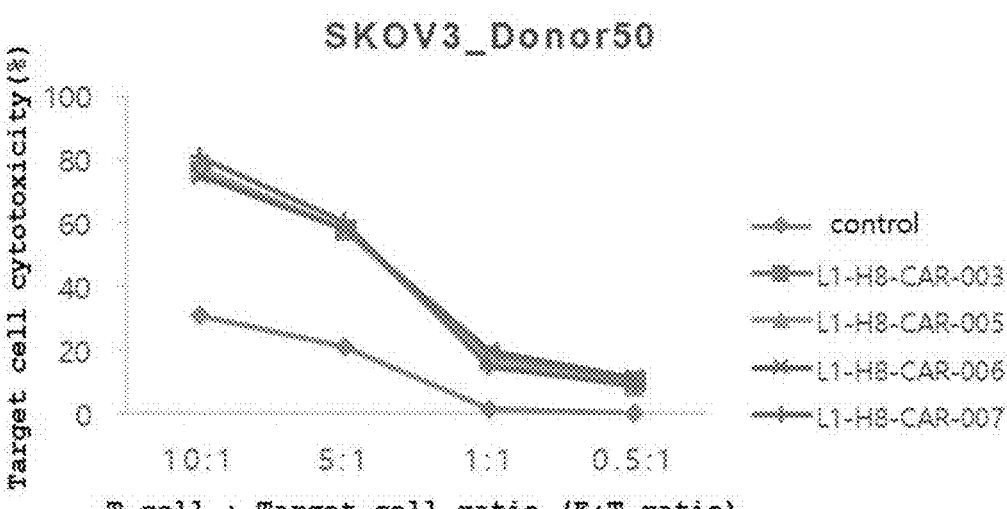

66 icity on SKOV3 cells compared with T cells not expressing L1-H8-CAR (control) (FIG. 62).

Figure 63:
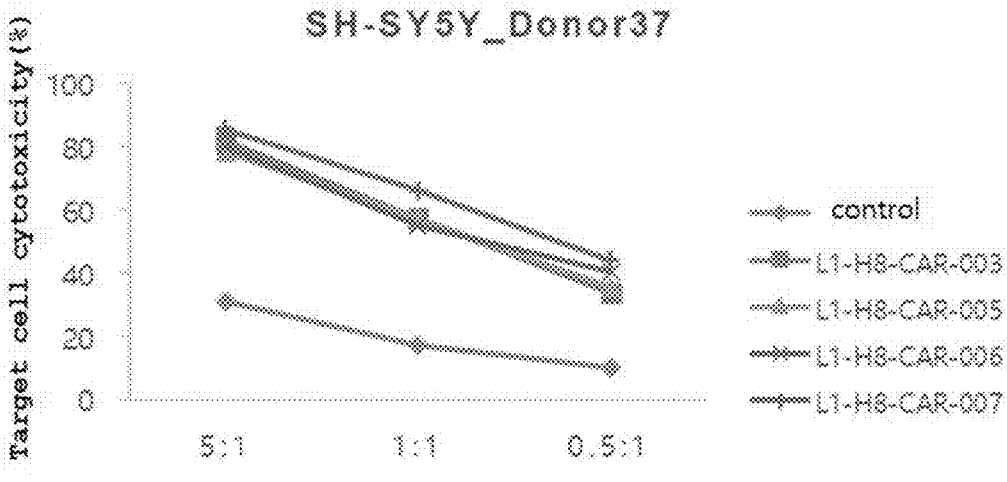
FIG. 63 shows anticancer activity of anti-L1CAM-CAR-expressing T cells of the present disclosure on SH-SY5Y cells (high expression of L1CAM).
Figure 63:
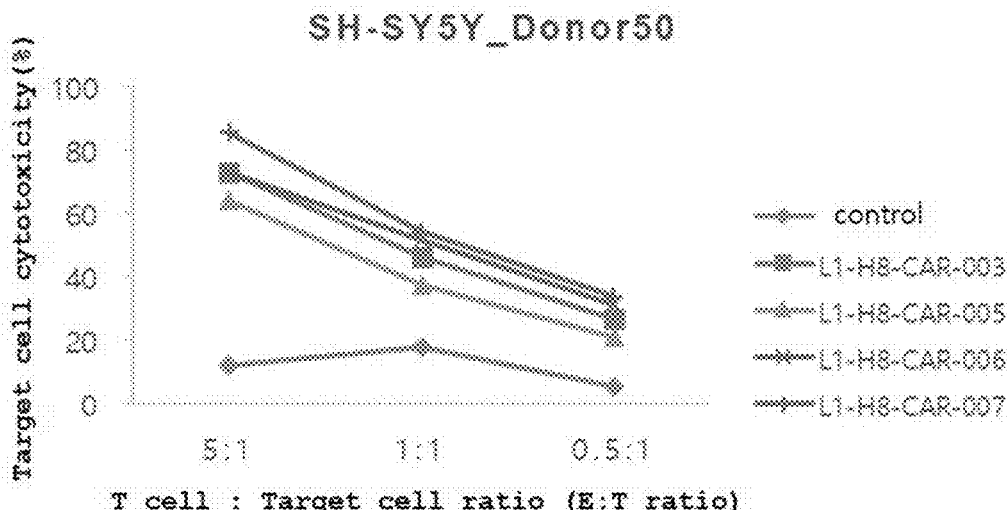

The cytotoxicity on SH-SY5Y cells were investigated by the same method as in Example 4.4.2.1. The target cells were added at $1.0 \times 10^5$ to 50 uL of culture media, and after about 21 hours, L1-H8-CAR-expressing T cells were prepared at $5.0 \times 10^4$, $1.0 \times 10^5$, and $5.0 \times 10^5$ (E:T ratio=0.5, 1, and 5) in 50 uL of AIMV media comprising human serum and human IL-2, and added to wells comprising target cells, to check the cell index value in real time for 30 hours. In addition, wells comprising only target cells were prepared, and the anticancer activity of L1-H8-CAR-expressing T cells was calculated in the same manner as in the above tests. As a result, four types of T cells expressing L1-H8-CAR-003 and L1-H8-CAR-005, -006, and -007 showed high cytotoxicity on SH-SY5Y cells compared with T cells not expressing L1-H8-CAR (control) (FIG. 63).

6.4.2.2. Verification of Anticancer Activity Using CellTox™ Green Dye

Figure 64:
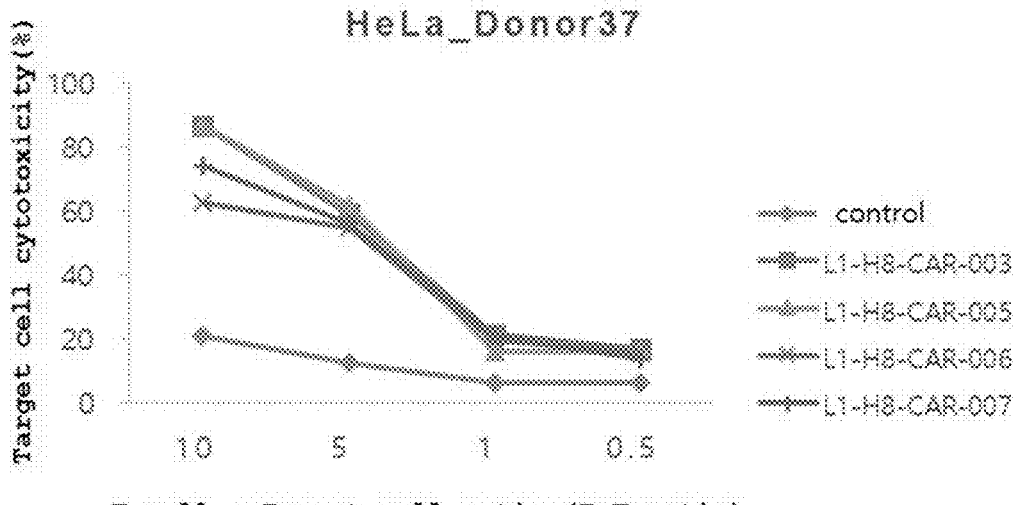
FIG. 64 shows anticancer activity of anti-L1CAM-CAR-expressing T cells of the present disclosure on HeLa cells (high expression of L1CAM).
Figure 64:
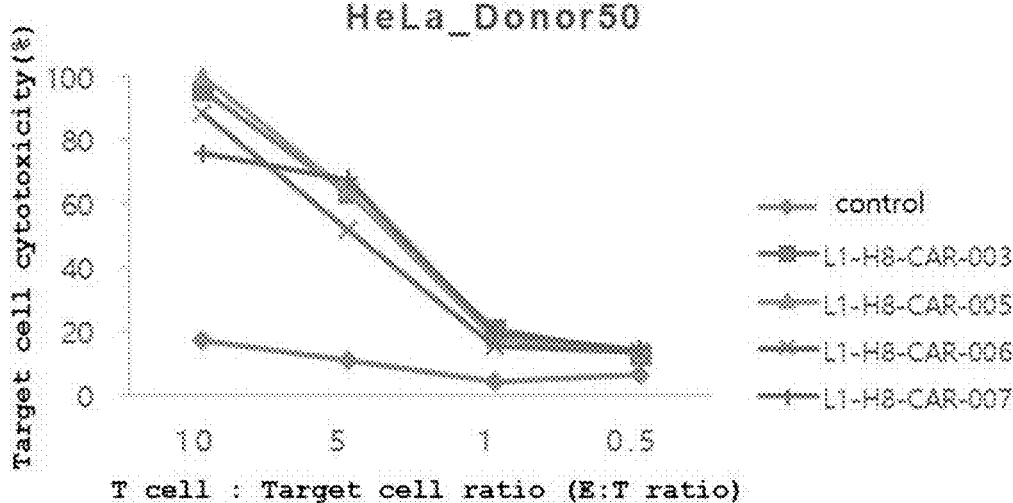

The activity of four types of L1-H8-CAR on HeLa cells were investigated by the same method as in Example 4.4.2.2. As a result, four types of T cells expressing L1-H8-CAR-003 and L1-H8-CAR-005, -006, and -007 showed high cytotoxicity on HeLa cells compared with T cells not expressing L1-H8-CAR (control) (FIG. 64).

The cytotoxicity on 293T cancer cells were investigated by the same method as in Example 4.4.2.2. The target cells were prepared at $1.0 \times 10^4$ in 50 uL of culture media, and 0.2 uL of CellTox™ Green dye was added, and the mix was added to 96-well black plates. The L1-H8-CAR-expressing T cells were prepared at $5.0 \times 10^3$, $1.0 \times 10^4$, $5.0 \times 10^4$, and $1.0 \times 10^5$ (E:T ratio=0.5, 1, 5, and 10) in 50 uL of AIMV media comprising human serum and human IL-2, and added to wells comprising target cells, followed by incubation in a $CO_2$ incubator at 37° C. for 24 hours. The cytotoxicity on the target cells was corrected and calculated by the same method.

Figure 65:
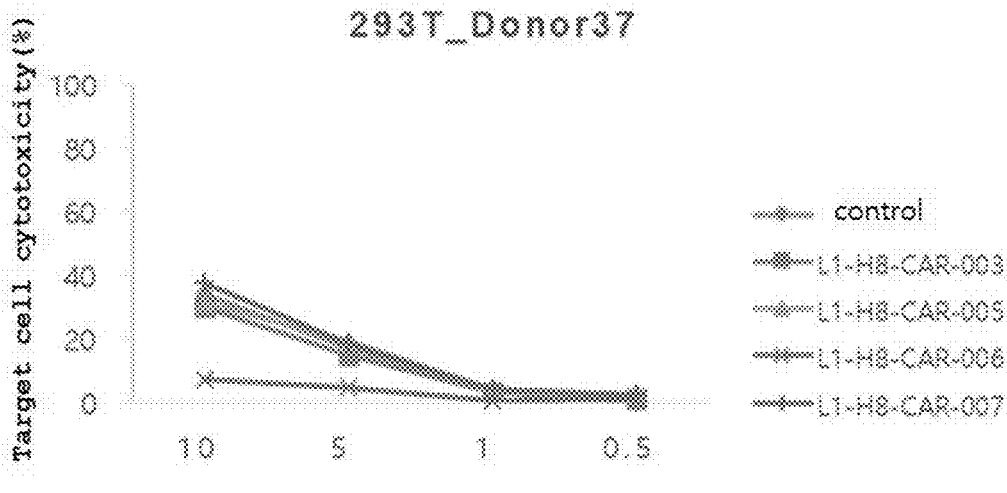
FIG. 65 shows anticancer activity of anti-L1CAM-CAR-expressing T cells of the present disclosure on 293T cells (low expression of L1CAM).
Figure 65:
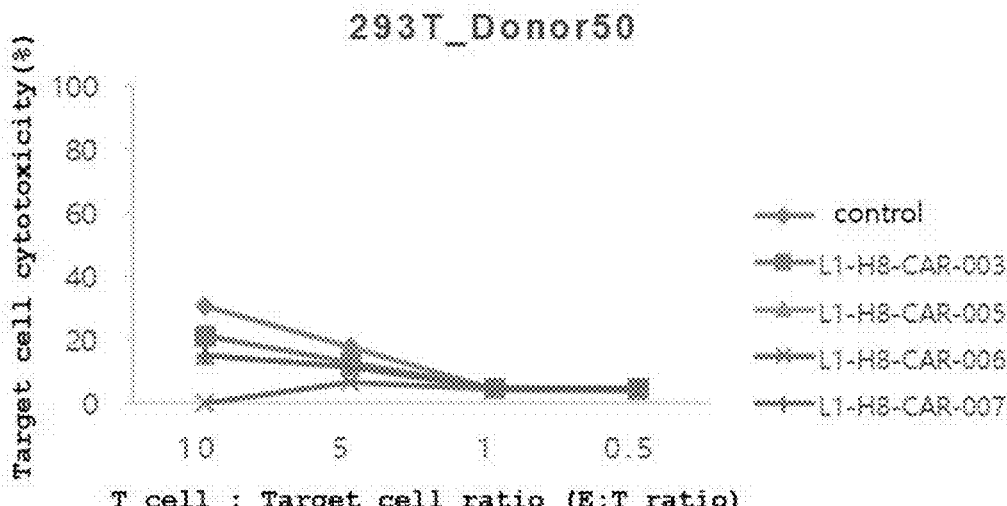

As a result, all the four types showed cytotoxicity similar to or lower than that of the control in 293T cells showing a low expression rate of L1CMA (FIG. 65).

---

What is claimed is:

1. A chimeric antigen receptor polypeptide comprising:

(a) an L1CAM binding domain;

(b) a transmembrane domain (TM);

(c) a costimulatory domain; and (d) an intracellular signaling domain (ICD), wherein the L1CAM binding domain comprises the anti-L1CAM antibody or antigen-binding fragment thereof comprising a heavy chain variable region (VH) comprising CDRH1 (complementarity determining region 1 of heavy chain), CDRH2, and CDRH3 below and a light chain variable region (VL) comprising CDRL1, CDRL2, and CDRL3 below:

i) CDRH1 consisting of the amino acid sequence of SEQ ID NO: 1, CDRH2 consisting of the amino acid sequence of SEQ ID NO: 8, and CDRH3 consisting of the amino acid sequence of SEQ ID NO: 15; and CDRL1 consisting of the amino acid sequence of SEQ ID NO: 32, CDRL2 consisting of the amino acid sequence of SEQ ID NO: 37, and CDRL3 consisting of the amino acid sequence of SEQ ID NO: 43;

ii) CDRH1 consisting of the amino acid sequence of SEQ ID NO: 2, CDRH2 consisting of the amino acid sequence of SEQ ID NO: 9, and CDRH3 consisting of the amino acid sequence of SEQ ID NO: 16; and CDRL1 consisting of the amino acid sequence of SEQ ID NO: 33, CDRL2 consisting of the amino acid sequence of SEQ ID NO: 38, and CDRL3 consisting of the amino acid sequence of SEQ ID NO: 44;

iii) CDRH1 consisting of the amino acid sequence of SEQ ID NO: 3, CDRH2 consisting of the amino acid sequence of SEQ ID NO: 10, and CDRH3 consisting of the amino acid sequence of SEQ ID NO: 17; and CDRL1 consisting of the amino acid sequence of SEQ ID NO: 34, CDRL2 consisting of the amino acid sequence of SEQ ID NO: 38, and CDRL3 consisting of the amino acid sequence of SEQ ID NO: 44;

iv) CDRH1 consisting of the amino acid sequence of SEQ ID NO: 4, CDRH2 consisting of the amino acid sequence of SEQ ID NO: 11, and CDRH3 consisting of the amino acid sequence of SEQ ID NO: 18; and CDRL1 consisting of the amino acid sequence of SEQ ID NO: 34, CDRL2 consisting of the amino acid sequence of SEQ ID NO: 39, and CDRL3 consisting of the amino acid sequence of SEQ ID NO: 45;

v) CDRH1 consisting of the amino acid sequence of SEQ ID NO: 3, CDRH2 consisting of the amino acid sequence of SEQ ID NO: 9, and CDRH3 consisting of the amino acid sequence of SEQ ID NO: 19; and CDRL1 consisting of the amino acid sequence of SEQ ID NO: 35, CDRL2 consisting of the amino acid sequence of SEQ ID NO: 39, and CDRL3 consisting of the amino acid sequence of SEQ ID NO: 46;

vi) CDRH1 consisting of the amino acid sequence of SEQ ID NO: 5, CDRH2 consisting of the amino acid sequence of SEQ ID NO: 12, and CDRH3 consisting of the amino acid sequence of SEQ ID NO: 20; and CDRL1 consisting of the amino acid sequence of SEQ ID NO: 33, CDRL2 consisting of the amino acid sequence of SEQ ID NO: 40, and CDRL3 consisting of the amino acid sequence of SEQ ID NO: 47;

vii) CDRH1 consisting of the amino acid sequence of SEQ ID NO: 6, CDRH2 consisting of the amino acid sequence of SEQ ID NO: 13, and CDRH3 consisting of the amino acid sequence of SEQ ID NO: 21; and CDRL1 consisting of the amino acid sequence of SEQ ID NO: 34, CDRL2 consisting of the amino acid sequence of SEQ ID NO: 41, and CDRL3 consisting of the amino acid sequence of SEQ ID NO: 44;

viii) CDRH1 consisting of the amino acid sequence of SEQ ID NO: 7, CDRH2 consisting of the amino acid sequence of SEQ ID NO: 9, and CDRH3 consisting of the amino acid sequence of SEQ ID NO: 22; and CDRL1 consisting of the amino acid sequence of SEQ ID NO: 36, CDRL2 consisting of the amino acid sequence of SEQ ID NO: 42, and CDRL3 consisting of the amino acid sequence of SEQ ID NO: 43; or ix) CDRH1 consisting of the amino acid sequence of SEQ ID NO: 3, CDRH2 consisting of the amino acid sequence of SEQ ID NO: 14, and CDRH3 consisting of the amino acid sequence of SEQ ID NO: 23; and CDRL1 consisting of the amino acid sequence of SEQ ID NO: 34, CDRL2 consisting of the amino acid sequence of SEQ ID NO: 37, and CDRL3 consisting of the amino acid sequence of SEQ ID NO: 44.

2. The chimeric antigen receptor polypeptide of claim 1, wherein the transmembrane domain includes a transmembrane domain of a protein selected from the group consisting of a T-cell receptor alpha, beta, or zeta chain, CD28, CD3 epsilon, CD45, CD4, CD5, CD8, CD9, CD16, CD22, CD33, CD37, CD64, CD80, CD86, CD134, CD137, and CD154.

3. The chimeric antigen receptor polypeptide of claim 1, wherein the costimulatory domain is a functional signaling domain obtained from a protein selected from the group consisting of TNF receptor proteins, cytokine receptors, integrins, signaling lymphocytic activation molecules (SLAMs), B and T lymphocyte attenuators (BTLAs), Toll-like ligand receptors, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and CD83.

4. The chimeric antigen receptor polypeptide of claim 1, wherein the intracellular signaling domain includes a functional signaling domain of 4-1BB, CD28, OX40, or CD3 zeta, or a combination thereof.

5. The chimeric antigen receptor polypeptide of claim 1, wherein the anti-L1CAM antibody or antigen-binding fragment thereof comprising VH and VL below:

i) VH consisting of the amino acid sequence of SEQ ID NO: 52, and VL consisting of the amino acid sequence of SEQ ID NO: 56;

ii) VH consisting of the amino acid sequence of SEQ ID NO: 53, and VL consisting of the amino acid sequence of SEQ ID NO: 57;

iii) VH consisting of the amino acid sequence of SEQ ID NO: 54, and VL consisting of the amino acid sequence of SEQ ID NO: 58; or iv) VH consisting of the amino acid sequence of SEQ ID NO: 55, and VL consisting of the amino acid sequence of SEQ ID NO: 59.

* * * * *

SEQUENCE LISTING

<160> NUMBER OF SEQ ID NOS: 130

<210> SEQ ID NO 1
<211> LENGTH: 5
<212> TYPE: PRT
<213> ORGANISM: Artificial Sequence
<220> FEATURE:
<223> OTHER INFORMATION: CDRH1 of mL1CAM-3R-H8

<400> SEQUENCE: 1

Asp Tyr Ala Met Asn
1               5

<210> SEQ ID NO 2
<211> LENGTH: 5
<212> TYPE: PRT
<213> ORGANISM: Artificial Sequence
<220> FEATURE:
<223> OTHER INFORMATION: CDRH1 of mL1CAM-3R-C9

<400> SEQUENCE: 2

Ser Tyr Ala Met His
1               5

<210> SEQ ID NO 3
<211> LENGTH: 5
<212> TYPE: PRT
<213> ORGANISM: Artificial Sequence
<220> FEATURE:
<223> OTHER INFORMATION: CDRH1 of mL1CAM-3R-E1, mL1CAM-3R-F1, and
      mL1CAM-2R-F8

<400> SEQUENCE: 3

Ser Tyr Ala Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: CDRH1 of mL1CAM-3R-F6

```
<400> SEQUENCE: 4

Ser Tyr Ala Met His
1               5

<210> SEQ ID NO 5
<211> LENGTH: 5
<212> TYPE: PRT
<213> ORGANISM: Artificial Sequence
<220> FEATURE:
<223> OTHER INFORMATION: CDRH1 of mL1CAM-3R-G6

<400> SEQUENCE: 5

Asn Tyr Ala Met His
1               5

<210> SEQ ID NO 6
<211> LENGTH: 5
<212> TYPE: PRT
<213> ORGANISM: Artificial Sequence
<220> FEATURE:
<223> OTHER INFORMATION: CDRH1 of mL1CAM-3R-A2

<400> SEQUENCE: 6

Ser Tyr Ala Met Asn
1               5

<210> SEQ ID NO 7
<211> LENGTH: 5
<212> TYPE: PRT
<213> ORGANISM: Artificial Sequence
<220> FEATURE:
<223> OTHER INFORMATION: CDRH1 of mL1CAM-3R-E9

<400> SEQUENCE: 7

Asp Tyr Ala Met His
1               5

<210> SEQ ID NO 8
<211> LENGTH: 17
<212> TYPE: PRT
<213> ORGANISM: Artificial Sequence
<220> FEATURE:
<223> OTHER INFORMATION: CDRH2 of mL1CAM-3R-H8

<400> SEQUENCE: 8

Ala Ile Ser Ser Thr Gly Ser Thr Ile Tyr Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: CDRH2 of mL1CAM-3R-C9, mL1CAM-3R-F1, and
     mL1CAM-3R-E9

<400> SEQUENCE: 9

Ala Ile Ser Ser Ser Gly Gly Ser Thr Tyr Tyr Ala Asp Ser Val Lys
1               5                   10                  15

Gly

<210> SEQ ID NO 10
<211> LENGTH: 17
<212> TYPE: PRT
```

<210> ORGANISM: Artificial Sequence
<220> FEATURE:
<223> OTHER INFORMATION: CDRH2 of mL1CAM-3R-E1

<400> SEQUENCE: 10

Ala Ile Ser Ser Ser Gly Ser Ser Thr Tyr Tyr Ala Asp Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: CDRH2 of mL1CAM-3R-F6

<400> SEQUENCE: 11

Ala Ile Ser Ser Ser Gly Ser Ser Lys Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: CDRH2 of mL1CAM-3R-G6

<400> SEQUENCE: 12

Ala Ile Tyr Gln Ser Gly Gly Asp Thr Tyr Tyr Ala Asp Ser Val Lys
1               5                   10                  15

Gly

<210> SEQ ID NO 13
<211> LENGTH: 16
<212> TYPE: PRT
<213> ORGANISM: Artificial Sequence
<220> FEATURE:
<223> OTHER INFORMATION: CDRH2 of mL1CAM-3R-A2

<400> SEQUENCE: 13

Arg Ile Ser Ser Ser Gly Thr Thr Phe Tyr Ala Asp Ser Val Lys Gly
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: CDRH2 of mL1CAM-2R-F8

<400> SEQUENCE: 14

Ala Ile Ser Ser Ser Gly Gly Thr Lys Tyr Tyr Ala Asp Ser Val Lys
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: CDRH3 of mL1CAM-3R-H8

<400> SEQUENCE: 15

Gln Ser Thr Tyr Phe Tyr Ser Tyr Phe Asp Val
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CDRH3 of mL1CAM-3R-C9

<400> SEQUENCE: 16

Asp Glu Gly Ser Gly Leu Gly Ala Phe Asp Ile
1               5                   10

<210> SEQ ID NO 17
<211> LENGTH: 11
<212> TYPE: PRT
<213> ORGANISM: Artificial Sequence
<220> FEATURE:
<223> OTHER INFORMATION: CDRH3 of mL1CAM-3R-E1

<400> SEQUENCE: 17

Asp Glu Ser Thr Gly Leu Gly Ala Phe Asp Tyr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: CDRH3 of mL1CAM-3R-F6

<400> SEQUENCE: 18

Asp Glu Ser Tyr Gly Trp Leu Tyr Ala Phe Asp Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: CDRH3 of mL1CAM-3R-F1

<400> SEQUENCE: 19

Val Leu Glu Leu Trp Glu Gly Leu Asp Tyr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: CDRH3 of mL1CAM-3R-G6

<400> SEQUENCE: 20

Val Arg Gly Thr Tyr Tyr Gly Ser Tyr Leu Asp Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: CDRH3 of mL1CAM-3R-A2

<400> SEQUENCE: 21

Val Glu Glu Gly Arg Tyr Val Gln Ala Phe Asp Tyr

```
1               5               10
```

<210> SEQ ID NO 22
<211> LENGTH: 12
<212> TYPE: PRT
<213> ORGANISM: Artificial Sequence
<220> FEATURE:
<223> OTHER INFORMATION: CDRH3 of mL1CAM-3R-E9

<400> SEQUENCE: 22

```
His Gly Gly Thr Trp Trp Gly Arg Ala Phe Asp Tyr
1               5               10
```

<210> SEQ ID NO 23
<211> LENGTH: 10
<212> TYPE: PRT
<213> ORGANISM: Artificial Sequence
<220> FEATURE:
<223> OTHER INFORMATION: CDRH3 of mL1CAM-2R-F8

<400> SEQUENCE: 23

```
His Gly Ser Tyr Ala Phe Val Phe Asp Tyr
1               5               10
```

<210> SEQ ID NO 24
<211> LENGTH: 30
<212> TYPE: PRT
<213> ORGANISM: Artificial Sequence
<220> FEATURE:
<223> OTHER INFORMATION: FRH1 of mL1CAM-3R-H8, mL1CAM-3R-C9,
     mL1CAM-3R-E1, mL1CAM-3R-F6, mL1CAM-3R-F1, mL1CAM-3R-A2, and
     mL1CAM-3R-E9

<400> SEQUENCE: 24

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser
            20              25              30
```

<210> SEQ ID NO 25
<211> LENGTH: 30
<212> TYPE: PRT
<213> ORGANISM: Artificial Sequence
<220> FEATURE:
<223> OTHER INFORMATION: FRH1 of mL1CAM-3R-G6

<400> SEQUENCE: 25

```
Glu Val Gln Leu Val Glu Ser Gly Gly Gly Leu Leu Gln Pro Gly Gly
1               5               10              15

Ser Leu Arg Leu Ser Cys Ala Ala Ser Gly Phe Thr Phe Ser
            20              25              30
```

<210> SEQ ID NO 26
<211> LENGTH: 30
<212> TYPE: PRT
<213> ORGANISM: Artificial Sequence
<220> FEATURE:
<223> OTHER INFORMATION: FRH1 of mL1CAM-2R-F8

<400> SEQUENCE: 26

```
Glu Val Gln Leu Val Glu Ser Gly Gly Gly Leu Ala Gln Pro Gly Gly
1               5               10              15

Ser Leu Arg Leu Ser Cys Ala Ala Ser Gly Phe Thr Phe Ser
            20              25              30
```

```
<210> SEQ ID NO 27
<211> LENGTH: 14
<212> TYPE: PRT
<213> ORGANISM: Artificial Sequence
<220> FEATURE:
<223> OTHER INFORMATION: FRH2 of mL1CAM-3R-H8, mL1CAM-3R-C9,
      mL1CAM-3R-E1, mL1CAM-3R-F6, mL1CAM-3R-F1, mL1CAM-3R-G6,
      mL1CAM-3R-A2, mL1CAM-3R-E9, and mL1CAM-2R-F8

<400> SEQUENCE: 27

Trp Val Arg Gln Ala Pro Gly Lys Gly Leu Glu Trp Val Ser
1               5                   10

<210> SEQ ID NO 28
<211> LENGTH: 32
<212> TYPE: PRT
<213> ORGANISM: Artificial Sequence
<220> FEATURE:
<223> OTHER INFORMATION: FRH3 of mL1CAM-3R-H8, mL1CAM-3R-C9,
      mL1CAM-3R-E1, mL1CAM-3R-F1, mL1CAM-3R-G6, mL1CAM-3R-A2,
      mL1CAM-3R-E9, and mL1CAM-2R-F8

<400> SEQUENCE: 28

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: FRH3 of mL1CAM-3R-F6

<400> SEQUENCE: 29

Arg Phe Thr Ile Ser Arg Asp Asn Ser Lys Asn Thr Leu Tyr Leu Gln
1               5                   10                  15

Ile Asn Ser Leu Arg Ala Glu Asp Thr Ala Val Tyr Tyr Cys Ala Lys
            20                  25                  30

<210> SEQ ID NO 30
<211> LENGTH: 11
<212> TYPE: PRT
<213> ORGANISM: Artificial Sequence
<220> FEATURE:
<223> OTHER INFORMATION: FRH4 of mL1CAM-3R-H8, mL1CAM-3R-C9,
      mL1CAM-3R-E1, mL1CAM-3R-F6, mL1CAM-3R-F1, mL1CAM-3R-G6,
      mL1CAM-3R-A2, mL1CAM-3R-E9, and mL1CAM-2R-F8

<400> SEQUENCE: 30

Trp Gly Gln Gly Thr Leu Val Thr Val Ser Ser
1               5                   10

<210> SEQ ID NO 31
<211> LENGTH: 15
<212> TYPE: PRT
<213> ORGANISM: Artificial Sequence
<220> FEATURE:
<223> OTHER INFORMATION: (G4S1)3 linker

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 11
```

<212> TYPE: PRT
<213> ORGANISM: Artificial Sequence
<220> FEATURE:
<223> OTHER INFORMATION: CDRL1 of mL1CAM-3R-H8

<400> SEQUENCE: 32

Arg Ala Ser Gln Ser Ile Ser Arg Asp Leu Asn
1               5                   10

<210> SEQ ID NO 33
<211> LENGTH: 11
<212> TYPE: PRT
<213> ORGANISM: Artificial Sequence
<220> FEATURE:
<223> OTHER INFORMATION: CDRL1 of mL1CAM-3R-C9, and mL1CAM-3R-G6

<400> SEQUENCE: 33

Arg Ala Ser Gln Ser Ile Ser Arg Tyr Leu Asn
1               5                   10

<210> SEQ ID NO 34
<211> LENGTH: 11
<212> TYPE: PRT
<213> ORGANISM: Artificial Sequence
<220> FEATURE:
<223> OTHER INFORMATION: CDRL1 of mL1CAM-3R-E1, mL1CAM-3R-F6,
     mL1CAM-3R-A2, and mL1CAM-2R-F8

<400> SEQUENCE: 34

Arg Ala Ser Gln Ser Ile Ser Asn Tyr Leu Asn
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CDRL1 of mL1CAM-3R-F1

<400> SEQUENCE: 35

Arg Ala Ser Gln Ser Ile Ser Ser Tyr Leu Asn
1               5                   10

<210> SEQ ID NO 36
<211> LENGTH: 11
<212> TYPE: PRT
<213> ORGANISM: Artificial Sequence
<220> FEATURE:
<223> OTHER INFORMATION: CDRL1 of mL1CAM-3R-E9

<400> SEQUENCE: 36

Arg Ala Ser Gln Ser Ile Gly Ser Tyr Leu Asn
1               5                   10

<210> SEQ ID NO 37
<211> LENGTH: 7
<212> TYPE: PRT
<213> ORGANISM: Artificial Sequence
<220> FEATURE:
<223> OTHER INFORMATION: CDRL2 of mL1CAM-3R-H8 and mL1CAM-2R-F8

<400> SEQUENCE: 37

Ala Ala Ser Ser Leu Gln Ser
1               5

<210> SEQ ID NO 38
<211> LENGTH: 7

```
<212> TYPE: PRT
<213> ORGANISM: Artificial Sequence
<220> FEATURE:
<223> OTHER INFORMATION: CDRL2 of mL1CAM-3R-C9, and mL1CAM-3R-E1

<400> SEQUENCE: 38

Ala Ala Ser Asn Leu Gln Ser
1               5

<210> SEQ ID NO 39
<211> LENGTH: 7
<212> TYPE: PRT
<213> ORGANISM: Artificial Sequence
<220> FEATURE:
<223> OTHER INFORMATION: CDRL2 of mL1CAM-3R-F6, and mL1CAM-3R-F1

<400> SEQUENCE: 39

Ala Ala Ser Arg Leu Gln Ser
1               5

<210> SEQ ID NO 40
<211> LENGTH: 7
<212> TYPE: PRT
<213> ORGANISM: Artificial Sequence
<220> FEATURE:
<223> OTHER INFORMATION: CDRL2 of mL1CAM-3R-G6

<400> SEQUENCE: 40

Ala Ala Ser Thr Leu Gln Ser
1               5

<210> SEQ ID NO 41
<211> LENGTH: 7
<212> TYPE: PRT
<213> ORGANISM: Artificial Sequence
<220> FEATURE:
<223> OTHER INFORMATION: CDRL2 of mL1CAM-3R-A2

<400> SEQUENCE: 41

Ala Thr Ser Arg Leu Gln Ser
1               5

<210> SEQ ID NO 42
<211> LENGTH: 7
<212> TYPE: PRT
<213> ORGANISM: Artificial Sequence
<220> FEATURE:
<223> OTHER INFORMATION: CDRL2 of mL1CAM-3R-E9

<400> SEQUENCE: 42

Ala Thr Ser Ser Leu Gln Ser
1               5

<210> SEQ ID NO 43
<211> LENGTH: 9
<212> TYPE: PRT
<213> ORGANISM: Artificial Sequence
<220> FEATURE:
<223> OTHER INFORMATION: CDRL3 of mL1CAM-3R-H8, and mL1CAM-3R-E9

<400> SEQUENCE: 43

Gln Gln Ser Tyr Ser Thr Pro Tyr Thr
1               5

<210> SEQ ID NO 44
<211> LENGTH: 9
<212> TYPE: PRT
```

```
<213> ORGANISM: Artificial Sequence
<220> FEATURE:
<223> OTHER INFORMATION: CDRL3 of mL1CAM-3R-C9, mL1CAM-3R-E1,
      mL1CAM-3R-A2, and mL1CAM-2R-F8

<400> SEQUENCE: 44

Gln Gln Ser Tyr Ser Phe Pro Trp Thr
1               5

<210> SEQ ID NO 45
<211> LENGTH: 9
<212> TYPE: PRT
<213> ORGANISM: Artificial Sequence
<220> FEATURE:
<223> OTHER INFORMATION: CDRL3 of mL1CAM-3R-F6

<400> SEQUENCE: 45

Gln Gln Ser Tyr Ser Phe Pro Leu Thr
1               5

<210> SEQ ID NO 46
<211> LENGTH: 9
<212> TYPE: PRT
<213> ORGANISM: Artificial Sequence
<220> FEATURE:
<223> OTHER INFORMATION: CDRL3 of mL1CAM-3R-F1

<400> SEQUENCE: 46

Gln Gln Ser Glu Ser Phe Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: CDRL3 of mL1CAM-3R-G6

<400> SEQUENCE: 47

Gln Gln Ser Tyr Ser Tyr Pro Phe Thr
1               5

<210> SEQ ID NO 48
<211> LENGTH: 23
<212> TYPE: PRT
<213> ORGANISM: Artificial Sequence
<220> FEATURE:
<223> OTHER INFORMATION: FRL1 of mL1CAM-3R-H8, mL1CAM-3R-C9,
      mL1CAM-3R-E1, mL1CAM-3R-F6, mL1CAM-3R-F1, mL1CAM-3R-G6,
      mL1CAM-3R-A2, mL1CAM-3R-E9, and mL1CAM-2R-F8

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 49
<211> LENGTH: 15
<212> TYPE: PRT
<213> ORGANISM: Artificial Sequence
<220> FEATURE:
<223> OTHER INFORMATION: FRL2 of mL1CAM-3R-H8, mL1CAM-3R-C9,
      mL1CAM-3R-E1, mL1CAM-3R-F6, mL1CAM-3R-F1, mL1CAM-3R-G6,
      mL1CAM-3R-A2, mL1CAM-3R-E9, and mL1CAM-2R-F8

<400> SEQUENCE: 49
```

```
Trp Tyr Gln Gln Lys Pro Gly Lys Ala Pro Lys Leu Leu Ile Tyr
1               5                   10                  15
```

<210> SEQ ID NO 50
<211> LENGTH: 32
<212> TYPE: PRT
<213> ORGANISM: Artificial Sequence
<220> FEATURE:
<223> OTHER INFORMATION: FRL3_of mL1CAM-3R-H8, mL1CAM-3R-C9,
      mL1CAM-3R-E1, mL1CAM-3R-F6, mL1CAM-3R-F1, mL1CAM-3R-G6,
      mL1CAM-3R-A2, mL1CAM-3R-E9, and mL1CAM-2R-F8

<400> SEQUENCE: 50

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 51
<211> LENGTH: 10
<212> TYPE: PRT
<213> ORGANISM: Artificial Sequence
<220> FEATURE:
<223> OTHER INFORMATION: FRL4_of mL1CAM-3R-H8, mL1CAM-3R-C9,
      mL1CAM-3R-E1, mL1CAM-3R-F6, mL1CAM-3R-F1, mL1CAM-3R-G6,
      mL1CAM-3R-A2, mL1CAM-3R-E9, and mL1CAM-2R-F8

<400> SEQUENCE: 51

```
Phe Gly Gln Gly Thr Lys Val Glu Ile Lys
1               5                   10
```

<210> SEQ ID NO 52
<211> LENGTH: 120
<212> TYPE: PRT
<213> ORGANISM: Artificial Sequence
<220> FEATURE:
<223> OTHER INFORMATION: heavy chain variable region_of mL1CAM-3R-H8

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Asn Trp Val Arg Gln Ala Pro Gly Lys Gly Leu Glu Trp Val
        35                  40                  45

Ser Ala Ile Ser Ser Thr Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ser Thr Tyr Phe Tyr Ser Tyr Phe Asp Val Trp Gly Gln
            100                 105                 110

Gly Thr Leu Val Thr Val Ser Ser
        115                 120
```

<210> SEQ ID NO 53
<211> LENGTH: 120
<212> TYPE: PRT
<213> ORGANISM: Artificial Sequence
<220> FEATURE:
<223> OTHER INFORMATION: heavy chain variable region_of mL1CAM-3R-C9

<400> SEQUENCE: 53

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Gly Ser Gly Leu Gly Ala Phe Asp Ile Trp Gly Gln
            100                 105                 110

Gly Thr Leu Val Thr Val Ser Ser
        115                 120
```

<210> SEQ ID NO 54
<211> LENGTH: 120
<212> TYPE: PRT
<213> ORGANISM: Artificial Sequence
<220> FEATURE:
<223> OTHER INFORMATION: heavy chain variable region_of mL1CAM-3R-E1

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Ser Thr Gly Leu Gly Ala Phe Asp Tyr Trp Gly Gln
            100                 105                 110

Gly Thr Leu Val Thr Val Ser Ser
        115                 120
```

<210> SEQ ID NO 55
<211> LENGTH: 121
<212> TYPE: PRT
<213> ORGANISM: Artificial Sequence
<220> FEATURE:
<223> OTHER INFORMATION: heavy chain variable region_of mL1CAM-3R-E9

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
```

```
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys His Gly Gly Thr Trp Trp Gly Arg Ala Phe Asp Tyr Trp Gly
            100             105             110

Gln Gly Thr Leu Val Thr Val Ser Ser
        115             120

<210> SEQ ID NO 56
<211> LENGTH: 107
<212> TYPE: PRT
<213> ORGANISM: Artificial Sequence
<220> FEATURE:
<223> OTHER INFORMATION: light chain variable region_of mL1CAM-3R-H8

<400> SEQUENCE: 56

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Arg Asp
                20              25              30

Leu Asn Trp Tyr Gln Gln Lys Pro Gly Lys Ala Pro Lys Leu Leu Ile
            35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Tyr
                85              90              95

Thr Phe Gly Gln Gly Thr Lys Val Glu Ile Lys
            100             105

<210> SEQ ID NO 57
<211> LENGTH: 107
<212> TYPE: PRT
<213> ORGANISM: Artificial Sequence
<220> FEATURE:
<223> OTHER INFORMATION: light chain variable region_of mL1CAM-3R-C9

<400> SEQUENCE: 57

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Arg Tyr
                20              25              30

Leu Asn Trp Tyr Gln Gln Lys Pro Gly Lys Ala Pro Lys Leu Leu Ile
            35              40              45

Tyr Ala Ala Ser Asn Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Phe Pro Trp
                85              90              95

Thr Phe Gly Gln Gly Thr Lys Val Glu Ile Lys
            100             105

<210> SEQ ID NO 58
<211> LENGTH: 107
```

<212> TYPE: PRT
<213> ORGANISM: Artificial Sequence
<220> FEATURE:
<223> OTHER INFORMATION: light chain variable region_of mL1CAM-3R-E1

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105
```

<210> SEQ ID NO 59
<211> LENGTH: 107
<212> TYPE: PRT
<213> ORGANISM: Artificial Sequence
<220> FEATURE:
<223> OTHER INFORMATION: light chain variable region_of mL1CAM-3R-E9

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105
```

<210> SEQ ID NO 60
<211> LENGTH: 726
<212> TYPE: DNA
<213> ORGANISM: Artificial Sequence
<220> FEATURE:
<223> OTHER INFORMATION: nucleotide sequence of scFv of mL1CAM-3R-H8

<400> SEQUENCE: 60

```
gaagtacagt tggtcgaaag tggcggtggc ctcgtgcaac cgggtggttc actgcgtctg      60
agctgcgccg cctcgggttt tactttctct gattatgcaa tgaattgggt tcgtcaggcg     120
ccgggcaagg gtctcgaatg ggtttcagca atctcttcta ctggttctac tatctactat     180
gccgattcag tgaagggtcg ctttaccatt tcccgtgaca actctaagaa tactctgtat     240
ctgcagatga actcgctgcg tgccgaagac acggccgtct attattgcgc caaacagtct     300
```

-continued

```
acttactttt actcttactt tgatgtttgg ggtcagggca ctttagtgac cgtctcatcg    360
ggtggaggcg gttcaggcgg aggtggatcc ggcggtggcg gatcggacat tcaaatgacg    420
cagagtccct cctcactgag tgctagcgtg ggcgatcgtg tgacaattac ttgtcgcgct    480
agccagtcta tctctcgtga tctgaactgg tatcagcaga aaccgggcaa ggcgccaaaa    540
ttgctgattt acgcagcatc ctctctgcag tctggtgtac cgtcccgttt ctctggcagc    600
ggttctggta cggattttac cctgaccatc tcaagcctcc agcctgaaga ttttgccacc    660
tattattgtc agcaatctta ctctactccg tacacgttcg ggcagggaac taaagtggaa    720
attaaa                                                              726
```

<210> SEQ ID NO 61
<211> LENGTH: 726
<212> TYPE: DNA
<213> ORGANISM: Artificial Sequence
<220> FEATURE:
<223> OTHER INFORMATION: nucleotide sequence of scFv of mL1CAM-3R-C9

<400> SEQUENCE: 61

```
gaagtacagt tggtcgaaag tggcggtggc ctcgtgcaac cgggtggttc actgcgtctg     60
agctgcgccg cctcgggttt tactttctct tcttatgcaa tgcactgggt tcgtcaggcg    120
ccgggcaagg gtctcgaatg ggtttcagca atctcttctt ctggtggttc tacttactat    180
gccgattcag tgaagggtcg ctttaccatt tcccgtgaca actctaagaa tactctgtat    240
ctgcagatga actcgctgcg tgccgaagac acggccgtct attattgcgc caaagatgaa    300
ggttctggtc tgggtgcatt tgatatctgg ggtcagggca ctttagtgac cgtctcatcg    360
ggtggaggcg gttcaggcgg aggtggatcc ggcggtggcg gatcggacat tcaaatgacg    420
cagagtccct cctcactgag tgctagcgtg ggcgatcgtg tgacaattac ttgtcgcgct    480
agccagtcta tctctcgtta cctgaactgg tatcagcaga aaccgggcaa ggcgccaaaa    540
ttgctgattt acgcagcatc caatctgcag tctggtgtac cgtcccgttt ctctggcagc    600
ggttctggta cggattttac cctgaccatc tcaagcctcc agcctgaaga ttttgccacc    660
tattattgtc agcaatctta ctcttttccg tggacgttcg ggcagggaac taaagtggaa    720
attaaa                                                              726
```

<210> SEQ ID NO 62
<211> LENGTH: 726
<212> TYPE: DNA
<213> ORGANISM: Artificial Sequence
<220> FEATURE:
<223> OTHER INFORMATION: nucleotide sequence of scFv of mL1CAM-3R-E1

<400> SEQUENCE: 62

```
gaagtacagt tggtcgaaag tggcggtggc ctcgtgcaac cgggtggttc actgcgtctg     60
agctgcgccg cctcgggttt tactttctct tcttatgcaa tgtcttgggt tcgtcaggcg    120
ccgggcaagg gtctcgaatg ggtttcagca atctcttctt ctggttcttc tacttactat    180
gccgattcag tgaagggtcg ctttaccatt tcccgtgaca actctaagaa tactctgtat    240
ctgcagatga actcgctgcg tgccgaagac acggccgtct attattgcgc caaagatgaa    300
tctactggtc tgggtgcatt tgattactgg ggtcagggca ctttagtgac cgtctcatcg    360
ggtggaggcg gttcaggcgg aggtggatcc ggcggtggcg gatcggacat tcaaatgacg    420
cagagtccct cctcactgag tgctagcgtg ggcgatcgtg tgacaattac ttgtcgcgct    480
agccagtcta tctctaatta cctgaactgg tatcagcaga aaccgggcaa ggcgccaaaa    540
```

-continued

```
ttgctgattt acgcagcatc caatctgcag tctggtgtac cgtcccgttt ctctggcagc      600
ggttctggta cggattttac cctgaccatc tcaagcctcc agcctgaaga ttttgccacc      660
tattattgtc agcaatctta ctcttttccg tggacgttcg ggcagggaac taaagtggaa      720
attaaa                                                                 726
```

```
<210> SEQ ID NO 63
<211> LENGTH: 729
<212> TYPE: DNA
<213> ORGANISM: Artificial Sequence
<220> FEATURE:
<223> OTHER INFORMATION: nucleotide sequence of scFv of mL1CAM-3R-E9

<400> SEQUENCE: 63
gaagtacagt tggtcgaaag tggcggtggc ctcgtgcaac cgggtggttc actgcgtctg       60
agctgcgccg cctcgggttt tactttctct gattatgcaa tgcactgggt tcgtcaggcg      120
ccgggcaagg gtctcgaatg ggtttcagca atctcttctt ctggtggttc tacttactat      180
gccgattcag tgaagggtcg ctttaccatt tcccgtgaca actctaagaa tactctgtat      240
ctgcagatga actcgctgcg tgccgaagac acggccgtct attattgcgc caaacatggt      300
ggtacttggt ggggtcgtgc attcgattac tggggtcagg gcactttagt gaccgtctca      360
tcgggtggag cggttcagg cggaggtgga tccggcggtg cggatcgga cattcaaatg      420 acgcagagtc cctcctcact gagtgctagc gtgggcgatc gtgtgacaat tacttgtcgc      480
gctagccagt ctatcggttc ttacctgaac tggtatcagc agaaaccggg caaggcgcca      540
aaattgctga tttacgcaac ttcctctctg cagtctggtg taccgtcccg tttctctggc      600
agcggttctg gtacggattt taccctgacc atctcaagcc tccagcctga agattttgcc      660
acctattatt gtcagcaatc ttactctact ccgtacacgt tcgggcaggg aactaaagtg      720
gaaattaaa                                                              729
```

```
<210> SEQ ID NO 64
<211> LENGTH: 242
<212> TYPE: PRT
<213> ORGANISM: Artificial Sequence
<220> FEATURE:
<223> OTHER INFORMATION: amino acid sequence of scFv of mL1CAM-3R-H8

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Asn Trp Val Arg Gln Ala Pro Gly Lys Gly Leu Glu Trp Val
        35                  40                  45

Ser Ala Ile Ser Ser Thr Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ser Thr Tyr Phe Tyr Ser Tyr Phe Asp Val Trp Gly Gln
            100                 105                 110

Gly Thr Leu Val Thr Val Ser Ser Gly Gly Gly Gly Ser Gly Gly Gly
        115                 120                 125
```

-continued

```
Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Arg Asp Leu Asn Trp Tyr Gln Gln Lys Pro Gly
                165                 170                 175

Lys Ala Pro Lys Leu Leu Ile Tyr Ala Ala Ser Ser Leu Gln Ser Gly
                180                 185                 190

Val Pro Ser Arg Phe Ser Gly Ser Gly Ser Gly Thr Asp Phe Thr Leu
                195                 200                 205

Thr Ile Ser Ser Leu Gln Pro Glu Asp Phe Ala Thr Tyr Tyr Cys Gln
    210                 215                 220

Gln Ser Tyr Ser Thr Pro Tyr Thr Phe Gly Gln Gly Thr Lys Val Glu
225                 230                 235                 240

Ile Lys
```

```
<210> SEQ ID NO 65
<211> LENGTH: 242
<212> TYPE: PRT
<213> ORGANISM: Artificial Sequence
<220> FEATURE:
<223> OTHER INFORMATION: amino acid sequence of scFv of mL1CAM-3R-C9

<400> SEQUENCE: 65
```

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Gly Ser Gly Leu Gly Ala Phe Asp Ile Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Arg Tyr Leu Asn Trp Tyr Gln Gln Lys Pro Gly
                165                 170                 175

Lys Ala Pro Lys Leu Leu Ile Tyr Ala Ala Ser Asn Leu Gln Ser Gly
                180                 185                 190

Val Pro Ser Arg Phe Ser Gly Ser Gly Ser Gly Thr Asp Phe Thr Leu
                195                 200                 205

Thr Ile Ser Ser Leu Gln Pro Glu Asp Phe Ala Thr Tyr Tyr Cys Gln
    210                 215                 220

Gln Ser Tyr Ser Phe Pro Trp Thr Phe Gly Gln Gly Thr Lys Val Glu
225                 230                 235                 240

Ile Lys
```

```
<210> SEQ ID NO 66
<211> LENGTH: 242
<212> TYPE: PRT
<213> ORGANISM: Artificial Sequence
<220> FEATURE:
<223> OTHER INFORMATION: amino acid sequence of scFv of mL1CAM-3R-E1

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Ser Thr Gly Leu Gly Ala Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Asn Tyr Leu Asn Trp Tyr Gln Gln Lys Pro Gly
                165                 170                 175

Lys Ala Pro Lys Leu Leu Ile Tyr Ala Ala Ser Asn Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Phe Pro Trp Thr Phe Gly Gln Gly Thr Lys Val Glu
225                 230                 235                 240

Ile Lys

<210> SEQ ID NO 67
<211> LENGTH: 243
<212> TYPE: PRT
<213> ORGANISM: Artificial Sequence
<220> FEATURE:
<223> OTHER INFORMATION: amino acid sequence of scFv of mL1CAM-3R-E9

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Thr Trp Trp Gly Arg Ala Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Gly Ser Tyr Leu Asn Trp Tyr Gln Gln Lys Pro
                165                 170                 175

Gly Lys Ala Pro Lys Leu Leu Ile Tyr Ala Thr Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Thr Pro Tyr Thr Phe Gly Gln Gly Thr Lys Val
225                 230                 235                 240

Glu Ile Lys
```

```
<210> SEQ ID NO 68
<211> LENGTH: 27
<212> TYPE: DNA
<213> ORGANISM: Artificial Sequence
<220> FEATURE:
<223> OTHER INFORMATION: primer for 3E8 VH_LS+ L1 ScFv(F)

<400> SEQUENCE: 68
ggtgtccact ccgaagtaca gttggtc                                        27

<210> SEQ ID NO 69
<211> LENGTH: 27
<212> TYPE: DNA
<213> ORGANISM: Artificial Sequence
<220> FEATURE:
<223> OTHER INFORMATION: primer for L1 ScFv+ hIgD hinge(R)

<400> SEQUENCE: 69
acctggccag cgtttaattt ccacttt                                        27

<210> SEQ ID NO 70
<211> LENGTH: 24
<212> TYPE: DNA
<213> ORGANISM: Artificial Sequence
<220> FEATURE:
<223> OTHER INFORMATION: primer for Mlu 1+3E8 VH(F)

<400> SEQUENCE: 70
acgcgtatgg aatggagctg ggtc                                           24

<210> SEQ ID NO 71
<211> LENGTH: 27
<212> TYPE: DNA
<213> ORGANISM: Artificial Sequence
<220> FEATURE:
<223> OTHER INFORMATION: primer for 3E8 VH+L1 ScFv(R)
```

<400> SEQUENCE: 71
caactgtact tcggagtgga cacctgt                                                          27

<210> SEQ ID NO 72
<211> LENGTH: 27
<212> TYPE: DNA
<213> ORGANISM: Artificial Sequence
<220> FEATURE:
<223> OTHER INFORMATION: primer for L1 ScFv+ hIgD hinge(F)

<400> SEQUENCE: 72
gtggaaatta aacgctggcc aggttct                                                          27

<210> SEQ ID NO 73
<211> LENGTH: 27
<212> TYPE: DNA
<213> ORGANISM: Artificial Sequence
<220> FEATURE:
<223> OTHER INFORMATION: primer for XhoI+CD3zeta(R)

<400> SEQUENCE: 73
ccgctcgagt tagcgagggg gcagggc                                                          27

<210> SEQ ID NO 74
<211> LENGTH: 19
<212> TYPE: DNA
<213> ORGANISM: Artificial Sequence
<220> FEATURE:
<223> OTHER INFORMATION: primer for T7(F)

<400> SEQUENCE: 74
tatacgactc actataggg                                                                   19

<210> SEQ ID NO 75
<211> LENGTH: 18
<212> TYPE: DNA
<213> ORGANISM: Artificial Sequence
<220> FEATURE:
<223> OTHER INFORMATION: primer for SP6(R)

<400> SEQUENCE: 75
atttaggtga cactatag                                                                    18

<210> SEQ ID NO 76
<211> LENGTH: 63
<212> TYPE: DNA
<213> ORGANISM: Artificial Sequence
<220> FEATURE:
<223> OTHER INFORMATION: Mlu I-start codon-3E8 LS

<400> SEQUENCE: 76
acgcgtatgg aatggagctg ggtctttctc ttcttcctgt cagtaactac aggtgtccac      60
tcc                                                                                    63

<210> SEQ ID NO 77
<211> LENGTH: 192
<212> TYPE: DNA
<213> ORGANISM: Artificial Sequence
<220> FEATURE:
<223> OTHER INFORMATION: IgD hinge

<400> SEQUENCE: 77
cgctggccag gttctccaaa ggcacaggcc tcctccgtgc ccactgcaca accccaagca      60

-continued

```
gagggcagcc tcgccaaggc aaccacagcc ccagccacca cccgtaacac aggtagagga      120
ggagaagaga agaagaagga gaaggagaaa gaggaacaag aagagagaga gacaaagaca      180
ccaggttgtc cg                                                          192

<210> SEQ ID NO 78
<211> LENGTH: 81
<212> TYPE: DNA
<213> ORGANISM: Artificial Sequence
<220> FEATURE:
<223> OTHER INFORMATION: CD28 TM

<400> SEQUENCE: 78
ttttgggtgc tggtggtggt tggtggagtc ctggcttgct atagcttgct agtaacagtg       60
gcctttatta ttttctgggt g                                                 81

<210> SEQ ID NO 79
<211> LENGTH: 123
<212> TYPE: DNA
<213> ORGANISM: Artificial Sequence
<220> FEATURE:
<223> OTHER INFORMATION: CD28 ICD

<400> SEQUENCE: 79
aggagtaaga ggagcaggct cctgcacagt gactacatga acatgactcc ccgccgcccc       60
gggcccaccc gcaagcatta ccagccctat gccccaccac gcgacttcgc agcctatcgc      120
tcc                                                                    123

<210> SEQ ID NO 80
<211> LENGTH: 126
<212> TYPE: DNA
<213> ORGANISM: Artificial Sequence
<220> FEATURE:
<223> OTHER INFORMATION: OX40

<400> SEQUENCE: 80
gccctgtacc tgctccggag ggaccagagg ctgccccccg atgcccacaa gccccctggg       60
ggaggcagtt ccggacccc catccaagag gagcaggccg acgcccactc caccctggcc      120
aagatc                                                                 126

<210> SEQ ID NO 81
<211> LENGTH: 339
<212> TYPE: DNA
<213> ORGANISM: Artificial Sequence
<220> FEATURE:
<223> OTHER INFORMATION: CD3zeta

<400> SEQUENCE: 81
agagtgaagt tcagcaggag cgcagacgcc cccgcgtacc agcagggcca gaaccagctc       60
tataacgagc tcaatctagg acgaagagag gagtacgatg ttttggacaa gagacgtggc      120
cgggaccctg agatggggg aaagccgcag agaaggaaga accctcagga aggcctgtac      180
aatgaactgc agaaagataa gatggcggag gcctacagtg agattgggat gaaaggcgag      240
cgccggaggg gcaagggca cgatggcctt taccagggtc tcagtacagc caccaaggac      300
acctacgacg cccttcacat gcaggccctg ccccctcgc                             339

<210> SEQ ID NO 82
<211> LENGTH: 348
<212> TYPE: DNA
<213> ORGANISM: Artificial Sequence
```

-continued

```
<220> FEATURE:
<223> OTHER INFORMATION: CD3zeta-stop codon-Xho I

<400> SEQUENCE: 82
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgcag agaaggaaga accctcagga aggcctgtac    180
aatgaactgc agaaagataa gatggcggag gcctacagtg agattgggat gaaaggcgag     240
cgccggaggg gcaagggggca cgatggcctt taccagggtc tcagtacagc caccaaggac    300
acctacgacg cccttcacat gcaggccctg cccctcgct aactcgag                   348

<210> SEQ ID NO 83
<211> LENGTH: 27
<212> TYPE: DNA
<213> ORGANISM: Artificial Sequence
<220> FEATURE:
<223> OTHER INFORMATION: primer for L1-H8 scFv+ IgG1 hinge(R)

<400> SEQUENCE: 83
agatttgggc tctttaattt ccacttt                                          27

<210> SEQ ID NO 84
<211> LENGTH: 27
<212> TYPE: DNA
<213> ORGANISM: Artificial Sequence
<220> FEATURE:
<223> OTHER INFORMATION: primer for L1-H8 scFv+ IgG1 hinge(F)

<400> SEQUENCE: 84
gtggaaatta aagagcccaa atcttgt                                          27

<210> SEQ ID NO 85
<211> LENGTH: 45
<212> TYPE: DNA
<213> ORGANISM: Artificial Sequence
<220> FEATURE:
<223> OTHER INFORMATION: IgG1 hinge

<400> SEQUENCE: 85
gagcccaaat cttgtgacaa aactcacaca tgcccaccgt gccca                      45

<210> SEQ ID NO 86
<211> LENGTH: 321
<212> TYPE: DNA
<213> ORGANISM: Artificial Sequence
<220> FEATURE:
<223> OTHER INFORMATION: IgG1 CH3

<400> SEQUENCE: 86
gggcagcccc gagaaccaca ggtgtacacc ctgcccccat cccgggatga gctgaccaag      60
aaccaggtca gcctgacctg cctggtcaaa ggcttctatc ccagcgacat cgccgtggag     120
tgggagagca atgggcagcc ggagaacaac tacaagacca cgcctcccgt gctggactcc     180
gacggctcct tcttcctcta cagcaagctc accgtggaca gagcaggtg gcagcagggg      240 aacgtcttct catgctccgt gatgcatgag gctctgcaca accactacac gcagaagagc     300
ctctccctgt ctccgggtaa a                                               321

<210> SEQ ID NO 87
<211> LENGTH: 27
<212> TYPE: DNA
```

-continued

<213> ORGANISM: Artificial Sequence
<220> FEATURE:
<223> OTHER INFORMATION: primer for CD28 ICD+41BB(R)

<400> SEQUENCE: 87
tctgccccgt ttggagcgat aggctgc                                        27

<210> SEQ ID NO 88
<211> LENGTH: 27
<212> TYPE: DNA
<213> ORGANISM: Artificial Sequence
<220> FEATURE:
<223> OTHER INFORMATION: primer for CD28 ICD+41BB(F)

<400> SEQUENCE: 88
gcctatcgct ccaaacgggg cagaaag                                        27

<210> SEQ ID NO 89
<211> LENGTH: 27
<212> TYPE: DNA
<213> ORGANISM: Artificial Sequence
<220> FEATURE:
<223> OTHER INFORMATION: primer for CD28 ICD+ICOS ICD (R)

<400> SEQUENCE: 89
ggatgaatac ttggagcgat aggctgc                                        27

<210> SEQ ID NO 90
<211> LENGTH: 27
<212> TYPE: DNA
<213> ORGANISM: Artificial Sequence
<220> FEATURE:
<223> OTHER INFORMATION: primer for CD28 ICD+ICOS ICD (F)

<400> SEQUENCE: 90
gcctatcgct ccaagtattc atccagt                                        27

<210> SEQ ID NO 91
<211> LENGTH: 27
<212> TYPE: DNA
<213> ORGANISM: Artificial Sequence
<220> FEATURE:
<223> OTHER INFORMATION: primer for ICOS ICD+CD3zeta(R)

<400> SEQUENCE: 91
gaacttcact ctggtcacat ctgtgag                                        27

<210> SEQ ID NO 92
<211> LENGTH: 27
<212> TYPE: DNA
<213> ORGANISM: Artificial Sequence
<220> FEATURE:
<223> OTHER INFORMATION: primer for ICOS ICD+CD3zeta(F)

<400> SEQUENCE: 92
acagatgtga ccagagtgaa gttcagc                                        27

<210> SEQ ID NO 93
<211> LENGTH: 27
<212> TYPE: DNA
<213> ORGANISM: Artificial Sequence
<220> FEATURE:
<223> OTHER INFORMATION: primer for CD28 ICD+CD3zeta(R)

<400> SEQUENCE: 93
gaacttcact ctggagcgat aggctgc                                        27

<210> SEQ ID NO 94
<211> LENGTH: 27
<212> TYPE: DNA
<213> ORGANISM: Artificial Sequence
<220> FEATURE:
<223> OTHER INFORMATION: primer for CD28 ICD+CD3zeta(F)

<400> SEQUENCE: 94
gcctatcgct ccagagtgaa gttcagc                                              27

<210> SEQ ID NO 95
<211> LENGTH: 27
<212> TYPE: DNA
<213> ORGANISM: Artificial Sequence
<220> FEATURE:
<223> OTHER INFORMATION: primer for CD28 TM+OX40(R)

<400> SEQUENCE: 95
caggtacagg gccacccaga aaataat                                              27

<210> SEQ ID NO 96
<211> LENGTH: 27
<212> TYPE: DNA
<213> ORGANISM: Artificial Sequence
<220> FEATURE:
<223> OTHER INFORMATION: primer for CD28 TM+OX40(F)

<400> SEQUENCE: 96
attttctggg tggccctgta cctgctc                                              27

<210> SEQ ID NO 97
<211> LENGTH: 27
<212> TYPE: DNA
<213> ORGANISM: Artificial Sequence
<220> FEATURE:
<223> OTHER INFORMATION: primer for CD28 TM+41BB(R)

<400> SEQUENCE: 97
tctgccccgt ttcacccaga aaataat                                              27

<210> SEQ ID NO 98
<211> LENGTH: 27
<212> TYPE: DNA
<213> ORGANISM: Artificial Sequence
<220> FEATURE:
<223> OTHER INFORMATION: primer for CD28 TM+41BB(F)

<400> SEQUENCE: 98
attttctggg tgaaacgggg cagaaag                                              27

<210> SEQ ID NO 99
<211> LENGTH: 29
<212> TYPE: DNA
<213> ORGANISM: Artificial Sequence
<220> FEATURE:
<223> OTHER INFORMATION: primer for CD28TM+ICOS ICD(R)

<400> SEQUENCE: 99
tggatgaata cttcacccag aaaataata                                            29

<210> SEQ ID NO 100
<211> LENGTH: 27
<212> TYPE: DNA
<213> ORGANISM: Artificial Sequence
<220> FEATURE:

<223> OTHER INFORMATION: primer for CD28TM+ICOS ICD(F)

<400> SEQUENCE: 100
attttctggg tgaagtattc atccagt                                              27

<210> SEQ ID NO 101
<211> LENGTH: 126
<212> TYPE: DNA
<213> ORGANISM: Artificial Sequence
<220> FEATURE:
<223> OTHER INFORMATION: 4-1BB

<400> SEQUENCE: 101
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                  126

<210> SEQ ID NO 102
<211> LENGTH: 93
<212> TYPE: DNA
<213> ORGANISM: Artificial Sequence
<220> FEATURE:
<223> OTHER INFORMATION: ICOS

<400> SEQUENCE: 102
aagtattcat ccagtgtgca cgaccctaac ggtgaataca tgttcatgag agcagtgaac      60
acagccaaaa aatctagact cacagatgtg acc                                     93

<210> SEQ ID NO 103
<211> LENGTH: 27
<212> TYPE: DNA
<213> ORGANISM: Artificial Sequence
<220> FEATURE:
<223> OTHER INFORMATION: primer for L1-H8 HC+IgD hinge(R)

<400> SEQUENCE: 103
acctggccag cgcgatgaga cggtcac                                              27

<210> SEQ ID NO 104
<211> LENGTH: 27
<212> TYPE: DNA
<213> ORGANISM: Artificial Sequence
<220> FEATURE:
<223> OTHER INFORMATION: primer for L1-H8 HC+IgD hinge(F)

<400> SEQUENCE: 104
accgtctcat cgcgctggcc aggttct                                              27

<210> SEQ ID NO 105
<211> LENGTH: 27
<212> TYPE: DNA
<213> ORGANISM: Artificial Sequence
<220> FEATURE:
<223> OTHER INFORMATION: primer for AS+MluI+2173-CD8a_LS(F)

<400> SEQUENCE: 105
cgacgcgtat ggccctccct gtcaccg                                              27

<210> SEQ ID NO 106
<211> LENGTH: 27
<212> TYPE: DNA
<213> ORGANISM: Artificial Sequence
<220> FEATURE:
<223> OTHER INFORMATION: primer for 2173-CD8a_LS+C9 ScFv(R)

<400> SEQUENCE: 106
caactgtact tcgggccgag cggcgtg                                                    27

<210> SEQ ID NO 107
<211> LENGTH: 27
<212> TYPE: DNA
<213> ORGANISM: Artificial Sequence
<220> FEATURE:
<223> OTHER INFORMATION: primer for 2173-CD8a_LS+C9 ScFv(F)

<400> SEQUENCE: 107
gccgctcggc ccgaagtaca gttggtc                                                    27

<210> SEQ ID NO 108
<211> LENGTH: 27
<212> TYPE: DNA
<213> ORGANISM: Artificial Sequence
<220> FEATURE:
<223> OTHER INFORMATION: primer for C9 ScFv+hCD8a_Hinge(R)

<400> SEQUENCE: 108
tggggtagtg gttttaattt ccacttt                                                    27

<210> SEQ ID NO 109
<211> LENGTH: 27
<212> TYPE: DNA
<213> ORGANISM: Artificial Sequence
<220> FEATURE:
<223> OTHER INFORMATION: primer for C9 ScFv+hCD8a_Hinge(F)

<400> SEQUENCE: 109
gtggaaatta aaaccactac cccagca                                                    27

<210> SEQ ID NO 110
<211> LENGTH: 27
<212> TYPE: DNA
<213> ORGANISM: Artificial Sequence
<220> FEATURE:
<223> OTHER INFORMATION: primer for AS+Xho1+2173-CD3 zeta(R)

<400> SEQUENCE: 110
ccgctcgagt taccgaggcg gcagggc                                                    27

<210> SEQ ID NO 111
<211> LENGTH: 27
<212> TYPE: DNA
<213> ORGANISM: Artificial Sequence
<220> FEATURE:
<223> OTHER INFORMATION: primer for AS+MluI+GMCSF rec.a LS(F)

<400> SEQUENCE: 111
cgacgcgtat gcttctcctg gtgacaa                                                    27

<210> SEQ ID NO 112
<211> LENGTH: 27
<212> TYPE: DNA
<213> ORGANISM: Artificial Sequence
<220> FEATURE:
<223> OTHER INFORMATION: primer for GMCSF rec.a LS+L1-H8 scFv(R)

<400> SEQUENCE: 112
caactgtact tctgggatca ggaggaa                                                    27

<210> SEQ ID NO 113

<211> LENGTH: 27
<212> TYPE: DNA
<213> ORGANISM: Artificial Sequence
<220> FEATURE:
<223> OTHER INFORMATION: primer for GMCSF rec.a LS+L1-H8 scFv(F)

<400> SEQUENCE: 113
ctcctgatcc cagaagtaca gttggtc                                              27

<210> SEQ ID NO 114
<211> LENGTH: 27
<212> TYPE: DNA
<213> ORGANISM: Artificial Sequence
<220> FEATURE:
<223> OTHER INFORMATION: primer for L1-H8 scFv+hinge+hCD28(R)

<400> SEQUENCE: 114
aattgcggcc gctttaattt ccacttt                                             27

<210> SEQ ID NO 115
<211> LENGTH: 27
<212> TYPE: DNA
<213> ORGANISM: Artificial Sequence
<220> FEATURE:
<223> OTHER INFORMATION: primer for L1-H8 scFv+hinge+hCD28(F)

<400> SEQUENCE: 115
gtggaaatta aagcggccgc aattgaa                                             27

<210> SEQ ID NO 116
<211> LENGTH: 25
<212> TYPE: DNA
<213> ORGANISM: Artificial Sequence
<220> FEATURE:
<223> OTHER INFORMATION: primer for AS+Xho1+CD3-zeta (R)

<400> SEQUENCE: 116
ccgctcgagt tagcgagggg gcagg                                               25

<210> SEQ ID NO 117
<211> LENGTH: 69
<212> TYPE: DNA
<213> ORGANISM: Artificial Sequence
<220> FEATURE:
<223> OTHER INFORMATION: Mlu I-start codon-hCD8a LS

<400> SEQUENCE: 117
acgcgtatgg ccctccctgt caccgccctg ctgcttccgc tggctcttct gctccacgcc      60
gctcggccc                                                                69

<210> SEQ ID NO 118
<211> LENGTH: 135
<212> TYPE: DNA
<213> ORGANISM: Artificial Sequence
<220> FEATURE:
<223> OTHER INFORMATION: hCD8a hinge

<400> SEQUENCE: 118
accactaccc cagcaccgag gccacccacc ccggctccta ccatcgcctc ccagcctctg      60
tccctgcgtc cggaggcatg tagacccgca gctggtgggg ccgtgcatac ccggggtctt      120
gacttcgcct gcgat                                                          135

<210> SEQ ID NO 119
<211> LENGTH: 72

<212> TYPE: DNA
<213> ORGANISM: Artificial Sequence
<220> FEATURE:
<223> OTHER INFORMATION: hCD8a TM

<400> SEQUENCE: 119
atctacattt gggccctct ggctggtact tgcgggtcc tgctgctttc actcgtgatc      60
actctttact gt                                                        72

<210> SEQ ID NO 120
<211> LENGTH: 126
<212> TYPE: DNA
<213> ORGANISM: Artificial Sequence
<220> FEATURE:
<223> OTHER INFORMATION: 4-1BB

<400> SEQUENCE: 120
aagcgcggtc ggaagaagct gctgtacatc tttaagcaac ccttcatgag gcctgtgcag     60
actactcaag aggaggacgg ctgttcatgc cggttcccag aggaggagga aggcggctgc    120
gaactg                                                              126

<210> SEQ ID NO 121
<211> LENGTH: 336
<212> TYPE: DNA
<213> ORGANISM: Artificial Sequence
<220> FEATURE:
<223> OTHER INFORMATION: CD3zeta-iso2M

<400> SEQUENCE: 121
cgcgtgaaat tcagccgcag cgcagatgct ccagcctaca agcaggggca gaaccagctc     60
tacaacgaac tcaatcttgg tcggagagag gagtacgacg tgctggacaa gcggagagga    120
cgggacccag aaatgggcgg gaagccgcgc agaaagaatc cccaagaggg cctgtacaac    180
gagctccaaa aggataagat ggcagaagcc tatagcgaga ttggtatgaa aggggaacgc    240
agaagaggca aaggccacga cggactgtac cagggactca gcaccgccac caaggacacc    300
tatgacgctc ttcacatgca ggccctgccg cctcgg                              336

<210> SEQ ID NO 122
<211> LENGTH: 345
<212> TYPE: DNA
<213> ORGANISM: Artificial Sequence
<220> FEATURE:
<223> OTHER INFORMATION: CD3zeta-iso2M-stop codon-Xho I

<400> SEQUENCE: 122
cgcgtgaaat tcagccgcag cgcagatgct ccagcctaca agcaggggca gaaccagctc     60
tacaacgaac tcaatcttgg tcggagagag gagtacgacg tgctggacaa gcggagagga    120
cgggacccag aaatgggcgg gaagccgcgc agaaagaatc cccaagaggg cctgtacaac    180
gagctccaaa aggataagat ggcagaagcc tatagcgaga ttggtatgaa aggggaacgc    240
agaagaggca aaggccacga cggactgtac cagggactca gcaccgccac caaggacacc    300
tatgacgctc ttcacatgca ggccctgccg cctcggtaac tcgag                    345

<210> SEQ ID NO 123
<211> LENGTH: 72
<212> TYPE: DNA
<213> ORGANISM: Artificial Sequence
<220> FEATURE:
<223> OTHER INFORMATION: Mlu I-start codon-hGM-CSF rec.a LS -continued

```
<400> SEQUENCE: 123
acgcgtatgc ttctcctggt gacaagcctt ctgctctgtg agttaccaca cccagcattc      60
ctcctgatcc ca                                                          72

<210> SEQ ID NO 124
<211> LENGTH: 9
<212> TYPE: DNA
<213> ORGANISM: Artificial Sequence
<220> FEATURE:
<223> OTHER INFORMATION: hinge

<400> SEQUENCE: 124 gcggccgca                                                               9

<210> SEQ ID NO 125
<211> LENGTH: 117
<212> TYPE: DNA
<213> ORGANISM: Artificial Sequence
<220> FEATURE:
<223> OTHER INFORMATION: hCD28 pECD

<400> SEQUENCE: 125
attgaagtta tgtatcctcc tccttaccta gacaatgaga agagcaatgg aaccattatc      60
catgtgaaag ggaaacacct ttgtccaagt cccctatttc ccggaccttc taagccc        117

<210> SEQ ID NO 126
<211> LENGTH: 339
<212> TYPE: DNA
<213> ORGANISM: Artificial Sequence
<220> FEATURE:
<223> OTHER INFORMATION: CD3zeta-iso2

<400> SEQUENCE: 126
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240 cggagggca aggggcacga tggcctttac caggtctca gtacagccac caaggacacc       300
tacgacgccc ttcacatgca ggccctgccc cctcgctaa                            339

<210> SEQ ID NO 127
<211> LENGTH: 348
<212> TYPE: DNA
<213> ORGANISM: Artificial Sequence
<220> FEATURE:
<223> OTHER INFORMATION: CD3zeta-iso2-stop codon-Xho I

<400> SEQUENCE: 127
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240 cggagggca aggggcacga tggcctttac caggtctca gtacagccac caaggacacc       300
tacgacgccc ttcacatgca ggccctgccc cctcgctaat aactcgag                  348

<210> SEQ ID NO 128
<211> LENGTH: 49
```

-continued

```
<212> TYPE: DNA
<213> ORGANISM: Artificial Sequence
<220> FEATURE:
<223> OTHER INFORMATION: 3E8 leader sequence

<400> SEQUENCE: 128
gagctgggtc tttctcttct tcctgtcagt aactacaggt gtccactcc          49

<210> SEQ ID NO 129
<211> LENGTH: 60
<212> TYPE: DNA
<213> ORGANISM: Artificial Sequence
<220> FEATURE:
<223> OTHER INFORMATION: hCD8 alpha leader sequence

<400> SEQUENCE: 129
gccctccctg tcaccgccct gctgcttccg ctggctcttc tgctccacgc cgctcggccc     60

<210> SEQ ID NO 130
<211> LENGTH: 63
<212> TYPE: DNA
<213> ORGANISM: Artificial Sequence
<220> FEATURE:
<223> OTHER INFORMATION: hGM-CSF receptor alpha-chain leader sequence

<400> SEQUENCE: 130
cttctcctgg tgacaagcct tctgctctgt gagttaccac acccagcatt cctcctgatc     60
cca                                                             63
```